United States Patent [19]
Atsumi et al.

[11] Patent Number: 5,663,162
[45] Date of Patent: Sep. 2, 1997

[54] CEPHEM DERIVATIVES

[75] Inventors: Kunio Atsumi; Eijiro Umemura; Yuko Kano; Sohjiro Shiokawa; Toshiaki Kudo; Masaki Tsushima; Katsuyoshi Iwamatsu; Atsushi Tamura; Seiji Shibahara, all of Kanagawa-ken, Japan

[73] Assignee: Meiji Seika Kabushiki Kaisha, Tokyo, Japan

[21] Appl. No.: 436,280

[22] PCT Filed: Sep. 16, 1994

[86] PCT No.: PCT/JP94/01529

§ 371 Date: Jul. 25, 1995

§ 102(e) Date: Jul. 25, 1995

[87] PCT Pub. No.: WO95/07912

PCT Pub. Date: Mar. 23, 1995

[30] Foreign Application Priority Data

Sep. 16, 1993 [JP] Japan .................... 5-230573
Aug. 12, 1994 [JP] Japan .................... 6-211908

[51] Int. Cl.[6] ............... C07D 501/46; A61K 31/545
[52] U.S. Cl. ............... 514/202; 514/201; 540/226; 540/227
[58] Field of Search ............... 540/226, 227; 514/201, 202

[56] References Cited

FOREIGN PATENT DOCUMENTS

| 097961A-2 | 1/1984 | European Pat. Off. . |
| 0097961 | 1/1984 | European Pat. Off. . |
| 59-10593 | 1/1984 | Japan . |
| 61-286388 | 12/1986 | Japan . |

OTHER PUBLICATIONS

Derwent Abstract of JP–61–286388, 1986.

*Primary Examiner*—Mukund J. Shah
*Assistant Examiner*—Pavanaram K. Sripada
*Attorney, Agent, or Firm*—Wenderoth, Lind & Ponack

[57] ABSTRACT

Compounds represented by the following formula (I), that is, cephem derivatives having substituted or unsubstituted imidazo[5,1-b]thiazolium-6-yl as a substituent at the 3-position of the cephem ring:

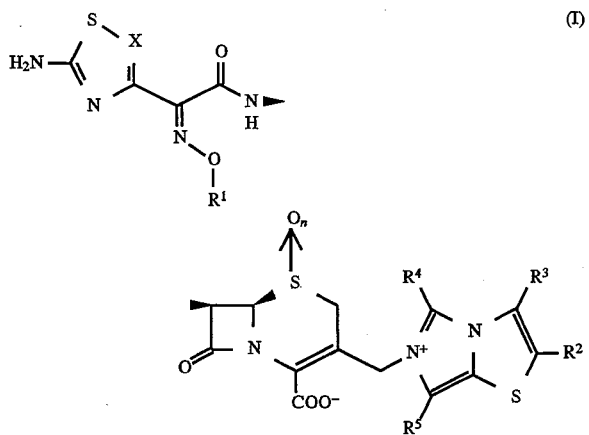

wherein X represents CH or N, $R^1$ represents H, alkyl, alkenyl or the like, and $R^2$, $R^3$, $R^4$ and $R^5$ represent H, alkyl, carbamoyl, amino or the like. The above compounds have excellent antibacterial activity, and useful as medicines for the treatment of various infectious diseases caused by bacteria.

21 Claims, No Drawings

CEPHEM DERIVATIVES

This application is a 371 of PCT/JP94/01529, Sep. 16, 1994, published as WO95/07412, Mar. 23, 1995.

BACKGROUND OF THE INVENTION

1. Field of the Invention

The present invention relates to cephem derivatives having antibacterial activity effective against a wide spectrum of bacteria. More particularly, the present invention relates to novel cephem derivatives having substituted or unsubstituted imidazo[5,1-b]-thiazolium-6-yl as a substituent at the 3-position of the cephem ring.

2. Background Art

Cephem antibiotics exhibit excellent antibacterial activity with a low toxic for mammals. They are therefore remarkably effective in the treatment of infectious diseases in mammals. Those cephem derivatives which have an aminothiazolylacetyl group at the 7-position of the cephem ring have potent antibacterial activity and stability agaist beta-lactamase. For this reason, numerous studies and developments in these cephem derivatives have been made in recent years.

Onium-salt-type cephem antibiotics, such as ceftazidime and cefpirome, which have an aminothiazolylacetyl group at the 7-position and a quaternary salt substituent at the 3-position have potent antibacterial activity effective against a wide spectrum of bacteria from Gram-positive bacteria to *Pseudomonas aeruginosa*. Thus, numerous studies and developments in the antibiotics of this type have been made in many countries in the world. However, even the onium-salt-type cephem compounds such as ceftazidime and cefpirome may not be satisfactory in the antibacterial activity against *Pseudomonas aeruginosa* or Gram-positive bacteria such as *Staphylococcus aureus* which have brought about a clinical problem in recent years. In addition, infectious diseases caused by methicillin-resistant *Staphylococcus aureus* (MRSA) or penicillin-resistant streptococcus pneumoniae (PRSP) have been a serious clinical problem these days. It is therefore strongly demanded to obtain novel cephem antibiotics which have improved antibacterial activity also against these bacteria (Chapter 11 by W. E. Wick, "Cephalosporins and Penicillins, Chemistry and Biology" edited by E. H. Flynn, Academic Press, New York, N.Y., 1972; 18.1 "Cephalosporins" by Hatsuo Aoki, "The Leading Studies in Antibiotics" edited by Masaji Oho and Satoshi Omura, Tokyo Kagaku Dojin Kabushiki Kaisha, Japan, 1987; and "Manifestation of Resistance and Molecular Genetics" by Ryoichi Okamoto and Matsuhisa Inoue, "*Sogo Rinsho*", Vol. 42, No. 2, 1993).

SUMMARY OF THE INVENTION

We have made studies in order to provide cephem derivatives characterized by having potent antibacterial activity effective against a wide spectrum of bacteria. As a result, we now found cephem compounds which have an imidazo[5,1-b]-thiazolium-6-yl structure at the 3-position having excellent antibacterial activity.

Accordingly, compounds provided by the present invention are cephem derivatives represented by the following formula (I):

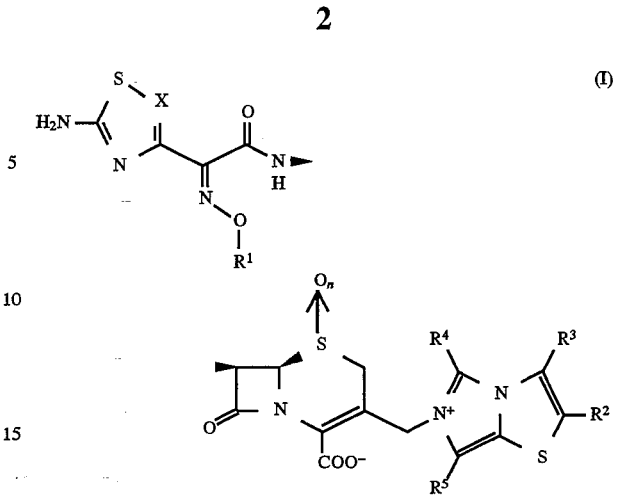

wherein X represents CH or N, $R^1$ represents a hydrogen atom, a $C_{1-4}$ alkyl group in which one or more hydrogen atoms may be substituted by a group selected from a group consisting of a halogen atom, hydroxyl, carboxyl, $C_{1-4}$ alkoxycarbonyl, carbamoyl, N-$C_{1-4}$ alkylcarbamoyl, cyano, amino and $C_{1-4}$ alkylamino; $C_{2-4}$ alkenyl; $C_{2-4}$ alkynyl; or $C_{3-6}$ cycloalkyl, $R^2$, $R^3$, $R^4$ and $R^5$ which may be the same or different, each independently represent hydrogen; $C_{1-4}$ alkoxy; $C_{1-4}$ alkylthio; cyano; carboxyl; $C_{1-4}$ alkoxycarbonyl; carbamoyl; N-$C_{1-4}$ alkylcarbamoyl; formyl; amino in which one or more hydrogen atoms may be substituted by a group selected from a group consisting of formyl, $C_{1-4}$ alkylcarbonyl and $C_{1-4}$ alkylsulfonyl; halogen; $C_{1-4}$ alkyl in which one or more hydrogen atoms may be substituted by a group selected from a group consisting of hydroxyl, $C_{1-4}$ alkoxy, mercapto, $C_{1-4}$ alkylthio, cyano, halogen, carboxyl, $C_{1-4}$ alkoxycarbonyl, carbamoyl, N-$C_{1-4}$ alkylcarbamoyl, formyl, alkylcarbonyl, hydroxyimino, $C_{1-4}$ alkoxyimino, amino, formylamino, $C_{1-4}$ alkylcarbonylamino, $C_{1-4}$ alkylcarbonylamino (which may be substituted by a halogen atom), carbamoyloxy, N-$C_{1-4}$ alkylcarbamoyloxy, $C_{1-4}$ alkylsulfonylamino, ureido, N-$C_{1-4}$ alkylureido, $C_{1-4}$ alkoxycarbonylamino and imino $C_{1-4}$ alkylamino; $C_{3-6}$ cycloalkyl, $C_{2-4}$ alkenyl group; $C_{3-4}$ alkynyl, or a saturated five-membered heterocyclic ring which contains one oxygen atom and one nitrogen atom and may be substituted by oxo (=O), or any two of $R^2$, $R^3$, $R^4$ and $R^5$ may form $C_{3-6}$ alkylene where one or more methylene groups in this alkylene group may be substituted by —NH—, —O—, —S— or —CO—, and n is 0 or 1; and pharmaceutically acceptable salts thereof.

An antibacterial composition according to the present invention comprises a compound of formula (I) together with a pharmaceutically acceptable carrier.

The compounds of the above formula (I) have potent antibacterial activity effective against a wide variety of Gram-positive and Gram-negative bacteria.

DETAILED DESCRIPTION OF THE INVENTION

In this disclosure, "a $C_{1-4}$ alkyl group" as a group or a part of a group means a straight or branched chain $C_{1-4}$ alkyl group. Specific examples of this group include methyl, ethyl, propyl, iso-propyl, n-butyl, iso-butyl, s-butyl and t-butyl. Further, "an alkylene group" means a divalent group derived from a straight or branched alkane chain by removing one hydrogen atom from each terminal end thereof. Further, "a halogen atom" means a fluorine, chlorine, bromine or iodine atom.

Preferable examples of the $C_{1-4}$ alkyl group represented by $R^1$ in the formula (I) include methyl, ethyl, propyl, 1-methylethyl, fluoromethyl, difluoromethyl, 2-fluoroethyl, 3-fluoropropyl, 2-hydroxyethyl, cyanomethyl, carbamoylmethyl, (S)-1-carboxyethyl and 1-carboxy-1-methylethyl. Preferable examples of the $C_{3-6}$ cycloalkyl group represented by $R^1$ include cyclopentyl and cyclohexyl. Preferable examples of the $C_{2-4}$ alkenyl group represented by $R^1$ include 2-propenyl, 2-butenyl and 3-butenyl. Preferable examples of the $C_{2-4}$ alkynyl group represented by $R^1$ include 2-propynyl, 2-butynyl and 3-butynyl.

In the formula (I), $R^2$, $R^3$, $R^4$ and $R^5$ may be the same or different, and represent a $C_{1-4}$ alkoxy group (e.g., methoxy, ethoxy); a $C_{1-4}$ alkylthio group (e.g., methylthio); a cyano group; a carboxyl group; a $C_{1-4}$ alkoxycarbonyl group (e.g., methoxycarbonyl, ethoxycarbonyl); a carbamoyl group; an N-$C_{1-4}$ alkylcarbamoyl group (e.g., N-methylcarbamoyl, N-ethyl- carbamoyl); a formyl group; an amino group; a halogen atom; a $C_{1-4}$ alkyl group; a $C_{3-6}$ cycloalkyl group (e.g., cyclopentyl, cyclohexyl); a $C_{2-4}$ alkenyl group (e.g., 2-propenyl); or a $C_{2-4}$ alkynyl group (e.g., 2-propynyl); or a saturated five-membered heterocyclic ring which contains one oxygen atom and one nitrogen atom and may be substituted by oxo (=O) (e.g., 2-, 4-, or 5-oxazolidinyl, 2-oxo-4- or 5-oxazolidinyl). One or more hydrogen atoms in the above $C_{1-4}$ alkyl group may be substituted by a substituent, and specific examples of the substituent include a hydroxyl group, a $C_{1-4}$ alkoxy group, a mercapto group, a $C_{1-4}$ alkylthio group, a cyano group, a halogen atom, a carboxyl group, a $C_{1-4}$ alkoxycarbonyl group, a carbamoyl group, an N-$C_{1-4}$ alkylcarbamoyl group, a formyl group, an alkylcarbonyl group, a hydroxyimino group, a $C_{1-4}$ alkoxyimino group, an amino group, a formylamino group, a $C_{1-4}$ alkylcarbonylamino group, a $C_{1-4}$ alkylcarbonylamino group (which may be substituted by a halogen atom), a carbamoyloxy group, an N-$C_{1-4}$ alkylcarbamoyloxy group, a $C_{1-4}$ alkylsulfonylamino group, a ureido group, an N-$C_{1-4}$ alkylureido group, a $C_{1-4}$ alkoxycarbonylamino group and a $C_{1-4}$ acetylamino group. Specific examples of the $C_{1-4}$ alkyl group substituted by the above substituent(s) include carboxylmethyl, carbamoylmethyl, hydroxymethyl, hydroxyethyl, (formylamino)-methyl, fluoromethyl, difluoromethyl, (hydroxyimino)methyl, dimethoxymethyl, acetoxymethyl, methoxymethyl, (R)-1-(formyl-amino) methyl, (S)-1-(formylamino)methyl, 2-(formylamino) methyl, (N-formyl-N-methylamino)methyl, ureidomethyl, (carbamoyloxy)methyl, (N-methylcarbamoyloxy)methyl, 2-(carbamoyloxy)ethyl, (acetylamino)methyl, (trifluoroacetylamino)methyl, (N-methyl-ureido)methyl and 1-formylamino-2-hydroxyethyl.

Further, it is also possible that any two of $R^2$, $R^3$, $R^4$ and $R^5$ may form a $C_{3-6}$ alkylene group to form a ring structure. Moreover, one or more methylene groups in this $C_{3-6}$ alkylene group may be substituted by —NH—, —O—, —S— or —CO—. Preferable examples of such a structure include one in which $R^2$ and $R^3$ form a propano group, and one and in which $R^3$ and $R^4$ form a 1-oxo-2-azapropano group. The structures of these groups are as follows:

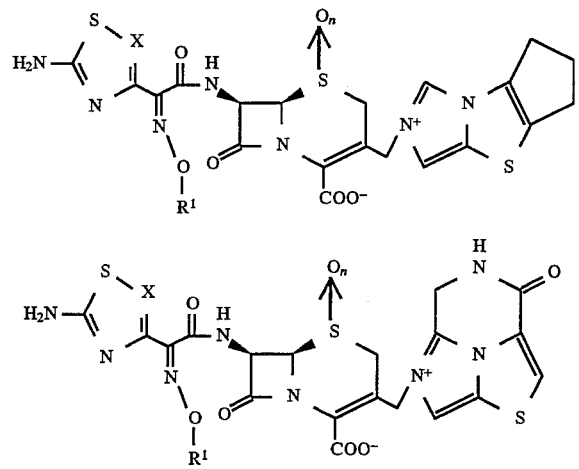

A preferred group of compounds according to the present invention is that wherein $R^2$, $R^4$ and $R^5$ represent a hydrogen atom, and $R^3$ represents a hydrogen atom or a methyl group.

Another preferred group of compounds according to the present invention is that wherein $R^3$ is a group selected from carbamoyl, hydroxymethyl, fluoromethyl, (carbamoyloxy) methyl, (N-methylcarbamoyloxy)methyl, 2-(carbamoyloxy) ethyl, cyano, difluoromethyl, formyl, (hydroxyimino)methyl and methoxymethyl. Of these compounds, more preferable ones are those in which $R^2$, $R^4$ and $R^5$ represent a hydrogen atom.

A further preferred group of compounds according to the present invention is that wherein $R^4$ is a group selected from hydroxymethyl, (formylamino)methyl, (R)-1-(formylamino)ethyl, (S)-1-(formylamino)ethyl, (N-formyl-N-methyl)aminomethyl, ureidomethyl, aminomethyl, 2-hydroxyethyl, formyl, dimethoxymethyl, 2-(formylamino)ethyl, carbamoylmethyl, 2-(carbamoyloxy) ethyl, methylthio, carbamoyl, methoxymethyl, acetoxymethyl, (N-methylureido)methyl, (acetylamino) methyl, (trifluoroacetylamino)methyl, cyano, carboxyl and ethoxycarbonyl. Of these compounds, those in which $R^2$, $R^3$ and $R^5$ represent a hydrogen atom are more preferable.

A yet preferred group of compounds according to the present invention is that wherein $R^2$ is a hydrogen atom, $R^3$ is a methyl group, $R^4$ is a (formylamino)methyl group, and $R^5$ is a hydrogen atom.

A preferred group of compounds according to the present invention is that wherein $R^3$ is a carbamoyl group, and $R^4$ is a (formylamino)methyl group. Of these compounds, those in which $R^2$ and $R^5$ represent a hydrogen atom are more preferable.

A preferred group of compounds according to the present invention is that wherein $R^3$ and $R^4$ are combined to represent 1-oxo-2-azapropylene. Of these compounds, those in which $R^2$ and $R^5$ represent a hydrogen atom are more preferable.

A preferred group of compounds according to the present invention is that wherein $R^5$ is a hydroxymethyl group. Of these compounds, those in which $R^2$, $R^3$ and $R^4$ represent a hydrogen atom are more preferable.

A preferred group of compounds according to the present invention is that wherein $R^2$ is a carbamoyl group. Of these compounds, those in which $R^3$ is a methyl group, and $R^4$ and $R^5$ represent a hydrogen atom are more preferable.

Specific examples of more preferable compounds of the invention are as follows:

(6R,7R)-7-[(Z)-2-(5-amino-1,2,4-thiadiazol-3-yl)-2-methoxyiminoacetamide]-3-(5-(formylamino)methylimidazo[5,1-b]-thiazolium-6-yl)methyl-3-cephem-4-carboxylate (internal salt);

(6R,7R)-7-[(Z)-2-(5-amino-1,2,4-thiadiazol-3-yl)-2-(2-fluoroethoxyimino)acetamide]-3-(imidazo[5,1-b]thiazolium-6-yl)methyl- 3-cephem-4-carboxylate (internal salt);

(6R,7R)-7-[(Z)-2-(5-amino-1,2,4-thiadiazol-3-yl)-2-fluoromethoxyiminoacetamide]-3-(5-((S)-1-formylamino)ethylimidazo-[5,1-b]thiazolium-6-yl)methyl-3-cephem-4-carboxylate (internal salt);

(6R,7R)-7-[(Z)-2-(5-amino-1,2,4-thiadiazol-3-yl)-2-fluoromethoxyiminoacetamide]-3-[5-((R)-1-formylamino-2-hydroxyethyl)-imidazo[5,1-b]thiazolium-6-yl]methyl-3-cephem-4-carboxylate (internal salt);

(6R,7R)-7-[(Z)-2-(5-Amino-1,2,4-thiadiazol-3-yl)-2-ethoxyiminoacetamide]-3-[5-(formylamino)methyl)methylimidazo[5,1-b]thiazolium-6-yl]methyl-3-cephem-4-carboxylate (internal salt), (6R,7R)-7-[(Z)-2-(5-Amino-1,2,4-thiadiazol-3-yl)-2-(fluoromethoxyimino)acetamide]-3-[5-[(R)-1-(formylamino)ethyl]imidazo-[5,1-b]thiazolium-6-yl]methyl-3-cephem-4-carboxylate (internal salt), and (6R,7R)-7-[(Z)-2-(5-amino-1,2,4-thiadiazol-3-yl)-2-fluoromethoxyiminoacetamido]-3-[5-(S)-1(formylamino)-2-hydroxyethyl]imidazo[5,1-b]thiazolium-6yl)methyl-3-cephem-4-carboxylate (inner salt).

include salts of halogen hydroacid such as hydrofluoric acid, hydrochloric acid, hydrobromic acid or hydriodic acid; inorganic acid salts such as sulfate, nitrate, phosphate, perchlorate and carbonate; salts of carboxylic acid such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid or malic acid; salts of acidic amino acid such as aspartic acid or glutamic acid; salts of sulfonic acid such as methanesulfonic acid or p-toluenesulfonic acid; and organic acid salts such as ascorbate. Examples of a salt formed at the carboxyl group include alkaline metallic salts such as a sodium salt, a potassium salt and a lithium salt; alkaline earth metallic salts such as a calcium salt and a magnesium salt; ammonium salts; salts of an organic amine such as triethylamine, trimethylamine, diethylamine, pyridine, ethanolamine, triethanolamine, dicyclohexylamine, procaine, benzylamine, N-methylpiperidine, N-methylmorpholine or diethylaniline; and salts of basic amino acid such as lysine, arginine or histidine.

Preparation of the Compounds

The compounds of the formula (I) according to the present invention can be preferably prepared in accordance with the following scheme:

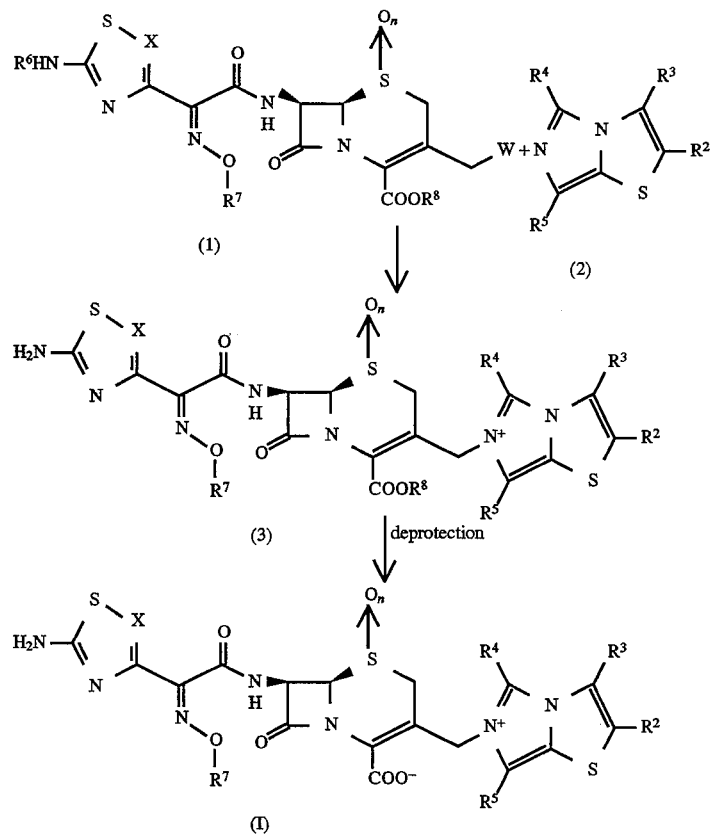

The compounds of the formula (I) according to the present invention may be in the form of pharmaceutically acceptable salts thereof. Examples of such salts include medically acceptable nontoxic salts. Preferable examples of a salt formed at the amino and/or imidazothiazolium group wherein X, $R^1$, $R^2$, $R^3$, $R^4$, $R^5$ and n are as defined in the formula (I), $R^6$ represents a hydrogen atom or an amino protective group (e.g., a trityl, chloroacetyl or formyl group), $R^7$ has the same meaning of $R^1$, provided that when $R^1$ has a carboxyl group, the carboxyl group may be protected by a protective group (e.g., a diphenyl, benzyl, p-methoxybenzyl, p-nitrobenzyl, tert-butyl, allyl or 2,2,2-trichloroethyl group), or represents an oxime protective group (e.g., a trityl group), $R^8$ represents a hydrogen atom or a carboxy protective group (e.g., a diphenylmethyl, benzyl, p-methoxybenzyl, p-nitrobenzyl, tert-butyl or allyl group), and W represents a leaving group, preferably a halogen atom, or a diphenylphosphoryloxy, methanesulfonyloxy, p-toluenesulfonyloxy, trifluoromethanesulfonyloxy or acetoxy group.

The reaction of compound (1) and compound (2) in the scheme can be completed by reacting the compound (1) with an equal or excess amount of the compound (2) in a proper solvent (e.g., acetone, methyl ethyl ketone, ethylacetate, chloroform, dichloromethane, tetrahydrofuran, dioxane, N,N-dimethylformamide, acetonitrile, hexamethylphosphoric triamide, toluene, methanol or ethanol) at a temperature of −20° C. to 50° C. for 0.5 to 72 hours. After the reaction is completed, the reaction solution is post-treated in a conventional manner. If necessary, the compound (3) thus obtained is purified by column chromatography using silica gel or Sephadex LH 20, or by means of crystallization or the like.

In the case where both $R^6$ and $R^8$ represent a hydrogen atom, and $R^7$ and $R^1$ the same, a compound represented by the formula (I) of the present invention can be obtained without conducting the step of deprotection, which is described below.

On the other hand, in the case where a compound (I) of the present invention can be obtained by removing the protective groups $R^6$, $R^7$ and $R^8$, the deprotection of these groups can be carried out in a conventional manner. When the protective groups $R^6$, $R^7$ and $R^8$ can be removed under the acidic condition, it is suitable to treat the compound (3) with trifluoroacetic acid, formic acid, hydrochloric acid or the like. When any one of or all of the groups $R^6$, $R^7$ and $R^8$ can be removed under the conditions for reduction, it is proper to treat the compound (3) by means of catalytic reduction using one of a variety of catalysts, or with a metal reducing agent such as zinc. Further, when $R^6$ is a chloroacetyl group, it can be removed by reacting the compound (3) with one of various thioamides.

By properly adjusting the pH of the aqueous reaction solution, the compound (I) can be crystallized and precipitated. If necessary, the compound (I) may be purified and isolated by chromatography using a nonionic macroporous resin, or by gel filtration using Sephadex or the like.

The above compound (1) can be synthesized by a known method or a method analogous thereto. .Specifically, it can be synthesized in accordance with the method described in the article by S. Torii, H. Hatanaka, N. Saitoh, M. Sasaoka and J. Nokami, Tetrahedron Lett., 23, 2187–2188, 1982.

Use of the Compounds/Pharmaceutical Compositions

The compounds according to the present invention have potent antibacterial activity effective against a wide variety of Gram-positive and Gram-negative bacteria. In particular, they are effective against beta-lactamase-producing bacteria, methicillin-resistant Staphylococcus aureus (MRSA), and the like. Moreover, their toxicity is low, and their absorbability is high.

Therefore, the compounds according to the present invention can be used for the treatment of infectious diseases in animals including humans, caused by various pathogenic fungi.

A pharmaceutical composition comprising as an active ingredient a compound of the present invention or a pharmaceutically acceptable salt thereof can be administered either orally or parenterally (e.g., intravenous injection, intramuscular injection, subcutaneous administration, rectal administration, percutaneous administration) to humans or animals other than humans.

The pharmaceutical composition comprising as an active ingredient a compound of the present invention may be made into a preparation suitable for an administration route to be adopted. Specifically, it may be made into any of the following preparations: an injection for intravenous or intramuscular injection; a capsule, a tablet, a granule, a powder, a pill or a troche for oral administration; a parenteral preparation; and an oily or aqueous suppository.

The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include milk sugar, fruit sugar, grape sugar, starch, gelatin, magnesium carbonate, synthetic magnesium silicate, talc, magnesium stearate, methyl cellulose or a salt thereof, gum arabic, polyethylene glycol, syrup, vaseline, glycerol, ethanol, propylene glycol, citric acid, sodium chloride, sodium sulfite and sodium phosphate.

The dosage of the compound of the present invention is properly determined in consideration of the regimen, the age and sex of a patient, and the conditions of disease. However, for the treatment of infectious disease, approximately 100 mg to 4000 mg, preferably 500 mg to 2000 mg of the compound is generally administered per day for adult human, desirably at one time or several times.

The present invention will now be explained more specifically by referring to the following examples. However, the present invention is not limited by these examples.

Preparation 1

Imidazo[5,1-b]thiazole 0.930 g (6.54 mmol) of 2-(formylamino)methylthiazole (obtained by N-formylating, in a conventional manner, 2-aminomethylthiazole synthesized by the method described in R. G. Jones, E. C. Kornfeld and K. C. McLaughlin, J. Am. Chem. Soc., Vol. 72, 1950, pp. 4525–4529) was dissolved in 20 ml of methylene chloride. 1.2 ml (13 mmol) of phosphorus oxychloride was added dropwise to the solution at −20° C., and the temperature of the mixture was raised to room temperature. The mixture was stirred for 30 minutes, and then concentrated to dryness under reduced pressure. To this was added 12 ml of phosphorus oxychloride, and the mixture was stirred at 100° C. for 30 minutes. The reaction solution was cooled to room temperature, and then concentrated to dryness under reduced pressure. Approximately 20 g of ice was added to the residue. The pH of the mixture was adjusted to 10.5 by a 2N aqueous solution of sodium hydroxide with ice-cooling. The mixture was extracted with methylene chloride (50 ml×3). The organic layer was dried over potassium carbonate, and concentrated. The residue was purified by flash column chromatography using silica gel, eluting first with ethyl acetate and then with a 20:1 mixture of ethyl acetate and methanol to give 0.488 g (yield 60%) of the title compound as light yellow crystals.

NMR (CDCl$_3$) d: 6.83 (1H, d, J=4.4.Hz), 7.10 (1H, s), 7.41 (1H, d, J=4.4 Hz), 8.01 (1H, s) MS (EI, CHCl$_3$, 100° C.): 124 (M$^+$)

Preparation 2

3-Methylimidazo[5,1-b]thiazole 0.795 g (yield 58%) of the title compound was obtained as light yellow crystals from 1.56 g (10.0 mmol) of 2-(formylamino)methyl-4-methylthiazole in the same manner as in Preparation 1.

NMR (CDCl$_3$) d: 2.41 (3H, s), 6.41 (1H, s), 7.10 (1H, s), 7.89 (1H, s). MS (EI, CHCl$_3$, 100° C.): 138 (M$^+$)

Preparation 3

5-Methylimidazo[5,1-b]thiazole 1.272 g (yield 92%) of the title compound was obtained as light yellow crystals from 1.56 g (10.0 mmol) of 2-(acetylamino)methylthiazole in the same manner as in Preparation 1.

NMR (CDCl$_3$) d: 2.57 (3H, s), 6.77 (1H, d, J=4.2 Hz), 6.94 (1H, s), 7.20 (1H, d, J=4.2 Hz) MS (EI, CHCl$_3$, 100° C.): 138 (M$^+$)

Preparation 4

3-Ethylimidazo[5,1-b]thiazole

The title compound (yield 90%) was obtained as light yellow crystals from 2-(formylamino)methyl-4-ethylthiazole in the same manner as in Preparation 1.

NMR (CDCl$_3$) d: 1.39 (3H, t, J=7.5 Hz), 2.76 (2H, qd, J=7.5 Hz, 4 Hz), 6.40 (1H, d, J=1.4 Hz), 7.09 (1H, s), 7.91 (1H, s) MS (EI, CHCl$_3$, 100° C.): 152 (M$^+$)

Preparation 5

2,3-Dimethylimidazo[5,1-b]thiazole 0.637 g (yield 77%) of the title compound was obtained as light yellow crystals from 0.930 g of 2-(formylamino)methyl-4,5-dimethylthiazole in the same manner as in Preparation 1.

NMR (CDCl$_3$) d: 2.28 (1H, s), 2.31 (3H, s), 7.03 (1H, s), 7.79 (1H, s) MS (EI, CHCl$_3$, 100° C.): 152 (M$^+$)

Preparation 6

2,3-Propanoimidazo[5,1-b]thiazole 0.285 g (yield 60%) of the title compound was obtained as light yellow crystals from 0.530 g of 2-(formylamino)methyl-4,5-propanothiazole in the same manner as in Preparation 1.

NMR (CDCl$_3$) d: 2.54–2.67 (2H, m), 2.80–2.90 (4H, m), 7.06 (1H, s), 7.81 (1H, s)

Preparation 7

2-Methylimidazo[5,1-b]thiazole 0.094 g (yield 70%) of the title compound was obtained as light yellow crystals from 0.152 g of 2-(formylamino)methyl-5-methylthiazole in the same manner as in Preparation 1.

NMR (CDCl$_3$) d: 2.35 (3H, s), 7.00 (1H, s), 7.13 (1H, s), 7.87 (1H, s)

Preparation 8

7-Methylimidazo[5,1-b]thiazole

The title compound was obtained as light yellow crystals from 2-(1-formylaminoethyl)thiazole in the same manner as in Preparation 1.

NMR (CDCl$_3$) d: 2.35 (3H, s), 6.76 (1H, d, J=4.2 Hz), 7.32 (1H, d, J=4.2 Hz), 7.90 (1H, s)

Preparation 9

Ethyl imidazo[5,1-b]thiazole-5-carboxylate

To a solution of 3.43 g (30 mmol) of 2-aminomethylthiazole and 3.34 g (33 mmol) of triethylamine in 60 ml of dichloromethane, a solution of 4.512 g of ethyl chloroxalate in 10 ml of dichloromethane was added dropwise with ice-cooling. The reaction solution was stirred for 30 minutes. 20 ml of water was added to the solution, and the mixture was stirred for 10 minutes. The organic layer was separated, and the aqueous layer was extracted with dichloromethane (30 ml×5). The organic layers were combined, washed with a small amount of a saturated aqueous solution of sodium hydrogencarbonate, and dried over anhydrous sodium sulfate. The resultant was concentrated to dryness under reduced pressure to give solid 2-(ethoxalylamino)methylthiazole. To this was added 50 ml of phosphorus oxychloride with ice-cooling. The mixture was refluxed for 12 hours, cooled to room temperature, and concentrated to dryness under reduced pressure. To the residue were added 50 ml of water and 50 ml of dichloromethane to obtain a solution. 50 g of potassium carbonate was added to the solution little by little with ice-cooling. The reaction solution was stirred for 10 minutes, and then filtered to remove insoluble matters. The organic layer was separated, and the aqueous layer was extracted with dichloromethane (30 ml×2). The combined organic layers were dried over anhydrous potassium carbonate, and purified by flash column chromatography using silica gel, eluting with ethyl acetate to give 4.68 g (yield 80%) of the title compound as light yellow crystals.

NMR (CDCl$_3$) d: 1.46 (3H, t, J=7.1 Hz), 4.47 (2H, q, J=7.1 Hz), 7.08 (1H, d, J=4.2 Hz), 7.31 (1H, s), 8.28 (1H, d, J=4.2 Hz) MS (EI, CHCl$_3$, 100° C.): 196 (M$^+$)

Preparation 10

5-Hydroxymethylimidazo[5,1-b]thiazole

To a solution of 0.929 g of the ethyl imidazo[5,1-b]-thiazole-5-carboxylate obtained in Preparation 9 in 20 ml of methanol was added 0.897 g of sodium borohydride, and the mixture was stirred overnight at room temperature. 2 ml of concentrated hydrochloric acid was added dropwise to the reaction solution with ice-cooling. The mixture was stirred for 10 minutes, and then concentrated to dryness under reduced pressure. The residue was dissolved in 50 ml of methanol, and concentrated to dryness again. To the residue were added 30 ml of an aqueous potassium carbonate solution (50 wt. %) and 30 ml of dichloromethane with ice-cooling. The mixture was stirred for 10 minutes, and then filtered to remove insoluble matters. The organic layer was separated, and the aqueous layer was extracted with dichloromethane (30 ml×2). The combined organic layers were dried over anhydrous potassium carbonate, and purified by flash column chromatography using silica gel, eluting first with ethyl acetate and then with a 20:1 mixture of ethyl acetate and methanol to give 0.628 g (yield 86%) of the title compound as light yellow crystals.

NMR (CDCl$_3$) d: 1.7–2.1 (1H, br), 4.85 (2H, s), 6.83 (1H, d, J=4.2 Hz), 6.91 (1H, s), 7.56 (1H, d, J=4.2 Hz) MS (EI, CHCl$_3$, 100° C.): 154 (M$^+$)

Preparation 11

Ethyl imidazo[5,1-b]thiazole-3-carboxylate a) (tert-Butoxycarbonylamino)acetothioamide 25 g of ammonia gas and 50 g of hydrogen sulfide gas were successively dissolved in 230 ml of methanol with ice-cooling and stirring. To this was added 71.45 g of (tert-butoxycarbonylamino)acetonitrile, and the mixture was stirred overnight at room temperature. The reaction solution was cooled with ice. To this was slowly added 500 ml of water, and the mixture was stirred for an additional 2 hours with ice-cooling. The crystals precipitated were collected by filtration, washed with 300 ml of cold water, and then dried under reduced pressure to give 65.88 g of (tert-butoxycarbonyl-amino)acetothioamide as colorless crystals.

NMR (CDCl$_3$) d: 1.46 (9H, s), 4.16 (2H, d, J=6.2 Hz), 5.2–5.3 (1H, br), 7.4–7.7 (1H, br), 7.7–8.0 (1H, br)

b) Ethyl 2-(tert-butoxycarbonylamino)methylthiazole-4-carboxylate

To a solution of 10 g of the above-obtained (tert-butoxycarbonylamino)acetothioamide in 150 ml of ethanol were added 7.3 ml of ethyl bromopyruvate and 2.7 g of calcium carbonate, and the mixture was stirred at room temperature for 6 hours. The reaction solution was filtered, and the filtrate was concentrated to dryness under reduced pressure. The residue was dissolved in chloroform. The solution was washed with a saturated aqueous solution of sodium hydrogencarbonate and a small amount of water, and then dried over anhydrous magnesium sulfate. The resultant was concentrated under reduced pressure, and isopropyl ether was added to the residue. The crystals precipitated were collected by filtration, and dried under reduced pressure to give 11.2 g (yield 74%) of ethyl 2-(tert-butoxycarbonylamino)methylthiazole-4-carboxylate.

NMR (CDCl$_3$) d: 1.44 (3H, t, J=7 Hz), 1.47 (9H, s), 4.57 (2H, q, J=7 Hz), 4.60 (2H, s), 7.12 (1H, s)

c) Ethyl imidazo[5,1-b]thiazole-3-carboxylate

To 1.50 g of the above-obtained ethyl 2-(tert-butoxycarbonylamino)methylthiazole-4-carboxylate was added 5 ml of trifluoroacetic acid, and the mixture was stirred at room temperature for 30 minutes. The reaction solution was concentrated under reduced pressure. A saturated aqueous solution of sodium hydrogencarbonate was added to the residue to adjust the pH of the mixture to approximately 8. To this was added 30 ml of dichloromethane. To the mixture was added with vigorous stirring a mixture which had been prepared by reacting 1 ml of formic acid with 1 ml of acetic anhydride at 50° C. for 30 minutes, and the resulting mixture were stirred for an additional one hour. The organic layer was separated, and the aqueous layer was extracted twice with dichloromethane. The combined organic layers were dried over anhydrous magnesium sulfate, and concentrated to dryness under reduced pressure to give 1.15 g of crude ethyl 2-(formylamino)methylthiazole-4-carboxylate. This compound was dissolved in 30 ml of dichloromethane. To the solution was added 1.2 ml of phosphorus oxychloride at –20 C., and the mixture was stirred at room temperature for 30 minutes. The reaction solution was concentrated under reduced pressure. To this was added 12 ml of phosphorus oxychloride, and the mixture was stirred at 100° C. for 30 minutes. The reaction solution was cooled to room temperature, and then concentrated to dryness under reduced pressure. The residue was dissolved in 30 ml of water, and the solution was washed with 20 ml of dichloromethane. To this was added sodium hydrogencarbonate to adjust the pH of the solution to 8, and the mixture was extracted with dichloromethane (30 ml×2). The combined organic layers were dried over anhydrous magnesium sulfate, and concentrated to dryness under reduced pressure to give 0.885 g (yield 85%) of the title compound as light brown crystals.

NMR (CDCl$_3$) d: 1.43 (2H, t, J=7 Hz), 4.44 (2H, q, J=7 Hz), 7.17 (1H, s), 7.77 (1H, s), 8.57 (1H, s)

Preparation 12 jImidazo[5,1-b]thiazole-3-carboxyamide 1.25 g of the ethyl imidazo[5,1-b]thiazole-3-carboxylate obtained in Preparation 11 was dissolved in 30 ml of methanol saturated with ammonia, and the solution was stirred for 16 hours. The reaction solution was concentrated under reduced pressure. To this was added 50 ml of water. The precipitate was collected by filtration, and dried under reduced pressure to give 1.00 g of the title compound.

NMR (DMSO-d$_6$) d: 7.12 (1H, s), 7.72 (1H, br), 8.09 (1H, s), 8.20 (1H, br), 8.54 (1H, br)

Preparation 13

Methyl imidazo[5,1-b]thiazol-5-yl-acetate

The title compound was obtained as light brown crystals (yield 63%) from 2-(methylmalonylamino)methylthiazole in the same manner as in Preparation 1 (anhydrous potassium carbonate was used instead of 2N sodium hydroxide, and the pH was adjusted to 8).

NMR (CDCl$_3$) d: 3.72 (3H, s), 4.00 (2H, s), 6.82 (1H, d, J=4.2 Hz), 7.02 (1H, s), 7.39 (1H, d, J=4.2 Hz) MS (EI, CHCl$_3$, 100° C.): 196 (M$^+$)

Preparation 14

Imidazo[5,1-b]thiazol-5-yl-acetamide

The title compound was obtained (yield 85%) from the ethyl imidazo[5,1-b]thiazol-5-yl-acetate obtained in Preparation 13 in the same manner as in Preparation 11.

NMR (DMSO-d$_6$) d: 3.78 (2H, s), 6.93 (1H, s), 7.07 (1H, br), 7.17 (1H, d, J=3.6 Hz), 7.62 (1H, br), 7.78 (1H, d, J=3.6 Hz) MS (EI, CHCl$_3$, 100° C.): 181 (M$^+$)

Preparation 15

5-(Formylamino)methylimidazo[5,1-b]thiazole a) 5-(Phthalimide)methylimidazo[5,1-b]thiazole To a solution of 0.548 g (3.55 mmol) of the 5-hydroxymethylimidazo[5,1-b]thiazole obtained in Preparation 9, 1.045 g (7.10 mmol) of phthalimide and 1.86 g (7.10 mmol) of triphenylphosphine in 30 ml of anhydrous tetrahydrofuran, a solution of 1.237 g (7.10 mmol) of diethylazodicarboxylate in 5 ml of anhydrous tetrahydrofuran was added dropwise at room temperature, and the mixture was stirred at room temperature for one hour. The reaction solution was concentrated under reduced pressure. To the residue were added 20 ml of ethyl acetate and 10 ml of hexane for crystallization. The crystals were collected by filtration, washed with a small amount of a 2:1 mixture of ethyl acetate and hexane, and dried under reduced pressure to give 0.725 g (yield 72%) of 5-(phthalimide)methylimidazo[5,1-b]thiazole as colorless crystals.

NMR (CDCl$_3$) d: 5.14 (2H, s), 6.64 (1H, d, J =4.3 Hz), 7.04 (1H, s), 7.7–7.4 (2H, m), 7.83 (1H, d, J=4.3 Hz), 7.85–7.9 (2H, m) b) 5-Aminomethylimidazo[5,1-b]thiazole To 20 ml of methanol were added 0.483 g of the aboveobtained 5-(phthalimide)methylimidazo[5,1-b]thiazole and 0.072 g of anhydrous hydrazine, and the mixture was refluxed for one hour. The reaction solution was cooled with ice. The crystals precipitated were removed by filtration, and washed with a small amount of cold methanol. The filtrate was concentrated under reduced pressure to give crude 5-aminomethylimidazo-[5,1-b]thiazole.

NMR (CDCl$_3$) d: 1.76 (2H, br), 4.15 (2H, s), 6.80 (1H, d, J=4.2 Hz), 6.98 (1H, s), 7.55 (1H, d, J=4.3 Hz)

c) 5-(Formylamino)methylimidazo[5,1-b]thiazole

To the whole quantity of the above-obtained crude 5-aminomethylimidazo[5,1-b]thiazole was added 20 ml of dichloromethane. To this mixture was added a mixture which had been prepared by reacting 1 ml of formic acid with 0.8 ml of acetic anhydride at 50° C. for 10 minutes, and the resulting mixture was stirred for an additional one hour. To the reaction solution were added 10 ml of water and 30 ml of dichloromethane. 10 g of anhydrous potassium carbonate was further added to the mixture with ice-cooling, and the mixture was thoroughly stirred. Insoluble matters were removed by filtration. The organic layer was separated, and the aqueous layer was extracted with dichloromethane (30 ml×2). The combined organic layers were dried over anhydrous potassium carbonate, concentrated under reduced pressure, and purified by flash column chromatography using silica gel, eluting first with ethyl acetate and then with a 20:1 mixture of ethyl acetate and methanol to give 0.304 g of the title compound as light yellow crystals.

NMR (CDCl$_3$) d: 4.75 (2H, d, J=6.5 Hz), 6.82 (1H, d, J=4.3 Hz), 6.75–6.85 (1H, br), 6.96 (2H, s), 7.69 (1H, d, J=4.3 Hz), 8.27 (1H, s)

Preparation 16

5-(Trifluoroacetylamino)methylimidazo[5,1-b]thiazole a) 2-[(N-tert-Butoxycarbonylglycyl)amino]methylthiazole 60 ml of methylene chloride was added to 3.854 g of N-tert-butoxycarbonylglycine and 2.97 g of 1-hydroxybenzotriazole. To this mixture was further added 4.54 g of dicyclohexylcarbodiimide with stirring and ice-cooling. The mixture was stirred for 2 hours with ice-cooling. To this was added 2.28 g of 2-aminomethylthiazole, and the resulting mixture was stirred for an additional 16 hours. The crystals precipitated were removed by filtration. The filtrate was washed with a 5% aqueous solution of sodium hydrogencarbonate, and dried over anhydrous magnesium sulfate. The methylene chloride was evaporated under reduced pressure. The residue was purified by flash column chromatography using silica gel, eluting with ethyl acetate to give 5.29 g (yield 97%) of 2-[(N-tert-butoxycarbonylglycyl)amino]methylthiazole.

NMR (CDCl$_3$) d: 1.44 (9H, s), 3.87 (2H, d, J=5.8 Hz), 4.79 (2H, d, J=5.8 Hz), 5.1–5.3 (1H, br), 7.0–7.15 (1H, br), 7.30 (1H, d, J=3.3 Hz), 7.71 (1H, d, J=3.3 Hz)

b) 2-[(N-Trifluoroacetylglycyl)amino]methylthiazole

To 2.05 g of the above-obtained 2-[(N-tert-butoxycarbonylglycyl)amino]methylthiazole was added 10 ml of trifluoroacetic acid, and the mixture was stirred at room temperature for 30 minutes. The reaction solution was concentrated under reduced pressure. To the residue were added 10.74 g of ethyl trifluoroacetate and 3.83 g of triethylamine, and the mixture was stirred at room temperature for 30 minutes. The mixture was then concentrated under reduced pressure; and purified by flash column chromatography using silica gel, eluting first with ethyl acetate and then with a 20:1 mixture of ethyl acetate and methanol to give 1.98 g (yield 98%) of 2-[(N-trifluoroacetylglycyl)amino]methylthiazole as colorless crystals.

NMR (CDCl$_3$) d: 4.10 (2H, d, J=4.7 Hz), 4.82 (2H, J=5.6 Hz), 6.75–6.85 (1H, br), 7.34 (1H, d, J=3.3 Hz), 7.25–7.4 (1H, br), 7.73 (1H, d, J=3.3 Hz)

c) 5- (Trifluoroacetylamino)methylimidazo[5,1-b]thiazole

To 1.98 g of the above-obtained 2-[(N-trifluoroacetylglycyl)amino]methylthiazole was added 20 ml of phosphorus oxychloride, and the mixture was heated and stirred at 100° C. for 4.5 hours. The reaction solution was cooled to room temperature, and concentrated to dryness under reduced pressure. The residue was dissolved in 30 ml of methylene chloride. To this solution was added 50 ml of water with ice- cooling. The pH of the mixture was adjusted to 8 by adding potassium carbonate little by little with ice-cooling, and the mixture was stirred for one hour. The crystals precipitated were collected by filtration, washed with cold water and a small amount of cold methylene chloride, and dried under reduced pressure to give 1.12 g (yield 60%) of 5-(trifluoro- acetylamino)methylimidazo[5, 1-b]thiazole as light yellow crystals.

NMR (CDCl$_3$) d: 4.77 (0.8H, d, J=2.9 Hz), 4.78 (1.2H, d, J=3.2 Hz), 6.88 (1H, d, J=4.2 Hz), 7.00 (1H, s), 7.76 (0.4H, d, J=4.2 Hz), 7.77 (0.6H, d, J=4.2 Hz)

Preparation 17

5-[(S)-1-(Formylamino)ethyl]imidazo[5,1-b]thiazole a) 2-[(N-tert-Butoxycarbonyl-L-alanyl)amino]methylthiazole 1.427 g (yield 100%) of the title compound was obtained from 0.946 g of N-tert-butoxycarbonyl-L-alanine, 0.743 g of 1-hydroxybenzotriazole, 1.135 g of dicyclohexylcarbodiimide and 0.628 g of 21aminomethylthiazole in the same manner as in Preparation 16 a).

NMR (CDCl$_3$) d: 1.40 (3H, d, J=7.1 Hz), 1.43 (9H, s), 4.15–4.3 (1H, m), 4.77 (3H, dd, J=5.8 Hz, J=12.2 Hz), 4.78 (1H, dd, J=5.8 Hz, J=12.2 Hz), 4.9–5.1 (1H, br), 7.0–7.2 (1H, br), 7.28 (1H, d, J=3.3 Hz), 7.70 (1H, J=3.3 Hz)

b) 2-[(N-Trifluoroacetyl-L-alanyl)amino]methylthiazole 1.368 g (yield 97%) of the title compound was obtained by treating 1.427 g of the above-obtained 2-[(N-tert-butoxycarbonyl-L-alanyl)amino]methylthiazole in the same manner as in Preparation 16 b).

NMR (CDCl$_3$) d: 1.51 (3H, d, J=7.0 Hz), 4.56 (1H, quintet, J=7.0 Hz), 4.78 (1H,.dd, J=5.5 Hz, J=16.0 Hz), 4.79 (1H, dd, J=5.5 Hz, J=16.0 Hz), 6.9–7.1 (1H, br), 7.33 (1H, d, J=3.3 Hz), 7.25–7.45 (1H, br), 7.73 (1H, d, J=3.3 Hz)

c) 5-[(S)-1-(Trifluoroacetylamino)ethyl]imidazo[5,1-b]thiazole 1.108 g (yield 87%) of the title compound was obtained by treating 1.360 g of the above-obtained 2-[(N-trifluoroacetyl-L-alanyl)amino]methylthiazole in the same manner as in Preparation 16 c).

NMR (CDCl$_3$) d: 1.63 (0.3H, d, J=7.1 Hz), 1.74 (2.7H, d, J=7.1 Hz), 5.43–5.75 (1H, m), 6.87 (1H, d, J=4.2 Hz), 6.99 (0.9H, s), 7.02 (0.1H, s), 7.51 (0.9H, d, J=4.2 Hz), 7.4–7.6 (1H, br), 7.65 (0.1H, d, J=4.2 Hz)

d) 5-[(S)-1-(Formylamino)ethyl]imidazo[5,1-b]thiazole

To a solution of 1.108 of the above-obtained 5-[(S)-1-(trifluoroacetylamino)ethyl]imidazo[5,1-b]thiazole in 20 ml of methanol was added a solution of 2.70 g of potassium carbonate in 20 ml of water, and the mixture was stirred at room temperature under argon atmosphere for 14 hours. To the reaction solution was added 50 ml of methylene chloride. To this mixture was added with ice-cooling a mixture of 0.50 g of formic acid and 0.25 g of acetic anhydride, which had been heated to 50° C. for 10 minutes and then cooled to room temperature, and the resulting mixture was stirred for an additional 30 minutes. 2.70 g of potassium carbonate was added to this reaction solution to obtain a solution, to which was added again with ice-cooling a mixture of 0.50 g of formic acid and 0.25 g of acetic anhydride, which had been heated to 50° C. for 10 minutes and then cooled to room temperature, and the resulting mixture was stirred for 30 minutes. Insoluble matters were removed by filtration. The organic layer was separated, and the aqueous layer was extracted with methylene chloride (30 ml×2). The combined organic layers were dried over anhydrous potassium carbonate, concentrated under reduced pressure, and purified by flash column chromatography using silica gel, eluting first with ethyl acetate and then with a 20:1 mixture of ethyl acetate and methanol to give 0.763 g (yield 93%) of the title compound.

NMR (CDCl$_3$) d: 1.70 (3H, J=6.9 Mz), 5.61 (3H, dq, J=7 Hz, 6.9 Hz), 6.25–6.45 (1H,. br), 6.81 (1H, d, J=4.3 Hz), 6.98 (1H, s), 7.59 (1H, d, J=4.3 Hz), 8.20 (1H, s)

Preparation 18

5-[(R)-1-(Formylamino)ethyl]imidazo[5,1-b]thiazole a) 2-[(N-tert-Butoxycarbonyl-D-alanyl)amino]methylthiazole 1.480 g (yield 100%) of the title compound was obtained from 0.946 g of N-tert-butoxycarbonyl-D-alanine, 0.743 g of 1-hydroxybenzotriazole, 1.135 g of dicyclohexylcarbodiimide and 0.628 g of 2-aminomethylthiazole in the same manner as in Preparation 16 a).

NMR (CDCl$_3$) d: 1.39 (3H, d, J=7.1 Hz), 1.43 (9H, s), 4.15–4.3 (1H, m), 4.76 (1H, dd, J=5.8 Hz, J=12.2 Hz), 4.77 (1H, dd, J=5.8 Hz, J=12.2 Hz), 4.9–5.1 (1H, br), 6.95–7.15 (1H, br), 7.28 (1H, d, J=3.3 Hz), 7.70 (1H, J=3.3 Hz)

2-[(N-Trifluoroacetyl-D-alanyl)amino]methylthiazole 1.406 g (yield 100%) of the title compound was obtained by treating 1.480 g of the above-obtained 2-[(N-tert-butoxycarbonyl-D-alanyl)amino]methylthiazole in the same manner as in Preparation 16 b).

NMR (CDCl$_3$) d: 1.51 (3H, d, J=7.0 Hz), 4.57 (1H, quintet, J=7.0 Hz), 4.77 (1H, dd, J=5.5 Hz, J=16.0 Hz), 4.78 (1H, dd, J=5.5 Hz, J=16.0 Hz), 6.9–7.1 (1H, br), 7.33 (1H, d, J=3.3 Hz), 7.35–7.55 (1H, br), 7.73 (1H, d, J=3.3 Hz)

c) 5-[(R)-1-(Trifluoroacetylamino)ethyl]imidazo[5,1-b]thiazole 1.165 g (yield 89%) of the title compound was obtained by treating 1.406 g of the above-obtained 2-[(N-trifluoroacetyl-D-alanyl)amino]methylthiazole in the same manner as in Preparation 16 c).

NMR (CDCl$_3$) d: 1.63 (0.3H, d, J=7.1 Hz), 1.74 (2.7H, d, J=7.1 Hz), 5.43–5.75 (1H, m), 6.87 (1H, d, J=4.2 Hz), 6.98 (0.9H, s), 7.01 (0.1H, s), 7.51 (0.9H, d, J=4.2 Hz), 7.64 (0.1H, d, J=4.2 Hz), 7.55–7.75 (1H, br)

d) 5-[(R)-1-(Formylamino)ethyl]imidazo[5,1-b]thiazole 0.839 g (yield 86%) of the title compound was obtained by treating 1.165 g of the above-obtained 5-[(R)-1-(trifluoroacetylamino)ethyl]imidazo[5,1-b]thiazole in the same manner as in Preparation 17 d).

NMR (CDCl$_3$) d: 1.70 (3H, J=6.9 Hz), 5.61 (1H, dq, J=7 Hz, 6.9 Hz), 6.4–6.55 (1H, br), 6.81 (1H, d, J=4.3 Hz), 6.97 (1H, s), 7.59 (1H, d, J=4.3 Hz), 8.19 (1H, s)

Preparation 19

Ethyl imidazo[5,1-b]thiazole-5-carboxylate

A solution of 0.117 g of the ethyl imidazo[5,1-b]thiazole-5-carboxylate obtained in Preparation 9 in 50 ml of absolute methanol was saturated with ammonia gas with ice-cooling. This was sealed tightly, and stirred at room temperature for 3 days. The reaction solution was concentrated to dryness under reduced pressure to give 0.949 9 (yield 100%) of the title compound as light yellow crystals.

NMR (CDCl$_3$) d: 5.3–5.6 (1H, br), 6.8–7.2 (1H, br), 7.02 (1H, d, J=4.3 Hz), 7.19 (1H, s), 8.37 (1H, d, J=4.2 Hz)

Preparation 20

Ethyl 5-(trifluoroacetylamino)methylimidazo[5,1-b]thiazole-5-carboxylate a) Ethyl 2-aminomethylthiazole-4-carboxylate To 20.55 g of the ethyl 2-(tert-butoxycarbonylamino)methylthiazole-4-carboxylate obtained in Preparation 11 b) was added 144 ml of trifluoroacetic acid, and the mixture was stirred at room temperature for 30 minutes. The reaction solution was concentrated under reduced pressure. To the residue were added 200 ml of methylene chloride and 50 ml of water with ice-cooling, and the mixture was stirred to obtain a solution. To the solution was added 50 g of potassium carbonate little by little with stirring and ice-cooling, and the mixture was stirred for an additional 30 minutes. Insoluble matters were removed by filtration. The organic layer (upper layer) was separated, and the aqueous layer was extracted with methylene chloride (30 ml×15). The combined organic layers were dried over anhydrous sodium sulfate, and concentrated to dryness to give 9.91 g (yield 79%) of the title compound as light yellow crystals.

NMR (CDCl$_3$) d: 1.41 (3H, t, J=7.1 Hz), 1.6–1.9 (2H, br), 4.24 (2H, s), 4.43 (1H, q, J=7.1 Hz), 8.12 (1H, s)

b) Ethyl 2-[(N-tert-butoxycarbonylglycyl)amino]methylthiazole-4-carboxylate 6.869 g (yield 100%) of the title compound was obtained from 3.854 g of N-tert-butoxycarbonylglycine, 2.97 g of 1-hydroxybenzotriazole, 4.54 g of dicyclohexylcarbodiimide and 0.3725 g of the above-obtained ethyl 2-aminomethylthiazole-4-carboxylate in the same manner as in Preparation 16 a).

NMR (CDCl$_3$) d: 1.40 (3H, t, J=7.1 Hz), 1.44 (9H, s), 3.87 (2H, d, J=6.0 Hz), 4.42 (2H, q, J=7.1 Hz), 4.79 (2H, d, J=6.2 Hz), 5.05–5.25 (1H, br), 7.0–7.2 (1H, br), 8.13 (1H, s)

c) Ethyl 2-[(N-trifluoroacetylglycyl)amino]methylthiazole-4-carboxylate 1.782 g (yield 100%) of the title compound was obtained by treating 1.717 g of the above-obtained ethyl 2-[(N-tert-butoxycarbonylglycyl)amino]methylthiazole-4-carboxylate in the same manner as in Preparation 16 b).

NMR (CDCl$_3$) d: 1.40 (3H, t, J=7.1 Hz), 4.15 (2H, J=4.9 Hz), 4.41 (2H, q, J=7.1 Hz), 4.78 (2H, d, J=5.8 Hz), 7.4–7.7 (2H, br), 8.14 (1H, s)

d) Ethyl 5-(trifluoroacetylamino)methylimidazo[5,1-b]thiazole-4-carboxylate

To 1.782 g of the above-obtained ethyl 2-[(N-trifluoroacetylglycyl)amino]methylthiazole-4-carboxylate was added 20 ml of phosphorus oxychloride, and the mixture was stirred at 100° C. for 30 minutes and then at 115° C. for one hour. The reaction solution was cooled to room temperature, and concentrated to dryness under reduced pressure. The residue was dissolved in 100 ml of methylene chloride, and to this solution was added 100 ml of water with ice-cooling. The pH of the mixture was adjusted to 8 by adding sodium hydrogencarbonate little by little with stirring and ice-cooling, and the mixture was stirred for an additional one hour. The organic layer was separated, and the aqueous layer was extracted with 30 ml of methylene chloride. The combined organic layers were dried over anhydrous sodium sulfate, concentrated under reduced pressure, and purified by flash column chromatography using silica gel, eluting with a 2:1 mixture of ethyl acetate and hexane to give 1.382 g (yield 86%) of the title compound.

NMR (CDCl$_3$) d: 1.43 (3H, t, J=7.1 Hz), 4.44 (2H, q, J=7.1 Hz), 5.06 (2H, d, J=5.2 Hz), 7.13 (1H, s), 7.7–7.9 (1H, br), 7.84 (1H, s) MS (EI, CHCl$_3$, 100° C.): 321 (M$^+$)

Preparation 21

5-(N-tert-Butoxycarbonylamino)methylimidazo[5,1-b]thiazole-3-carboxylic acid, 5-(N-tert-butoxycarbonylamino)methylimidazo-[5,1-b]thiazole-3-carboxyamide and 3,5-(1-oxo-2-azapropano)-imidazo[5,1-b]thiazole To a solution of 0.643 g of ethyl 5-(trifluoroacetylamino)methylimidazo[5,1-b]thiazole-4-carboxylate in 10 ml of methanol was added 20 ml of concentrated aqueous ammonia, and the mixture was stirred at room temperature for 14 hours. The reaction solution was concentrated to dryness under reduced pressure. To the residue were added 10 ml of water and 20 ml of tetrahydrofuran to obtain a solution. To the solution were added 2 ml of a saturated aqueous solution of sodium hydrogencarbonate and 0.655 g of di-tert-butyldicarbonate with ice-cooling, and the mixture was stirred overnight at room temperature. The reaction solution was concentrated to dryness under reduced pressure, and the residue was dissolved in 20 ml of water. The pH of the solution was adjusted to 7.5 by a saturated aqueous solution of sodium hydrogencarbonate. The mixture was then extracted with methylene chloride (30 ml×3 ). The combined organic layers were concentrated under reduced pressure, and purified by flash column chromatography using silica gel, eluting with a 20:1 mixture of ethyl acetate and methanol to give 0.310 g (yield 50%) of 5-(N-tert-butoxy-carbonylamino)methylimidazo[5,1-b]thiazole-3-carboxyamide and 0.020 g (yield 5%) of 3,5-(1-oxo-2-azapropano)imidazo[5,1-b]-thiazole. On the other hand, the pH of the aqueous layer was adjusted to 3.5 by 1N hydrochloric acid, and the mixture was concentrated to dryness. The residue was triturated with 50 ml of ethyl acetate, and the mixture was thoroughly stirred. Insoluble matters were removed by filtration, and the filtrate was concentrated to dryness under reduced pressure to obtain 0.180 g (yield 30%) of 5-(N-tert-butoxycarbonylamino)methyl-imidazo[5,1-b]thiazole-3-carboxylic acid. The whole quantity of this carboxylic acid and 0.135 g of 1-hydroxybenzotriazole were dissolved in 5 ml of N,N-dimethylformamide. To this solution was added 0.206 g of dicyclohexylcarbodiimide with ice-cooling, and the mixture was stirred overnight with ice-cooling. Insoluble matters were removed by filtration, and the filtrate was concentrated to dryness under reduced pressure. To the residue was added 5 mi of trifluoroacetic acid. The mixture was stirred at room temperature for 20 minutes, and then concentrated to dryness under reduced pressure. To the residue were added 100 ml of methylene chloride and 2 ml of triethylamine, and the mixture was stirred overnight at room temperature. The reaction solution was concentrated to dryness, and the residue was dissolved in 500 ml of methylene chloride and 10 ml of methanol. To this solution was added 10 ml of a 50% (w/w) aqueous solution of potassium carbonate, and the mixture was thoroughly stirred. The organic layer was decanted, and dried over anhydrous potassium carbonate. The resultant was concentrated under reduced pressure, and then purified by using a Sephadex LH 20 column (500 ml), eluting with a 1:1 mixture of methanol and chloroform to give 0.079 g (yield 22% with respect to the starting material) of 3,5-(1-oxo-2-azapropano)imidazo[5,1-b]thiazole.

5-(N-tert-Butoxycarbonylamino)methylimidazo[5,1-b]-thiazole-3-carboxyamide: NMR (DMSO-d$_6$) d: 1.37 (9H, s), 4.43 (2H, d, J=6.0 Hz), 6.7–6.9 (1H, br), 7.02 (1H, s), 7.71 (1H, s), 7.65–7.9 (1H, br), 8.15–8.4 (1H, br)

3,5-(1-Oxo-2-azapropano)imidazo[5,1-b]thiazole: NMR (DMSO-d$_6$) d: 4.85 (2H, d, J=1.9 Hz), 7.02 (1H, s), 7.79 (1H, s); 8.4–8.6 (1H, br) MS (EI, DMSO, 150° C.): 179 (M$^+$)

5-(N-tert-Butoxycarbonylamino)methylimidazo[5,1-b]-thiazole-3-carboxylic acid: NMR (DMSO-d$_6$) d: 1.36 (9H, s), 4.58 (2H, d, J=5.8 Hz), 6.9–7.1 (1H, br), 7.00 (1H, s), 7.1–7.5 (1H, br), 7.76 (1H, s)

Preparation 22

5-(N-tert-Butoxycarbonylamino)methylimidazo[5,1-b]thiazole

To 0.306 g of the 5-aminomethylimidazo[5,1-b]thiazole obtained in Preparation 15 b) and 0.276 g of potassium carbonate were added 20 ml of tetrahydrofuran and 10 ml of water to obtain a solution. To this reaction solution was added 0.465 g of di-tert-butyldicarbonate with ice-cooling. The mixture was stirred overnight at room temperature, and concentrated under reduced pressure. To the residue were added 50 ml of methylene chloride and 20 ml of water, and the mixture was thoroughly stirred. The organic layer was separated, and the aqueous layer was extracted with 30 ml of methylene chloride. The combined organic layers were dried over anhydrous sodium sulfate, concentrated under reduced pressure, and purified by flash column chromatography using silica gel, eluting with ethyl acetate to give 0.380 g (yield 75%) of the title compound.

NMR(CDCl$_3$) d: 1.45 (9H, s), 4.60 (2H, d, J=6.4 Hz), 5.1–5.3 (1H, br), 6.79 (1H, d, J=4.2 Hz), 6.97 (1H, s), 7.68 (1H, d, J=4.2 Hz)

Preparation 23

Ethyl 3-methylimidazo[5,1-b]thiazole-5-carboxylate

To a solution of 2.564 g (20 mmol) of 2-aminomethyl-4-methylthiazole and 2.226 g (22 mmol) of triethylamine in 50 ml of dichloromethane, a solution of 3.004 g of ethyl chloroxalate in 10 ml of dichloromethane was added dropwise with ice-cooling. The mixture was stirred for 30 minutes. To this was then added 20 ml of water, and the mixture was stirred for 10 minutes. The organic layer was separated, and the aqueous layer was extracted with dichloromethane (30 ml×5). The combined organic layers were washed with a small amount of a saturated aqueous solution of sodium hydrogencarbonate, dried over anhydrous sodium sulfate, and concentrated to dryness under reduced pressure to obtain solid 2-(ethoxalylamino)-methyl-4-methylthiazole. To this compound was added 20 ml of phosphorus oxychloride with ice-cooling. The mixture was refluxed for 10.5 hours, cooled to room temperature, and concentrated to dryness under reduced pressure. To the residue were added 50 ml of water and 50 ml of dichloromethane to obtain a solution, to which was added 50 g of potassium carbonate little by little with ice-cooling. The mixture was stirred for 10 minutes, and insoluble matters were removed by filtration. The organic layer was separated, and the aqueous layer was extracted with dichloromethane (30 ml×2). The combined organic layers were dried over anhydrous potassium carbonate, concentrated under reduced pressure, and purified by flash column chromatography using silica gel, eluting with a 2:1 mixture of ethyl acetate and hexane to give 1.773 g (yield 42% ) of the title compound as yellow crystals.

NMR (CDCl$_3$) d: 1.45 (3H, t, J=7.1 Hz), 2.76 (3H, d, J=1.1 Hz), 4.42 (2H, q, J=7.1 Hz), 6.57 (1H, q, J=1.1 Hz), 7.25 (1H, s)

Preparation 24

5-Hydroxymethyl-3-methylimidazo[5,1-b]thiazole 1.298 g of the title compound was obtained from 1.770 g of the ethyl 3-methylimidazo[5,1-b]thiazole-5-carboxylate obtained in Preparation 23 and 1.593 g of sodium borohydride in the same manner as in Preparation 10.

Preparation 25

5-(Formylamino)methyl-3-methylimidazo[5,1-b]thiazole a) 5-(Phthalimide)methyl-3-methylimidazo[5,1-b]thiazole 1.574 g (yield 75%) of the title compound was obtained as colorless crystals from 1.19 g of the 5-hydroxymethyl-3-methylimidazo[5,1-b]thiazole in Preparation 24, 2.081 g of phthalimide, 3.71 g of triphenylphosphine and 2.463 g of diethyl azodicarboxylate in the same manner as in Preparation 15 a).

NMR (CDCl$_3$) d: 2.72 (3H, d, J=1.3 Hz), 5.28 (2H, s), 6.40 (1H, q, J=1.3 Hz), 6.95 (1H, s), 7.68–7.76 (2H, m), 7.83–7.90 (2H, m)

b) 5-(Formylamino)methyl-3-methylimidazo[5,1-b]thiazole 0.453 g (yield 88%) of the title compound was obtained from 0.885 g of the above-obtained 5-(phthalimide)methyl-3-methylimidazo[5,1-b]thiazole in the same manner as in Preparation 15 a) and b).

NMR (CDCl$_3$) d: 2.58 (3H, d, J=1.3 Hz), 4.89 (2H, d, J=5.0 Hz), 6.38 (1H, q, J=1.3 Hz), 6.7–6.95 (1H, br), 6.96 (1H, s), 8.26 (1H, s)

Preparation 26

Ethyl 2-(imidazo[5,1-b]thiazol-5-yl)acrylate a) Ethyl N-(thiazol-2-yl-methyl) fumaramide ester To a solution of 1.585 g of monomethyl fumaric acid ester and 1.486 g of 1-hydroxybenzotriazole in 100 ml of methylene chloride was added 2.27 g of dicyclohexylcarbodiimide with ice-cooling, and the mixture was stirred for one hour. To this reaction solution was added 1.142 g of 2-aminomethylthiazole, and the mixture was stirred at 4° C. for 3 days. Insoluble matters were removed by filtration. The filtrate was washed with 50 ml of a saturated aqueous solution of sodium hydrogencarbonate. The organic layer was dried over anhydrous magnesium sulfate, concentrated under reduced pressure, and purified by flash column chromatography using silica gel, eluting with a 2:1 mixture of ethyl acetate and hexane to give 2.108 g (yield 88%) of the title compound as light yellow crystals.

NMR (CDCl$_3$) d: 1.31 (3H, t, J=7.1 Hz), 4.25 (2H, q, J=7.1 Hz), 4.87 (2H, d, J=5.6 Hz), 6.7–7.1 (1H, br), 6.88 (1H, d, J=15.4 Hz), 6.97 (1H, d, J=15.4 Hz), 7.32 (1H, d, J=3.3 Hz), 7.73 (1H, d, J=3.3 Hz)

b) Ethyl 2-(imidazo[5,1-b]thiazol-5-yl)acrylate

To 2.108 g of the above-obtained ethyl N-(thiazol-2-yl-methyl)fumaramide ester was added 30ml of phosphorus oxychloride. The mixture was stirred at 110° C. for 5 hours, and allowed to stand to cool to room temperature. The mixture was then concentrated under reduced pressure. The residue was dissolved in 100 ml of methylene chloride. To this solution was added 100 ml of a saturated aqueous solution of sodium hydrogencarbonate little by little with good stirring and ice-cooling, and the mixture was stirred at room temperature for an additional 30 minutes. The organic layer was separated, and the aqueous layer was extracted with methylene chloride (30ml×3). The combined organic layers were dried over anhydrous magnesium sulfate, concentrated under reduced pressure, and purified by flash column chromatography using silica gel, eluting with a 2:1 mixture of ethyl acetate and hexane to give 1.727 g (yield 89%) of the title compound as light yellow crystals.

NMR (CDCl$_3$) d: 1.34 (1H, t, J=7.1 Hz), 4.28 (2H, q, J=7.1 Hz), 6.69 (1H, d, J=15.7 Hz), 7.02 (1H, d, J=4.2 Hz), 7.30 (1H, s), 7.65 (1H, d, J=4.2 Hz), 7.68 (1H, d, J=15.7 Hz)

Preparation 27

2-(Imidazo[5,1-b]thiazol-5-yl)acrylamide

A solution of 0.445 g of the ethyl 2-(imidazo[5,1-b]thiazol-5-yl)acrylate obtained in Preparation 26 in 20 ml of methanol was saturated with ammonia gas with ice-cooling. This was sealed tightly, and stirred at room temperature for 7 days. The reaction solution was concentrated, and then purified by using a Sephadex LH 20 column (500 ml), eluting with a 1:1 mixture of methanol and chloroform to give 0.320 g (yield 83%) of the title compound.

NMR (DMSO-d$_6$) d: 6.74 (1H, d, J=15.4 Hz), 7.05–7.15 (1H, br), 7.25 (1H, s), 7.42 (1H, d, J=4.2 Hz), 7.5–7.6 (1H, br), 7.58 (1H, d, J=15.4 Hz), 8.29 (1H, d, J=4.2 Hz)

Preparation 28

5-Cyanoimidazo[5,1-b]thiazole

To a suspension of 0.237 g of the imidazo[5,1-b]thiazole-5-carboxyamide obtained in Preparation 19 in 20 ml of methylene chloride, 1.302 g of diisopropylethylemine and 0.52 ml of phosphorus oxychloride were successively added with ice-cooling. The mixture was stirred at room temperature for 2 hours. 30 g of ice was then added to the mixture, and the resulting mixture was thoroughly stirred. The organic layer was separated, and the aqueous layer was extracted with 30 ml of methylene chloride. The combined organic layers were washed with 20 ml of a saturated aqueous solution of sodium hydrogencarbonate, dried over anhydrous potassium carbonate, and then concentrated under reduced pressure. The residue was purified by flash column chromatography using silica gel, eluting with a 2:1 mixture of ethyl acetate and hexane to give 0.132 g (yield 62%) of the title compound as light yellow crystals.

NMR (CDCl$_3$) d: 7.18 (1H, d, J=4.1 Hz), 7.30 (1H, s), 7.70 (1H, d, J=4.2 Hz) MS (EI, MeOH, 100° C.): 149 (M$^+$)

Preparation 29

Diphenylmethyl imidazo[5,1-b]thiazole-5-carboxylic acid ester

To a solution of 0.393 g of ethyl imidazo[5,1-b]thiazole-5-carboxylate in 20 ml of methanol was added 2 ml of a 2N aqueous solution of sodium hydroxide, and the mixture was stirred at room temperature for 6 hours. The solution was made weakly acidic (checked by a pH test paper) by 0.5N hydrochloric acid with ice-cooling. To this were added 20 ml of ethyl acetate and 0.427 g of diphenyldiazomethane, and the mixture was stirred overnight. The reaction solution was concentrated under reduced pressure. To the residue were added 30 ml of methylene chloride and 30 ml of water, and the mixture was thoroughly stirred. The organic layer was separated, dried over anhydrous magnesium sulfate, concentrated under reduced pressure, and purified by flash column chromatography using silica gel, eluting with a 1:1 mixture of ethyl acetate and hexane to give 0.602 g (yield 90%) of the title compound as light yellow crystals.

NMR (CDCl$_3$) d: 7.05 (1H, d, J=4.2 Hz), 7.15 (1H, s), 7.28–7.52 (11H, m), 8.26(1H, d, J=4.2 Hz)

Preparation 30

5-(Acetylamino)methylimidazo[5,1-b]thiazole

To a solution of 150 mg (0.98 mmol) of 5-aminomethylimidazo[5,1-b]thiazole in 1 ml of methylene chloride were added 1 ml of acetic anhydride and 0.5 ml of pyridine, and the mixture was stirred overnight at room temperature. The reaction solution was concentrated. The residue was dissolved in methylene chloride, and washed with water. The organic layer was dried over anhydrous magnesium sulfate, and concentrated under reduced pressure. The residue was purified by flash column chromatography using silica gel, eluting with ethyl acetate to give 159 mg (yield 83%) of the title compound as colorless crystals.

NMR (CDCl$_3$) d: 2.03 (3H, s), 4.68 (2H, d, J=6.1 Hz), 6.79 (1H, d, J=4.1 Hz), 6.95 (1H, s), 7.30 (1H, br), 7.75 (1H, d, J=4.1 Hz) MS (EI, MeOH, 120° C.): 195 (M$^+$)

Preparation 31

5-Ureidomethylimidazo[5,1-b]thiazole

To 220 mg (1.42 mmol) of 5-aminomethylimidazo[5,1-b]-thiazole and 0.3 mg of ice were added 1 ml of ice-cooled water and 1 ml of 5N hydrochloric acid, and the mixture was stirred at 80° C. for 5 minutes. To this mixture was added 111 mg of sodium cyanate, and the resulting mixture was stirred at the temperature for 2 hours. 123 mg of sodium cyanate was further added to the mixture, and the resulting mixture was stirred for one hour. 122 mg of sodium cyanate was added again to the mixture, and the stirring was continued for 2 hours. The mixture was cooled to room temperature, and then made alkali by the addition of potassium carbonate. This mixture was washed with methylene chloride. MeOH was added to the aqueous layer, and the mixture was thoroughly stirred. Insoluble matters were removed by filtration. The filtrate was concentrated under reduced pressure, and then allowed to stand at 0° C. overnight. The crystals precipitated were collected by filtration to obtain 160 mg (yield 57%) of 5-ureidomethyl-imidazo[5,1-b]thiazole.

NMR (DMSO-$d_6$) d: 4.41 (2H, d, J=6.0 Hz), 5.60 (2H, br), 6.55 (1H, t, J=6.0 Hz), 6.92 (1H, s), 7.20 (1H, d, 4.2 Hz), 7.84 (1H, d, J=4.2 Hz) MS (EI, MeOH, 190° C.): 196 ($M^+$)

Preparation 32

5-Dimethoxymethylimidazo[5,1-b]thiazole a) 5-Formylimidazo[5,1-b]thiazole

To a solution of 480 mg (3.12 mmol) of 5-hydroxymethylimidazo[5,1-b]thiazole in 10 ml of methylene chloride was added 5 g of manganese dioxide, and the mixture was stirred vigorously at room temperature for 2 hours. The reaction solution was filtered through Celite to remove the manganese dioxide. The filtrate was concentrated under reduced pressure to give 442 mg (yield 93%) of the title compound.

NMR (CDCl$_3$) d: 7.18 (1H, d, J=4.1 Hz), 7.46 (1H, s), 8.45 (1H, d, J=4.1 Hz), 9.76 (1M, s) MS (EI, CHCl$_3$, 110° C.): 152 ($M^+$)

b) 5-Dimethoxymethylimidazo[5,1-b]thiazole

To a solution of 650 mg (4.23 mmol) of the above-obtained 5-formylimidazo[5,1-b]thiazole in 10 ml of methanol were added 30 ml of methyl orthoformate and 486 mg of p-toluenesulfonic acid monohydride. The mixture was refluxed for 4 hours, and then cooled to room temperature. To this was added 2 ml of a 28% sodium methoxide/methanol solution, and the mixture was stirred for 10 minutes. The reaction solution was concentrated under reduced pressure. The residue was dissolved in methylene chloride, and the solution was successively washed with water and a saturated saline solution. The organic layer was dried over anhydrous magnesium sulfate, concentrated under reduced pressure, and purified by flash column chromatography using silica gel, eluting with a 1:9 mixture of hexane and ethyl acetate to give 694 mg (yield 83%).of the title compound as an red-brown oil.

NMR (CDCl$_3$) d: 3.43 (6H, s), 5.56 (1H, s), 6.79 (1H, d, J=4.2 Hz), 7.05 (1H, s), 7.68 (1H, d, J=4.2 Hz)

Preparation 33

5-(N-Methylformylamino)methylimidazo[5,1-b]thiazole a) 2-(N-Methyl-N-trifluoroacetylaminomethylcarbonyl) aminomethylthiazole To a solution of 3.78 g (20 mmol) of N-tert-butoxycarbonylsarcosine in 60 ml of methylene chloride were added with ice-cooling 4.54 g (22mmol) of dicyclohexylcarbodiimide and 3.24 g (24 mmol) of 1-hydroxybenzotriazole, and the mixture was stirred with ice-cooling for one hour. To this was added a solution of 2.28 g (20 mmol) of 2-aminomethylthiazole in 5 ml of methylene chloride, and the mixture was stirred overnight. The methylene chloride layer with insoluble matters removed by filtration was washed with a 10% aqueous solution of potassium carbonate, dried over anhydrous potassium carbonate, and concentrated under reduced pressure. The residue was purified by flash column chromatography using silica gel, eluting with ethyl acetate to give 6.33 g of 2-((N-tert-butoxycarbonyl-N-methyl) aminomethylcarbonyl)aminomethylthiazole.

NMR (CDCl$_3$) d: 1.44 (9H, s), 2.96 (3H, s), 3.93 (2H, s), 4.79 (2H, d, J=5.8 Hz), 7.30 (1H, d, J=3.2 Hz), 7.71 (1H, d, J=3.2 Hz)

To 5.80 g (20 mmol) of the above-obtained 2-((N-tert-butoxycarbonyl-N-methyl)aminomethylcarbonyl) aminomethylthiazole was added 15 ml of trifluoroacetic acid, and the mixture was stirred at room temperature for 30 minutes. The trifluoroacetic acid was evaporated under reduced pressure, and the residue was dissolved in 60 ml of methylene chloride. To this solution were added 25 g of ethyl trifluoroacetic acid ester and 2.78 ml of triethylamine, and the mixture was stirred overnight at room temperature. The reaction solution was washed 4 times with a 5% aqueous solution of sodium hydrogencarbonate, dried over anhydrous magnesium sulfate, and concentrated under reduced pressure. The residue was purified by flash column chromatography using silica gel, eluting with ethyl acetate. A fraction containing the desired compound was concentrated to dryness. The residue was further purified by column chromatography using Sephadex LH 20, eluting with a 1:1 mixture of chloroform and water to give 5.34 g (yield 95%) of 2-(N-methyl-N-trifluoroacetylaminomethylcarbonyl) aminomethylthiazole.

NMR (CDCl$_3$) d: 3.12 (1/4×3H, s), 3.28 (3/4×3H, s), 4.12 (3/4×2H, s), 4.16 (1/4×2H, s), 4.76 (3/4×2H, d, J=5.6 Hz), 4.78 (1/4 33 2H, d, J=5.6 Hz), 6.98 (1/4×1H, br), 7.05 (3/4×1H, br), 7.30 (3/4×1H, d, J=3.3 Hz), 7.32 (1/4×1H, d, J=3.3 Hz), 7.71 (1H, s) MS (EI, CHCl$_3$, 120° C.): 281 ($M^+$)

b) 5-(N-Methyl-N-trifluoroacetylamino)methylimidazo-[5,1-b]thiazole

To 3.02 g (10.3 mmol) of the above-obtained 2-(N-methyl-N-trifluoroacetylaminomethylcarbonyl) aminomethylthiazole was added 40 ml of phosphorus oxychloride, and the mixture was stirred at 10° C. for 1.5 hours and then at 120° C. for 5 hours. The reaction solution was cooled to room temperature, and concentrated under reduced pressure. To the residue were added a small amount of ice and 15 ml of a 50% aqueous solution of potassium carbonate. The mixture was stirred, and then extracted three times with methylene chloride. The organic layer was dried over anhydrous potassium carbonate, concentrated under reduced pressure, and purified by flash column chromatography using silica gel, eluting with a 1:9 mixture of hexane and ethyl acetate to give 490 mg (yield 18%) of 5-(N-methyl-N-trifluoroacetylamino)methylimidazo[5,1-b] thiazole as colorless crystals.

NMR (CDCl$_3$) d: 3.20 (3H, s), 4.89 (2H, s), 6.82 (1H, d, J=4.3 Hz), 7.04 (1H, s), 7.69 (1H, d, J=4.3 Hz) MS (EI, CHCl$_3$, 120° C.): 263 ($M^+$)

c) 5-(N-Methylamino)methylimidazo[5,1-b]thiazole

To a solution of 394 mg (1.49 mmol) of the above-obtained 5-(N-methyl-N-trifluoroacetylamino) methylimidazo[5,1-b]thiazole in 3 ml of methanol was added 3 ml of a 10% aqueous solution of sodium hydroxide, and the mixture was stirred at room temperature for 1 hour. The methanol was distilled off under reduced pressure. The resultant was extracted three times with chloroform. The organic layer was dried over anhydrous potassium carbonate, and concentrated under reduced pressure to give 272 mg of the title compound as an oil.

NMR (CDCl$_3$) d: 2.45 (3H, s), 4.03 (2H, s), 6.77(1H, d, J=4.2 Hz), 6.97 (1H, s), 7.69 (1H, s)

d) 5-(N-Methylformylamino)methylimidazo[5,1-b]thiazole

To a solution of 100 mg (0.59 mmol) of the above-obtained 5-(N-methylamino)methylimidazo[5,1-b]thiazole in 3 ml of methylene chloride was added a mixture which had been prepared in advance by reacting 1 ml of formic acid with 0.2 ml of acetic anhydride at 50° C. for 10 minutes. The mixture was stirred at room temperature for one hour, and then refluxed for 3 hours. To this was added a mixture which had been prepared in advance by reacting 5 ml of formic acid with 2 ml of acetic anhydride at 50° C. for 10 minutes, and the mixture was refluxed for an additional 2 hours. To the reaction solution cooled to room temperature was added 3 ml of toluene, and the mixture was concentrated to dryness under reduced pressure. To the residue were added methylene chloride and a 50% aqueous solution of potassium carbonate, and the mixture was stirred for 10 minutes. The organic layer was separated, and the aqueous layer was extracted three times with methylene chloride. The combined organic layers were dried over anhydrous potassium carbonate, concentrated under reduced pressure, and purified by flash column chromatography using silica gel, eluting with a 9:1 mixture of ethyl acetate and methanol to give 89 mg (yield 77%) of the title compound as colorless crystals.

NMR (CDCl$_3$) d: 2.81 (1/9×3H, s), 2.96 (8/9×3H, s), 4.71 (1/9×2H, s), 4.79 (8/9×2H, s), 6.78 (8/9×1H, d, J=4.3 Hz), 6.91 (1/9×1H, d, J=4.3 Hz), 6.99 (8/9×1H, s), 7.07 (1/9×1H, s), 7.36 (1/9×1H, d, J=3.5 Hz), 7.73 (8/9×1H, d, J =3.5 Hz), 8.08 (8/9×1H, s), 8.37 (1/9×1H, s) MS (EI, CHC13, 110° C.): 195 (M$^+$)

Preparation 34

5-(1-Methylureido)methylimidazo[5,1-b]thiazole

To 137 mg (0.82 mmol) of the 5-(N-methylamino) methylimidazo[S,1-b]thiazole prepared in Preparation 33 c) and 0.3 mg of ice was added 1 ml of ice-cooled water. To the mixture was added 0.5 ml of 5N hydrochloric acid, and the resulting mixture was stirred at 80° C. for 5 minutes. 160 mg of sodium cyanate was further added to the mixture, followed by stirring at the temperature for 2 hours. The reaction solution was cooled to room temperature, and then made alkali by the addition of potassium carbonate. The mixture was extracted four times with methylene chloride. The organic layer was dried over anhydrous potassium carbonate. The solvent was distilled off under reduced pressure to give 150 mg (yield 87%) of 5-(1-methylureido) methylimidazo[5,1-b]thiazole as colorless crystals.

NMR (DMSO-d$_6$) d: 2.74 (3H, s), 4.60 (2H, s), 6.04 (2H, br), 6.95 (1H, s), 7.21 (1H, d, J=4.1 Hz), 7.81 (1H, d, J=4.1 Hz) MS (EI, MeOH, 200° C.): 210 (M$^+$)

Preparation 35

5-Methoxymethylimidazo[5,1-b]thiazole a) 2-(Methoxyacetylamino)methylthiazole

To a solution of 342 mg (3.0 mmol) of 2-aminomethylthiazole and 0.50 ml (3.6 mmol) of triethylamine in 5 ml of methylene chloride was added dropwise with ice-cooling a solution of 390 mg (3.6 mmol) of methoxyacetyl chloride in 2 ml of methylene chloride, and the mixture was stirred at the temperature for 15 minutes. To this was added 2 ml of water, and the mixture was stirred for 5 minutes. The organic layer was separated, and the aqueous layer was extracted two times with methylene chloride. The combined organic layers were washed with a small amount of a50% aqueous solution of potassium carbonate, dried over anhydrous potassium carbonate, and concentrated under reduced pressure. The residue was purified by flash column chromatography using silica gel, eluting with ethyl acetate to give 570 mg of the title compound.

NMR (CDCl$_3$) d: 3.43 (3H, s), 3.97 (2H, s), 4.81 (2H, d, J=6.0 Hz), 7.29 (1H, d, J=3.3 Hz), 7.35 (1H, br), 7.72 (1H, d, J=3.3 Hz)

b) 5-Methoxymethylimidazo[5,1-b]thiazole

To 570 mg (3.1 mmol) of the above-obtained 2-(methoxyacetylamino)methylthiazole was added 5 ml of phosphorus oxychloride. The mixture was refluxed for 4 hours, cooled to room temperature, and concentrated to dryness under reduced pressure. To the residue were added 2 ml of water and 5 ml of methylene chloride to obtain a solution, to which was added 2 g of potassium carbonate little by little. The mixture was stirred for 5 minutes. The organic layer was separated, and the aqueous layer was extracted two times with methylene chloride. The combined organic layers were dried over anhydrous potassium carbonate, concentrated under reduced pressure, and purified by flash column chromatography using silica gel, eluting with ethyl acetate. A fraction containing the desired compound was concentrated to dryness. The residue was further purified by column chromatography using Sephadex LH 20, eluting with a 1:1 mixture of chloroform and methanol to give 110 mg (yield 21%) of the title compound.

NMR (CDCl$_3$) d: 3.35 (3H, s), 4.73 (2H, s), 6.82 (1H, d, J=4.2 Hz), 7.02 (1H, s), 7.50 (1H, d, J=4.2 Hz) MS (EI, CDCl$_3$, 120° C.): 168 (M$^+$)

Preparation 36

5-(2-Hydroxyethyl)imidazo[5,1-b]thiazole

To a solution of 1.10 g (5.62 mmol) of methyl (imidazo-[5,1-b]thiazol-5-yl)acetate in 15 ml of ethanol was added 61 mg (2.8 mmol) of lithium borohydride with ice-cooling, and the mixture was stirred at room temperature for 30 minutes. To this was added 130 mg (5.6 mmol) of lithium borohydride. The mixture was stirred at room temperature for 3 hours, and allowed to stand overnight in a refrigerator. 20 ml of methanol and 2 ml of concentrated hydrochloric acid were added to the reaction solution with ice-cooling. The mixture was stirred, and then concentrated under reduced pressure. To this was added 30 ml of methanol, and the mixture was concentrated to dryness under reduced pressure. The residue was dissolved in ethyl acetate, and the solution was concentrated to approximately half the original volume under reduced pressure. The crystals precipitated were collected by filtration to give 640 mg of the title compound.

NMR (CDCl$_3$) d: 3.07 (2H, t, J=5.4 Hz), 3.60 (1H, br), 4.08 (2H, t, J=5.4 Hz), 6.80 (1H, d, J=4.3 Hz), 6.97 (1H, s), 7.30 (1H, d, J=4.3 Hz) MS (EI, MeOH, 100° C.): 168 (M$^+$)

Preparation 37

5-(2-Formylaminoethyl)imidazo[5,1-b]thiazole a) 5-(2-Phthalimidethyl)imidazo[5,1-b]thiazole To a solution of 550 mg (3.27 mmol) of the 5-(2-hydroxyethyl)imidazo[5,1-b]thiazole prepared in Preparation 36 in 15 ml of anhydrous tetrahydrofuran were added 1.03 g (3.93 mmol) of triphenylphosphine and 578 mg (3.93mmol) of phthalimide at room temperature, and the mixture was stirred for 4 minutes. To this mixture was added a solution of 0.59 ml (3.93 mmol) of diethyl azodicarboxylate in 5 ml of anhydrous tetrahydrofuran, and the resulting mixture was allowed to stand overnight in a refrigerator. The crystals precipitated were collected by filtration, washed with a small amount of ethyl acetate, and dried under reduced pressure to give 710 mg (yield 73%) of 5-(2-phthalimidethyl)imidazo[5,1-b]thiazole as colorless crystals.

NMR (CDCl₃) d: 5.14 (2H, s), 6.83 (1H, d, J=4.3 Hz), 7.04 (1H, s), 7.70–7.73 (2H, m), 7.83 (1H, d, J=4.3 Hz), 7.84–4.87 (2H, m)

b) 5-(2-Formylaminoethyl)imidazo[5,1-b]thiazole

To a solution of 710 mg (2.39 mmol) of the above-obtained 5-(2-phthalimidethyl)imidazo[5,1-b]thiazole in 10 ml of methanol was added 0.11 ml (3.58 mol) of anhydrous hydrazine, and the mixture was refluxed for one hour. The reaction solution was cooled with ice. The crystals precipitated were removed by filtration, and the filtrate was concentrated under reduced pressure to give crude 5-(2-aminoethyl)imidazo[5,1-b]-thiazole. This compound was dissolved in 20 ml of ethyl formate, and the solution was stirred at room temperature for one hour and then at 50° C. for one hour. To this reaction solution was added 0.78 ml of triethylamine with ice-cooling, and the mixture was stirred at 50° C. for 3 hours. 0.36 ml of triethylamine was further added, and the resulting mixture was stirred at 70° C. for 4 hours. The reaction solution was concentrated under reduced pressure. The residue was purified by flash column chromatography using silica gel, eluting with a 1:9 mixture of methanol and chloroform to give 423 mg (yield 90%) of 5-(2-formylaminoethyl)imidazo[5,1-b]thiazole.

NMR (CDCl₃) d: 3.10 (2H, t, J=6.4 Hz), 3.80 (2H, dr, J=6.2 Hz, 6.0 Hz), 6.75 (1H, br), 6.84 (1H, d, J=4.2 Hz), 6.99 (1H, s), 7.30 (1H, d, J=4.2 Hz), 8.17 (1H, s) MS (EI, MeOH, 100° C.): 195 (M⁺)

Preparation 38

7-Hydroxymethylimidazo[5,1-b]thiazole a) 7-Ethoxycarbonylimidazo[5,1-b]thiazole

A solution of 270 mg (1.26 mmol) of ethyl 2-(N-formylamino)-2-(2-thiazolyl)acetic acid ester (obtained by formylating, in a conventional manner, ethyl 2-amino-2-(2-thiazolyl)acetic acid ester synthesized by the method described in M. Hatanaka and T. Ishimaru, Bull. Chem. Soc. Jpn., Vol. 46, 1973, pp. 3600–3601) in 25 ml of phosphorus oxychloride was stirred at 100° C. (the oil bath temperature) for one hour..The reaction solution was cooled to room temperature, and the phosphorus oxychloride was evaporated under reduced pressure. To the residue were added a small amount of ice and 15 ml of a 50% aqueous solution of potassium carbonate. The mixture was stirred, and extracted three times with methylene chloride. The organic layer was dried over anhydrous potassium carbonate, concentrated under reduced pressure, and purified by flash column chromatography using silica gel, eluting with a 1:4 mixture of hexane and ethyl acetate to give 140 mg (yield 57%) of the title compound.

NMR (CDCl₃) d: 1.43 (3H, t, J=7.0 Hz), 4.42 (2H, q, J=7.0 Hz), 7.05 (1H, d, J=4.1 Hz), 7.53 (1H, d, J=4.1 Hz), 8.01 (1H, s) MS (EI, CHCl₃, 170° C.): 196 (M⁺)

b) 7-Hydroxymethylimidazo[5,1-b]thiazole

To a solution of 95 mg (0.49 mmol) of the above-obtained 7-ethoxycarbonylimidazo[5,1-b]thiazole in 10 ml of tetrahydrofuran (THF) was added 300 mg of lithium borohydride. The mixture was stirred at 80° C. (the oil bath temperature) for one hour, and then cooled. To this reaction solution, 15 ml of methanol was added little by little with ice-cooling, and the mixture was stirred at room temperature for 30 minutes. Concentrated hydrochloric acid was added to this solution little by little with ice-cooling. The resulting mixture was stirred at room temperature for one hour, and concentrated under reduced pressure. To the residue was added a 50% aqueous solution of potassium carbonate to obtain a solution, which was then extracted four times with methylene chloride. The organic layer was dried over anhydrous potassium carbonate, concentrated under reduced pressure, and purified by flash column chromatography using silica gel, eluting with a 3:17 mixture of methanol and ethyl acetate to give 30 mg (yield 40%) of 7-hydroxymethylimidazo[5,1-b]thiazole.

NMR (CDCl₃) d: 4.75 (2H, s), 6.81 (1H, d, J=4.4 Hz), 7.36 (1H, d, J=4.4 Hz), 7.94 (1H, s) MS (EI, CHCl₃, 150° C.): 154 (M⁺)

Preparation 39

3-(Carbamoyloxymethyl)imidazo[5,1-b]thiazole

To a solution of 0.5 g (3.24 mmol) of the 3-(hydroxymethyl)imidazo[5,1-b]thiazole prepared in Preparation 55 in 5 ml of pyridine was added 0.54 ml (4.22 mmol) of phenyl chlorocarbonate with ice-cooling, and the mixture was stirred at the temperature for 40 minutes and then at room temperature for 2.5 hours. To this solution was added with ice-cooling 20 ml of methanol saturated with ammonia, and the mixture was stirred at the temperature for 30 minutes and then at room temperature for 41 hours. The resulting mixture was concentrated under reduced pressure. The residue was purified by column chromatography using Sephadex LH 20, eluting with a 1:1 mixture of chloroform and methanol to give 0.4 g (yield 62.6%) of the title compound as light yellow crystals.

NMR (DMSO-d₆) d: 5.18 (2H, s), 6.55–6.95 (2H, br), 7.08 (1H, s), 7.28 (1H, s), 8.17 (1H, s) MS (EI, DMSO, 110° C.): 197 (M⁺)

Preparation 40

5-(Methylthio)imidazo[5,1-b]thiazole 0.5 g (4.38 mmol) of 2-(aminomethyl)thiazole and 1.22 ml (8.76 mmol) of triethylamine were dissolved in 13 ml of chloroform. To this solution, a solution of 0.35 ml (4.60 mmol) of thiophosgene in 10 ml of chloroform was added dropwise with ice-cooling. The mixture was stirred at the temperature for 1.5 hours, and then concentrated under reduced pressure. The residue was purified by flash column chromatography using silica gel, eluting with a 3:1 mixture of ethyl acetate and chloroform to give 0.37 g (yield 53.8%) of 5,6-dihydro-5-(thIoxo)imidazo[5,1-b]thiazole as red crystals. The crystals were dissolved in 4 ml of N,N-dimethylformamide (DMF). To this solution was added 0.081 ml of methyl iodide with ice-cooling, and the mixture was stirred at the temperature for 1.5 hours. The reaction solution was concentrated under reduced pressure. The residue was purified by flash column chromatography using silica gel, eluting with a 1:1 mixture of ethyl acetate and chloroform to give 0.616 g (yield 27.5%) of the title compound as a red oil.

NMR (CDCl₃) d: 2.52 (3H, s), 6.86 (1H, d, J=4.2 Hz), 7.15 (1H, s), 7.43 (1H, d, J=4.2 Hz)

Preparation 41

3-(Formylamino)methylimidazo[5,1-b]thiazole a) 3-(Phthalimide)methylimidazo[5,1-b]thiazole To a solution of 1 g (6.48 mmol) of 3-hydroxymethylimidazo[5,1-b]thiazole, 1.91 g (13mmol) of phthalimide and 3.39 g (13 mmol) of triphenylphosphine in 30 ml of anhydrous tetrahydrofuran was added 2.26 g (13 mmol) of diethyl azocarboxylate at room temperature, and the mixture was stirred at room temperature for one hour. The reaction solution was concentrated under reduced pressure. The residue was purified by column chromatography using silica gel, eluting with a 5:1 mixture of toluene and ethyl acetate to give 1.41 g (yield 77%) of the title compound.

NMR (CDCl$_3$) d: 1.65 (2H, s), 6.70 (1H, s), 7.12 (1H, s), 7.7–7.9 (4H, m), 8.12 (1H, s)

b) 3-Aminomethylimidazo[5,1-b]thiazole 0.72 g of the above-obtained 3-(phthalimide) methylimidazo-[5,1-b]thiazole was dissolved in 15 ml of ethanol, and to this solution was added 0.1 ml of anhydrous hydrazine. The mixture was refluxed for one hour, and then cooled. The crystals precipitated were removed by filtration. The filtrate was concentrated under reduced pressure, and water was added to the residue. The mixture was washed two times with ether, and then concentrated under reduced pressure to give 0.338 g (yield 87%) of the title compound.

NMR (CDCl$_3$) d: 4.47 (2H, s), 6.75 (1H, s), 7.11 (1H, s), 8.27 (1H, s)

c) 3-(Formylamino)methylimidazo[5,1-b]thiazole 0.33 g of the above-obtained 3-aminomethylimidazo[5,1-b]-thiazole was dissolved in 10 ml of dichloromethane. To this solution, a mixture which had been prepared in advance by reacting 0.5 ml of formic acid with 0.5 ml of acetic anhydride at 50° C. for 10 minutes was added with stirring, and the resulting mixture was stirred at room temperature for an additional one hour. To the reaction solution was added 20 ml of a saturated aqueous solution of sodium hydrogencarbonate, and the organic layer was separated. The aqueous layer was extracted with dichloromethane (10 ml×2). The combined organic layers were dried over anhydrous magnesium sulfate, and concentrated to dryness under reduced pressure to give 0.338 g (yield 87%) of the title compound.

NMR (CDCl$_3$) d: 1.75 (2H, s), 6.66 (1H, s), 7.10 (1H, s), 8.15 (1H, s)

Preparation 42

3-(tert-Butoxycarbonylamino)methylimidazo[5,1-b]thiazole 0.33 g of 3-aminomethylimidazo[5,1-b]thiazole was dissolved in 10 ml of dichloromethane. To this solution were added 1 ml of triethylamine, 200 mg of di-tert-butyl- dicarbonate and 5 ml of concentrated aqueous ammonia, and the mixture was stirred at room temperature for 30 minutes. The organic layer was separated, and the aqueous layer was extracted with dichloromethane (10 ml×2). The combined organic layers were dehydrated over anhydrous magnesium sulfate, and then concentrated to dryness under reduced pressure to give 0.49 g (yield 91%) of the title compound.

NMR (CDCl$_3$) d: 1.46 (9H, s), 1.88 (2H, s), 6.58 (1H, s), 7.11 (1H, s), 8.17 (1H, s)

Preparation 43

Imidazo[5,1-b]thiazole-3-carbaldehyde 0.211 g of the 3-hydroxymethylimidazo[5,1-b]thiazole prepared in Preparation 55 was suspended in 20 ml of dichloromethane. To this suspension was added 1.1 g of manganese dioxide, and the mixture was stirred at room temperature for 16 hours. The reaction solution was filtered, and then concentrated to dryness under reduced pressure to give 0.146 g (yield 71%) of the title compound.

NMR (CDCl$_3$) d: 7.11 (1H, s), 7.42 (1H, s), 8.16 (1H, s), 8.66 (1H, s)

Preparation 44

Imidazo[5,1-b]thiazole-3-carbaldehydoxime 0.12 g of the imidazo[5,1-b]thiazole-3-carbaldehyde prepared in Preparation 43 was dissolved in 3 ml of ethanol. To this solution were added 1 ml of triethylamine and 0.06 g of hydroxylamine hydrochloride, and the mixture was stirred at 60° C. for 1 hour. The reaction solution was concentrated under reduced pressure. The residue was purified by silica gel column chromatography, eluting with a 20:1 mixture of chloroform and methanol to give 0.72 g (yield 56%) of the title compound.

NMR (CDCl$_3$) d: 7.11 (1H, s), 7.42 (1H, s), 8.16 (1H, s), 8.66 (1H, s)

Preparation 45

3-Acetoxymethylimidazo[5,1-b]thiazole 0.15 g of the 3-hydroxymethylimidazo[5,1-b]thiazole prepared in Preparation 55 was dissolved in 4 ml of dichloromethane, and the solution was stirred. To this was added 0.1 ml of acetic anhydride, and the mixture was stirred at room temperature for 3 hours. To the reaction solution was added 5 ml of a saturated aqueous solution of sodium hydrogencarbonate, and the organic layer was separated. The aqueous layer was extracted with dichloromethane (5 ml×2). The combined organic layers were dried over anhydrous magnesium sulfate, and concentrated to dryness under reduced pressure to give 0.181 g (yield 95%) of the title compound.

NMR (CDCl$_3$) d: 2.13 (3H, s), 5.23 (2H, s), 6.87 (1H, s), 7.13 (1H, s), 8.03 (1H, s)

Preparation 46

3-Fluoromethylimidazo[5,1-b]thiazole a) 2-(tert-Butoxycarbonylamino)methyl-4-hydroxymethylthiazole To a solution of 0.52 g of ethyl 2-(tert-butoxycarbonylamino)methylthiazole-3-carboxylate in 10 ml of ethanol was added 200 mg of lithium borohydride, and the mixture was stirred at room temperature for 30 minutes. To this reaction solution was added 2 ml of acetone. The mixture was stirred for an additional 30 minutes, and then concentrated under reduced pressure. To the residue were added 15 ml of dichloromethane and 15 ml of a saturated saline solution, and the mixture was stirred for 10 minutes. The organic layer was separated, and the aqueous layer was extracted with dichloromethane (5 ml×2). The combined organic layers were dried over anhydrous magnesium sulfate, and concentrated to dryness under reduced pressure to give 0.357 g (yield 81%) of the title compound.

NMR (CDCl$_3$) d: 1.46 (9H, s), 4.57 (1H, s), 4.59 (1H, s), 4.71 (2H, s), 5.50 (1H, s), 7.12 (1H, s)

b) 2-(tert-Butoxycarbonylamino)methyl-4-fluoromethylthiazole

To a solution of 1.0 g of the above-obtained 2-(tert-butoxycarbonylamino)methyl-4-hydroxymethylthiazole in 20 ml of dichloromethane was added 0.6 ml of diethylaminosulphur trifluoride with ice-cooling, and the mixture was stirred at room temperature for 30 minutes. To this reaction solution was added 20 ml of a saturated aqueous solution of sodium hydrogencarbonate, and the mixture was stirred for 10 minutes. The organic layer was separated, and the aqueous layer was extracted with dichloromethane (10 ml×2). The combined organic layers were dried over anhydrous magnesium sulfate, and concentrated under reduced pressure. The residue was purified by silica gel column chromatography, eluting with a 50:1 mixture of chloroform and methanol to give 0.535 g (yield 47%) of the title compound.

NMR (CDCl$_3$) d: 1.47 (9H, s), 4.60 (1H, s), 4.62 (1H, s), 5.43 (2H, d, J=47 Hz), 7.32 (1H, s)

c) 3-Fluoromethylimidazo[5,1-b]thiazole

To 0.66 g of the above-obtained 2-(tert-butoxycarbonylamino)methyl-4-fluoromethylthiazole was added 2 ml of trifluoroacetic acid, and the mixture was stirred at room temperature for 30 minutes. The reaction solution was concentrated under reduced pressure. To the residue was added a saturated aqueous solution of sodium hydrogencarbonate to adjust the pH of the mixture to approximately 8. To this reaction solution was added 20 ml of dichloromethane. To the mixture was added with stirring a solution which had been prepared in advance by reacting 0.33 ml of formic acid with 0.33 ml of acetic anhydride at 50° C. for 10 minutes, and the resulting mixture was stirred at room temperature for an additional one hour. The organic layer was separated, and the aqueous layer was extracted with dichloromethane (10ml×2). The combined organic layers were dried over anhydrous magnesium sulfate, and concentrated to dryness under reduced pressure to give 0.27 g of crude 3-fluoromethyl-2-(formylamino)methylthiazole. This compound was dissolved in 6 ml of dichloromethane. 4.2 ml of phosphorus oxychloride was added to the solution at −20° C., and the mixture was stirred at room temperature for 30 minutes. The reaction solution was concentrated under reduced pressure. To the residue was added 4.2 ml of phosphorus oxychloride, and the mixture was stirred at 100° C. for 30 minutes. The reaction solution was cooled to room temperature, and then concentrated to dryness under reduced pressure. The residue was dissolved in 10 ml of water, and the solution was washed with 5 ml of dichloromethane. To this was added a saturated aqueous solution of sodium hydrogencarbonate to adjust the pH to approximately 8. The mixture was further extracted with dichloromethane (10ml×2). The combined organic layers were dried over anhydrous magnesium sulfate, and concentrated to dryness under reduced pressure to give 0.241 g (yield 58%) of the title compound.

NMR (CDCl$_3$) d: 5.46 (2H, d, J=48 Hz), 6.92 (1H, d, J=6 Hz), 7.15 (1H, s), 8.07 (1H, s)

Preparation 47

3-(Difluoromethyl)imidazo[5,1-b]thiazole a) 2-(tert-Butoxycarbonylamino)methylthiazole-4-carbaldehyde 0.05 g (yield 78%) of the title compound was obtained from 0.651 g of 2-(tert-butoxycarbonylamino)methyl-4-hydroxymethylthiazole in the same manner as in Preparation 43.

NMR (CDCl$_3$) d: 1.46 (9H, s), 4.57 (1H, s), 4.59 (1H, s), 8.70 (1H, s)

b) 2-(tert-Butoxycarbonylamino)methyl-4,4-difluoromethylthiazole 0.535 g (yield 47%) of the title compound was obtained from 0.533 g of the above-obtained 2-(tert-butoxycarbonylamino)methylthiazole-4-carbaldehyde in the same manner as in Preparation 46 b).

NMR (CDCl$_3$) d: 1.47 (9H, s), 4.62 (2H, d, J=6 Hz), 6.72 (2H, t, J=56 Hz), 7.57 (1H, s)

c) 3- (Difluoromethyl)imidazo[5,1-b]thiazole 0.873 g (yield 83% ) of the title compound was obtained from 1.6 g of the above-obtained 2-(tert-butoxycarbonylamino)methyl-4-(difluoromethyl)thiazole in the same manner as in Preparation 46 c).

NMR (CDCl$_3$) d: 6.75 (1H, t, J=53 Mz), 7.16 (1H, s), 7.17 (1H, s), 8.11 (1H, s)

Preparation 48

3-Methoxymethylimidazo [5,1-hi thiazole a) 2-(tert-Butoxycarbonylamino)methyl-4-methoxymethylthiazole 0.412 g of 2-(tert-butoxycarbonylamino)methyl-4-hydroxymethylthiazole was dissolved in 8 ml of acetonitrile. To this solution were added 0.98 g of silver oxide and 0.5 ml of methyl iodide, and the mixture was stirred at room temperature for 6 hours. The reaction solution was filtered, and then concentrated to dryness to give 0.385 g (yield 89%) of the title compound.

NMR (CDCl$_3$) d: 3.35 (3H, s), 4.56 (2H, s), 4.72 (1H, s), 7.15 (1H, s)

b) 3-Methoxymethylimidazo[5,1-b]thiazole 0.211 g (yield 81%) of the title compound was obtained from 0.385 g of the above-obtained 2-(tert-butoxycarbonylamino)methyl-4-methoxymethylthiazole in the same manner as in Preparation 46 c).

NMR (CDCl$_3$) d: 3.39 (3H, s), 4.57 (2H, s), 6.73 (1H, s), 7.11 (1H, s), 8.06 (1H, s)

Preparation 49

3-Methylimidazo[5,1-b]thiazole-2-carboxyamide a) Ethyl 2-(tert-butoxycarbonylamino)methyl-4-methylthiazole-5-carboxylate To a solution of 5.02 g of (tert-butoxycarbonylamino)acetothioamide in 75 ml of ethanol were added 3.92 ml of ethyl 2-chloroacetoacetate and 2.75 g of calcium carbonate, and the mixture was stirred at 50° C. for 6 hours. The reaction solution was filtered, and the filtrate was concentrated under reduced pressure. The residue was purified by silica gel column chromatography, eluting with a 5:1 mixture of toluene and ethyl acetate to give 5.65 g (yield 71%) of the title compound.

NMR (CDCl$_3$) d: 1.36 (3H, t, J=7 Hz), 1.47 (9H, s), 2.80 (3H, s), 4.32 (1H, s), 4.55 (2H, d, J=7 Hz), 7.27 (1H, s)

b) Ethyl 3-methylimidazo[5,1-b]thlazole-2-carboxylate 2.85 g (yield 73%) of the title compound was obtained from 5.6 g of the above-obtained 2-(tert-butoxycarbonylamino)methyl-4-methoxythiazole-5-carboxylate in the same manner as in Preparation 6 c).

NMR (CDCl$_3$) d: 1.39 (3H, t, J=7 Hz), 2.79 (3H, S), 4.57 (2H, d, J=7 Hz), 7.10 (1H, s), 8.01 (1H, s)

c) 3-Methylimidazo[5,1-b]thiazole-2-carboxyamide 0.5 g of the above-obtained ethyl 3-methylimidazo[5,1-b]-thiazole-2-carboxylate was dissolved in 30 ml of methanol saturated with ammonia, and reaction was conducted at room temperature for 40 hours. The reaction solution was concentrated under reduced pressure, and to the residue was added 100 ml of water. The precipitate was collected by filtration, and then dried under reduced pressure to give 0.342 g (yield 79%) of the title compound.

NMR (DMSO-d6) d: 2.82 (3H, s), 7.12 (1H, s), 8.13 (1H, s), 8.21 (1H, br), 8.53 (1H, br)

Preparation 50

3-(Ethoxycarbonylmethyl)imidazo[5,1-b]thiazole a) 2-(tert-Butoxycarbonylaminomethyl)-4-(ethoxycarbonylmethyl)thiazole 2 g of (tert-hutoxycarbonylamino)acetothioamide was dissolved in 30 ml of N,N-dimethylformamide. To this solution were added 1.903 g of ethyl 4-chloroacetoacetic acid ester, 526 mg of Calcium carbonate and 1.190 g of sodium bromide, and the mixture was stirred at room temperature for 3 hours and then at 40° C. for one hour. Insoluble matters were removed by filtration. The filtrate was placed in a mixture of 300 ml of ethyl acetate and 200 ml of a 20% saline solution. The mixture was stirred, and then subjected to distribution. The organic layer was washed with a 20% saline solution, and dried over anhydrous magnesium sulfate. The solvent was distilled off under reduced pressure, and the residue was purified by column chromatography using 150 g of silica gel, eluting with a 3:1 mixture of toluene and ethyl acetate to give 3.053 g (yield 97%) of the title compound.

NMR (CDCl$_3$) d: 1.27 (3H, t, J=7 Hz), 1.47 (9H, s), 3.79 (2H, s), 4.19 (1H, q, J=7 Hz), 4.58 (1H, s), 4.60 (1H, s), 5.53 (1H, br-s), 7.12 (1H, s) MS (EI, CHCl$_3$, 110° C.): 300 (M$^+$)

b) 3-(Ethoxycarbonylmethyl)imidazo[5,1-b]thiazole 574 mg (yield 81%) of the title compound was obtained from 1.00 g of the above-obtained 2-(tert-butoxycarbonylaminomethyl)-4-(ethoxycarbonylmethyl)thiazole in the same manner as in Preparation 11 b).

NMR (CDCl$_3$) d: 1.29 (1H, t, J=7 Hz), 3.78 (2H, s), 4.22 (2H, q, J=7 Hz), 6.74 (1H, s), 7.11 (1H, s), 7.96 (1H, s) MS (EI, CHCl$_3$, 110° C.): 210 (M$^+$)

Preparation 51

3-(Carbamoylmethyl)imidazo[5,1-b]thiazole 352 mg (yield 71%) of the title compound was obtained from 574 mg Of the 3-.(ethoxycarbonylmethyl)imidazo[5,1-b]thiazole prepared in Preparation 50 in the same manner as in Preparation 12.

NMR (DMSO-d$_6$) d: 3.69 (2H, s), 6.94 (1H, s), 7.01 (1H, s), 7.19 (1H, br-s), 7.70 (1H, br-s), 8.08 (1H, s) MS (EI, DMSO, 310° C.): 181 (M$^+$)

Preparation 52

3-(2-Hydroxyethyl)imidazo[5,1-b]thiazole 900 mg of the 3-(ethoxycarbonylmethyl)imidazo[5,1-b]thiazole prepared in Preparation 50 was dissolved in 20 ml of methanol. To this solution was added 810 mg of sodium borohydride with ice-cooling, and the mixture was stirred at room temperature for 2.5 hours. To this was added 2 ml of concentrated hydrochloric acid, and the mixture was stirred at room temperature for 15 minutes. The solvent was distilled off under reduced pressure. To the residue was added 20 ml of water, and the pH of the mixture was adjusted to 7.5 by sodium hydrogencarbonate. The water was evaporated from the mixture under reduced pressure. To the residue were successively added 50 ml of dichloromethane and anhydrous magnesium sulfate. Insoluble matters were removed by filtration, and the solvent was distilled off under reduced pressure. The residue was washed with a mixture of 10 ml of ethyl acetate and 50 ml of ether to give 476 mg (yield 66%) of the title compound. NMR (CDCl$_3$) d: 1.95 (1H, br-s), 3.01 (3H, t, J=6 Hz), 4.02 (1H, t, J=6 Hz), 6.57 (1H, s), 7.04 (1H, s), 7.90 (1H, s) MS (EI, CHCl$_3$, 100° C.): 168 (M$^+$)

Preparation 53

5-Acetoxymethylimidazo[5,1-b]thiazole

To a solution of 0.231 g (1.50 mmol) of the 5-Hydroxymethylimidazo[5,1-b]thiazole prepared in Preparation 10 in 8 ml of dichloromethane was added 0.156 ml (1.65 mmol) of acetic anhydride with ice-cooling, and the mixture was stirred at room temperature for 20 hours. To the reaction solution were added water and a saturated aqueous solution of sodium hydrogencarbonate, and the mixture was extracted with dichloromethane. The organic layer was dried over anhydrous magnesium sulfate, and concentrated to dryness under reduced pressure. The residue was purified by flash column chromatography using silica gel, eluting with a 30:1 mixture of chloroform and methanol to give 0.237 g (yield 81%) of the title compound.

NMR (CDCl$_3$) d: 2.09 (3H, s), 5.37 (2H, s), 6.86 (1H, d, J=4.2 Hz), 7.10 (1H, s), 7.61 (1H, d, J=4.2 Hz)

Preparation 54

5-(Formylamino)methylimidazo[5,1-b]thiazole-3-carboxyamide

To 0.296 mg of the 5-(tert-butoxycarbonylamino)methylimidazo[5,1-b]thiazole-3-carboxyamide was added 8 ml of trifluoroacetic acid. The mixture was stirred at room temperature for 30 minutes, and then concentrated to dryness under reduced pressure. To the residue were added 50 ml of methylene chloride, 50 ml of tetrahydrofuran and i ml of triethylamine, and the mixture was thoroughly stirred. To this was added a mixture of 2 ml of formic acid and i ml of acetic anhydride, which had been heated to 50° C. for 10 minutes and then cooled to room temperature, and the mixture was stirred for 14 hours. The crystals precipitated were collected by filtration, and dried under reduced pressure to give 0.214 g of the title compound.

NMR (DMSO-d$_6$) d: 4.63 (0.85H, d, J=5.5 Hz), 4.68 (0.15H, d, J=6.3 Hz), 7.06 (0.85H, s), 7.07 (0.15H, s), 7.6–7.9 (1H, br), 7.74 (0.85H, s), 7.75 (0.15H, s), 8.00 (0.15H, s), 8.03 (0.85H, s), 8.1–8.4 (2H, br)

Preparation 55

3-Hydroxymethylimidazo[5,1-b]thiazole

To a solution of 0.80 g of the ethyl imidazo[5,1-b]thiazole-3-carboxylate prepared in Preparation 11 in 16 ml of methanol was added 400 mg of sodium borohydride, and the mixture was stirred at room temperature for 30 minutes. To the reaction solution was added dropwise 3 ml of acetone. The mixture was stirred for 30 minutes, and then concentrated to dryness under reduced pressure. To the residue were added 20 ml of methylene chloride and 20 ml of a saturated saline solution, and the mixture was stirred for 10 minutes. The organic layer was separated, and the aqueous layer was extracted with methylene chloride (20 ml×2). The combined organic layers were dried over anhydrous magnesium sulfate, and concentrated to dryness under reduced pressure to give 0.615 of the title compound as light brown crystals.

NMR (CDCl$_3$) d: 4.97 (2H, s), 6.71 (1H, s), 7.04 (1H, s), 8.06 (1H, s)

Preparation 56

3-Cyanoimidazo[5,1-b]thiazole 0.149 g (yield 50%) of the title compound was obtained from 0.334 g of the imidazo[5,1-b]thiazole-3-carboxyamide prepared in Preparation 12 in the same manner as in Preparation 28.

NMR (CDCl$_3$) d: 7.26 (1H, s), 7.70 (1H, s), 8.18 (1H, s)

EXAMPLE 1

(6R,7R)-7-[(Z)-2-(2-Aminothiazol-4-yl)-2-methoxyimino-acetamide]-3-(imidazo[5,1-b]thiazolium-6-yl)methyl-3-cephem-4-carboxylate (internal salt)

To a 0.397 g (0.5 mmol) of p-methoxybenzyl (6R,7R)-7-[(Z)-2-(2-tritylaminothiazol-4-yl)-2-methoxyimino]acetamide-3-chloromethyl-3-cephem-4-carboxylic acid ester in acetone (8 ml), 0.075 g (0.6mmol) of imidazo[5,1-b]thiazole (Preparation 1) and 0.0824 g (0.55 mmol) of sodium iodide were added at room temperature under argon atmosphere, and the mixture was thoroughly stirred for 10 minutes. The reaction solution was shielded from the light, and allowed to stand overnight. The acetone was distilled off under reduced pressure. To the residue were added 30 ml of dichloromethane and 20 ml of water, and the mixture was thoroughly stirred. The organic layer was separated, dried over anhydrous magnesium sulfate, and then concentrated to dryness under reduced pressure. To the residue was added 1 ml of anisole, and the mixture was thoroughly stirred. To this was added 10 ml of trifluoroacetic acid with ice-cooling, and the mixture was stirred for one hour. To the reaction solution was added 50 ml of isopropyl ether cooled to −10° C. The precipitate was collected by filtration, washed with isopropyl ether (50 ml×2), dried under reduced pressure, and then suspended in 30 ml of water. To this suspension was added sodium hydrogencarbonate with stirring to adjust the pH to 7.5. The mixture was purified by column chromatography using 50 ml of Diaion HP 20 Resin, eluting with 200 ml of water, 200 ml of a 10% aqueous solution of methanol and 200 ml of a 20% aqueous solution of methanol. A fraction containing the desired compound was concentrated to dryness. The residue was further purified by column chromatography using 100 ml of Sephadex LH 20, eluting with a 50% aqueous solution of methanol, concentrated under reduced pressure, and then freeze-dried to give 0.032 g of the title compound.

NMR ($D_2O$) d (HDO=4.80): 3.25 (1H, d, J=17.7 Hz), 3.66 (1H, d, J=17.7 Hz), 3.97 (3H, s), 5.14 (1H, d, J=14.6 Hz), 5.27 (1H, d, J=4.9 Hz), 5.29 (1H, d, J=14.6 Hz), 5.84 (1H, d, J=4.9 Hz), 6.97 (1H, s), 7.53 (1H, d, J=4.2 Hz), 7.77 (1H, s ), 7.93 (1H, d, J=4.2 Hz), 9.37 (1H, s)

EXAMPLE 2

(6R,7R)-7-[(Z)-2-(2-Aminothiazol-4-yl)-2-((S)-1-carboxyethoxy-imino)acetamide]-3-(imidazo[5,1-b]thiazolium-6-yl)methyl-3-cephem-4-carboxylate (internal salt)

0.310 g of a monosodium salt of the title compound was obtained from 1.019 g (1.00 mmol) of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.137 g (1.1 mmol) of imidazo[5,1-b]-thiazole (Preparation 1) and 0.165 g (1.1mmol) of sodium iodide in the same manner as in Example 1.

NMR ($D_2O$) d (HDO=4.80): 1.44 (3H, d, J=7.0 Hz), 3.24 (1H, d, J=17.9 Hz), 3.66 (1H, d, J=17.9 Hz), 4.66 (1H, q, J=7.0 Hz), 5.11 (1H, d, J=14.7 Hz), 5.28 (1H, d, J=4.8 Hz), 5.33 (1H, d, J=14.7 Hz), 5.86 (1H, d, J=4.8 Hz), 6.95 (1H, s), 7.52 (1H, d, J=4.4 Hz), 7.78 (1H, s), 7.91 (1H, d, J=4.4 Hz), 9.37 (1H, s)

EXAMPLE 3

(6R,7R)-7-[(Z)-2-(2-Aminothiazol-4-yl)-2-(1-carboxy-1-methylethoxyimino)acetamide]-3-(imidazo[5,1-b]thiazolium-6-yl)methyl-3-cephem-4-carboxylate (internal salt)

0.067 g of a monosodium salt of the title compound was obtained from 0.516 g (0.50 mmol) of p-methoxybenzyl (6R, 7R)-7-[(Z)-2-(2-tritylaminothiazol-4-yl)-2-(1-diphenylmethoxycarbonyl-1-methylethoxyimino) acetamide]-3-chloromethyl-3-cephem-4-carboxylic acid ester, 0.0745 g (0.60 mmol) of imidazo[5,1-b]thiazole (Preparation 1) and 0.090 g (0.60 mmol) of sodium iodide in the same manner as in Example 1.

NMR ($D_2O$) d (HDO=4.80): 1.48 (6H, s), 3.25 (1H, d, J=17.9 Hz), 3.65 (1H, d, J=17.9 Hz), 5.13 (1H, d, J=14.8 Hz), 5.28 (1H, d, J=4.8 Hz), 5.33 (1H, q, J=14.8 Hz), 5.86 (1H, d, J=4.7 Hz), 6.98 (1H, s), 7.53 (1H, d, J=4.3 Hz), 7.78 (1H, s), 7.93 (1H, d, J=4.3 Hz), 9.37 (1H, s)

EXAMPLE 4

(6R,7R)-7-[(Z)-2-(2-Aminothiazol-4-yl)-2-methoxyimino-acetamide]-3-(3-methylimidazo[5,1-b]thiazolium-6-yl)methyl-3-cephem-4-carboxylate (internal salt)

The title compound was obtained from 0.397 g (0.5 mmol) of p-methoxybenzyl (6R,7R)-7-[(Z)-2-(2-tritylaminothiazol-4-yl)-2-methoxyimino]acetamide-3-chloromethyl-3-cephem-4-carboxylic acid ester, 0.083 g (0.6 mmol) of 3-methylimidazo[5,1-b]-thiazole (Preparation 2) and 0.090 g (0.60 mmol) of sodium iodide in the same manner as in Example 1.

NMR (D20) d (HDO=4.80): 2.49 (3H, s), 3.23 (1H, d, J=17.8 Hz), 3.65 (1H, d, J=17.8 Hz), 3.97 (3H, s), 5.15 (1H, d, J=14.8 Hz), 5.27 (1H, d, J=4.9 Hz), 5.31 (1H, q, J=14.8 Hz), 5.84 (1H, d, J=4.9 Hz), 6.97 (1H, s), 7.12 (1H, s), 7.75 (1H, s), 9.35 (1H, s)

EXAMPLE 5

(6R,7R)-7-[(Z)-2-(2-Aminothiazol-4-yl)-2-((S)-1-carboxyethoxy-imino)acetamide]-3-(3-methylimidazo[5,1-b]thiazolium-6-yl)methyl-3-cephem-4-carboxylate (internal salt)

0.072 g of a monosodium salt of the title compound was obtained from 0.509 g (0.50 mmol) of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.083 g (0.6 mmol) of 3-methylimidazo[5,1-b]thiazole (Preparation 2) and 0.075 g (0.5mmol) of sodium iodide in the same manner as in Example 1.

NMR ($D_2O$) d (HDO=4.80): 1.44 (1H, d, J=7.0 Hz), 2.49 (3H, s), 3.23 (1H, d, J=17.9 Hz), 3.65 (1H, d, J=17.9 Hz), 4.64 (1H, q, J=7.0 Hz), 5.13 (1H, d, J=14.8 Hz), 5.28 (1H, d, J=4.8 Hz), 5.32 (1H, J=14.8 Hz), 5.86 (1H, q, J=4.8 Hz), 6.95 (1H, s), 7.12 (1H, s), 7.76 (1H, s), 9.35 (approx. 1H, s) (this seems to be due to D-substitution)

EXAMPLE 6

(6R,7R)-7-[(Z)-2-(2-Aminothiazol-4-yl)-2-methoxyimino-acetamide]-3-(5-methylimidazo[5,1-b]thiazolium-6-yl)methyl-3-cephem-4-carboxylate (internal salt)

0.037 g of the title compound was obtained from 0.397 g (0.5 mmol) of p-methoxybenzyl (6R,7R)-7-[(Z)-2-(2-tritylaminothiazol-4-yl)-2-methoxyimino]acetamide-3-chloromethyl-3-cephem-4-carboxylic acid ester, 0.0835 g (0.6 mmol) of 5-methylimidazo[5,1-b]thiazole (Preparation 3) and 0.090 g (0.60 mmol) of sodium iodide in the same manner as in Example 1.

NMR (D20) d (HDO=4.80): 2.84 (3H, s), 3.23 (1H, d, J=17.7 Hz), 3.53 (1H, d, J=17.7 Hz), 3.99 (3H, s), 5.12 (1H, d, J=15.3 Hz), 5.24 (1H, d, J=4.8 Hz), 5.28 (1H, d, J=15.3 Hz), 5.84 (1H, d, J=4.8 Hz), 6.99 (1H, s), 7.48 (1H, d, J=4.3 Hz), 7.61 (1H, s), 7.84 (1H, d, J=4.3 Hz)

EXAMPLE 7

(6R,7R)-7-[(Z)-2-(2-Aminothiazol-4-yl)-2-((S)-1-carboxyethoxy-imino)acetamide]-3-(5-methylimidazo[5,1-b]thiazolium-6-yl)-methyl-3-cephem-4-carboxylate (internal salt)

0.045 g of a monosodium salt of the title compound was obtained from 0.509 g (0.50 mmol) of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.083 g (0.6 mmol) of 5-methylimidazo-[5,1-b]thiazole (Preparation 3) and 0.090 g (0.6mmol) of sodium iodide in the same manner as in Example 1.

NMR ($D_2O$) d (HDO=4.80): 1.46 (3H, d, J=7.0 Hz), 2.85 (3H, s), 3.23 (1H, d, J=17.9 Hz), 3.52 (1H, d, J=17.9 Hz), 4.68 (1H, q, J=7.0 Hz), 5.14 (1H, d, J=15.3 Hz), 5.26 (1H, d, J=4.8 Hz), 5.28 (1H, d, J=15.3 Hz), 7.00 (1H, s), 7.48 (1H, d, J=4.3 Hz), 7.63 (1H, s), 7.84 (1H, d, J=4.3 Hz)

EXAMPLE 8

(6R,7R)-7-[(Z)-2-(2-Aminothiazol-4-yl)-2-methoxyimino-acetamide]-3-(3-ethylimidazo[5,1-b]thiazolium-6-yl)methyl-3-cephem-4-carboxylate (internal salt)

The title compound (yield 40%) was obtained from p-methoxybenzyl (6R,7R)-7-[(Z)-2-(2-tritylaminothiazol-4-yl)-2-methoxyimino]acetamide]-3-chloromethyl-3-cephem-4-carboxylic acid ester, 3-ethylimidazo[5,1-b]thiazole (Preparation 4) and sodium iodide in the same manner as in Example 1.

NMR (D$_2$O) d (HDO =4.80): 1.36 (3H, t, J=7.4 Hz), 2.85 (2H, q, J=7.4 Hz), 3.24 (1H, d, J=17.9 Hz), 3.67 (1H, d, J=17.9 Hz), 3.98 (3H, s), 5.14 (1H, d, J=14.8 Hz), 5.28 (1H, d, J=4.7 Hz), 5.32 (1H, d, J=14.8 Hz), 5.83 (1H, d, J=4.7 Hz), 6.92 (1H, s), 7.13 (1H, s), 7.77 (1H, s), 9.40 (1H, s) MS (SIMS): 548 (M$^+$)

EXAMPLE 9

(6R,7R)-7-[(Z)-2-(2-Aminothiazol-4-yl)-2-((S))-1-carboxyethoxyimino)acetamide]- 3-(3-ethylimidazo[5,1-b]thiazolium-6-yl)methyl-3-cephem-4-carboxylate (internal salt)

A monosodium salt of the title compound was obtained (yield 38%) from p-methoxybenzyl (6R,7R)-7-[(Z)-2-(2-trityl-aminothiazol-4-yl)-2-((S)-1-diphenylmethoxycarbonylethoxyimino)acetamide]-3-chloromethyl-3-cephem-4-carboxylic acid ester, 3-ethylimidazo[5,1-b]thiazole (Preparation 4) and sodium iodide in the same manner as in Example 1.

NMR (D$_2$O) d (HDO=4.80): 1.34 (3H, t, J=7.4 Hz), 1.46 (3H, t, J=7.1 Hz), 2.81 (2H, q, J=7.4 Hz), 3.23 (1H, d, J=17.8 Hz), 3.96 (1H, d, J=17.8 Hz), 4.66 (1H, q, J=7.1 Hz), 5.08 (1H, d, J=13.8 Hz), 5.30 (1H, d, J=4.9 Hz), 5.33 (1H, J=13.8 Hz), 5.81 (1H, d, J=4.9 Hz), 6.80 (1H, s), 7.08 (1H, s), 7.78 (1H, s), 9.41 (1H, s) MS (SIMS): 606 (M$^+$)

EXAMPLE 10

(6R, 7R)-7-[(Z)-2-(2-Aminothiazol-4-yl)-2-methoxyimino-acetamide]-3-(2,3-dimethylimidazo[5,1-b]thiazolium-6-yl)methyl-3-cephem-4-carboxylate (internal salt)

0.035 g of the title compound was obtained from 0.238 g of p-methoxybenzyl (6R,7R)-7-[(Z)-2-(2-tritylaminothiazol-4-yl)-2-methoxyimino]acetamide]-3-chloromethyl-3-cephem-4-carboxylic acid ester, 0.055 g of 2,3-dimethylimidazo[5,1-b]thiazole (Preparation 5) and sodium iodide in the same manner as in Example 1.

NMR (D$_2$O) d (HDO=4.80): 2.36 (6H, s), 3.21 (1H, d, J=18 Hz), 3.67 (1H, d, J=18 Hz), 3.95 (3H, s), 5.08 (1H, q, J=13 Hz), 5.2–5.35 (3H, m), 5.79 (1H, d, J=5 Hz), 6.82 (1H, s), 7.12 (1H, s), 7.68 (1H, s)

EXAMPLE 11

(6R,7R)-7-[(Z)-2-(2-Aminothiazol-4-yl)-2-((S))-1-carboxyethoxyimino)acetamide]-3-(2,3-dimethylimidazo[5,1-b]thiazolium-6-yl)methyl-3-cephem-4-carboxylate (internal salt)

0.061 g of a monosodium salt of the title compound was obtained from 0.305 g of p-methoxybenzyl (6R,7R)-7-[(Z)-2-(2-tritylaminothiazol-4-yl)-2-((S)-1-diphenylmethoxycarbonyl-ethoxyimino)acetamide]-3-chloromethyl-3-cephem-4-carboxylic acid ester, 0.055 g of 2,3-dimethylimidazo[5,1-b]thiazole (Preparation 5) and sodium iodide in the same manner as in Example 1.

NMR (D$_2$O) d (HDO=4.80): 1.48 (3H, t, J=7 Hz), 2.34 (3H, s), 2.36 (3H, s), 3.22 (1H, d, J=18 Hz), 3.69 (1H, d, J=18 Hz), 4.69 (1H, q, J=7 Hz), 5.06 (1H, d, J=13 Hz), 5.25–5.35 (3H, m), 5.82 (1H, d, J=5 Hz), 6.81 (1H, s), 7.70 (1H, s), 9.23 (1H, s)

EXAMPLE 12

(6R,7R)-7-[(Z)-2-(2-Aminothiazol-4-yl)-2-methoxyiminoacetamide]-3-(2,3-propanoimidazo[5,1-b]thiazolium-6-yl)methyl-3-cephem-4-carboxylate (internal salt)

0.031 g of the title compound was obtained from 0.238 g of p-methoxybenzyl (6R,7R)-7-[(Z)-2-(2-tritylaminothiazol-4-yl)-2-methoxyimino]acetamide-3-chloromethyl-3-cephem-4-carboxylic acid ester, 0.059 g of 2,3-propanoimidazo[5,1-b]thlazole (Preparation 6) and sodium iodide in the same manner as in Example 1.

NMR (D$_2$O) d (HDO=4.80): 2.6–2.7 (2H, m), 2.85–3.0 (4H, m), 3.24 (1H, d, J=18 Hz), 3.69 (1H, d, J=18 Hz), 3.99 (3H, s), 5.12 (1H; d, J=13 Hz), 5.28 (1H, d, J=5 Hz), 5.29 (1H, d, J=13 Hz), 5.84 (1H, d, J=5 Hz), 6.93 (1H, s), 7.72 (1H, s), 9.21 (1H, s)

EXAMPLE 13

(6R,7R)-7-[(Z)-2-(2-Aminothiazol-4-yl)-2-((S)-1-carboxyethoxyimino)acetamide]-3-(2,3-propanoimidazo[5,1-b]thiazolium-6-yl)methyl-3-cephem-4-carboxylate (internal salt)

0.042 g of a monosodium salt of the title compound was obtained from 0.305 g of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.059 g of 2,3-propanoimidazo[5,1-b]thiazole (Preparation 6) and sodium iodide in the same manner as in Example 1.

NMR (D30) d (HDO=4.80): 1.45 (3H, d, J=7 Hz), 2.56–2.71 (2H, m), 2.80–3.00 (4H, m), 3.21 (1H, d, J=18 Hz), 3.71 (1H, d, J=18 Hz), 4.65 (1H, q, J=7 Hz), 5.05 (1H, d, J=13 Hz), 5.31 (1H, d, J=5 Hz), 5.33 (1H, d, J=13 Hz), 5.82 (1H, d, J=5 Hz), 6.80 (1H, s), 7.76 (1H, s), 9.21 (1H, s)

EXAMPLE 14

(6R,7R)-7-[(Z)-2-(2-Aminothiazol-4-yl)-2-((S)-1-carboxyethoxyimino)acetamide]-3-(5-ethoxycarbonylimidazo[5,1-b]thiazolium-6-yl)methyl-3-cephem-4-carboxylate (internal salt)

0.013 g of a monosodium salt of the title compound was obtained from 0.509 g (50 mmol) of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.118 g (0.6 mmol) of ethyl imidazo-[5,1b]thiazole-5-carboxylate (Preparation 9) and 0.090 g (0.6 mmol) of sodium iodide in the same manner as in Example 1.

NMR (D$_2$O) d (HDO=4.80): 1.44 (3H, d, J=7 Hz), 1.48 (3H, t, J=7 Hz), 3.28 (1H, d, J=18 Hz), 3.62 (1H, d, J=18 Hz), 4.65 (2H, q, J=7 Hz), 4.70 (1H, d, J=7 Hz), 5.27 (1H, d, J=5 Hz), 5.51 (1H, d, J=15 Hz), 5.85 (1H, J=15 Hz), 5.85 (1H, J=5 Hz), 6.95 (1H, s), 7.85 (1H, d, J=4 Hz), 8.21 (1H, s), 8.47 (1H, J=4 Hz)

EXAMPLE 15

(6R,7R)-7-[(Z)-2-(2-Aminothiazol-4-yl)-2-((S)-1-carboxyethoxyimino)acetamide]-3-(5-Hydroxymethylimidazo[5,1-b]thiazolium-6-yl)methyl-3-cephem-4-carboxylate (internal salt)

0.056 g of a monosodium salt of the title compound was obtained from 0.509 g (50 mmol) of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.093 g (0.6 mmol) of 5-hydroxymethylimidazo[5,1-b]thiazole (Preparation 3) and 0.090 g (0.6 mmol) of sodium iodide in the same manner as in Example 1.

NMR ($D_2O$) d (HDO=4.80): 1.45 (3H, d, J=7.0 Hz), 3.21 (1H, J=17.9 Hz), 3.59 (1H, d, J=17.9 Hz), 4.65 (2H, q, J=7.0 Hz), 5.19 (2H, s), 5.26 (1H, d, J=4.9 Hz), 5.27 (2H, s), 5.83 (1H, J=4.9 Hz), 6.86 (1H, s), 7.53 (1H, d, J=4.2 Hz), 7.77 (1H, s), 8.01 (1H, d, J=4.2 Hz)

EXAMPLE 16

(6R,7R)-7-[(Z)-2-(2-Aminothiazol-4-yl)-2-methoxyiminoacetamide]-3-(2-methylimidazo[5,1-b]thiazolium-6-yl)methyl-3-cephem-4-carboxylate (internal salt)

0.031 g of the title compound was obtained from 0.165 g of p-methoxybenzyl (6R,7R)-7-[(Z)-2-(2-tritylaminothiazol-4-yl)-2-methoxyimino]acetamide-3-chloromethyl-3-cephem-4-carboxylic acid ester, 0.034 g of 2-methylimidazo[5,1-b]thiazole (Preparation 7) and sodium iodide in the same manner as in Example 1.

NMR ($D_2O$) d (HDO=4.80): 2.47 (3H, s), 3.24 (1H, d, J=18 Hz), 3.67 (1H, d, J=18 Hz), 3.99 (3H, s), 5.09 (1H, q, J=15 Hz), 5.28 (1H, d, J=15 Hz), 5.28 (1H, d, J=5 Hz), 5.84 (1H, d, J=5 Hz), 6.95 (1H, s), 7.66 (1H, s), 7.68 (1H, s), 9.22 (1H, s)

EXAMPLE 17

(6R,7R)-7-[(Z)-2-(2-Aminothiazol-4-yl)-2-((S)-1-carboxyethoxyimino)acetamide]-3-(2-methylimidazo[5,1-b]thiazolium-6-yl)methyl-3-cephem-4-carboxylate (internal salt)

0.022 g of a monosodium salt of the title compound was obtained from 0.151 g of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.025 g of 2-methylimidazo[5,1-b]-thiazole (Preparation 7) and sodium iodide in the same manner as in Example 1.

NMR ($D_2O$) d (HDO=4.80): 1.47 (3H, d, J=7 Hz), 2.46 (3H, s), 3.24 (1H, d,,J,=18 Hz), 3.67 (1H, d, J=18 Hz), 4.68 (1H, q, J=7 Hz), 5.06 (1H, d, J=15 Hz), 5.29 (1H, d, J=5 Hz), 5.30 (1H, d, J=15 Hz), 5.86 (1H, d, J=15 Hz), 6.92 (1H, s), 7.65 (1H, s), 7.69 (1H, s), 9.22 (1H, s)

EXAMPLE 18

(6R,7R)-7-[(Z)-2-(2-Aminothiazol-4-yl)-2-((S)-1-carboxyethoxyimino)acetamide]-3-(3-ethoxycarbonylimidazo[5,1-b]thiazolium-6-yl)methyl-3-cephem-4-carboxylate (internal salt)

0.049 g (yield 24%) of a monosodium salt of the title compound was obtained from 0.303 g of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.065 g of ethyl imidazo[5,1-b]thiazole-3-carboxylate (Preparation 11) and 0.047 g of sodium iodide in the same manner as in Example 1.

NMR ($D_2O$) d (HDO=4.80): 1.42 (3H, t, J=7 Hz), 1.45 (3H, d, J=7 Hz), 3.20 (1H, d, J=18 Hz), 3.72 (1H, d, J=18 Hz), 4.49 (2H, q, J=7 Hz), 4.66 (1H, q, J=7 Hz), 5.09 (1H, d, J=14 Hz), 5.30 (1H, d, J=5 Hz), 5.38 (1H, d, J=14 Hz), 5.78 (1H, d, J=5 Hz), 6.77 (1H, s), 7.96 (1H, s), 8.56 (1H, s)

EXAMPLE 19

(6R,7R)-7-[(Z)-2-(2-Aminothiazol-4-yl)-2-((S)-1-carboxyethoxyimino)acetamide]-3-(3-hydroxymethylimidazo[5,1-b]thiazolium-6-yl)methyl-3-cephem-4-carboxylate (internal salt)

0.051 g (yield 27%) of a monosodium salt of the title compound was obtained from 0.303 g of p-methoxyhenzyl (6R,7R)-7-[(Z)-2-(2-tritylaminothiazol-4-yl)-2-((S)-1-diphenylmethoxy-carbonylethoxyimino)acetamide]-3-chloromethyl-3-cephem-4-carboxylic acid ester, 0.051 g of 3-hydroxymethylimidazo-[5,1-b]thiazole (Preparation 11) and 0.047 g of sodium iodide in the same manner as in Example 1.

NMR ($D_2O$) d (HDO=4.80): 1.44 (1H, d, J=7 Hz), 3.24 (1H, d, J=17 Hz), 3.64 (1H, d, J=17 Hz), 4.64 (1H, q, J=7 Hz), 4.86 (2H, s), 5.13 (1H, q, J=15 Hz), 5.28 (1H, d, J=5 Hz), 5.33 (1H, d, J=15 Hz), 5.86 (1H, d, J=5 Hz), 6.96 (1H, s), 7.46 (1H, s), 7.81 (1H, s), 9.43 (1H, s)

EXAMPLE 20

(6R,7R)-7-[(Z)-2-(2-Aminothiazol-4-yl)-2-((S)-1-carboxyethoxyimino)acetamide]-3-(3-fluoromethylimidazo[5,1-b]thiazolium-6-yl)methyl-3-cephem-4-carboxylate (internal salt)

0.048 g (yield 25%) of a monosodium salt of the title compound was obtained from 0.303 g of p-methoxybenzyl (6R,7R)-7-[(Z)-2-(2-tritylaminothiazol-4-yl)-2-((S)-1-diphenylmethoxy-carbonylethoxyimino)acetamide]-3-chloromethyl-3-cephem-4-carboxylic acid ester, 0.052 g of 3-fluoromethylimidazo-[5,1-b]thiazole and 0.047 g of sodium iodide in the same manner as in Example 1.

NMR ($D_2O$) d (HDO=4.80): 1.44 (1H, d, J=7 Hz), 3.23 (1H, d, J=18 Hz), 3.66 (1H, d, J=18 Hz), 4.64 (1H, q, J=7 Hz), 5.12 (1H, d, J=15 Hz), 5.28 (1H, d, J=4 Hz), 5.34 (1H, d, J=15 Hz), 5.66 (2H, J=47 Hz), 5.84 (1H, d, J=4 Hz), 6.90 (1H, s), 7.74 (1H, s), 7.85 (1H, s), 9.54 (1H, s)

EXAMPLE 21

(6R,7R)-7-[(Z)-2-(2-Aminothiazol-4-yl)-2-((S)-1-carboxyethoxyimino)acetamide]-3-(3-(N-methylcarbamoyl)imidazo[5,1-b]-thiazolium-6-yl)methyl-3-cephem-4-carboxylate (internal salt)

0.036 g (yield 25%) of a monosodium salt of the title compound was obtained from 0.303 g of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.065 g of imidazo[5,1-b]thiazole-3-N-methylcarboxyamide and 0.060 g of sodium iodide in the same manner as in Example 1.

NMR ($D_2O$) d (HDO=4.80): 1.44 (3H, d, J=3 Hz), 2.93 (3H, s), 3.21 (1H, d, J=18 Hz), 3.69 (1H, d, J=18 Hz), 4.64 (1H, q, J=7 Hz), 5.11 (1M, d, J=15 Hz), 5.29 (1H, d, J=5 Hz), 5.36 (1H, d, J=15 Hz), 5.81 (1H, d, J=5 Hz), 7.89 (1H, s), 8.20 (1H, s), 9.77 (1H, s)

EXAMPLE 22

(6R,7R)-7-[(Z)-2-(2-Aminothiazol-4-yl)-2-((S)-1-carboxyethoxy-imino)acetamide]-3-(3-cyanoimidazo[5,1-b]thiazolium-6 -yl)methyl-3-cephem-4-carboxylate (internal salt)

0.041 g (yield 22%) of a monosodium salt of the title compound was obtained from 0.303 g of p-methoxybenzyl (6R,7R)-7-[(Z)-2-(2-tritylaminothiazol-4-yl)-2-((S)-1-diphenylmethoxy-carbonylethoxyimino)acetamide]-3-chloromethyl-3-cephem-4-carboxylic acid ester, 0.049 g of 3-cyanoimidazo[5,1-b]thiazole (Preparation 56) and 0.047 g of sodium iodide in the same manner as in Example 1.

NMR (D₂O) d (HDO=4.80): 1.45 (3H, d, J=7 Hz), 3.22 (1H, d, J=18 Hz), 3.69 (1H, d, J=18 Hz), 4.66 (1H, q, J=7 Hz), 5.16, (1H, d, J=15 Hz), 5.30 (1H, d, J=5 Hz), 5.40 (1H, d, J=15 Hz), 5.85 (1H, d, J=5 Hz), 6.93 (1H, s), 8.01 (1H, s), 8.66 (1H, s), 9.77 (1H, s)

EXAMPLE 23

(6R,7R)-7-[(Z)-2-(2-Aminothiazol-4-yl)-2-methoxyimino-acetamide]-3-(7-methylimidazo[5,1-b]thiazolium-6-yl)methyl-3-cephem-4-carboxylate (internal salt)

0.032 g of the title compound was obtained from 0.238 g (0.30 mmol) of p-methoxybenzyl (6R,7R)-7-[(Z)-2-(2-tritylaminothiazol-4-yl)-2-methoxyiminoacetamide]-3-chloromethyl-3-cephem-4-carboxylic acid ester, 0.050 g (0.36 mmol) of 7-methylimidazo[5,1-b]thiazole (Preparation 8) and 0.090 g (0.60 mmol) of sodium iodide in the same manner as in Example 1.

NMR (D₂O) d (HDO=4.80): 2.49 (3H, s), 3.28 (1H, d, J=17.9 Hz), 3.53 (1H, d, J=17.9 Hz), 4.00 (3H, s), 5.17 (1H, d, J=15.1 Hz), 5.27 (1H, d, J=4.9 Hz), 5.32 (1H, d, J=15.1 Hz), 5.86 (1H, d, J=4.9 Hz), 7.01 (1H, s), 7.53 (1H, d, J=4.3 Hz), 8.87 (1H, d, J=4.3 Hz), 9.27 (1H, s)

EXAMPLE 24

(6R,7R)-7-[(Z)-2-(2-Aminothiazol-4-yl)-2-((S)-1-carboxyethoxyimino)acetamide]-3-(7-methylimidazo[5,1-b]thiazolium-6-yl)methyl-3-cephem-4-carboxylate (internal salt)

0.066 g of a monosodium salt of the title compound was obtained from 0.305 g (0.30 mmol) of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.050 g (0.36 mmol) of 7-methylimidazo-[5,1-b]thiazole (Preparation 8) and 0.090 g (0.60 mmol) of sodium iodide in the same manner as in Example 1.

NMR (D₂O) d (HDO=4.80): 1.48 (3H, d, J=7.1 Hz), 2.50 (3H, s), 3.28 (1H, d, J=17.7 Hz), 3.54 (1H, d, J=17.7 Hz), 4.68 (1H, q, J=7.1 Hz), 5.18 (1H, d, J=15.0 Hz), 5.29 (1H, d, J=4.9 Hz), 5.31 (1H, d, J=15.0 Hz), 5.90 (1H, d, J=4.9 Hz), 7.03 (1H, s), 7.53 (1H, d, J=4.3 Hz), 7.88 (1H, d, J=4.3 Hz), 9.28 (1H, s)

EXAMPLE 25

(6R,7R)-7-[(Z)-2-(2-Aminothiazol-4-yl)-2-((S)-1-carboxyethoxy-imino)acetamide]- 3-(3-carbamoylimidazo[5,1-b]thiazolium-6-yl)methyl-3-cephem-4-carboxylate (internal salt)

To a solution of 0.303 g of p-methoxybenzyl (6R,7R)-7-[(Z)-2-(2-tritylaminothiazol-4-yl)-2-((S)-1-diphenylmethoxy-carbonylethoxyimino)acetamide]-3-chloromethyl-3-cephem-4-carboxylic acid ester in 5 ml of acetone was added 0.047 g of sodium iodide, and the mixture was stirred for 3 hours. The reaction solution was concentrated under reduced pressure. The residue was dissolved in 1.5 ml of N,N-dimethylformamide (DMF). To this solution was added 0.055 g of imidazo[5,1-b]thiazole-3-carboxyamide (Preparation 12), and the mixture was stirred at room temperature for 16 hours. The reaction solution was diluted with 20 ml of ethyl acetate. The diluted solution was washed with water, dried over anhydrous magnesium sulfate, and then concentrated to dryness under reduced pressure. To the residue were added 1 ml of anisole and 2 ml of trifluoroacetic acid, and the mixture was stirred for one hour with ice-cooling. To this reaction solution was added isopropyl ether. The precipitate was collected by filtration, and dissolved in an aqueous solution of sodium hydrogencarbonate. The solution was purified by column chromatography successively using Diaion HP 20 and Sephadex LH 20 to give 0.050 g (yield .26%) of a monosodium salt of the title compound.

NMR (D₂O) d (HDO=4.80): 1.46 (3H, d, J=7 Hz), 3.21 (1H, d, J=18 Hz), 3.67,(1H, d, J=18 Hz), 4.64 (1H, q, J=7 Hz), 5.12 (1H, d, J=15 Hz), 5.29 (1H, d, J=15 Hz), 5.36 (1H, d, J=15 Hz), 5.83 (1H, d, J=5 Hz), 6.85 (1H, s), 7.90 (1H, s), 8.36 (1H, s), 9.78 (1H, s)

EXAMPLE 26

(6R,7R)-7-[(Z)-2-(2-Aminothiazol-4-yl)-2-((S)-1-carboxyethoxy-imino)acetamide]-3-(3-carbamoyl-5-methylimidazo[5,1-b]-thiazolium-6-yl)methyl-3-cephem-4-carboxylate (internal salt)

0.006 g (yield 3%) of a monosodium salt of the title compound was obtained from 0.303 g of p-methoxybenzyl (6R,7R)-7-[(Z)-2-(2-trityleminothiazol-4-yl)-2-((S)-1-diphenylmethoxycarbonylethoxyimino)acetamide]-3-chloromethyl-3-cephem-4-carboxylic acid ester, 0.065 g of 5-methylimidazo[5,1-b]-thiazole-3-carboxyamide and 0.047 g of sodium iodide in the same manner as in Example 25.

NMR (D₂₀) d (HDO=4.80): 1.48 (3H, d, J=7 Hz), 2.84 (3H, s), 3.20 (1H, d, J=18 Hz), 3.52 (1H, J=18 Hz), 4.65 (1H, q, J=7 Hz), 5.18 (1H, d, J=15 Hz), 5.25 (1H, d, J=5 Hz), 5.28 (1H, J=15 Hz), 5.86 (1H, d, J=5 Hz), 6.97 (1H, s), 7.75 (1H, s), 8.09 (1H, s)

EXAMPLE 27

(6R,7R)-7-[(Z)-2-(2-Aminothiazol-4-yl)-2-methoxyimino-acetamide]-3-(3-carbamoylimidazo[5,1-b]thiazolium-6-yl)methyl-3-cephem-4-carboxylate (internal salt)

0.032 g (yield 19%) of the title compound was obtained from 0.235 g of p-methoxybenzyl (6R,7R)-7-[(Z)-2-(2-tritylaminothiazol-4-yl)-2-methoxyimino]acetamide]-3-chloromethyl-3-cephem-4-carboxylic acid ester, 0.055 g of imidazo[5,1-b]-thiazole-3-carboxyamide (Preparation 12) and 0.047 g of sodium iodide in the same manner as in Example 25.

NMR (D₂O) d (HDO=4.80): 3.23 (1H, d, J=18 Hz), 3.74 (1H, d, J=18 Hz), 3.96 (3H, s), 5.13 (1H, d, J=15 Hz), 5.27 (1H, d, J=5 Hz), 5.32 (1H, d, J=15 Hz), 5.81 (1H, d, J=5 Hz), 6.92 (1H, s), 7.88 (1H, s), 8.36 (1H, s)

EXAMPLE 28

(6R,7R)-7-[(Z)-2-(5-(Amino-1,2,4-thiadiazol-3-yl)-2-((S)-1-carboxyethoxyimino)acetamide]-3-(3-carbamoylimidazo[5,1-b]-thiazolium-6-yl)methyl-3-cephem-4-carboxylate (internal salt)

0.048 g (yield 25%) of a monosodium salt of the title compound was obtained from 0.303 g of p-methoxybenzyl (6R,7R)-7-[(Z)-2-(5-tritylamino-1,2,4-thiadiazol-3-yl)-2-((S)-1-diphenylmethoxycarbonylethoxyimino)acetamide]-3-chloromethyl-3-cephem-4-carboxylic acid ester, 0.055 g of imidazo[5,1-b]-thiazole-3-carboxyamide and 0.047 g of sodium iodide in the same manner as in Example 25.

NMR (D$_2$O) d (HDO=4.80): 1.46 (3H, d, J=7 Hz), 3.23 (1H, d, J=18 Hz), 3.63 (1H, d, J=18 Hz), 4.72 (1H, q, J=7 Hz), 5.13 (1H, d, J=15 Hz), 5.28 (1H, d, J=5 Hz), 5.34 (1H, d, J=15 Hz), 5.89 (1H, J=5 Hz), 7.89 (1H, s), 8.37 (1H, s), 9.77 (1H, s)

EXAMPLE 29

(6R,7R)-7-[(Z)-2-(2-Aminothiazol-4-yl)-2-((S)-1-carboxyethoxy-imino)acetamide]-3-(3-carbamoyl-5-hydroxymethylimidazo[5,1-b]-thiazolium-6-yl)methyl-3-cephem-4-carboxylate (internal salt)

0.026 g (yield 13%) of a monosodium salt of the title compound was obtained from 0.303 g of p-methoxybenzyl (6R,7R)-7-[(Z)-2-(2-tritylaminothiazol-4-yl)-2-((S)-1-diphenylmethoxycarbonylethoxyimino)acetamide]-3-chloromethyl-3-cephem-4-carboxylic acid ester, 0.065 g of 5-hydroxymethylimidazo-[5,1-b]thiazole-3-carboxyamide and 0.047 g of sodium iodide in the same manner as in Example 25.

NMR (D$_2$O) d (HDO=4.80): 1.45 (3H, d, J=7 Hz), 3.23 (1H, d, J=17 Hz), 3.58 (1H, J=17 Hz), 4.65 (1H, q, J=7 Hz), 5.21 (2H, s), 5.28 (1H, d, J=5 Hz), 5.36 (2H, s), 5.88 (1H, d, J=5 Hz), 7.00 (1H, s), 7.91 (1H, s), 8.22 (1H, s)

EXAMPLE 30

(6R,7R)-7-[(Z)-2-(5-Amino-1,2,4-thiadiazol-3-yl)-2-methoxyiminoacetamide]-3- (imidazo [5, 1-b]thiazolium-6-yl)methyl-3-cephem-4-carboxylate (internal salt)

To a solution of 0.215 g of sodium (6R,7R)-7-[(Z)-2-(5-amino-1,2,4-thiadiazol-3-yl)-2-methoxyiminoacetamide]-3-acetoxymethyl-3-cephem-4-carboxylate in a mixture of 1 ml of water and 1 ml of acetonitrile were added 0.675 g of sodium iodide and 0.168 g of imidazo[5,1-b]thlazole, and the mixture was stirred at 70° C. for 4 hours. The reaction solution was cooled to room temperature. To this was added 20 ml of acetone. The precipitate was collected by filtration, and purified by column chromatography successively using Dialon HP 20 and Sephadex LH 20 to give 0.007 g of the title compound.

NMR (D$_3$O) d (HDO=4.80): 3.24 (1H, d, J=18.0 Hz), 3.64 (1H, d, J=18.0 Hz), 4.06 (3H, s), 5.14 (1H, d, J=14.6 Hz), 5.26 (1H, d, J=4.7 Hz), 5.29 (1H, d, J=14.6 Hz), 5.88 (1H, d, J=4.7 Hz), 7.54 (1H, d, J=4.3 Hz), 7.76 (1H, s), 7.93 (1H, d, J=4.3 Hz)

EXAMPLE 31

(6R,7R)-7-[(Z)-2-(5-(Amino-1,2,4-thiadiazol-3-yl)-2-methoxyiminoacetamide]-3-(5-hydroxymethylimidazo[5,1-b]thiazolium-6-yl)methyl-3-cephem-4-carboxylate (internal salt)

To a solution of 0.553 g (1.00 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester in 10 ml of acetone were successively added 0.180 g (1.20 mmol) of sodium iodide and 0,093 g (1.20 mmol) of 5-hydroxymethylimidazo[5,1-b]thiazole (Preparation 10), and the mixture shielded from the light was stirred overnight at room temperature under argon atmosphere. To the reaction solution was added 20 ml of ethyl acetate, and the mixture was stirred. The precipitate was collected by filtration, and dried under reduced pressure. The powder obtained was dissolved in 30 ml of methanol. To this solution was added 20 ml of a 2N aqueous solution of sodium trifluoroacetate of which pH had been adjusted to 5.5–6 by trifluoroacetic acid. The mixture was stirred, and then concentrated to approximately 10 ml under reduced pressure. The precipitate was collected by filtration, and dried under reduced pressure. To this was successively added 2 ml of anisole and 10 ml of trifluoroacetic acid with ice-cooling, and the mixture was stirred for one hour. To the reaction solution was added 50 ml of isopropyl ether which had been cooled to −10° C. The precipitate was collected by filtration, and dried under reduced pressure. To this was added 30 ml of water to obtain a suspension, to which was then added sodium hydrogencarbonate with good stirring to adjust the pH of the suspension to 7.5. The mixture was purified by column chromatography using 50 ml of Diaion HP 20 Resin, eluting with 200 ml of water, 200 ml of a 10% aqueous solution of methanol, 200 ml of a 20% aqueous solution of methanol and 200 ml of a 30% aqueous solution of methanol. A fraction containing the desired compound was concentrated to dryness. The residue was further purified by column chromatography using 200 ml of Sephadex LH 20, eluting with a 50% aqueous solution of methanol, concentrated under reduced pressure, and then freeze-dried to give 0.133 g of the title compound. NMR (D$_2$O) d (HDO=4.80): 3.22 (1H, J=17.9 Hz), 3.54 (1H, d, J=17.9 Hz), 4.06 (3H, s), 5.19 (2H, s), 5.25 (1H, d, J=5.2 Hz), 5.26 (1H, d, J=15.0 Hz), 5.32 (1H, d, J=15.0 Hz), 5.87 (1H, d, J=5.2 Hz), 7.57 (1H, d, J=4.3 Hz), 7.75 (1H, s), 8.05 (1H, d, J=4.3 Hz)

EXAMPLE 32

(6R,7R)-7-[(Z)-2-(5-Amino-1,2,4-thiadiazol-3-yl)-2-methoxyiminoacetamide]-3-(3-methylimidazo[5,1-b]thiazolium-6-yl)methyl-3-cephem-4-carboxylate (internal salt)

0.052 g of the title compound was obtained from 0.276 g (0.5 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.083 g (0.6 mmol) of 3-methylimidazo[5,1-b]thiazole (Preparation 2) and 0.090 g (0.60 mmol) of sodium iodide in the same manner as in Example 31.

NMR (D$_2$O) d (HDO=4.80): 2.48 (3H, s), 3.23 (1H, d, J=17.9 Hz), 3.63 (1H, d, J=17.9 Hz), 4.05 (3H, s), 5.15 (1H, d, J=14.8 Hz), 5.26 (1H, d, J=4.8 Hz), 5.30 (1H, d, J=14.8 Hz), 5.86 (1H, d, J=4.8 Hz), 7.11 (1H, s), 7.75 (1H, s), 9.34 (1H, s)

EXAMPLE 33

(6R,7R)-7-[(Z)-2-(5-Amino-1,2,4-thiadiazol-3-yl)-2-methoxyiminoacetamide]-3-(5-methylimidazo[5,1-b]thiazolium-6-yl)methyl-3-cephem-4-carboxylate (internal salt)

0.037 g of the title compound was obtained from 0.276 g (0.5 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.083 g (0.6 mmol) of 5-methylimidazo[5,1-b]thiazole (Preparation 3) and 0.090 g (0.60 mmol) of sodium iodide in the same manner as in Example 31.

NMR (D$_2$O) d (HDO=4.80): 2.84 (3H, s), 3.22 (1H, d, J=17.9 Hz), 3.52 (1H, d, J=17.9 Hz), 4.06 (1H, s), 5.12 (1H, d, J=15.1 Hz), 5.23 (1H, d, J=4.8 Hz), 5.23 (1H, d, J=4.8 Hz), 5.86 (1H, d, J=5.8 Hz), 7.47 (1H, d, J=4.3 Hz), 7.61 (1H, s), 7.82 (1H, d, J=4.3 Hz)

EXAMPLE 34

(6R,7R)-7-[(Z)-2-(5-Amino-1,2,4-thiadiazol-3-yl)-2-methoxyiminoacetemide]-3-(5-(formylamino)methylimidazo[5,1-b]-thiazolium-6-yl)methyl-3-cephem-4-carboxylate (internal salt)

0.012 g of the title compound was obtained from 0.221 g (0.4 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.091 g (0.5 mmol) of 5-(formylamino)methylimidazo[5,1-b]thiazole (Preparation 15) and 0.075 g (0.50 mmol) of sodium iodide in the same manner as in Example 31.

NMR ($D_2O$) d (HDO=4.80): 3.15 (1H, d, J=17.8 Hz), 3.58 (1H, d, J=17.8 Hz), 4.05 (3H, s), 5.02 (2H, s), 5.27 (1H, d, J=5.0 Hz), 5.28 (1H, d, J=14.8 Hz), 5.33 (1H, d, J=14.8 Hz), 5.86 (1H, d, J=5.0 Hz), 7.58 (1H, d, J=4.3 Hz), 7.73 (1H, s), 8.03 (1H, d, J=4.3 Hz), 8.20 (1H, s)

EXAMPLE 35

(6R,7R)-7-[(Z)-2-(5-Amino-1,2,4-thiadiazol-3-yl)-2-methoxyiminoacetamide]-3-(7-methylimidazo[5,1-b]thiazolium-6-yl)methyl-3-cephem-4-carboxylate (internal salt)

0.023 g of the title compound was obtained from 0.166 g (0.30 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.050 g (0.36 mmol) of 7-methylimidazo-[5,1-b]thiazole (Preparation 8) and 0.090 g (0.60mmol) of sodium iodide in the same manner as in Example 31.

NMR ($D_2O$) d (HDO=4.80): 2.47 (3H, s), 3.26 (1H, d, J=17.6 Hz), 3.51 (1H, d, J=17.6 Hz), 4.08 (3H, s), 5.16 (1H, d, J=15.9 Hz), 5.25 (1H, d, J=4.5 Hz), 5.30 (1H, d, J=15.9 Hz), 5.89 (1H, d, J=4.5 Hz), 7.51 (1H, d, J=3.7 Hz), 7.85 (1H, d, J=3.7 Hz)

EXAMPLE 36

(6R,7R)-7-[(Z)-2-(5-Amino-1,2,4-thiadiazol-3-yl)-2-methoxyiminoacetamide]-3-(3-hydroxymethylimidazo[5,1-b]thiazolium-6-yl)methyl-3-cepham-4-carboxylate (internal salt)

0.031 g (yield 19%) of the title compound was obtained from 0.161 g of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.051 g of 3-hydroxymethylimidazo[5,1-b]thiazole (Preparation 9) and 0.047 g of sodium iodide in the same manner as in Example 31.

NMR ($D_2O$) d (HDO=4.80): 3.50 (1H, d, J=18 Hz), 3.89 (1H, d, J=18 Hz), 4.31 (3H, s), 5.12 (2H, s), 5.41 (1H, d, J=15 Hz), 5.52 (1H, d, J=5 Hz), 5.57 (1H, d, J=15 Hz), 6.12 (1H, d, J=5 Hz), 7.72 (1H, s), 8.06 (1H, s)

EXAMPLE 37

(6R,7R)-7-[(Z)-2-(5-Amino-1,2,4-thiadiazol-3-yl)-2-methoxyiminoacetamide]-3-(3-fluoromethylimidazo[5,1-b]thiazolium-6-yl)methyl-3-cephem-4-carboxylate (internal salt)

0.023 g of the title compound was obtained from 0.161 g of p-methoxybenzyl (6R,7R)-7-[(Z)-2-(5-amino-1,2,4-thiadiazol-3-yl)-2-methoxyiminoacetamide]-3-chloromethyl-3-cephem-4- carboxylic acid ester, 0.052 g of 3-fluoromethylimidazo[5,1-b]-thiazole and 0.047 g of sodium iodide in the same manner as in Example 31

NMR ($D_2O$) d (HDO=4.80): 3.24 (1H, d, J=18 Hz), 3.63 (1H, d, J=18 Hz), 4.03 (3H, s), 5.15 (1H, d, J=15 Hz), 5.25 (1H, d, J=5 Hz), 5.33 (1H, d, J=15 Hz), 5.66 (2H, d, J=47 Hz), 5.85 (1H, d, J=5 Hz), 7.74 (1H, d, J=4 Hz), 7.84 (1H, s), 9.53 (1H, s)

EXAMPLE 38

(6R,7R)-7-[(Z)-2-(5-Amino-1,2,4-thiadiazol-3-yl)-2-methoxyiminoacetamide]-3-(3-(N-methylcarbamoyl)imidazo[5,1-b]-thiazolium-6-yl)methyl-3-cephem-4-carboxylate (internal salt)

0.045 g (yield 26%) of the title compound was obtained from 0.161 g of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.060 g of imidazo[5,1-b]-thiazole-3-N-methylcarboxyamide and 0.047 g of sodium iodide in the same manner as in Example 31.

NMR ($D_2O$) d (HDO=4.80): 2.92 (3H, s), 3.23 (1H, d, J=18 Hz), 3.64 (1H, d, J=18 Hz), 4.03 (3H, s), 5.15 (1H, d, J=14 Hz), 5.26 (1H, d, J=4 Hz), 5.33 (1H, d, J=14 Hz), 5.85 (1H, d, J=4 Hz), 7.87 (1H, s), 8.20 (1H, s), 9.85 (1H, s)

EXAMPLE 39

(6R,7R)-7-[(Z)-2-(5-Amino-1,2,4-thiadiazol-3-yl)-2-methoxyiminoacetamide]-3-(3-cyanoimidazo[5,1-b]thiazolium-6-yl)methyl-3-cephem-4-carboxylate (internal salt)

0.030 g (yield 18%) of the title compound was obtained from 0.161 g of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.049 g of 3-cyanoimidazo-[5,1-b]thiazole (Preparation 56) and 0.047 g of sodium iodide in the same manner as in Example 31.

NMR ($D_2O$) d (HDO=4.80): 3.23 (1H, d, J=18 Hz), 3.64 (1H, d, J=18 Hz), 4.04 (3H, s), 5.16 (1H, d, J=15 Hz), 5.26 (1H, d, J=5 Hz), 5.33 (1H, d, J=15 Hz), 5.86 (1H, d, J=5 Hz), 7.88 (1H, s), 8.36 (1H, s), 9.77 (1H, s)

EXAMPLE 40

(6R,7R)-7-[(Z)-2-(5-Amino-1,2,4-thiadiazol-3-yl)-2-methoxyiminoacetamide]-3-(5-(methoxycarbonylmethyl)imidazo[5,1-b]-thiazolium-6-yl)methyl-3-cepham-4-carboxylate (internal salt)

The title compound was obtained (yield 6.9%) from p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, methyl imidazo[5,1-b]thiazol-5-yl-acetate (Preparation 13) and sodium iodide in the same manner as in Example 31.

NMR ($D_2O$) d (HDO=4.80): 3.14 (1H, d, J=18.1 Hz), 3.55 (1H, d, J=18.1 Hz), 3.79 (3H, s), 4.08 (2H, s), 4.12 (3H, s), 5.26 (1H, d, J=15.5 Hz), 5.26 (1H, J=4.8 Hz), 5.43 (1H, J=15.5 Hz), 5.88 (1H, d, J=4.8 Hz), 7.62 (1H, d, J=4.1 Hz), 7.81 (1H, s), 7.97 (1H, d, J=4.1 Hz) MS (SIMS): 592 ($M^+$)

EXAMPLE 41

(6R,7R)-7-[(Z)-2-(5-Amino-1,2,4-thiadiazol-3-yl)-2-methoxyiminoacetamide]-3-(5-(carbamoylmethyl)imidazo[5,1-b]thiazolium-6-yl)methyl-3-cephem-4-carboxylate (internal salt)

The title compound was obtained (yield 13%) from p-methoxybenzyl (6R, 7R)-7-[(Z)-2-(5-amino-1,2,4-thiadiazol-3-yl)-2-methoxyiminoacetamide]-3- chloromethyl-3-cephem-4-carboxylic acid ester, imidazo[5,1-b]thiazole-5-acetamide (Preparation 14) and sodium iodide in the same manner as in Example 31.

NMR (D$_2$O) d (HDO=4.80): 3.10 (1H, d, J=17.9 Hz), 3.48 (1H, d, J=17.9 Hz), 4.08 (5H, s), 5.23 (1H, d, J=4.7 Hz), 5.25 (1H, d, J=15.1 Hz), 5.42 (1H, d, J=15.1 Hz), 5.86 (1H, d, J=4.7 Hz), 7.60 (1H, d, J=4.4 Hz), 7.80 (1H, s), 7.82 (1H, d, J=4.4 Hz) MS (SIMS): 577 (M$^+$)

EXAMPLE 42

(6R, 7R)-7-[(Z)-2-(5-Amino-1,2,4-thiadiazol-3-yl)-2-methoxyiminoacetamide]-3-(2,3-dimethylimidazo[5,1-b]thiazolium-6-yl)methyl-3-cephem-4-carboxylate (internal salt)

0.041 g (yield 25%) of the title compound was obtained from 0.166 g of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.055 g of 2,3-dimethylimidazo[5,1-b]thiazole (Preparation 5) and sodium iodide in the same manner as in Example 31.

NMR (D$_2$O) d (HDO=4.80): 2.48 (3H, s), 2.50 (3H, s), 3.25 (1H, d, J=18 Hz), 3.64 (1H, d, J=18 Hz), 4.06 (3H, s), 5.12 (1H, d, J=13 Hz), 5.25–5.30 (2H, m), 5.88 (1H, d, J=5 Hz), 7.68 (1H, s), 9.22 (1H, s)

EXAMPLE 43

(6R,7R)-7-[(Z)-2-(5-Amino-1,2,4-thiadiazol-3-yl)-2-methoxyiminoacetamide]-3-(2-methylimidazo[5,1-b]thiazolium-6-yl)methyl-3-cephem-4-carboxylate (internal salt)

0.041 g (yield 3.8%) of the title compound was obtained from 0.111 g of p-methoxybenzyl (6R,7R)-7-[(Z)-2-(5-amino-1,2,4-thiadiazol-3-yl)-2-methoxyiminoacetamide]-3-chloromethyl- 3-cephem-4-carboxylic acid ester, 0.033 g of 2-methylimidazo-[5,1-b]thiazole (Preparation 7) and sodium iodide in the same manner as in Example 31.

NMR (D$_2$O) d (HDO=4.80): 2.47 (3H, s), 3.25 (1H, d, J=18 Hz) 3.65 (1H, d, J=18 Hz), 4.07 (3H, s), 5.11 (1H, d, J=15 Hz), 5.27 (1H, d, J=15 Hz), 5.27 (1H, d, J=5 Hz), 5.88 (1H, d, J=5 Hz), 7.67 (1H, s), 9.22 (1H, s)

EXAMPLE 44

(6R,7R)-7-[(Z)-2-(5-Amino-1,2,4-thiadiazol-3-yl)-2-methoxyiminoacetamide]-3-(3-carbamoylimidazo[5,1-b]thiazolium-6-yl)methyl-3-cephem-4-carboxylate (internal salt)

0.161 g of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester was dissolved in 5 ml of acetone. To this solution was added 0.047 g of sodium iodide, and the mixture was stirred for 3 hours. The reaction solution was concentrated under reduced pressure, and the residue was dissolved in 1.5 ml of N,N-dimethylformamide (DMF). To this solution was added 0.055 g of imidazo[5,1-b]thiazole-3-carboxyamide (Preparation 12), and the mixture was stirred at room temperature for 16 hours. To the reaction solution was added a 10% aqueous solution of sodium trifluoroacetate. The precipitate was collected by filtration, and dried under reduced pressure. To this were added 1 ml of anisole and 2 ml of trifluoroacetic acid, and the mixture was stirred for one hour with ice-cooling. To the mixture was further added isopropyl ether. The precipitate was collected by filtration, dissolved in an aqueous solution of sodium hydrogencarbonate, and purified by column chromatography successively using Diaion HP 20 and Sephadex LH 20 to give 0.037 g (yield 22%) of a monosodium salt of the title compound.

NMR (D$_2$O) d (HDO=4.80): 3.22 (1H, s, J=18 Hz), 3.63 (1H, s, J=18 Hz), 4.03 (3H, s), 5.14 (1H, d, J=15 Hz), 5.25 (1H, d, J=5 Hz), 5.34 (1H, d, J=15 Hz), 5.85 (1H, d, J=5 Hz), 7.88 (1H, s), 8.35 (1H, s), 9.77 (1H, s)

EXAMPLE 45

(6R,7R)-7-[(Z)-2-(5-Amino-1,2,4-thiadiazol-3-yl)-2-methoxyiminoacetamide]-3-(3-carbamoyl-5-methylimidazo[5,1-b]-thiazolium-6-yl)methyl-3-cephem-4-carboxylate (internal salt)

4.7 mg (yield 2.7%) of the title compound was obtained from 0.161 g of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.060 g of 5-methylimidazo-[5,1-b]thiazole-3-carboxyamide and 0.047 g of sodium iodide in the same manner as in Example 44.

NMR (D$_2$O) d (HDO=4.80): 2.85 (3H, s), 3.23 (1H, d, J=18 Hz), 3.53 (1H, d, J=18 Hz), 4.07 (3H, s), 5.17 (1H, d, J=15 Hz), 5.25 (1H, d, J=4 Hz), 5.32 (1H, d, J=15 Hz), 5.87 (1H, d, J=4 Hz), 7.76 (1H, s), 8.11 (1H, s)

EXAMPLE 46

(6R,7R)-7-[(Z)-2-(5-amino-1,2,4-thiadiazol-3-yl)-2-methoxyiminoacetamide]-3-(3-carbamoyl-5-hydroxymethylimidazo[5,1-b]-thiazolium-6-yl)methyl-3-cepham-4-carboxylate (internal salt)

0.013 g (yield 7%) of the title compound was obtained from 0.161 g of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.065 g of 5-hydroxymethylimidazo[5,1-b]thiazole-3-carboxyamide and 0.047 g of sodium iodide in the same manner as in Example 44.

NMR (D$_2$O) d (HDO=4.80): 3.22 (1H, d, J=18 Hz), 3.57 (1H, d, J=18 Hz), 4.08 (3H, s), 5.20 (2H, s), 5.26 (1H, d, J=6 Hz), 5.32 (1H, d, J=15 Hz), 5.40 (1H, d, J=15 Hz), 5.88 (1H, d, J=6 Hz), 7.90 (1H, s), 8.22 (1H, s)

EXAMPLE 47

(6R,7R)-7-[(Z)-2-(5-Amino-1,2,4-thiadiazol-3-yl)-2-methoxyiminoacetamide]-3-(3-carbamoylimidazo [5,1-b]thiazolium-6-yl)methyl-3-cephem-4-carboxylate (internal salt)

0.039 g (yield 24%) of the title compound was obtained from 0.166 g of p-methoxybenzyl (6R,7R)-7-[(Z)-2-(5-amino-1,2,4-thiadiazol-3-yl)-2-ethoxyiminoacetamide]-3-chloromethyl-3-cepham-4-carboxylic acid ester, 0.055 g of imidazo[5,1-b]-thiazole-3-carboxyamide (Preparation 12) and 0.047 g of sodium iodide in the same manner as in Example 44.

NMR (D20) d (HDO=4.80): 1.30 (3H, t, J=7 Hz), 3.24 (1H, d, J=18 Hz), 3.64 (1H, J=18 Hz), 4.33 (2H, q, J=7 Hz), 5.18 (1H, d, J=14 Hz), 5.27 (1H, d, J=5 Hz), 5.33 (1H, d, J=14 Hz), 5.87 (1H, d, J=5 Hz), 7.88 (1H, s), 8.37 (1H, s), 9.78 (1H, s)

EXAMPLE 48

(6R,7R)-7-[(Z)-2-(5-Amino-2,4-thiadiazol-3-yl)-2-(2-fluoroethoxyimino)acetamide]-3-(3-carbamoylimidazo[5,1-b]thiazolium-6-yl)methyl-3-cephem-4-carboxylate (internal salt)

0.037 g (yield 20%) of the title compound was obtained from 0.261 g of p-methoxybenzyl (6R,7R)-7-[(Z)-2-(5-tritylamino-1,2,4-thiadiazol-3-yl)-2-(2-fluoroethoxyimino) acetamide]-3-chloromethyl-3-cephem-4-carboxylic acid ester, 0.055 g of imidazo[5,1-b]thiazole-3-carboxyamide (Preparation 12) and 0.047 g of sodium iodide in the same manner as in Example 44.

NMR (D$_2$O) d (HDO=4.80): 3.24 (1H, d, J=18 Hz), 3.63 (1H, J=18 Hz), 4.49 (1H, m), 4.59 (1H, m), 4.68 (1H, m), 4.84(1H, m), 5.18 (1H, d, J=14 Hz), 5.27 (1H, d, J=5 Hz), 5.33 (1H, d, J=14 Hz), 5.87 (1H, d, J=5 Hz), 7.88 (1H, s), 8.37 (1H, s), 9.78 (1H, s)

EXAMPLE 49

(6R,7R)-7-[(Z)-2-(5-Amino-1,2,4-thiadiazol-3-yl)-2-ethoxyiminoacetamide]-3-[5-(formylamino)methylimidazo[5,1-b]thiazolium-6-yl]methyl-3-cephem-4-carboxylate (internal salt)

0.068 g of the title compound was obtained from 0.227 g (0.4 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 0.091 g (0.5 mmol) of 5-(formylamino)methylimidazo[5,1-b]thiazole (Preparation 15) and 0.075 g (0.50 mmol) of sodium iodide in the same manner as in Example 31.

NMR (D$_2$O) d (HDO=4.80): 1.31 (3H, t, J=7.1 Hz), 3.16 (1H, d, J=17.8 Hz), 3.58 (1H, d, J=17.8 Hz), 4.34 (2H, q, J=7.1 Hz), 5.03 (2H, s), 5.28 (1H, d, J=4.8 Hz), 5.29 (1H, d, J=15.6 Hz), 5.34 (1H, d, J=15.6 Hz), 5.87 (1H, d, J=4.8 Hz), 7.59 (1H, d, J=4.4 Hz), 7.73 (1H, s), 8.04 (1H, d, J=4.4 Hz), 8.20 (1H, s)

EXAMPLE 50

(6R,7R)-7-[(Z)-2-(2-Aminothiazol-4-yl)-2-methoxyiminoacetamide]-3-[5-(formylamino)methylimidazo[5,1-b]thiazolium-6-yl]methyl-3-cephem-4-carboxylate (internal salt)

0.093 g of the title compound was obtained from 0.397 g (0.5 mmol) of p-methoxybenzyl (6R,7R)-7-[(Z)-2-(2-tritylaminothiazol-4-yl)-2-methoxyimino]acetamide-3-chloromethyl-3-cephem-4-carboxylic acid ester, 0.110 g (0.61 mmol) of 5-(formylamino)methylimidazo[5,1-b]thiazole (Preparation 15) and 0.090 g (0.60 mmol) of sodium iodide in the same manner as in Example 1.

NMR (D$_2$O) d (HDO=4.80): 3.16 (1H, d, J=17.6 Hz), 3.59 (1H, d, J=17.6 Hz), 3.98 (3H, s), 5.03 (2H, s), 5.28 (1H, d, J=4.7 Hz), 5.29 (1H, d, J=15.3 Hz), 5.34 (1H, d, J=15.3 Hz), 5.83 (1H, d, J=4.7 Hz), 6.99 (1H, s), 7.59 (1H, d, J=4.3 Hz), 7.73 (1H, s), 8.04 (1H, d, J=4.3 Hz)

EXAMPLE 51

(6R,7R)-7-[(Z)-2-(2-Aminothiazol-4-yl)-2-hydroxyiminoacetamide]-3-[5-methylimidazo[5,1-b]thiazolium-6-yl]methyl-3-cephem-4-carboxylate (internal salt)

0.025 g of the title compound was obtained from 0.511 g (0.5 mmol) of p-methoxybenzyl (6R,7R)-7-[(Z)-2-(2-tritylaminothiazol-4-yl)-2-triphenylmethoxyimino]acetamide-3-chloromethyl-3-cephem-4-carboxylic acid ester, 0.083 g (0.60 mmol) of 5-methylimidazo[5,1-b]thiazole (Preparation 3) and 0.090 g (0.60 mmol) of sodium iodide in the same manner as in Example 1.

NMR (D$_2$O) d (HDO=4.80): 2.84 (3H, s), 3.23 (1H, d, J=17.8 Hz), 3.53 (1H, d, J=17.8 Hz), 5.12 (1H, d, J=15.1 Hz), 5.25 (1H, d, J=4.7 Hz), 5.28 (1H, d, J=15.1 Hz), 5.87 (1H, d, J=4.7 Hz), 6.96 (1H, s), 7.48 (1H, d, J=4.3 Hz), 7.61 (1H, s), 7.84 (1H, d, J=4.3 Hz)

EXAMPLE 52

(6R,7R)-7-[(Z)-2-(5-Amino-1,2,4-thiadiazol-3-yl)-2-methoxyiminoacetamide]-3-(5-aminomethylimidazo[5,1-b]thiazolium-6-yl]methyl-3-cephem-4-carboxylate (internal salt)

0.035 g of the title compound was obtained from 0.221 g (0.4 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.120 g (0.47 mmol) of 5-(tert-butoxycarbonylamino) methylimidazo[5,1-b]thiazole (Preparation 22) and 0.070 g (0.47 mmol) of sodium iodide in the same manner as in Example 31.

NMR (D$_3$O) d (HDO=4.80): 3.24 (1H, d, J=18.5 Hz), 3.71 (1H, d, J=18.5 Hz), 4.00 (3H, s), 4.95 (1H, d, J=16.1 Hz), 5.01 (1H, d, J=16.1 Hz), 5.24 (1H, d, J=15.2 Hz), 5.28 (1H, d, J=4.8 Hz), 5.70 (1H, d, J=15.2 Hz), 5.84 (1H, d, J=4.8 Hz), 7.68 (1H, d, J=4.4 Hz), 7.68 (1H, s), 8.12 (1H, d, J=4.4 Hz)

EXAMPLE 53

(6R,7R)-7-[(Z)-2-(5-Amino-1,2,4-thiadiazol-3-yl)-2-methoxyiminoacetamide]-3-(5-hydroxymethyl-3-methylimidazo[5,1-b]-thiazolium-6-y1]methyl-3-cephem-4-carboxylate (internal salt)

0.062 g of the title compound was obtained from 0.277 g (0.5 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester, 0.101 g (0.60 mmol) of 5-hydroxymethyl-3-methylimidazo[5,1-b] thiazole (Preparation 24) and 0.090 g (0.60 mmol) of sodium iodide in the same manner as in Example 31.

NMR (D$_2$O) d (HDO=4.80): 2.70 (3H, s), 3.21 (1H, d, J=17.7 Hz), 3.53 (1H, d, J=17.7 Hz), 4.08 (1H, s), 5.22 (2H, s), 5.25 (1H, d, J=4.9 Hz), 5.30 (1H, d, J=14.9 Hz), 5.38 (1H, d, J=14.9 Hz), 5.87 (1H, d, J=4.9 Hz), 7.18 (1H, s), 7.76 (1H, s)

EXAMPLE 54

(6R,7R)-7-[(Z)-2-(5-Amino-1,2,4-thiadiazol-3-yl)-2-methoxyiminoacetamide]-3-[5-(formylamino)methyl-3-methylimidazo-[5,1-b]thiazolium-6-yl]methyl-3-cepham-4-carboxylate (internal salt)

0.045 g of the title compound was obtained from 0.221 g (0.4 mmol) of p-methoxybenzyl (6R,7R)-7-[(Z)-2-(5-amino-1,2,4-thiadiazol-3-yl)-2-methoxyiminoacetamide]-3-chloromethyl-3-cepham-4-carboxylic acid ester, 0.098 g (0.50 mmol) of 5-(formylamino)methyl-3-methylimidazo[5,1-b]thiazole (Preparation 25) and 0.075 g (0.50 mmol) of sodium iodide in the same manner as in Example 31.

NMR (D$_2$O) d (HDO=4.80): 2.70 (3H, s), 3.12 (1H, d, J=17.9 Hz), 3.58 (1H, d, J=17.9 Hz), 4.05 (1H, s), 5.06 (1H, d, J=17.0 Hz), 5.13 (1H, d, J=17.0 Hz), 5.27 (1H, d, J=4.8 Hz), 5.32 (2H, s), 5.85 (1H, d, J=4.8 Hz), 7.14 (1H, s), 7.71 (1H, s), 8.17 (1H, s)

EXAMPLE 55

(6R,7R)-7-[(Z)-2-(5-Amino-1,2,4-thiadiazol-3-yl)-2-ethoxy-iminoacetamide]-3-[57(formylamino)methyl-3-methylimidazo-[5,1-b]thiazolium-6-yl]methyl-3-cephem-4-carboxylate (internal salt)

0.051 g of the title compound was obtained from 0.227 g (0.4 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 0.098 g (0.50 mmol) of 5-(formylamino)methyl-3-methylimidazo[5,1-b]thiazole (Preparation 25) and 0.075 g (0.50 mmol) of sodium iodide in the same manner as in Example 31.

NMR (D$_2$O) d (HDO=4.80): 1.30 (3H, t, J=7.1 Hz), 2.69 (3H, s), 3.13 (1H, d, J=17.9 Hz), 3.58 (1H, d, J=17.9 Hz), 4.32 (2H, q, J=7.1 Hz), 5.06 (1H, d, J=17.1 Hz), 5.12 (1H, d, J=17.1 Hz), 5.27 (1H, d, J=4.8 Hz), 5.32 (2H, s), 5.85 (1H, d, J=4.8 Hz), 7.14 (1H, :s), 7.71 (1H, s), 8.17 (1H, s)

EXAMPLE 56

(6R,7R)-7-[(Z)-2-(5-Amino-1,2,4-thiadiazol-3-yl)-2-ethoxyiminoacetamide]-3-[3,5-(1-oxo-2-azapropano)imidazo[5,1-b]-thiazolium-6-yl]-methyl-3-cephem-4-carboxylate (internal salt)

To 0.170 g (0.3 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester and 0.060 g (0.40 mmol) of sodium iodide was added 5 ml of acetone, and the mixture shielded from the light was stirred at room temperature under argon atmosphere for 30 minutes. The reaction solution was concentrated to dryness under reduced pressure. To the residue were added 30 ml of methylene chloride and 20 ml of a 2% aqueous solution of sodium thiosulfate, and the mixture was thoroughly stirred. The organic layer was separated, dried over anhydrous magnesium sulfate, and concentrated to dryness under reduced pressure. To the residue were added 0.078 g (0.44 mmol) of 3,5-(1-oxo-2-azapropano)imidazo[5,1-b]thiazole (Preparation 21) and 5 ml of N,N-dimethylformamide, and the mixture shielded from the light was stirred at room temperature under argon atmosphere for 16 hours. The reaction solution was concentrated under reduced pressure. The residue was triturated with 30 ml of ethyl acetate. The precipitate was collected by filtration, dried in the air, and then dissolved in 50 ml of methanol. To this solution was added 20 ml of a 2N aqueous solution of sodium trifluoroacetate of which pH had been adjusted to 6 by a small amount of trifluoroacetic acid. The mixture was stirred, and then concentrated to approximately 15 ml under reduced pressure. The precipitate was collected by filtration, and dried under reduced pressure. To this were successively added 1 ml of anisole and 6 ml of trifluoroacetic acid with ice-cooling, and the mixture was stirred for one hour. To the reaction solution was added 50 ml of isopropyl ether which had been cooled to −10° C. The precipitate was collected, dried under reduced pressure, and then suspended in 20 ml of water. Sodium hydrogencarbonate was added to the suspension with good stirring to adjust the pH to 7.5. This was purified by column chromatography using 30 ml of Dialon HP 20 Resin, eluting with 100 ml of water, 100 ml of a 10% aqueous solution of methanol, 100 ml of a 20% aqueous solution of methanol and 100 ml of a 30% aqueous solution of methanol. A fraction containing the desired compound was concentrated to dryness. The residue was further purified by column chromatography using 200 ml of Sephadex LH 20, eluting with 100 ml of a 50% aqueous solution of methanol, concentrated under reduced pressure, and then freeze-dried to give 0.035 g of the title compound.

NMR (D$_2$O) d (HDO=4.80): 1.32 (3H, t, J=7.1 Hz), 3.25 (1H, d, J=17.7 Hz), 3.62 (1H, d, J=17.7 Hz), 4.34 (2H, q, J=7.1 Hz), 5.17 (1H, d, J=15.2 Hz), 5.19 (1H, d, J=16 Hz), 5.25 (1H, d, J=15.2 Hz), 5.28 (1H, d, J=4.7 Hz), 5.30 (1H, d, J=16 Hz), 5.86 (1H, d, J=4.7 Hz), 7.71 (1H, s), 8.11 (1H, d)

EXAMPLE 57

(6R,7R)-7-[(Z)-2-(5-Amino-1,2,4-thiadiazol-3-yl)-2-ethoxyiminoacetamide]-3-[5-[(S)-1-(formylamino)ethyl]imidazo[5,1-b]-thiazolium-6-yl]methyl-3-cephem-4-carboxylate (internal salt)

0.068 g of the title compound was obtained from 0.227 g (0.4 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 0.098 g (0.50 mmol) of 5-[(S)-1-(formylamino)ethyl]imidazo[5,1-b]thiazole (Preparation 17) and 0.075 g (0.50 mmol) of sodium iodide in the same manner as in Example 31.

NMR (D$_2$O) d (HDO=4.80): 1.29 (3H, t, J=7.1 Hz), 1.68 (3H, d, J=7.2 Hz), 3.24 (1H, d, J=18.0 Hz), 3.58 (1H, d, J=18.0 Hz), 4.32 (2H, q, J=7.1 Hz), 5.27 (1H, d, J=4.7 Hz), 5.31 (1H, d, J=15.1 Hz), 5.38 (1H, d, J=15.1 Hz), 5.64 (1H, q, J=7.2 Hz), 5.86 (1H, d, J=4.7 Hz), 7.58 (1H, d, J=4.4 Hz), 7.73 (1H, S), 7.97 (1H, d, J=4.4 Hz), 8.14 (1H, s)

EXAMPLE 58

(6R,7R)-7-[(Z)-2-(5-Amino-1,2,4-thiadiazol-3-yl)-2-(ethoxyimino)acetamide]-3-[5-[(R)-1-(formylamino)ethyl]imidazo[5,1-b]-thiazolium-6-yl]methyl-3-cephem-4-carboxylate (internal salt)

0.052 g of the title compound was obtained from 0.227 g (0.4 mmol) of p-methoxybenzyl (6R, 7R)-7-[(Z)-2-(5-amino-1,2,4-thiadiazol-3-yl)-2-ethoxyiminoacetamide]-3-chloromethyl-3-cephem-4-carboxylic acid ester, 0.098 g (0.50 mmol) of 5-[(R)-1-(formylamino)ethyl]imidazo[5,1-b]thiazole (Preparation 18) and 0.075 g (0.50 mmol) of sodium iodide in the same manner as in Example 31.

NMR (D$_2$O) d (HDO=4.80): 1.31 (3H, t, a =7.1 Hz), 1.69 (3H, d, J=7.2 Hz), 3.25 (1H, d, J=17.7 Hz), 3.49 (1H, d, J=17.7 Hz), 4.33 (2H, q, J=7.1 Hz), 5.25 (1H, d, J=4.7 Hz), 5.33 (1H, d, J=15.3 Hz), 5.49 (1H, d, J=15.3 Hz), 5.59 (1H, q, J=7.2 Hz), 5.87 (1H, d, J=4.7 Hz), 7.60 (1H, d, J=4.5 Hz), 7.70 (1H, s), 7.98 (1H, d, J=4.5 Hz), 8.12 (1H, s)

EXAMPLE 59

(6R,7R)-7-[(Z)-2-(5-Amino-1,2,4-thiadiazol-3-yl)-2-(2-hydroxyethoxyimino)acetamide]-3-imidazo[5,1-b]thiazolium-6-yl]-5methyl-3-cephem-4-carboxylate (internal salt)

To a solution of 0.375 g (0.45 mmol) of p-methoxybenzyl (6R,7R)-7-[(Z)-2-(5-tritylamino-1,2,4-thiadiazol-3-yl)-2-(2-hydroxyethoxyimino)acetamide]-3-chloromethyl-3-cephem-4-carboxylic acid ester in 5 ml of acetone were added 0.068 g (0.55 mmol) of imidazo[5,1-b]thiazole (Preparation 1) and 0.082 g (0.55 mmol) of sodium iodide, and the mixture shielded from the light was stirred at room temperature under argon atmosphere for 18 hours. To the reaction solution were added 50 ml of methylene chloride and 30 ml of 2N sodium trifluoroacetate of which pH had been adjusted to 6 by a small amount of trifluoroacetic acid, and the mixture was thoroughly stirred. The organic layer was separated, dried over anhydrous magnesium sulfate, and then concentrated to dryness. To the residue were successively added 1 ml of anisole and 6 ml of trifluoroacetic acid with ice-cooling, and the mixture was stirred for one hour. To the reaction solution was added 50 ml of isopropyl ether which had been cooled to −10° C. The precipitate was collected by filtration, dried under reduced pressure, and then suspended in 20 ml of water. Sodium hydrogencarbonate was added with good stirring to the suspension to adjust the pH to 7.5. This was purified by column chromatography using 30 ml of Diaion HP 20 Resin, eluting with 100 ml of water, 100 ml of a 10% aqueous solution of methanol, 100 ml of a 20% aqueous solution of methanol and 100 ml of a 30% aqueous solution of methanol. A fraction containing the desired compound was concentrated to dryness. The residue was further purified by column chromatography using 200 ml of Sephadex LH 20, eluting with a 50% aqueous solution of methanol, concentrated under reduced pressure, and then freeze-dried to give 0.0135 g of the title compound.

NMR ($D_2O$) d (HDO=4.80): 3.24 (1H, d, J=18.0 Hz), 3.64 (1H, d, J=18.0 Hz), 3.85–3.92 (2H, m), 4.35–4.44 (2H, m), 5.14 (1H, d, J=14.6 Hz), 5.27 (1H, d, J=4.7 Hz), 5.30 (1H, d, J=14.6 Hz), 5.89 (1H, d, J=4.7 Hz), 7.53 (1H, d, J=4.3 Hz), 7.76 (1H, s), 7.93 (1H, d, J=4.3 Hz), 9.36 (1H, s)

EXAMPLE 60

(6R,7R)-7-[(Z)-2-(5-Amino-1,2,4-thiadiazol-3-yl)-2-(ethoxyimino)acetamide]-3-[5-(trifluoroacetylamino) methylimidazo-[5,1-b]-thiazolium-6-yl]methyl-3-cephem-4-carboxylate (internal salt) 0.042 g of the title compound was obtained from 0.227 g (0.4 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 0.125 g. (0.50 mmol) of 5-(trifluoroacetylamino)methylimidazo[5,1-b]thiazole (Preparation 16) and 0.075 g (0.50 mmol) of sodium iodide in the same manner as in Example 31.

NMR ($D_2O$) d (HDO=4.80): 1.31 (3H, t, J=7.1 Hz), 3.16 (1H, d, J=17.7 Hz), 3.60 (1H, d, J=17.7 Hz), 4.34 (2H, q, J=7.1 Hz), 5.13 (2H, s), 5.28 (1H, d, J=4.8 Hz), 5.30 (1H, d, J=15.3 Hz), 5.37 (1H, d, J=15.3 Hz), 5.87 (1H, d, J=4.8 Hz), 7.63 (1H, d, J=4.4 Hz), 7.78 (1H, s), 8.09 (1H, d, J=4.4 Hz)

EXAMPLE 61

(6R,7R)-7-[(Z)-2-(5-Amino-1,2,4-thiadiazol-3-yl)-2-(ethoxyimino)acetamide]-3-[3-carbamoyl-5-(formylamino) methylimidazo-[5,1-b]-thiazolium-6-yl]methyl-3-cephem-4-carboxylate (internal salt)

0.075 g of the title compound was obtained from 0.284 g (0.5 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 0.134 g (0.60 mmol) of 5-(formylamino)methylimidazo[5,1-b] thiazole-3-carboxyamide (Preparation 54) and 0.090 g (0.50mmol) of sodium iodide in the same manner as in Example 56.

NMR ($D_2O$) d (HDO=4.80): 1.31 (3H, t, J=7.1 Hz), 3.18 (1H, d, J=17.9 Hz), 3.60 (1H, d, J=17.9 Hz), 4.33 (1H, q, J=7.1 Hz), 5.06 (1H, d, J=16.3 Hz), 5.16 (1H, d, J=16.3 Hz), 5.28 (1H, d, J=4.7 Hz), 5.35 (1H, d, J=14.8 Hz), 5.41 (1H, d, J=14.8 Hz), 5.87 (1H, d, J=4.7 Hz), 7.86 (1H, s), 8.12 (1H, s), 8.25 (1H, s)

EXAMPLE 62

(6R,7R)-7-[(Z)-2-(5-Amino-1,2,4-thiadiazol-3-yl)-2-(ethoxyimino)acetamide]-3-(5-carbamoylimidazo[5,1-b] thiazolium-6-yl]methyl-3-cephem-4-carboxylate (internal salt) 0.021 g of the title compound was obtained from 1.134 g (2.0 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 0.502 g (3.0 mmol) of imidazo-[5,1-b]thiazole-3-carboxyamide (Preparation 19) and 0.33 g (2.2 mmol) of sodium iodide in the same manner as in Example 56.

NMR ($D_2O$) d (HDO=4.80): 1.29 (3H, t, J=7.1 Hz), 3.27 (1H, d, J=17.9 Hz), 3.55 (1H, d, J=17.9 Hz), 4.31 (2H, q, J=7.1 Hz), 5.24 (1H, d, J=4.7 Hz), 5.42 (1H, d, J=14.9 Hz), 5.59 (1H, d, J=14.9 Hz), 5.86 (1H, d, J=4.7 Hz), 7.73 (1H, d, J=4.2 Hz), 8.02 (1H, s), 8.18 (1H, d, J=4.2 Hz)

EXAMPLE 63

(6R,7R)-7-[(Z)-2-(5-Amino-1,2,4-thiadiazol-3-yl)-2-(2-hydroxyethoxyimino)acetamide]-3-[5-(formylamino) methylimidazo[5,1-b]-thiazolium-6-yl]methyl-3-cephem-4-carboxylate (internal salt) 0.015 g of the title compound was obtained from 0.136 g (0.16 mmol) of p-methoxybenzyl (6R,7R)-7-[(Z)-2-(5-tritylamino-1,2,4-thiadiazol-3-yl)-2-(2-hydroxyethoxy)iminoacetamide]-3-chloromethyl-3-cephem-4-carboxylic acid ester, 0.035 g (0.19 mmol) of 5-(formylamino)methylimidazo[5,1-b]thiazole (Preparation 15) and 0.026 g (0.18 mmol) of sodium iodide in the same manner as in Example 59.

NMR ($D_2O$) d (HDO=4.80): 3.15 (1H, d, J=17.8 Hz), 3.58 (1H, d, J=17.8 Hz), 3.85–3.95 (2H, m), 4.35–4.45 (2H, m), 5.02 (2H, s), 5.28 (1H, d, J=4.7 Hz), 5.28 (1H, d, J=16 Hz), 5.33 (1H, d, J=16 Hz), 5.88 (1H, d, J=4.7 Hz), 7.59 (1H, d, J=4.3 Hz), 7.72 (1H, s), 8.05 (1H, d, J=4.3 Hz), 8.20 (1H, s)

EXAMPLE 64

(6R,7R)-7-[(Z)-2-(5-Amino-1,2,4-thiadiazol-3-yl)-2-(ethoxyimino)acetamide]-3-[5-(2-carbamoylethenyl) imidazo[5,1-b]-thiazolium- 6-yl]methyl-3-cephem-4-carboxylate (internal salt)

0.252 g of the title compound was obtained from 0.783 g (1.38 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 0.320 g (1.66 mmol) of 2-(imidazo[5,1-b]thiazol-5-yl)acrylamide (Preparation 27) and 0.249 g (1.66 mmol) of sodium iodide in the same manner as in Example 56.

NMR ($D_2O$) d (HDO=4.80): 1.30 (1H, d, J=7.1 Hz), 3.17 (1H, d, J=17.9 Hz), 3.55 (1H, d, J=17.9 Hz), 4.33 (2H, q, J=7.1 Hz), 5.24 (1H, d, J=4.8 Hz), 5.33 (1H, d, J=14.8 Hz), 5.37 (1H, d, J=14.8 Hz), 5.86 (2H, d, J=4.8 Hz), 7.01 (1H, d, J=16.2 Hz), 7.74 (1H, d, J=4.4 Hz), 7.76 (1H, d, J=16.2 Hz), 7.92 (1H, s), 8.20 (1H, d, J=4.4 Hz)

EXAMPLE 65

(6R,7R)-7-[(Z)-2-(5-Amino-1,2,4-thiadiazol-3-yl)-2-(2-hydroxyethoxyimino)acetamide]-3-(3-carbamoylimidazo[5,1-b]thiazolium-6-yl]methyl-3-cephem-4-carboxylate (internal salt)

0.032 g of the title compound was obtained from 0.136 g (0.16 mmol) of p-methoxybenzyl (6R,7R)-7-[(Z)-2-(5-tritylamino-1,2,4-thiadiazol-3-yl)-2-(2-hydroxyethoxyimino)acetamide]-3-chloromethyl-3-cephem-4-carboxylic acid ester, 0.033 g (0.2 mmol) of imidazo[5,1-b]thiazole-3-carboxyamide (Preparation 12) and 0.030 g (0.2 mmol) of sodium iodide in the same manner as in Example 56.

NMR ($D_2O$) d (HDO=4.80): 3.22 (1H, d, J=17.7 Hz), 3.62 (1H, d, J=17.7 Hz), 3.83–3.92 (2H, m), 4.32–4.42 (2H, m), 5.15 (1H, d, J=14.6 Hz), 5.26 (1H, d, J=4.7 Hz), 5.23 (1H, d, J=14.6 Hz), 5.87 (1H, d, J=4.7 Hz), 7.87 (1H, s), 8.35 (1H, s), 9.76 (1H, s)

EXAMPLE 66

(6R,7R)-7-[(Z)-2-(5-Amino-1,2,4-thiadiazol-3-yl)-2-(fluoromethoxyimino)acetamide]-3-[5-[(R)-1-(formylamino)ethyl]imidazo-[5,1-b]thiazolium-6-yl] methyl-3-cepham-4-carboxylate (internal salt)

0.118 g of the title compound was obtained from 0.651 g (0.80 mmol) of p-methoxybenzyl (6R,7R)-7-[(Z)-2-(5-tritylamino- 1,2,4-thiadiazol-3-yl)-2-(fluoromethoxyimino) acetamide]-3-chloromethyl-3-cephem-4-carboxylic acid ester, 0.195 g (1.0mmol) of 5-[(R)-1-(formylamino)ethyl] imidazo[5,1-b]thiazole (Preparation 18) and 0.15 g (1.0mmol) of sodium iodide in the same manner as in Example 59. NMR (D$_2$O) d (HDO=4.80): 1.69 (1H, d, J=7.2 Hz), 3.23 (1H, d, J=17.8 Hz), 3.49 (1H, J=17.8 Hz), 5.25 (1H, d, J=4.7 Hz), 5.32 (1H, d, J=14.9 Hz), 5.49 (1H, d, J=14.9 Hz), 5.58 (1H, q, J=7.2 Hz), 5.82 (2H, d, J=54.2 Hz), 5.88 (1H, d, J=4.7 Hz), 7.58 (1H, d, J=4.3 Hz), 7.69 (1H, s), 7.97 (1H, d, J=4.3 Hz), 8.11 (1H, s)

EXAMPLE 67

(6R,7R)-7-[(Z)-2-(5-Amino-1,2,4-thiadiazol-3-yl)-2-methoxy- iminoacetamide]-3-[5-(2-hydroxyethyl)imidazo[5,1-b]thiazolium-6-yl]methyl-3-cephem-4-carboxylate (internal salt)

To a solution of 433 mg (0.54 mmol) of p-methoxybenzyl (6R, 7R)-7- [(Z)-2-(5-amino-1,2,4-thiadiazol-3-yl)-2-methoxyiminoacetamide]-3-chloromethyl-3-cephem-4-carboxylic acid ester in 10 ml of acetone were successively added. 90 mg (0.59 mmol) of sodium iodide and 110 mg (0.65 mmol) of 5-hydroxyethyl)imidazo[5,1-b]thiazole (Preparation 36), and the mixture were stirred overnight at room temperature. The solvent was distilled off, and the residue was dissolved in methylene chloride. To this solution was added a 2N aqueous solution of sodium trifluoroacetate, and the mixture was stirred. The organic layer was separated, dried over anhydrous magnesium sulfate, and concentrated under reduced pressure. To the residue were added i ml of anisole and 5 ml of trifluoroacetic acid ice-cooling, and the mixture was stirred for 30 minutes. To the reaction solution was added cold isopropyl ether, and the mixture was subjected to centrifugal separation. The precipitate washed with isopropyl ether, and dried under reduced pressure. To this was added a 5% aqueous solution of sodium hydrogencarbonate to obtain a solution. The solution was purified by column chromatography using Diaion HP 20 Resin, eluting with 200 ml of water, 200 ml of a 10% aqueous solution of methanol, 200 ml of a 20% aqueous solution of methanol, 200 ml of a 30% aqueous solution of methanol and 200 ml of a 40% aqueous solution of methanol. The desired compound was further purified by using a 1:1 mixture of methanol and water to give 63 mg (yield 21%) of the title compound. NMR (D$_2$O) d ( HDO=4.80): 3.23 (1H, d, J=17.7 Hz), 3.55 (1H, d, J=17.7 Hz), 3.56 (2H, t, J=5.6 Hz), 3.97 (2H, t, J=5.6 Hz), 4.08 (3H, s), 5.24 (1H, d, J=15.0 Hz), 5.26 (1H, d, J=4.7 Hz), 5.33 (1H, d, J=15.0 Hz), 5.88 (1H, d, J=4.7 Hz), 7.53 (1H, d, J=4.3 Hz), 7.70 (1H, s), 7.95 (1H, d, J=4.3 Hz)

EXAMPLE 68

(6R,7R)-7-[(Z)-2-(5-Amino-1,2,4-thiadiazol-3-yl)-2-methoxy- iminoacetamide]-3-[5-(2-formylaminoethyl) imidazo[5,1-b]- thiazolium-6-yl]methyl-3-cepham-4-carboxylate (internal salt)

42 mg (yield 24%) of the title compound was obtained from 238 mg (0.30 mmol) of p-methoxybenzyl (6R,7R)-7-[(Z)-2-(5- amino-1,2,4-thiadiazol-3-yl)-2-methoxyiminoacetamide]-3-chloromethyl-3-cephem-4-carboxylic acid ester, 82 mg (0.42 mmol) of 5-(2-formylaminoethyl)imidazo[5,1-b]thiazole (Preparation 37) and 54 mg (0.36 mmol) of sodium iodide in the same manner as in Example 67. NMR (D$_2$O) d (HDO=4.80): 3.27 (1H, d, J=17.9 Hz), 3.63 (5H, m), 4.08 (3H, s), 5.28 (1H, d, J=5.6 Hz), 5.30 (2H, s), 5.88 (1H, d, J=5.6 Hz), 7.56 (1H, d, J=3.8 Hz), 7.7 (1H, s), 7.95 (1H, s), 7.97 (1H, d, J=3.8 Hz)

EXAMPLE 69

(6R,7R)-7-[(Z)-2-(5-Amino-1,2,4-thiadiazol-3-yl)-2-methoxy- iminoacetamide]-3-[5-carboxyimidazo[5,1-b]thiazolium-6-yl]methyl-3-cephem-4-Carboxylate (internal salt)

238 mg (0.30 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester was dissolved in 5 ml of acetone. To this solution was added 54 mg (0.36 mmol) of sodium iodide, and the mixture was stirred for 30 minutes. The acetone was distilled off under reduced pressure. The residue was dissolved in 2 ml of N,N-dimethylformamide (DMF). To this solution was added a solution of 501 mg (1.50 mmol) of diphenylmethyl imidazo[5,1-b]thiazole-5-carboxylic acid ester (Preparation 29) in 1 ml of DMF, and the mixture was stirred overnight at room temperature. To the reaction solution was added a 2N aqueous solution of sodium trifluoroacetate, and the mixture was stirred. The precipitate was washed with a 2N aqueous solution of sodium trifluoroacetate, and dried under reduced pressure. To the residue were added 1 ml of anisole and 5 ml of trifluoroacetic acid with ice-cooling, and the mixture was stirred for one hour. To this was added cold isopropyl ether, and the mixture was subjected to centrifugal separation. The precipitate was washed with isopropyl ether, and dried under reduced pressure. To this was added a 5% aqueous solution of sodium hydrogencarbonate to obtain a solution. The solution was purified by column chromatography using Diaion HP 20 Resin, eluting with 200 ml of water, 200 ml of a 10% aqueous solution of methanol, 200 ml of a 20% aqueous solution of methanol, 200 ml of a 30% aqueous solution of methanol and 200 ml of a 40% aqueous solution of methanol. A fraction containing the desired compound was concentrated to dryness. The residue was further purified by column chromatography using Sephadex LH 20, eluting with a 1:1 mixture of methanol and water to give 7 mg of the title compound. NMR (D$_3$O) d (HDO=4.80): 3.26 (1H, d, J=18.2 Hz), 3.66 (1H, d, J=18.2 Hz), 4.08 (3H, s), 5.16 (1H, d, J=14.4 Hz), 5.28 (1H, d, J=4.7 Hz), 5.22 (1H, d, J=14.4 Hz), 5.89 (1H, d, J=4.7 Hz), 7.56 (1H, d, J=4.2 Hz), 7.78 (1H, s), 7.95 (1H, d, J=4.2 Hz)

EXAMPLE 70

(6R,7R)-7-[(Z)-2-(5-Amino-1,2,4-thiadiazol-3-yl)-2-ethoxy- iminoacetamide]-3-[5-(2-hydroxyethyl)imidazo[5,1-b]thiazolium-6-yl]methyl-3-cephem-4-carboxylate (internal salt)

To a solution of 160 mg (0.30 mmol) of p-methoxybenzyl (6R,7R)-7-[(Z)-2-(5-amino-1,2,4-thiadiazol-3-yl)-2-methoxyiminoacetamide]-3-chloromethyl-3-cephem-4-carboxylic acid ester in 3 ml of acetone were added 60 mg (0.36 mmol) of 5-(2-hydroxyethyl)imidazo[5,1-b]thiazole (Preparation 36) and 54 mg (0.36 mmol) of sodium iodide, and the mixture was stirred overnight at room temperature. The solvent was distilled off, and the residue was dissolved in methanol. To this solution was added a 2N aqueous solution of sodium trifluoroacetate. The mixture was stirred, and concentrated under reduced pressure. The precipitate was washed with a 2N aqueous solution of sodium trifluoroacetate, and dried under reduced pressure. To this were added 1 ml of anisole and 5 ml of trifluoroacetic acid with ice-cooling, and the mixture was stirred for 30 minutes. To the reaction solution was added cold isopropyl ether, and the mixture was subjected to centrifugal separation. The precipitate was washed with isopropyl ether, and dried under reduced pressure. To this was added a 5% aqueous solution of sodium hydrogencarbonate to obtain a solution. The solution was purified by column chromatography using Diaion HP 20 Resin, eluting with 200 ml of water, 200 ml of a 10% aqueous solution of methanol, 200 ml of a 20% aqueous solution of methanol, 200 ml of a 30% aqueous solution of methanol and 200 ml of a 40% aqueous solution of methanol. A fraction containing the desired compound was concentrated to dryness. The residue was further purified by column chromatography using Sephadex LH 20, eluting with a 1:1 mixture of methanol and water to give 16 mg (yield 9%) of the title compound. NMR ($D_2O$) d ($\underline{H}DO$=4.80): 1.33 (3H, t, J=7.1 Hz), 3.28 (1H, d, J=18.1 Hz), 3.56 (2H, t, J=0.8 Hz), 3.98 (2H, t, J=5.4 Hz), 4.36 (2H, q, J=6.9 Hz), 5.31 (1H, d, J=4.8 Hz), 5.31 (1H, d, J=14.8 Hz), 5.40 (1H, d, J=14.8 Hz), 5.92 (1H, d, J=4.8 Hz), 7.55 (1H, d, J=4.4 Hz), 7.70 (1H, s), 7.96 (1H, d, J=4.4 Hz)

EXAMPLE 71

(6R,7R)-7-[(Z)-2-(5-Amino-1,2,4-thiadiazol-3-yl)-2-ethoxy- iminoacetamide]-3-[5-(2-formylaminoethyl)imidazo[5,1-b]- thiazolium-6-yl]methyl-3-cephem-4-carboxylate (internal salt)

27 mg (yield 15%) of the title compound was obtained from 169 mg (0.30 mmol) of p-methoxybenzyl (6R,7R)-7-[(Z)-2-(5- amino-1,2,4-thiadiazol-3-yl)-2-ethoxyiminoacetamide]-3- chloromethyl-3-cephem-4-carboxylic acid ester, 76 mg (0.39mmol) of 5-(2-formylaminoethyl)imidazo[5,1-b]thiazole (Preparation 37) and 54 mg (0.36 mmol) of sodium iodide in the same manner as in Example 70. NMR ($D_2O$) d ($\underline{H}DO$=4.80): 1.33 (3H, t, J=7.1 Hz), 3.28 (1H, d, J=18.7 Hz), 3.63 (5H, m), 4.36 (2H, q, J=7.1 Hz), 5.28 (1H, d, J=4.8 Hz), 5.31 (2H, s), 5.88 (1H, d, J=4.8 Hz), 7.56 (1H, d, J=4.3 Hz), 7.70 (1H, s), 7.97 (1H, d, J=4.3 Hz)

EXAMPLE 72

(6R,7R)-7-[(Z)-2-(5-Amino-1,2,4-thiadiazol-3-yl)-2-ethoxy- iminoacetamide]-3-[5-cyanoimidazo[5,1-b]thiazolium-6-yl]methyl- 3-cephem-4-carboxylate (internal salt)

To a solution of 283 mg (0.50 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester in 10 mi of acetone was added 90 mg (0.60 mmol) of sodium iodide, and the mixture was stirred at room temperature for one hour. The acetone was distilled off under reduced pressure, and the residue was dissolved in methylene chloride. The solution was washed with a small amount of water, dried over anhydrous magnesium carbonate, and .concentrated under reduced pressure. The residue was dissolved in 5 ml of DMF. To this solution was added a solution of 372 mg (2.50 mmol) of 5-cyanoimidazo[5,1-b]thiazole (Preparation 28) in 1 ml of DMF, and the mixture was stirred overnight at room temperature. To the reaction solution was added a 2N aqueous solution of sodium trifluoroacetate, and the mixture was stirred. The precipitate was washed with a 2N aqueous solution of sodium trifluoroacetate, and dried under reduced pressure. To this were added 1 ml of anisole and 5 ml of trifluoroacetic acid with ice-cooling, and the mixture was stirred for one hour. To the reaction solution was added cold isopropyl ether, and the mixture was subjected to centrifugal separation. The precipitate was washed with isopropyl ether, and dried under reduced pressure. To this was added a 5% aqueous solution of sodium hydrogencarbonate to obtain a solution. The solution was purified by column chromatography using Diaion HP 20 Resin, eluting with 200 ml of water, 200 ml of a 10% aqueous solution of methanol, 200 ml of a 20% aqueous solution of methanol, 200 ml of a 30% aqueous solution of methanol and 200 ml of a 40% aqueous solution of methanol. A fraction containing the desired compound was concentrated to dryness. The residue was further purified by column chromatography using Sephadex LH 20, eluting with a 1:1 mixture of methanol and water to give 7 mg of the title compound. NMR ($D_2O$) d ($\underline{H}DO$=4.80): 1.33 (3H, t, J=5.1 Hz), 3.34 (1H, d, J=18.7 Hz), 3.69 (1H, d, J=18.7 Hz), 4.36 (2H, q, J=5.1 Hz), 5.31 (1H, d, J=4.9 Hz), 5.45 (1H, d, J=15.2 Hz), 5.56 (1H, d, J=15.2 Hz), 5.91 (1H, d, J=4.9 Hz), 8.04 (1H, d, J=3.8 Hz), 8.30 (1H, s), 8.37 (1H, d, J =3.8

EXAMPLE 73

(6R,7R)-7-[(Z)-2-(5-Amino-1,2,4-thiadiazol-3-yl)-2-ethoxy- iminoacetamide]-3-[5-(acetylamino)imidazo[5,1-b]thiazolium-6- yl]methyl-3-cephem-4-carboxylate (internal salt)

42 mg (yield 23%) of the title compound was obtained from 169 mg (0.30 mmol) of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 76 mg (0.39 mmol) of 5-(acetylamino)imidazo[5,1-b]thiazole (Preparation 30) and 54 mg (0.36 mmol) of sodium iodide in the same manner as in Example 72. NMR ($D_2O$) d ($\underline{H}DO$=4.80): 1.33 (3H, t, J=7.1 Hz), 2.02 (3H, s), 3.15 (1H, d, J=17.8 Hz), 3.59 (1H, d, J=17.8 Hz), 4.35 (2H, q, J=7.1 Hz), 4.95 (2H, d, J=2.7 Hz), 5.28 (1H, d, J=15.1. Hz), 5.29 (1H, d, J=4.8 Hz), 5.36 (1H, d, J=15.1 Hz), 5.88 (1H, d, J=4.8 Hz), 7.59 (1H, d, J=4.2 Hz), 7.74 (1H, s), 8.04 (1H, d, J=4.2 Hz)

EXAMPLE 74

(6R,7R)-7-[(Z)-2-(5-Amino-1,2,4-thiadiazol-3-yl)-2-ethoxy- iminoacetamide]-3-[5-ureidomethylimidazo[5,1-b]thiazolium-6-yl]methyl-3-cephem-4-carboxylate (internal salt)

To a solution of 142 mg (0.25 mmol) of p-methoxybenzyl (6R,7R)-7-[(Z)-2-(5-amino-1,2,4-thiadiazol-3-yl)-2-methoxyiminoacetamide]-3- chloromethyl-3-cephem-4-carboxylic acid ester in 3 ml of acetone was added 41 mg (0.28 mmol) of sodium iodide, and the mixture was stirred at room temperature for one hour. The acetone was distilled off under reduced pressure, and the residue was dissolved in methylene chloride. The solution was washed with a small amount of a saturated aqueous solution of sodium thiosulfate and a saturated saline solution, dried over anhydrous magnesium sulfate, and concentrated under reduced pressure. The residue was dissolved in 1 ml of DMF. To this solution was added a solution of 59 mg (0.3 mmol) of 5-ureidomethylimidazo[5,1-b]thiazole (Preparation 31) in 1ml of DMF, and the mixture was stirred overnight at room temperature. To the reaction solution was added a 2N aqueous solution of sodium trifluoroacetate, and the mixture was stirred. The precipitate was washed with a 2N aqueous solution of sodium trifluoroacetate, and dried under reduced pressure. To this were added 1 ml of anisole and 5 ml of trifluoroacetic acid with ice-cooling, and the mixture was stirred for one hour. To the reaction solution was added cold isopropyl ether, and the mixture was subjected to centrifugal separation. The precipitate was washed with isopropyl ether, and dried under reduced pressure. To this was: added a 5% aqueous solution of sodium hydrogencarbonate to obtain a solution. The solution was purified by column chromatography using Diaion HP 20 Resin, eluting with 200 ml of water, 200 ml of a 10% aqueous solution of methanol, 200 ml of a 20% aqueous solution of methanol, 200 ml of a 30% aqueous solution of methanol and 200 ml of a 40% aqueous solution of methanol. A fraction containing the desired compound was concentrated to dryness. The residue was further purified by column chromatography using Sephadex LH 20, eluting with a 1:1 mixture of methanol and water to give 48 mg (yield 31%) of the title compound. NMR ($D_2O$) d ($\underline{H}DO=4.80$): 1.33 (3H, t, J=7.0 Hz), 3.17 (1H, d, J=17.6 Hz), 3.55 (1H, d, J=17.6 Hz), 4.36 (2H, q, J=7.0 Hz), 4.87 (2H, s), 5.28 (1H, d, J=3.7 Hz), 5.31 (2H, s), 5.88 (1H, d, J=3.7 Hz), 7.57 (1H, d, J=4.3 Hz), 7.73 (1H, s), 8.04 (1H, d, J=4.3 Hz)

EXAMPLE 75

(6R,7R)-7-[(Z)-2-(5-Amino-1,2,4-thiadiazol-3-yl)-2-ethoxy- iminoacetamide]-3-[5-methoxymethylimidazo[5,1-b]thiazolium-6- yl]methyl-3-cephem-4-carboxylate (internal salt)

38 mg (yield 27%) of the title compound was obtained from 142 mg (0.25 mmol) of p-methoxybenzyl (6R,7R)-7-[(Z)-2-(5- amino-1,2,4-thiadiazol-3-yl)-2-ethoxyiminoacetamide]-3- chloromethyl-3-cephem-4-carboxylic acid ester, 46 mg (0.28 mmol) of 5-methoxymethylimidazo[5,1-b]thiazole (Preparation 35) and 41 mg (0.28 mmol) of sodium iodide in the same manner as in Example 74. NMR ($D_2O$) d ($\underline{H}DO=4.80$): 1.33 (3H, t, J=7.1 Hz), 3.23 (1H, d, J=17.4 Hz), 3.50 (3H, s), 3.53 (1H, d, J=17.4), 4.36 (2H, q, J=7.1 Hz), 5.11 (2H, s), 5.29 (1H, d, J=15.5 Hz), 5.26 (1H, d, J=4.7 Hz), 5.31 (1H, d, 15.5 Hz), 5.89 (1H, d, J=4.7 Hz), 7.63 (1H, d, J=6.2 Hz), 7.84 (1H, s), 8.06 (1H, d, J=6.2 Hz)

EXAMPLE 76

(6R,7R)-7-[(Z)-2-(5-Amino-1,2,4-thiadiazol-3-yl)-2-fluoromethoxyiminoacetamide]-3-[5-(2-hydroxyethyl)imidazo[5, 1-b]- thiazolium-6-yl]methyl-3-cephem-4-carboxylate (internal salt)

48 mg (yield 19%) of the title compound was obtained from 349 mg (0.43 mmol) of p-methoxybenzyl (6R,7R)-7-[(Z)-2-(5- tritylamino-1,2,4-thiadiazol-3-yl)-2-fluoromethoxyimino- acetamide]-3-chloromethyl-3-cephem-4-carboxylic acid ester, 81 mg (0.47 mmol) Of 5-(2-hydroxyethyl)imidazo[5,1-b]thiazole (Preparation 36) and 64 mg (0.43 mmol) of sodium iodide in the same manner as in Example 74. NMR ($D_2O$) d ($\underline{H}DO=4.80$): 3.23 (1H, d, J=17.6 Hz), 3.57 (3H, m), 3.98 (2H, t, J=7.9 Hz), 5.23 (1H, d, J=15.4 Hz), 5.29 (1H, d, J=4.4 Hz), 5.86 (2H, d, J=54.3 Hz), 5.91 (1H, d, 4.4 Hz), 7.54 (1H, d, J=3.1 Hz), 7.70 (1H, s), 7.96 (1H, d, J=3.1 Hz)

EXAMPLE 77

(6R,7R)-7-[(Z)-2-(5-Amino-1,2,4-thiadiazol-3-yl)-2-fluoromethoxyiminoacetamide]-3-[5-ureidomethylimidazo[5,1-b]-thiazolium-6-yl]methyl-3-cephem-4-carboxylate (internal salt)

82 mg (yield 45%) of the title compound was obtained from 242 mg (0.30 mmol) of p-methoxybenzyl (6R,7R)-7-[(Z)-2-(5- tritylamino-1,2,4-thiadiazol-3-yl)-2-fluoromethoxyimino- acetamide]-3-chloromethyl-3-cephem-4-carboxylic acid ester, 71 mg (0.36mmol) of 5-ureidomethylimidazo[5,1-b]thiazole (Preparation 31) and 49 mg (0.30 mmol) of sodium iodide in the same manner as in Example 74. NMR ($D_2O$) d ($\underline{H}DO=4.80$): 3.17 (1H, d, J=17.7 Hz), 3.55 (1H, d, J=17.7 Hz), 4.87 (2H, s), 5.29 (1H, d, J=4.9 Hz), 5.31 (2H, s), 5.84 (2H, d, J=54.1 Hz), 5.90 (1H, d, J=4.9 Hz), 7.58 (1H, d, J=4.4 Hz), 7.74 (1H, s), 8.04 (1H, J=4.4 Hz)

EXAMPLE 78

(6R,7R)-7-[(Z)-2-(5-Amino-1,2,4-thiadiazol-3-yl)-2-ethoxy- iminoacetamide]-3-[5-dimethoxymethylimidazo[5, 1-b]thiazolium-6- yl]methyl-3-cephem-4-carboxylate (internal salt)

40 mg of the title compound was obtained from 195 mg (0.35 mmol) of p-methoxybenzyl (6R,7R)-7-[(Z)-2-(5- amino-1,2,4- thiadiazol-3-yl)-2-ethoxyiminoacetamide]-3- chloromethyl-3- cephem-4-carboxylic acid ester, 82 mg (0.41 mmol) of 5-dimethoxymethylimidazo[5,1-b]thiazole (Preparation 32) and 52 mg (0.35 mmol) of sodium iodide in the same manner as in Example 74. NMR ($D_2O$) d ($\underline{H}DO=4.80$): 1.33 (3H, t, J=7.0 Hz), 3.22 (1H, d, J=17.8 Hz), 3.54 (1H, d, J=7.0 Hz), 3.51 (3H, s), 3.56 (3H, s), 4.35 (2H, q, J=7.0 Hz), 5.26 (1H, d, J=4.9 Hz), 5.30 (1H, d, J=17.2 Hz), 5.43 (1H, d, J=17.2 Hz), 5.89 (1H, d, J=4.9 Hz), 6.22 (1H, s), 7.61 (1H, d, J=4.2 Hz), 7.84 (1H, s), 8.20 (1H, d, J=4.2 Hz)

EXAMPLE 79

(6R,7R)-7-[(Z)-2-(5-Amino-1,2,4-thiadiazol-3-yl)-2-ethoxy- iminoacetamide]-3-[5-formylimidazo[5,1-b] thiazolium-6- yl]methyl-3-cephem-4-carboxylate (internal salt).

23 mg (0.04 mmol) of (6R,7R)-7-[(Z)-2-(5-amino-1,2,4-thiadiazol-3-yl)-2-ethoxyiminoacetamide]-3-[5-dimethoxymethyl- imidazo[5,1-b]thiazolium-6-yl]methyl-3-cephem-4-carboxylate (internal salt) was dissolved in 2 ml of 1N hydrochloric acid. The solution was stirred at room temperature for 3 hours, and then concentrated under reduced pressure. To the residue was added a 5% aqueous solution of sodium hydrogencarbonate for neutralization. This mixture was purified by column chromatography using Diaion HP 20 Resin, eluting with 200 ml of water, 200 ml of a 20% aqueous solution of methanol, 200 ml of a 30% aqueous solution of methanol and 200 ml of a 40 % aqueous solution of methanol. A fraction containing the desired compound was concentrated to dryness. .The residue was further purified by column chromatography using Sephadex LH 20, eluting with a 1:1 mixture of methanol and water to give 4 mg of the title compound. NMR (DMSO-$d_6$) d: 1.21 (3H, t, J=6.9 Hz), 3.11 (1H, d, J=16.6 Hz), 3.64 (1H, d, J=16.6 Hz), 4.12 (2H, q, J=6.9 Hz), 4.88 (1H, d, J=15.1 Hz), 5.00 (1H, d, J=4.8 Hz), 5.36 (1H, d, J=15.1 Hz), 5.64 (1H, dd, J=8.4 Hz, 4.8 Hz), 7.67 (1H, d, J=3.9 Hz), 8.11 (2H, s), 8.21 (2H, m), 9.42 (1H, d, J=8.4 Hz), 9.79 (1H, s)

EXAMPLE 80

(6R,7R)-7-[(Z)-2-(5-Amino-1,2,4-thiadiazol-3-yl)-2-ethoxy- iminoacetemide]-3-[5-(N-methylformylamino) methylimidazo[5,1-b]- thiazolium-6-yl]methyl-3-cephem-4-carboxylate (internal salt)

27 mg of the title compound was obtained from 169 mg (0.30 mmol) of p-methoxybenzyl (6R,7R)-7-[(Z)-2-(5- amino-1,2,4- thiadiazol-3-yl)-2-ethoxyiminoacetamide]-3- chloromethyl-3- cephem-4-carboxylic acid ester, 89 mg (0.45 mmol) of 5-(N- methyl-formylamino)methylimidazo [5,1-b]thiazole (Preparation 33) and 54 mg (0.36 mmol) of sodium iodide in the same manner as in Example 74. NMR (D$_2$O) d (HDO=4.80): 1.32 (3H, t, J=6.9 Hz), 2.81 (¼×3H, s), 3.08 (¾×3H, s), 3.14 (¼×1H, d, J=18.7 Hz), 3.16 (¾×1H, d, J=17.9 Hz), 3.57 (¼×1H, d, J=18.7 Hz), 3.60 (¾×1H, d, J=17.9 Hz), 4.34 (2H, q, J=6.9 Hz), 5.15 (1H, d, J=16.7 Hz), 5.25 (1H, d, J=16.7 Hz), 5.28 (1H, d, J=4.9 Hz), 5.31 (1H, d, J=17.0 Hz), 5.38 (1H, d, J=17.0 Hz), 7.61 (¾×1H, d, J=4.2 Hz), 7.69 (¾×1H, d, J=3.9 Hz), 7.78 (¾×1H, s), 7.86 (¼×1H, s), 7.96 (¾×1H, d, J=3.9 Hz), 7.98 (¼×1H, d, J=4.2 Hz), 8.14 (¾×1H, s), 8.41 (¼×1H, s)

EXAMPLE 81

(6R,7R)-7-[(Z)-2-(5-Amino-1,2,4-thiadiazol-3-yl)-2-ethoxy- iminoacetamide]-3-[5-(1-methylureido) methylimidazo[5,1-b]- thiazolium-6-yl]methyl-3-cephem-4-carboxylate (internal salt)

22 mg of the title compound was obtained from 141 mg (0.25 mmol) of p-methoxybenzyl (6R,7R)-7-[(Z)-2-(5-amino-1,2,4- thiadiazol-3-yl)-2-ethoxyiminoacetamide]-3-chloromethyl-3- cephem-4-carboxylic acid ester, 63 mg (0.30 mmol) of 5-(1-methylureido)methylimidazo[5,1-b] thiazole (Preparation 34) and 41 mg (0.28 mmol) of sodium iodide in the same manner as in Example 74. NMR (D$_2$O) d (HDO=4.80): 1.30 (3H, t, J=7.8 Hz), 3.05 (3H, s), 3.13 (1H, d, J=18.1 Hz), 3.53 (1H, d, J=18.1 Hz), 4.32 (2H, q, J=7.8 Hz), 5.01 (2H, m), 5.25 (1H, d, J=4.6 Hz), 5.28 (2H, s), 5.87 (1H, d, J=4.6 Hz), 7.55 (1H, d, J=4.0 Hz), 7.73 (1H, s), 7.89 (1H, d, J=4.0 Hz)

EXAMPLE 82

(6R,7R)-7-[(Z)-2-(5-Amino-1,2,4-thiadiazol-3-yl)-2-fluoromethoxyiminoacetamide]-3-[5-formylimidazo[5,1-b] thiazolium-6- yl]methyl-3-cephem-4-carboxylate (internal salt)

227 mg of (6R,7R)-7-[(Z)-2-(5-amino-1,2,4-thiadiazol-3-yl)-2-fluoromethoxyiminoacetamide]-3-[5-dimethoxymethyl - imidazo[5,1-b]thiazolium-6-yl]methyl-3-cephem-4-carboxylate (internal salt) was obtained from 812 mg (1.0 mmol) of p-methoxybenzyl (6R,7R)-7-[(Z)-2-(5-tritylamino-1,2,4- thiadiazol-3-yl)-2-fluoromethoxyiminoacetamide]-3-chloromethyl-3-cephem-4-carboxylic acid ester, 237 mg (1.20 mmol) of 5-dimethoxymethylimidazo[5,1-b]thiazole (Preparation 32) and 163 mg (1.20 mmol) of sodium iodide in the same manner as in Example 74. This compound was treated with 5 ml of 1N hydrochloric acid in the same manner as in Example 79, and then purified by column chromatography using Diaion HP 20 Resin and Sephadex LH 20 to give 84 mg of the title compound. NMR (DMSO-d$_6$) d: 3.11 (1H, d, J=17.5 Hz), 3.50 (1H, d, J=17.5 Hz), 4.91 (1H, d, J=13.7 Hz), 5.03 (1H, d, J=4.9 Hz), 5.38 (1H, d, J=13.7 Hz), 5.66 (1H, m), 5.73 (1H, d, J=55.2 Hz), 7.67 (1H, d, J=4.2 Hz), 8.23 (4H, m), 9.65 (1H, d, J=8.0 Hz), 9.82 (1H, s)

EXAMPLE 83

(6R,7R)-7-[(Z)-2-(5-Amino-1,2,4-thiadiazol-3-yl)-2-ethoxy- iminoacetamide]-3-[7-hydroxymethylimidazo[5,1-b]thiazolium-6- yl]methyl-3-cephem-4-carboxylate (internal salt)

14 mg of the title compound was obtained from 110 mg (0.20 mmol) of p-methoxybenzyl (6R,7R)-7-[(Z)-2-(5-amino-1,2,4- thiadiazol-3-yl)-2-ethoxyiminoacetamide]-3-chloromethyl-3-cephem-4-carboxylic acid ester, 30 mg (0.20 mmol) of 7-hydroxymethylimidazo[5,1-b]thiazole (Preparation 38) and 29 mg (0.20 mmol) of sodium iodide in the same manner as in Example 74. NMR (D$_2$O) d ( HDO=4.80): 1.32 (3H, t, J=7.0 Hz), 3.26 (1H, d, J=17.9 Hz), 3.56 (1H, d, J=17.9 Hz), 4.35 (2H, q, J=7.0 Hz), 4.92 (2H, s), 5.27 (3H, m), 5.88 (1H, d, J=4.7 Hz), 7.55 (1H, d, J=3.9 Hz), 7.91 (1H, d, J=3.9 Hz), 9.35 (1H, s)

EXAMPLE 84

(6R,7R)-7-[(Z)-2-(5-Amino-1,2,4-thiadiazol-3-yl)-2-fluoroethoxyiminoacetamide]-3-[5-formylimidazo[5,1-b] thiazolium-6- yl]methyl-3-cephem-4-carboxylate (internal salt)

30 mg of the title compound was obtained from 250 mg (0.30 mmol) of p-methoxybenzyl (6R,7R)-7-[(Z)-2-(5-tritylamino-1,2,4- thiadiazol-3-yl)-2-fluoroethoxyiminoacetamide]-3-chloromethyl-3-cephem-4-carboxylic acid ester, 72 mg (0.36 mmol) of 5-dimethoxymethylimidazo[5,1-b]thiazole (Preparation 32) and 55 mg (0.36 mmol) of sodium iodide in the same manner as in Example 82. NMR (DMSO-d$_6$) d: 3.07 (1H, d, J=17.1 Hz), 3.50 (1H, d, J=17.1 Hz), 4.28 (1H, m), 4.37 (1H, m), 4.55 (1H, m), 4.70 (1H, m), 4.94 (1H, d, J=13.5 Hz), 5.03 (1H, d, J=6.2 Hz), 5.38 (1H, d, J=13.5 Hz), 5.67 (1H, dd, J=8.8 Hz, 4.4 Hz), 7.69 (1H, d, J=4.2 Hz), 8.16 (2H, s), 8.24 (2H, m), 9.51 (1H, d, J=8.8 Hz), 9.82 (1H, s)

EXAMPLE 85

(6R,7R)-7-[(Z)-2-(5-Amino-1,2,4-thiadiazol-3-yl)-2-(1-methyl- ethoxyimino)acetamide]-3-(imidazo[5,1-b] thiazolium-6-yl)methyl- 3-cephem-4-carboxylate (internal salt)

To a solution of 0.25 g (0.3 mmol) of p-methoxybenzyl (6R,7R)-7-[(Z)-2-(5-tritylamino-1,2,4-thiadiazol-3-yl)-2-(1- methylethoxyimino)acetamide]-3-chloromethyl-3-cephem-4-carboxylic acid ester in 3 ml of acetone were successively added 0.05 g (0.33 mmol) of sodium iodide and 0.045 g (0.36 mmol) of imidazo[5,1-b]thiazole (Preparation 1), and the mixture was stirred overnight at room temperature. The reaction solution was concentrated to dryness under reduced pressure. The residue was dissolved in 25 ml of methylene chloride, and the solution was washed with 16 ml of a 2N aqueous solution of sodium trifluoroacetate of which pH had been adjusted to 5.5–6 by trifluoroacetic acid. The methylene chloride layer was dried over anhydrous magnesium sulfate, and concentrated to dryness under reduced pressure. To the residue was added 1.1 ml of anisole, and the mixture was thoroughly stirred. To this was added 3.7 ml of trifluoroacetic acid with ice-cooling, and the mixture was stirred for one hour. To the reaction solution was added 50 ml of isopropyl ether which had been cooled to −10° C. The precipitate was collected by filtration, washed with isopropyl ether (50 ml×2), and dried under reduced pressure. The residue was suspended in 4 ml of water. To this suspension was added sodium hydrogencarbonate with good stirring to adjust the pH of the suspension to 7.5. This was purified by column chromatography using 20 ml of Diaion HP 20 Resin, eluting with 100 ml of water, 100 ml of a 20% aqueous solution of methanol and 200 ml of a 40% aqueous solution of methanol. A fraction containing the desired compound was concentrated to dryness. The residue was further purified by column chromatography using 100 ml of Sephadex LH 20, eluting with a 50% aqueous solution of methanol, concentrated under reduced pressure, and then freeze-dried to give 0.041 g (yield 24.6%)

of the title compound. NMR (D₂O) d (HDO=4.80): 1.30 (6H, d, J=6.4 Hz), 3.25 (1H, d, J=17.9 Hz), 3.64 (1H, d, J=17.9 Hz), 4.57 (1H, d, J=6.4 Hz), 5.14 (1H, d, J=14.5 Hz), 5.27 (1H; d, J=4.9 Hz), 5.30 (1H, d, J=14.5 Hz), 5.86 (1H, d, J=4.9 Hz), 7.53 (1H, d, J=4.3 Hz), 7.76 (1H, s), 7.92 (1H, d, J=4.3 Hz), 9.37 (1H, s)

EXAMPLE 86

(6R,7R)-7-[(Z)-2-(5-Amino-1,2,4-thiadiazol-3-yl)-2-(1-methylethoxyimino) acetamide]-3-(3-carbamoylimidazo[5,1-b]thiazolium- 6-yl)methyl-3-cephem-4-carboxylate (internal salt)

0.013 g (yield 7.3%) of the title compound was obtained from 0.25 g (0.3 mmol) of p-methoxybenzyl (6R,7R)-7-[(Z)-2-(5- tritylamino-1,2,4-thiadiazol-3-yl)-2-(1-methylethoxyimino)- acetamide]-3-chloromethyl-3-cephem-4-carboxylic acid ester, 0.093 g (0.56mmol) of imidazo[5,1-b]thiazole-3-carboxyamide (Preparation 11) and 0.05 g (0.33 mmol) of sodium iodide in the same manner as in Example 42. NMR (D₂O) d (HDO=4.80): 1.28 (6H, d, J=6.3 Hz), 3.24 (1H, d, J=18.3 Hz), 3.63 (1H, d, J=18.3 Hz), 4.56 (1H, quintet, J=6.3 Hz), 5.17 (1H, d, J=14.6 Hz), 5.27 (1H, d, J=4.8 Hz), 7.88 (1H, s), 8.36 (1H, s)

EXAMPLE 87

(6R,7R)-7-[(Z)-2-(5-Amino-1,2,4-thiadiazol-3-yl)-2-(1-methylethoxyimino) acetamide]-3-[5-(formylaminomethyl) imidazo[5,1-b]- thiazolium-6-yl]methyl-3-cephem-4-carboxylate (internal salt)

0.014 g (yield 7.5%) of the title compound was obtained from 0.25 g (0.3 mmol) of p-methoxybenzyl (6R, 7R)-7-[(Z)-2-(5- tritylamino-1,2,4-thiadiazol-3-yl)-2-(1-methylethoxyimino)- acetamide]-3-chloromethyl-3-cephem-4-carboxylic acid ester, 0.132 g (0.73 mmol) of 5-(formylaminomethyl)imidazo[5,1-b]-thiazole (Preparation 14) and 0.05 g (0.33 mmol) of sodium iodide in the same manner as in Example 85. NMR (D₂O) d (HDO=4.80): 1.30 (3H, d, J=6.3 Hz), 1.31 (3H, d, J=6.3 Hz), 3.16 (1H, d, J=17.8 Hz), 3.58 (1H, d, J=17.8 Hz), 4.58 (1H, quintet, J=6.3 Hz), 5.02 (2H, s), 5.28 (1H, d, J=4.9 Hz), 5.32 (2H, s), 5.86 (1H, d, J=4.9 Hz), 7.58 (1H, d, J=4.4 Hz), 7.73 (1H, s), 8.04 (1H, d, J=4.4 Hz), 8.20 (1H, s)

EXAMPLE 88

(6R,7R)-7-[(Z)-2-(5-Amino-1,2,4-thiadiazol-3-yl)-2-(propoxyimino)acetamide]-3-(imidazo[5,1-b]thiazolium-6-yl)methyl-3-cephem-4-carboxylate (internal salt)

0.037 g (yield 22.2%) of the title compound was obtained from 0.25 g (0.3 mmol) of p-methoxybenzyl (6R,7R)-7-[(Z)-2-(5- tritylamino-1,2,4-thiadiazol-3-yl)-2-(propoxyimino)acetamide]- 3-chloromethyl-3-cephem-4-carboxylic acid ester, 0.045 g (0.36 mmol) of imidazo[5,1-b]thiazole (Preparation 1) and 0.05 g (0.33 mmol) of sodium iodide in the same manner as in Example 85. NMR (D₂O) d (HDO=4.80): 0.89 (3H, t, J=7.4 Hz), 1.70 (2H, q, J=7.4 Hz), 3.24 (1H, d, J=17.9 Hz), 3.64 (1H, d, J=17.9 Hz), 4.23 (2H, t, J=7.4 Hz), 5.13 (1H, d, J=14.8 Hz), 5.26 (1H, d, J=4.7 Hz), 5.31 (1H, d, J=14.8 Hz), 5.86 (1H, d, J=4.7 Hz), 7.53 (1H, d, J =4.4 Hz), 7.77 (1H, s), 7.92 (1H, d, J=4.4 Hz), 9.37 (1H, s)

EXAMPLE 89

(6R,7R)-7-[(Z)-2-(5-Amino-1,2,4-thiadiazol-3-yl)-2-(propoxyimino) acetamide]-3-[5-(formylaminomethyl) imidazo[5,1-b]- thiazolium-6-yl)methyl-3-cephem-4-carboxylate (internal salt)

0.029 g (yield 15.6%) of the title compound was obtained from 0.25 g (0.3 mmol) of p-methoxybenzyl (6R,7R)-7-[(Z)-2-(5- tritylamino-1,2,4-thiadiazol-3-yl)-2-(propoxyimino)acetamide]- 3-chloromethyl-3-cephem-4-carboxylic acid ester, 0.083 g (0.46 mmol) of 5-(formylaminomethyl)imidazo[5,1-b]thiazole (Preparation 14) and 0.055 g (0.36 mmol) of sodium iodide in the same manner as in Example 85. NMR (D₂O) d (HDO=4.80): 0.90 (3H, t, J=7.4 Hz), 1.71 (2H, q, J=7.4 Hz), 3.14 (1H, d, J=18.0 Hz), 3.58 (1H, d, J=18.0 Hz), 4.24 (2H, t, J=7.4 Hz), 5.02 (2H, s), 5.27 (1H, d, J=4.7 Hz), 5.28 (1H, d, J=14.9 Hz), 5.35 (1H, d, J=14.9 Hz), 5.86 (1H, d, J=4.7 Hz), 7.58 (1H, d, J=4.3 Hz), 7.73 (1H, s), 8.03 (1H, d, J=4.3 Hz), 8.20 (1H, s)

EXAMPLE 90

(6R,7R)-7-[(Z)-2-(5-Amino-1,2,4-thiadiazol-3-yl)-2-(propoxy- imino)acetamide]-3-(3-carbamoylimidazo[5,1-b] thiazolium-6- yl)methyl-3-cephem-4-carboxylate (internal salt)

0.074 g (yield 40.9%) of the title compound was obtained from 0.25 g (0.3 mmol) of p-methoxybenzyl (6R,7R)-7-[(Z)-2-(5- tritylamino-1,2,4-thiadiazol-3-yl)-2-(propoxyimino)acetamide]- 3-chloromethyl-3-cephem-4-carboxylic acid ester, 0.076 g (0.46 mmol) of imidazo[5,1-b]thiazole-3-carboxyamide (Preparation 11) and 0.055 g (0.36 mmol) of sodium iodide in the same manner as in Example 42. NMR (D₂O) d (HDO=4.80): 0.89 (3H, t, J=7.1 Hz), 1.70 (2H, q, J=7.1 Hz), 3.23 (1H, d, J=17.9 Hz), 3.64 (1H, d, J=17.9 Hz), 4.23 (2H, t, J=7.1 Hz), 5.17 (1H, d, J=14.8 Hz), 5.27 (1H, d, J=4.7 Hz), 5.33 (1H, d, J=14.8 Hz), 5.86 (1H, d, J=4.7 Hz), 7.88 (1H, s), 8.37 (1H, s), 9.77 (1H, s)

EXAMPLE 91

(6R,7R)-7-[(Z)-2-(5-Amino-1,2,4-thiadiazol-3-yl)-2-(propoxyimino) acetamide]-3-[5-(2-hydroxyethyl)imidazo [5,1-b]-thiazolium-6-yl]methyl-3-cephem-4-carboxylate (internal salt)

0.030 g (yield 16.7%) of the title compound was obtained from 0.25 g (0.3 mmol) of p-methoxybenzyl (6R,7R)-7-[(Z)-2-(5-tritylamino-1,2,4-thiadiazol-3-yl)-2-(propoxyimino)acetamide]-3-chloromethyl-3-cephem-4-carboxylic acid ester, 0.077 g (0.46 mmol) of 5-(2-hydroxyethyl)imidazo[5,1-b]thiazole (Preparation 36) and 0.055 g (0.36 mmol) of sodium iodide in the same manner as in Example 85. NMR (D₂O) d (HDO=4.80): 0.91 (3H, t, J=7.3 Hz), 1.72 (2H, q, J=7.3 Hz), 3.21 (1H, d, J=17.9 Hz), 3.45–3.60 (3H, m), 3.96 (2H, t, J=7.3 Hz), 5.22 (1H, d, J=15.1 Hz), 5.25 (1H, d, J=4.8 Hz), 5.32 (1H, d, J=15.1 Hz), 5.86 (1H, d, J=4.8 Hz), 7.51 (1H, d, J=4.3 Hz), 7.69 (1H, s), 7.93 (1H, d, J=4.3 Hz)

EXAMPLE 92

(6R,7R)-7-[(Z)-2-(5-Amino-1,2,4-thiadiazol-3-yl)-2-(ethoxyimino) acetamide]-3-(3-methylimidazo[5,1-b] thiazolium-6- yl)methyl-3-cephem-4-carboxylate (internal salt)

0.07 g (yield 36.1%) of the title compound was obtained from 0.2 g (0.35 mmol) of p-methoxybenzyl (6R,7R)-7-[(Z)-2-(5-amino-1,2,4-thiadiazol-3-yl)-2-(ethoxyimino) acetamide]-3- chloromethyl-3-cephem-4-carboxylic acid ester, 0.059 g (0.42 mmol) of 3-methylimidazo[5,1-b] thiazole (Preparation 2) and 0.064 g (0.42 mmol) of sodium iodide in the same manner as in Example 31. NMR (D₂O) d (HDO=4.80): 1.28 (3H, t, J=7.1 Hz), 2.47 (3H, s), 3.23

(1H, d, J=18.1 Hz), 3.62 (1H, d, J=18.1 Hz), 4.30 (2H, q, J=7.1 Hz), 5.14 (1H, d, J=14.8 Hz), 5.25 (1H, d, J=4.7 Hz), 5.30 (1H, d, J=14.8 Hz), 5.84 (1H, d, J=4.7 Hz), 7.09 (1H, s), 7.75 (1H, s), 9.34 (1H, s)

EXAMPLE 93

(6R,7R)-7-[(Z)-2-(5-Amino-1,2,4-thiadiazol-3-yl)-2-(ethoxy- imino)acetamide]-3-[3-(carbamoyloxymethyl) imidazo[5,1-b]- thiazolium-6-yl]methyl-3-cephem-4-carboxylate (internal salt)

0.128 g (yield 47.8%) of the title compound was obtained from 0.25 g (0.44 mmol) of p-methoxybenzyl (6R,7R)-7-[(Z)-2-(5- amino-1,2,4-thiadiazol-3-yl)-2-(ethoxyimino) acetamide]-3- chloromethyl-3-cephem-4-carboxylic acid ester, 0.104 g (0.53 mmol) of 3-(carbamoyloxymethyl) imidazo[5,1-b]thiazole (Preparation 39) and 0.08 g (0.53 mmol) of sodium iodide in the same manner as in Example 42. NMR ($D_2O$) d (HDO=4.80): 1.29 (3H, t, J=7.1 Hz), 3.24 (1H, d, J=18.1 Hz), 3.64 (1H, d, J=18.1 Hz), 4.31 (2H, q, J=7.1 Hz), 5.15 (1H, d, J=14.8 Hz), 5.26 (1H, d, J=4.8 Hz), 5.31 (1H, d, J=14.8 Hz), 5.32 (2H, s), 5.85 (1H, d, J=4.8 Hz), 7.62 (1H, s), 7.81 (1H, d, J=1.6 Hz), 9.47 (1H, d, J=1.6 Hz)

EXAMPLE 94

(6R,7R)-7-[(Z)-2-(5-Amino-1,2,4-thiadiazol-3-yl)-2-(2-fluoro- ethoxyimino)acetamide]-3-(3-carbamoyloxymethylimidazo[5,1-b]- thiazolium-6-yl) methyl-3-cephem-4-carboxylate (internal salt)

0.06 g (yield 43.4%) of the title compound was obtained from 0.183 g (0.22 mmol) of p-methoxybenzyl (6R,7R)-7-[(Z)-2- (5-tritylamino-1,2,4-thiadiazol-3-yl)-2-(2-fluoroethoxyimino)- acetamide]-3-chloromethyl-3-cephem-4-carboxylic acid ester, 0.053 g (0.27 mmol) of 3-(carbamoyloxymethyl)imidazo[5,1-b]-thiazole (Preparation 39) and 0.04 g (0.27mmol) of sodium iodide in the same manner as in Example 42. NMR ($D_2O$) d ( HDO=4.80): 3.24 (1H, d, J=17.9 Hz), 3.64 (1H, d, J=17.9 Hz), 4.48 (1H, m), 4.58 (1H, m), 4.67 (1H, m), 4.82 (1H, m), 5.15 (1H, d, J=14.8 Hz), 5.26 (1H, d, J=4.8 Hz), 5.31 (1H, d, J=14.8 Hz), 5.32 (2H, s), 5.85 (1H, d, J=4.8 Hz), 7.62 (1H, s), 7.81 (1H, s)

EXAMPLE 95

(6R,7R)-7-[(Z)-2-(5-Amino-1,2,4-thiadiazol-3-yl)-2-(fluoro- ethoxyimino)acetamide]-3-[3-(carbamoyloxymethyl)imidazo[5,1-b]- thiazolium-6-yl] methyl-3-cephem-4-carboxylate (internal salt)

0.064 g (yield 47.3%) of the title compound was obtained from 0.18 g (0.22 mmol) of p-methoxybenzyl (6R,7R)-7-[(Z)-2-(5- tritylamino-1,2,4-thiadiazol-3-yl)-2-(fluoromethoxyimino)- acetamide]-3-chloromethyl-3-cephem-4-carboxylic acid ester, 0.053 g (0.27 mmol) of 3-(carbamoyloxymethyl)imidazo[5,1-b]-thiazole (Preparation 39) and 0.04 g (0.27 mmol) of sodium iodide in the same manner as in Example 42. NMR ($D_2O$) d (HDO=4.80): 3.23 (1H, d, J=18 Hz), 3.64 (1H, d, J=18 Hz), 5.13 (1H, d, J=14.8 Hz), 5.27 (1H, d, J=4.8 Hz), 5.30 (2H, s), 5.31 (1H, d, J=14.8 Hz), 5.72 (1H, s), 5.86 (1H, d, J=4.8 Hz), 5.90 (1H, s), 7.61 (1H, s), 7.81 (1H, s), 9.46 (1H, s)

EXAMPLE 96

(6R,7R)-7-[(Z)-2-(5-Amino-1,2,4-thiadiazol-3-yl)-2-(ethoxy- imino)acetamide]-3-[5-(methylthio)imidazo[5,1-b] thiazolium-6- yl]methyl-3-cephem-4-Carboxylate (internal salt)

0.04 g (yield 31.3%) of the title compound was obtained from 0.125 g (0.22 mmol) of p-methoxybenzyl (6R,7R)-7-[(Z)-2- (5-amino-1,2,4-thiadiazol-3-yl)-2-(ethoxyimino) acetamide]-3- chloromethyl-3-cephem-4-carboxylic acid ester, 0.045 g (0.26 mmol) of 5-(methylthio)imidazo[5,1-b] thiazole (Preparation 40) and 0.04 g (0.26mmol) of sodium iodide in the same manner as in Example 42. NMR ($D_2O$) d (HDO=4.80): 1.30 (3H, t, J=7.1 Hz), 2.52 (3H, s), 3.25 (1H, d, J=17.6 Hz), 3.50 (1H, d, J=17.6 Hz), 4.32 q, J=7.1 Hz), 5.20 (1H, d, J=14.8 Hz), 5.21 (1H, d, J=4.7 Hz), 5.64 (1H, d, J=14.8 Hz), 5.84 (1H, d, J=4.7 Hz), 7.64 (1H, d, J=4.3 Hz), 7.94 (1H, s), 8.06 (1H, d, J=4.3 Hz)

EXAMPLE 97

(6R,7R)-7-[(Z)-2-(5-Amino-1,2,4-thiadiazol-3-yl)-2-(fluoro- methoxyimino)acetamide]-3-[5-(methylthio) imidazo[5,1-b]- thiazolium-6-yl]methyl-3-cephem-4-carboxylate (internal salt)

0.039 g (yield 30.2%) of the title compound was obtained from 0.18 g (0.22 mmol) of p-methoxybenzyl (6R,7R)-7-[(Z)-2-(5- tritylamino-1,2,4-thiadiazol-3-yl)-2-(fluoromethoxyimino)- acetamide]-3-chloromethyl-3-cephem-4-carboxylic acid ester, 0.045 g (0.26mmol) of 5-(methylthio)imidazo[5,1-b]thiazole (Preparation 40) and 0.04 g (0.26 mmol) of sodium iodide in the same manner as in Example 42. NMR ($D_2O$) d (HDO=4.80): 2.52 (3H, s), 3.25 (1H, d, J=17.7 Hz), 3.51 (1H, d, J=17.7 Hz), 5.21 (1H, d, J=14.9 Hz), 5.23 (1H, d, J=4.7 Hz), 5.63 (1H, d, J=14.9 Hz), 5.74 (1H, s), 5.86 (1H, d, J=4.7 Hz), 5.92 (1H, s), 7.65 (1H, d, J=4.4 Hz), 7.94 (1H, s), 8.07 (1H, d, J=4.4 Hz)

EXAMPLE 98

(6R,7R)-7-[(Z)-2-(5-Amino-1,2,4-thiadiazol-3-yl)-2-hydroxy- iminoacetamide]-3-(3-carbamoylimidazo[5,1-b] thiazolium-6-yl)- methyl-3-cephem-4-carboxylate (internal salt)

0.233 g of p-methoxybenzyl (6R,7R)-7-[(Z)-2-(5-trityl-amino-1,2,4-thiadiazol-3-yl)-2-hydroxyiminoacetamide]-3-chloromethyl-3-cephem-4-carboxylic acid ester was dissolved in 5 ml of acetone. To this solution was added 0.047 g of sodium iodide, and the mixture was stirred for 3 hours. The reaction solution was concentrated under reduced pressure, and the residue was dissolved in 1.5 ml of N,N-dimethylformamide (DMF). To this solution was added 0.055 g of imidazo [5,1-b]thiazole-3- carboxyamide (Preparation 12), and the mixture was stirred at room temperature for 16 hours. To this was added a 10% aqueous solution of sodium trifluoroacetate. The precipitate was collected by filtration, and dried under reduced pressure, To the residue were added 1 ml of anisole and 2 ml of trifluoroacetic acid, and the mixture was stirred for one hour with ice-cooling. To the reaction solution was added isopropyl ether. The precipitate was collected by filtration, dissolved in an aqueous solution of sodium hydrogencarbonate, and purified by column chromatography successively using Diaion HP 20 and Sephadex LH 20 to give 0.028 g of the title compound. NMR ($D_2O$) d ( HDO=4.80): 3.24 (1H, d, J=18 Hz), 3.63 (1H, d, J=18 Hz), 5.17 (1H, d, J=15 Hz), 5.26 (1H, d, J=5 Hz), 5.33 (1H, d, J=15 Hz), 5.91 (1H, d, J=5 Hz), 7.88 (1H, s), 8.38 (1H, s), 8.46 (1H, s)

EXAMPLE 99

(6R,7R)-7-[(Z)-2-(5-Amino-1,2,4-thiadiazol-3-yl)-2-methoxy- iminoacetamide]-3-(3-(formylamino) methylimidazo[5,1-b]- thiazolium-6-yl)methyl-3-cephem-4-carboxylate (internal salt)

0.161 g of p-methoxybenzyl (6R,7R)-7-[(Z)-2-(5-amino-1,2,4-thiadiazol-3-yl)-2-methoxyiminoacetamide]-3-chloromethyl- 3-cephem-4-carboxylic acid ester was dissolved in 5 ml of acetone. To this solution was added 0.047 g of sodium iodide, and the mixture was stirred for 3 hours. To the reaction solution was added 0.061 g of 3-(formylamino)methylimidazo-[5,1-b]thiazole (Preparation 41), and the mixture was stirred at room temperature for 16 hours. To this was added a 10% aqueous solution of sodium trifluoroacetate. The precipitate was collected by filtration, and dried under reduced pressure. To the residue were added 1 ml of anisole and 2 ml of trifluoroacetic acid, and the mixture was stirred for one hour with ice-cooling. To this was added isopropyl ether. The precipitate was collected by filtration, dissolved in an aqueous solution of sodium hydrogencarbonate, and purified by column chromatography successively using Diaion HP 20 and Sephadex LH 20 to give 0.054 g of the title compound. NMR ($D_2O$) d (HDO=4.80): 3.23 (1H, d, J=18 Hz), 3.65 (1H, d, J=18 Hz), 4.06 (3H, s), 4.70 (2H, s), 5.15 (1H, d, J=15 Hz), 5.28 (1H, d, J=5 Hz), 5.32 (1H, d, J=15 Hz), 5.87 (1H, d, J=5 Hz), 7.46 (1H, s), 7.80 (1H, s), 8.22 (1H, s), 9.33 (1H, s)

EXAMPLE 100

(6R,7R)-7-[(Z)-2-(5-amino-1,2,4-thiadiazol-3-yl)-2-methoxy- iminoacetamide]-3-(3-aminomethylimidazo[5,1-b]thiazolium-6- yl)methyl-3-cephem-4-carboxylate (internal salt)

0.065 g of the title compound was obtained from 0.161 g of p-methoxybenzyl (6R,7R)-7-[(Z)-2-(5-amino-1,2,4-thiadiazol-3- yl)-2-methoxyiminoacetamide]-3-chloromethyl-3-cephem-4- carboxylic acid ester, 0.083 g of 3-(t-butoxycarbonylamino)-methylimidazo[5,1-b]thiazole (Preparation 42) and 0.047 mg of sodium iodide in the same manner as in Example 99. NMR ($D_2O$) d (HDO=4.80): 3.36 (1H, d, J=18 Hz), 3.76 (1H, d, J=18 Hz), 4.04 (3H, s), 5.15 (1H, d, J=15 Hz), 5.30 (1H, d, J=5 Hz), 5.60 (1H, d, J=15 Hz), 5.87 (1H, d, J=5 Hz), 7.78 (1H, s), 7.87 (1H, s)

EXAMPLE 101

(6R,7R)-7-[(Z)-2-(5-Amino-1,2,4-thiadiazol-3-yl)-2-(2,2-difluoroethoxyimino)acetamide]-3-(3-carbamoylimidazo[5,1-b]- thiazolium-6-yl)methyl-3-cephem-4-carboxylate (internal salt)

0.055 g of the title compound was obtained from 0.253 g of p-methoxybenzyl (6R,7R)-7-[(Z)-2-(5-tritylamino-1,2,4-thiadiazol-3-yl)-2-(2,2-difluoroethoxyimino)acetamide]-3-chloromethyl-3-cephem-4-carboxylic acid ester, 0.055 g of imidazo[5,1-b]thiazole-3-carboxyamide (Preparation 12) and 0.047 mg of sodium iodide in the same manner as in Example 98. NMR ($D_2O$) d (HDO=4.80): 3.31 (1H, d, J=18 Hz), 3.61 (1H, d, J=18 Hz), 4.50 (1H, dt, J=4 Hz, 15 Hz), 5.15 (1H, d, J=15 Hz), 5.24 (1H, d, J=5 Hz), 5.31 (1H, d, J=15 Hz), 5.84 (1H, d, J=5 Hz), 6.14 (1H, dd, J=4 Hz, 54 Hz), 7.85 (1H, s), 8.35 (1H, s), 9.75 (1H, s)

EXAMPLE 102

(6R,7R)-7-[(Z)-2-(5-Amino-1,2,4-thiadiazol-3-yl)-2-ethoxy- iminoacetamide]-3-(3-fluoromethylimidazo[5,1-b]thiazolium-6- yl)methyl-3-cephem-4-carboxylate (internal salt)

0.066 g of the title compound was obtained from 0.166 g of p-methoxybenzyl (6R,7R)-7-[(Z)-2-(5-amino-1,2,4-thiadiazol-3- yl)-2-ethoxyiminoacetamide]-3-chloromethyl-3-cephem-4- carboxylic acid ester, 0.052 g of 3-fluoromethylimidazo[5,1-b]-thiazole (Preparation 46) and 0.047 mg of sodium iodide in the same manner as in Example 98. NMR ($D_2O$) d (HDO=4.80): 1.31 (3H, t, J=7 Hz), 3.25 (1H, d, J=18 Hz), 3.65 (1H, d, J=18 Hz), 4.34 (2H, q, J=7 Hz), 5.18 (1H, d, J=15 Hz), 5.33 (1H, d, J=5 Hz), 5.69 (1H, d, J=15 Hz), 5.88 (1H, d, J=5 Hz), 7.77 (1H, s), 7.85 (1H, s), 9.54 (1H, s)

EXAMPLE 103

(6R,7R)-7-[(Z)-2-(5-Amino-1,2,4-thiadiazol-3-yl)-2-(2-fluoro- ethoxyimino)acetamide]-3-(3-fluoromethylimidazo[5,1-b]- thiazolium-6-yl)methyl-3-cephem-4-carboxylate (internal salt)

0.055 g of the title compound was obtained from 0.247 g of p-methoxybenzyl (6R,7R)-7-[(Z)-2-(5-tritylamino-1,2,4-thiadiazol-3-yl)-2-(2-fluoroethoxyimino)acetamide]-3-chloromethyl-3-cephem-4-carboxylic acid ester, 0.052 g of 3-fluoromethylimidazo[5,1-b]thiazole (Preparation 46) and 0.047 mg of sodium iodide in the same manner as in Example 98. NMR ($D_2O$) d (HDO=4.80): 3.24 (1H, d, J=18 Hz), 3.64 (1H, d, J=18 Hz), 4.50 (1H, m), 4.59 (1H, m), 4.69 (1H, m), 4.84 (1H, m), 5.18 (1H, d, J=15 Hz), 5.27 (1H, d, J=5 Hz), 5.33 (1H, d, J=15 Hz), 5.69 (2H, d, J=48 Hz), 5.88 (1H, d, J=5 Hz), 7.77 (1H, d, J=5 Hz), 7.84 (1H, s), 9.55 (1H, s)

EXAMPLE 104

(6R,7R)-7-[(Z)-2-(5-Amino-1,2,4-thiadiazol-3-yl)-2-fluoro-ethoxyiminoacetamide]-3-(3-carbamoylimidazo[5,1-b]thiazolium-6- yl)methyl-3-cephem-4-Carboxylate (internal salt)

0.048 g of the title compound was obtained from 0.243 g of p-methoxybenzyl (6R,7R)-7-[(Z)-2-(5-tritylamino-1,2,4-thiadiazol-3-yl)-2-fluoromethoxyiminoacetamide]-3-chloromethyl- 3-cephem-4-carboxylic acid ester, 0.055 g of imidazo[5,1-b]- thiazole-3-carboxyamide (Preparation 12) and 0.047 mg of sodium iodide in the same manner as in Example 98. NMR ($D_2O$) d (HDO=4.80): 3.23 (1H, d, J=18 Hz), 3.64 (1H, d, J=18 Hz), 5.15 (1H, d, J=15 Hz), 5.27 (1H, d, J=5 Hz), 5.33 (1H, d, J=15 Hz), 5.81 (2H, d, J=55 Hz), 5.87 (1H, d, J=5 Hz), 7.88 (1H, s), 8.36 (1H, s), 8.97 (1H, s)

EXAMPLE 105

(6R,7R)-7-[(Z)-2-(5-Amino-1,2,4-thiadiazol-3-yl)-2-fluoro-methoxyiminoacetamide]-3-(5-(formylamino) methylimidazo[5,1-b]- thiazolium-6-yl)methyl-3-cephem-4-carboxylate (internal salt)

0.027 g of the title compound was obtained from 0.065 g of p-methoxybenzyl (6R,7R)-7-[(Z)-2-(5-tritylamino-1,2,4-thiadiazol-3 -yl-2-fluoromethoxyiminoacetamide]-3-chloromethyl-3-cephem-4-carboxylic acid ester, 0.065 g of 5-(formylamino)-methylimidazo[5,1-b]thiazole (Preparation 15) and 0.047 mg of sodium iodide in the same manner as in Example 98. NMR ($D_2O$) d (HDO=4.80): 3.16 (1H, d, J=18 Hz), 3.60 (1H, d, J=18 Hz), 5.03 (2H, s), 5.20 (1H, d, J=15 Hz), 5.32 (1H, d, J=5 Hz), 5.36 (1H, d, J=15 Hz), 5.90 (2H, d, J=57 Hz), 5.84 (1H, d, J=5 Hz), 7.60 (1H, d, J=4 Hz), 7.73 (1H, s), 8.05 (1H, d, J=4 Hz), 8.21 (1H, s)

EXAMPLE 106

(6R,7R)-7-[(Z)-2-(2-aminothiazol-4-yl)-2-fluoromethoxyimino- acetamide]-3-(imidazo[5,1-b]thiazolium-6-yl)methyl-3-cephem-4- carboxylate (internal salt)

0.044 g of the title compound was obtained from 0.238 g of p-methoxybenzyl (6R,7R)-7-[(Z)-2-(2-tritylaminothiazol-4-yl)-2- fluoromethoxyimino]acetamide-3-chloromethyl-3-cephem-4- carboxylic acid ester, 0.041 g of imidazo[5,1-b]thiazole (Preparation 1) and 0.047 mg of sodium iodide in the same manner as in Example 99. NMR ($D_2O$) d ($\underline{H}DO$=4.80): 3.24 (1H, d, J=18 Hz), 3.66 (1H, d, J=18 Hz), 5.13 (1H, d, J=15 Hz), 5.28 (1H, d, J=5 Hz), 5.31 (1H, d, J=15 Hz), 5.77 (2H, d, J=55 Hz), 5.81 (1H, d, J=5 Hz), 7.13 (1H, s), 7.53 (1H, d, J=4 Hz), 7.77 (1H, s), 7.92 (1H, d, J=4 Hz), 9.36 (1H, s)

EXAMPLE 107

(6R,7R)-7-[(Z)-2-(2-Aminothiazol-4-yl)-2-fluoromethoxyimino- acetamide]-3-(3-carbamoylimidazo[5,1-b]thiazolium-6-yl)methyl- 3-cephem-4-carboxylate (internal salt)

0.072 g of the title compound was obtained from 0.238 g of p-methoxybenzyl (6R,7R)-7-[(Z)-2-(2-tritylaminothiazol-4-yl)-2- fluoromethoxyimino]acetamide-3-chloromethyl-3-cephem-4- carboxylic acid ester, 0.055 g of imidazo[5,1-b]thiazole-3- carboxyamide (Preparation 12) and 0.047 mg of sodium iodide in the same manner as in Example 98. NMR ($D_2O$) d ($\underline{H}DO$=4.80): 3.23 (1H, d, J=18 Hz), 3.67 (1H, d, J=18 Hz), 5.17 (1H, d, J=15 Hz), 5.29 (1H, d, J=5 Hz), 5.34 (1H, d, J=15 Hz), 5.77 (2H, d, J=55 Hz), 5.84 (1H, d, J=5 Hz), 7.08 (1H, s), 7.88 (1H, s), 8.36 (1H, s), 9.78 (1H, s)

EXAMPLE 108

(6R,7R)-7-[(Z)-2-(2-Aminothiazol-4-yl)-2-cyclopentyloxyimino- acetamide]-3-(imidazo[5,1-b]thiazolium-6-yl)methyl-3-cephem-4- carboxylate (internal salt)

0.072 g of the title compound was obtained from 0.254 g of p-methoxybenzyl (6R,7R)-7-[(Z)-2-(2-tritylaminothiazol-4-yl)-2- cyclopentyloxyimino]acetamide-3-chloromethyl-3-cephem-4-carboxylic acid ester, 0.041 g of imidazo[5,1-b]thiazole (Preparation 1) and 0.047 mg of sodium iodide in the same manner as in Example 99. NMR ($D_2O$) d ($\underline{H}DO$=4.80): 1.4–1.9 (8H, m), 3.23 (1H, d, J=18 Hz), 3.64 (1H, d, J=18 Hz), 5.13 (1H, d, J=15 Hz), 5.27 (1H, d, J=5 Hz), 5.30 (1H, d, J=15 Hz), 5.80 (1H, d, J=5 Hz), 6.95 (1H, s), 7.54 (1H, d, J=4 Hz), 7.78 (1H, s), 7.93 (1H, d, J=4 Hz), 9.37 (1H, s)

EXAMPLE 109

(6R,7R)-7-[(Z)-2-(2-Aminothiazol-4-yl)-2-cyclopentyloxyimino- acetamide]-3-(3-carbamoylimidazo[5,1-b]thiazolium-6-yl)methyl- 3-cephem-4-carboxylate (internal salt)

0.066 g of the title compound was obtained from 0.254 g of p-methoxybenzyl (6R,7R)-7-[(Z)-2-(2-tritylaminothiazol-4-yl)-2- cyclopentyloxyimino]acetamide-3-chloromethyl-3-cephem-4-carboxylic acid ester, 0.055 g of imidazo[5,1-b]thiazole-3-carboxyamide (Preparation 12) and 0.047 mg of sodium iodide in the same manner as in Example 98. NMR ($D_2O$) d ($\underline{H}DO$=4.80): 1.4–1.9 (8H, m), 3.24 (1H, d, J=18 Hz), 3.64 (1H, d, J=18 Hz), 5.17 (1H, d, J=15 Hz), 5.28 (1H, d, J=5 Hz), 5.33 (1H, d, J=15 Hz), 5.81 (1H, d, J=5 Hz), 6.96 (1H, s), 7.89 (1H, s), 8.39 (1H, s), 9.79 (1H, s)

EXAMPLE 110

(6R,7R)-7-[(Z)-2-(5-Amino-1,2,4-thiadiazol-3-yl)-2-(3-fluoro- propoxyimino)acetamide]-3-(imidazo[5,1-b]thiazolium-6- yl)methyl-3-cephem-4-carboxylate (internal salt)

0.063 g of the title compound was obtained from 0.251 g of p-methoxybenzyl (6R,7R)-7-[(Z)-2-(5-tritylamino-1,2,4-thiadiazol-3-yl)-2-(3-fluoropropoxyimino)acetamide]-3-chloromethyl-3-cephem-4-carboxylic acid ester, 0.041 g of imidazo[5,1-b]thiazole (Preparation 1) and 0.047 mg of sodium iodide in the same manner as in Example 99. NMR ($D_2O$) d ($\underline{H}DO$=4.80): 2.13 (2H, dquint, J=6 Hz, 23 Hz), 3.23 (1H, d, J=18 Hz), 3.63 (1H, d, J=18 Hz), 4.44 (2H, t, J=6 Hz), 4.60 (2H, dr, J=6 Hz, 47 Hz), 5.14 (1H, d, J=15 Hz), 5.27 (1H, d, J=5 Hz), 5.31 (1H, d, J=15 Hz), 5.86 (1H, d, J=5 Hz), 7.54 (1H, d, J=4 Hz), 7.77 (1H, s), 7.93 (1H, d, J=4 Hz), 9.36 (1H, s)

EXAMPLE 111

(6R,7R)-7-[(Z)-2-(5-Amino-1,2,4-thiadiazol-3-yl)-2-(3-fluoro- propoxyimino)acetamide]-3-(3-carbamoylimidazo[5,1-b]thiazolium- 6-yl)methyl-3-cephem-4-carboxylate (internal salt)

0.065 g of the title compound was obtained from 0.251 g of p-methoxybenzyl (6R,7R)-7-[(Z)-2-(5-tritylamino-1,2,4-thiadiazol-3-yl)-3-fluoropropoxyiminoacetamide]-3-chloromethyl- 3-cephem-4-carboxylic acid ester, 0.055 g of imidazo[5,1-b]-thiazole-3-carboxyamide (Preparation 12) and 0.047 mg of sodium iodide in the same manner as in Example 98. NMR ($D_2O$) d ($\underline{H}DO$=4.80): 2.11 (2H, dquint, J=6 Hz, 27 Hz), 3.21 (1H, d, J=18 Hz), 3.62 (1H, d, J=18 Hz), 4.39 (2H, t, J=6 Hz), 4.58 (2H, dr, J=6 Hz, 47 Hz), 5.15 (1H, d, J=15 Hz), 5.26 (1H, d, J=5 Hz), 5.31 (1H, d, J=15 Hz), 5.84 (1H, d, J=5 Hz), 7.97 (1H, s), 8.45 (1H, s), 9.75 (1H, s)

EXAMPLE 112

(6R,7R)-7-[(Z)-2-(5-Amino-1,2,4-thiadiazol-3-yl)-2-cyclopentyl- oxyiminoacetamide]-3-(imidazo[5,1-b]thiazolium-6-yl)methyl-3- cephem-4-carboxylate (internal salt)

0.071 9 of the title compound was obtained from 0.254 9 of p-methoxybenzyl (6R,7R)-7-[(Z)-2-(5-tritylamino-1,2,4-thiadiazol-3-yl)-2-cyclopentyloxyiminoacetamide]-3-chloromethyl-3-cepham-4-carboxylic acid ester, 0.041 g of imidazo[5,1-b]thiazole (Preparation 1) and 0.047 mg of sodium iodide in the same manner as in Example 99. NMR ($D_2O$) d ($\underline{H}DO$=4.80): 1.4–1.9 (8H, m), 3.23 (1H, d, J=18 Hz), 3.64 (1H, d, J=18 Hz), 4.89 (1H, m), 5.13 (1H, d, J=15 Hz), 5.27 (1H, d, J=5 Hz), 5.30 (1H, d, J=15 Hz), 5.81 (1H, d, J=5 Hz), 7.54 (1H, d, J=4 Hz), 7.77 (1H, s), 7.93 (1H, d, J=4 Hz), 9.37 (1H, s)

EXAMPLE 113

(6R,7R)-7-[(Z)-2-(5-Amino-1,2,4-thiadiazol-3-yl)-2-cyclopentyl- oxyiminoacetamide]-3-(3-carbamoylimidazo[5,1-b]thiazolium-6- yl)methyl-3-cephem-4-carboxylate (internal salt)

0.065 g of the title compound was obtained from 0.254 g of p-methoxybenzyl (6R,7R)-7-[(Z)-2-(5-tritylamino-1,2,4-thiadiazol-3-yl)-cyclopentyloxyiminoacetamide]-3-chloromethyl-3-cephem-4-carboxylic acid ester, 0.055 g of imidazo[5,1-b]-thiazole-3-carboxyamide (Preparation 12) and 0.047 mg of sodium iodide in the same manner as in Example 98. NMR ($D_2O$) d ($\underline{H}DO$=4.80): 1.4–1.9 (1H, m), 3.22 (1H, d, J=18 Hz), 3.64 (1H, d, J=18 Hz), 4.90 (1H, m), 5.16 (1H, d, J=15 Hz), 5.27 (1H, d, J=5 Hz), 5.33 (1H, d, J=15 Hz), 5.81 (1H, d, J=5 Hz), 7.89 (1H, s), 8.38 (1H, s), 9.78 (1H, s)

EXAMPLE 114

(6R,7R)-7-[(Z)-2-(5-Amino-1,2,4-thiadiazol-3-yl)-2-ethoxy- iminoacetamide]-3-(3-hydroxymethylimidazo[5,1-b]thiazolium-6- yl)methyl-3-cephem-4-carboxylate (internal salt)

0.057 g of the title compound was obtained from 0.166 g of p-methoxybenzyl (6R,7R)-7-[(Z)-2-(5-amino-1,2,4-thiadiazol-3-yl)-2-ethoxyiminoacetamide]-3-chloromethyl-3-cephem-4-carboxylic acid ester, 0.051 g of 3-hydroxymethylimidazo-[5,1-b]thiazole (Preparation 55) and 0.047 mg of sodium iodide in the same manner as in Example 98. NMR ($D_2O$) d ($\underline{H}DO$=4.80): 1.30 (3H, t, J=7 Hz), 3.25 (1H, d, J=18 Hz), 3.64 (1H, d, J=18 Hz), 4.33 (2H, q, J=7 Hz), 4.87 (2H, s), 5.17 (1H, d, J=15 Hz), 5.27 (1H, d, J=5 Hz), 5.31 (1H, d, J=15 Hz), 5.87 (1H, d, J=5 Hz), 7.47 (1H, s), 7.80 (1H, s), 9.43 (1H, s)

EXAMPLE 115

(6R,7R)-7-[(Z)-2-(5-Amino-1,2,4-thiadiazol-3-yl)-2-fluoromethoxyiminoacetamide]-3-(3-hydroxymethylimidazo[5,1-b]- thiazolium-6-yl)methyl-3-cephem-4-carboxylate (internal salt)

0.047 g of the title compound was obtained from 0.243 g of p-methoxybenzyl (6R,7R)-7-[(Z)-2-(5-tritylamino-1,2,4-thiadiazol-3-yl)- 2-fluoromethoxyiminoacetamide]-3-chloromethyl-3-cephem-4-carboxylic acid ester, 0.051 g of 3-hydroxymethyl-imidazo[5,1-b]thiazole (Preparation 55) and 0.047 mg of sodium iodide in the same manner as in Example 99. NMR ($D_2O$) d ($\underline{H}DO$=4.80): 3.24 (1H, d, J=18 Hz), 3.65 (1H, d, J=18 Hz), 4.86 (2H, s), 5.15 (1H, d, J=15 Hz), 5.27 (1H, d, J=5 Hz), 5.31 (1H, d, J=15 Hz), 5.82 (2H, d, J=55 Hz), 5.88 (1H, d, J=5 Hz), 7.46 (1H, s), 7.80 (1H, s), 9.42 (1H, s)

EXAMPLE 116

(6R,7R)-7-[(Z)-2-(5-Amino-1,2,4-thiadiazol-3-yl)-2-(2-fluoro- ethoxyimino)acetamide]-3-(3-hydroxymethylimidazo[5,1-b]- thiazolium-6-yl)methyl-3-cephem-4-carboxylate (internal salt)

0.051 g of the title compound was obtained from 0.247 g of p-methoxybenzyl (6R,7R)-7-[(Z)-2-(5-tritylamino-1,2,4-thiadiazol-3-yl)-2-(2-fluoroethoxyimino)acetamide]-3-chloromethyl-3-cephem-4-carboxylic acid ester, 0.052 g of 3-hydroxymethylimidazo[5,1-b]thiazole (Preparation 55) and 0.047 mg of sodium iodide in the same manner as in Example 99. NMR ($D_2O$) d ($\underline{H}DO$=4.80): 3.23 (1H, d, J=18 Hz), 3.63 (1H, d, J=18 Hz), 4.49 (1H, m), 4.58 (1H, m), 4.61 (1H, m), 4.79 (1H, m), 4.88 (2H, s), 5.16 (1H, d, J=15 Hz), 5.27 (1H, d, J=5 Hz), 5.30 (1H, d, J=15 Hz), 5.87 (1H, d, J=5 Hz), 7.47 (1H, s), 7.79 (1H, s), 9.42 (1H, s)

EXAMPLE 117

(6R,7R)-7-[(Z)-2-(5-Amino-1,2,4-thiadiazol-3-yl)-2-cyclopentyl- oxyiminoacetamide]-3-(3-hydroxymethylimidazo[5,1-b]thiazolium- 6-yl)methyl-3-cephem-4-carboxylate (internal salt)

0.061 g of the title compound was obtained from 0.254 g of p-methoxybenzyl (6R,7R)-7-[(Z)-2-(5-tritylamino-1,2,4-thiadiazol-3-yl)-2-cyclopentyloxyiminoacetamide]-3-chloromethyl-3-cephem-4-carboxylic acid ester, 0.051 g of 3-hydroxymethylimidazo[5,1-b]thiazole (Preparation 55) and 0. 047 mg of sodium iodide in the same manner as in Example 99. NMR ($D_2O$) d ($\underline{H}DO$=4.80): 1.4–1.9 (8H, m), 3.22 (1H, d, J=18 Hz), 3.63 (1H, d, J=18 Hz), 4.86 (2H, s), 4.89 (1H, m), 5.15 (1H, d, J=15 Hz), 5.26 (1H, d, J=5 Hz), 5.31 (1H, d, J=15 Hz), 5.81 (1H, d, J=5 Hz), 7.47 (1H, s), 7.80 (1H, s), 9.42 (1H, s)

EXAMPLE 118

(6R,7R)-7-[(Z)-2-(5-Amino-1,2,4-thiadiazol-3-yl)-2-fluoromethoxyiminoacetamide]-3-(3-formylimidazo[5,1-b] thiazolium-6- yl)methyl-3-cephem-4-carboxylate (internal salt)

0.047 g of the title compound was obtained from 0.243 g of p-methoxybenzyl (6R,7R)-7-[(Z)-2-(5-tritylamino-1,2,4-thiadiazol-3-yl)-2-fluoromethoxyiminoacetamide]-3-chloromethyl-3-cephem-4-carboxylic acid ester, 0.051 g of imidazo[5,1-b]-thiazole-3-carbaldehyde (Preparation 43) and 0.647 mg of sodium iodide in the same manner as in Example 99. NMR ($D_2O$) d ($\underline{H}DO$=4.80): 3.23 (1H, d, J=18 Hz), 3.64 (1H, d, J=18 Hz), 5.18 (1H, d, J=15 Hz), 5.28 (1H, d, J=5 Hz), 5.34 (1H, d, J=15 Hz), 5.81 (2H, d, J=55 Hz), 5.87 (1H, d, J=5 Hz), 7.96 (1H, s), 7.87 (1H, s), 9.85 (1H, s), 9.96 (1H, s)

EXAMPLE 119

(6R,7R)-7-[(Z)-2-(5-Amino-1,2,4-thiadiazol-3-yl)-2-fluoromethoxyiminoacetamide]-3-[3-(difluoromethyl)imidazo[5,1-b]- thiazolium-6-yl]methyl-3-cephem-4-carboxylate (internal salt)

0.051 g of the title compound was obtained from 0.243 g of p-methoxybenzyl (6R,7R)-7-[(Z)-2-(5-tritylamino-1,2,4-thiadiazol-3-yl)-2-fluoromethoxyiminoacetamide]-3-chloromethyl-3-cephem-4-carboxylic acid ester, 0.058 g of 3-difluoromethyl-imidazo[5,1-b]-thiazole (Preparation 47) and 0.047 mg of sodium iodide in the same manner as in Example 99. NMR ($D_2O$) d ($\underline{H}DO$=4.80): 3.24 (1H, d, J=18 Hz), 3.64 (1H, d, J=18 Hz), 5.18 (1H, d, J=15 Hz), 5.28 (1H, d, J=5 Hz), 5.33 (1H, d, J=15 Hz), 5.83 (2H, d, J=55 Hz), 5.89 (1H, d, J=5 Hz), 7.17 (1H, t, J=52 Hz), 7.90 (1H, s), 8.07 (1H, s), 9.64 (1H, s)

EXAMPLE 120

(6R,7R)-7-[(Z)-2-(5-Amino-1,2,4-thiadiazol-3-yl)-2-fluoromethoxyiminoacetamide]-3-(3-hydroxyiminomethylimidazo[5,1-b]- thiazolium-6-yl)methyl-3-cephem-4-carboxylate (internal salt)

0.044 g of the title compound was obtained from 0.243 g of p-methoxybenzyl (6R,7R)-7-[(Z)-2-(5-tritylamino-1,2,4-thiadiazol-3-yl)-2-fluoromethoxyiminoacetamide]-3-chloromethyl-3-cephem-4-carboxylic acid ester, 0.061 g of imidazo[5,1-b]-thiazole-3-carbaldehydoxime (Preparation 44) and 0.047 mg of sodium iodide in the same manner as in Example 99. NMR ($D_2O$) d ($\underline{H}DO$=4.80): 3.23 (1H, d, J=18 Hz), 3.65 (1H, d, J=18 Hz), 5.13 (1H, d, J=15 Hz), 5.27 (1H, d, J=5 Hz), 5.33 (1H, d, J=15,Hz), 5.81 (2H, d, J=55 Hz), 5.86 (1H, d, J=5 Hz), 7.84 (1H, s), 7.88 (1H, s), 8.35 (1H, s), 9.86 (1H, s)

EXAMPLE 121

(6R,7R)-7-[(Z)-2-(5-Amino-1,2,4-thiadiazol-3-yl)-2-fluoromethoxyiminoacetamide]-3-(3-ethylimidazo[5,1-b] thiazolium-6-yl)methyl-3-cephem-4-carboxylate (internal salt)

0.055 g of the title compound was obtained from 0.243 g of p-methoxybenzyl (6R,7R)-7-[(Z)-2-(5-tritylamino-1,2,4-thiadiazol-3-yl)-2-fluoromethoxyiminoacetamide]-3-chloromethyl-3-cephem-4-carboxylic acid ester, 0.048 g of 3-ethylimidazo-[5,1-b]thiazole (Preparation 4) and 0.047 mg of sodium iodide in the same manner as in Example 99. NMR ($D_2O$) d ($\underline{H}DO$=4.80): 1.34 (3H, t, J=7 Hz), 3.22 (1H, d, J=18 Hz), 3.63 (1H, d, J=18 Hz), 5.13 (1H, d, J=15 Hz), 5.27 (1H, d, J=5 Hz), 5.30 (1H, d, J=15 Hz), 5.82 (2H, d, J=55 Hz), 5.86 (1H, d, J=5 Hz), 7.11 (1H, s), 7.74 (1H, s), 9.37 (1H, s)

EXAMPLE 122

(6R,7R)-7-[(Z)-2-(5-Amino-1,2,4-thiadiazol-3-yl)-2-fluoromethoxyiminoacetamide]-3-(3-acetoxymethylimidazo[5,1-b]- thiazolium-6-yl)methyl-3-cephem-4-carboxylate (internal salt)

0.061 g of the title compound was obtained from 0.243 g of p-methoxybenzyl (6R,7R)-7-[(Z)-2-(5-tritylamino-1,2,4-thiadiazol-3-yl)-2-fluoromethoxyiminoacetamide]-3-chloromethyl-3-cephem-4-carboxylic acid ester, 0.055 g of 3-acetoxymethyl-imidazo[5,1-b]thiazole (Preparation 45) and 0.047 mg of sodium iodide in the same manner as in Example 99. NMR ($D_2O$) d (HDO=4.80): 2.12 (3H, s), 3.24 (1H, d, J=18 Hz), 3.66 (1H, d, J=18 Hz), 5.16 (1H, d, J=15 Hz), 5.29 (1H, d, J=5 Hz), 5.32 (1H, d, J=15 Hz), 5.39 (2H, s), 5.83 (2H, d, J=55 Hz), 5.89 (1H, d, J=5 Hz), 7.67 (1H, t, J=52 Hz), 7.82 (1H, s), 9.48 (1H, s)

EXAMPLE 123

(6R,7R)-7-[(Z)-2-(5-Amino-1,2,4-thiadiazol-3-yl)-2-fluoromethoxyiminoacetamide]-3-(3-methoxymethylimidazo[5,1-b]- thiazolium-6-yl)methyl-3-cephem-4-carboxylate (internal salt)

0.039 g of the title compound was obtained from 0.243 g of p-methoxybenzyl (6R,7R)-7-[(Z)-2-(5-tritylamino-1,2,4- thiadiazol-3-yl)-2-fluoromethoxyiminoacetamide]-3-chloromethyl-3-cephem-4-carboxylic acid ester, 0.055 g of 3-methoxymethyl-imidazo[5,1-b]thiazole (Preparation 48) and 0.047 mg of sodium iodide in the same manner as in Example 99. NMR ($D_2O$) d (HDO=4.80): 3.21 (1H, d, J=18 Hz), 3.40 (3H, s), 3.63 (1H, d, J=18 Hz), 4.76 (2H, s), 5.14 (1H, d, J=15 Hz), 5.27 (1H, d, J=5 Hz), 5.30 (1H, d, J=15 Hz), 5.81 (2H, d, J=55 Hz), 5.86 (1H, d, J=5 Hz), 7.56 (1H, s), 7.80 (1H, s), 9.39 (1H, s)

EXAMPLE 124

(6R,7R)-7-[(Z)-2-(5-Amino-1,2,4-thiadiazol-3-yl)-2-fluoromethoxyiminoacetamide]-3-(3-cyanoimidazo[5,1-b]thiazolium-6- yl)methyl-3-cephem-4-carboxylate (internal salt)

0.061 g of the title compound was obtained from 0.243 g of p-methoxybenzyl (6R,7R)-7-[(Z)-2-(5-tritylamino-1,2,4-thiadiazol-3-yl)-2-fluoromethoxyiminoacetamide]-3-chloromethyl-3-cephem-4-carboxylic acid ester, 0.053 g of 3-cyanoimidazo-[5,1-b]thiazole (Preparation 56) and 0.047 mg of sodium iodide in the same manner as in Example 99. NMR ($D_2O$) d (HDO=4.80): 3.21 (1H, d, J=18 Hz), 3.66 (1H, d, J=18 Hz), 5.17 (1H, d, J=15 Hz), 5.28 (1H, d, J=5 Hz), 5.38 (1H, d, J=15 Hz), 5.82 (2H, d, J=55 Hz), 5.87 (1H, d, J=5 Hz), 7.99 (1H, s), 8.65 (1H, s)

EXAMPLE 125

(6R,7R)-7-[(Z)-2-(5-Amino-1,2,4-thiadiazol-3-yl)-2-fluoromethoxyiminoacetamide]-3-(2-carbamoyl-3-methylimidazo[5,1-b]- thiazolium-6-yl)methyl-3-cephem-4-carboxylate (internal salt)

0.063 g of the title compound was obtained from 0.243 g of p-methoxybenzyl (6R,7R)-7-[(Z)-2-(5-tritylamino-1,2,4-thiadiazol-3- yl)-2-fluoromethoxyiminoacetamide]-3-chloromethyl-3-cephem-4-carboxylic acid ester, 0.063 g of 3-methylimidazo-[5,1-b]thiazole-2-carboxyamide (Preparation 49) and 0.047 mg of sodium iodide in the same manner as in Example 99. NMR ($D_2O$) d (HDO=4.80): 2.70 (3H, s), 3.21 (1H, d, J=18 Hz), 3.65 (1H, d, J=18 Hz), 5.14 (1H, d, J=15 Hz), 5.27 (1H, d, J=5 Hz), 5.34 (1H, d, J=15 Hz), 5.79 (2H, d, J=55 Hz), 5.84 (1H, d, J=5 Hz), 7.81 (1H, s), 9.53 (1H, s)

EXAMPLE 126

(6R,7R)-7-[(Z)-2-(5-Amino-1,2,4-thiadiazol-3-yl)-2-ethoxy- iminoacetamide]-3-(2-carbamoyl-3-methylimidazo [5,1-b]- thiazolium-6-yl)methyl-3-cephem-4-carboxylate (internal salt)

0.048 g of the title compound was obtained from 0.166 g of p-methoxybenzyl (6R,7R)-7-[(Z)-2-(5-amino-1,2,4-thiadiazol-3- yl)-2-ethoxyiminoacetamide]-3-chloromethyl-3-cephem-4-carboxylic acid ester, 0.059 g of 3-methylimidazo[5,1-b]-thiazole-2-carboxyamide (Preparation 49) and 0.047 mg of sodium iodide in the same manner as in Example 98. NMR ($D_2O$) d (HDO=4.80): 1.29 (3H, t, J=7 Hz), 2.70 (3H, s), 3.23 (1H, d, J=18 Hz), 3.64 (1H, d, J=18 Hz), 4.32 (2H, q, J=7 Hz), 5.25 (1H, d, J=15 Hz), 5.27 (1H, d, J=5 Hz), 5.33 (1H, d, J=15 Hz), 5.86 (1H, d, J=5 Hz), 7.81 (1H, s), 9.54 (1H, s)

EXAMPLE 127

(6R,7R)-7-[(Z)-2-(5-Amino-1,2,4-thiadiazol-3-yl)-2-(2-fluoro- ethoxyimino)acetamide]-3-(2-carbamoyl-3-methylimidazo[5,1-b]- thiazolium-6-yl)methyl-3-cephem-4-carboxylate (internal salt)

0.091 g of the title compound was obtained from 0.247 g of p-methoxybenzyl (6R,7R)-7-[(Z)-2-(5-tritylamino-1,2,4-thiadiazol-3-yl)-2-(2-fluoroethoxyimino)acetamide]-3-chloromethyl-3-cephem-4-carboxylic acid ester, 0.059 g of 3-methylimidazo[5,1-b]thiazole-2-carboxyamide (Preparation 49) and 0.047 mg of sodium iodide in the same manner as in Example 99. NMR ($D_2O$) d (HDO=4.80): 2.71 (3H, s), 3.22 (1H, d, J=18 Hz), 3.63 (1H, d, J=18 Hz), 4.4–4.7 (4H, m), 5.17 (1H, d, J=15 Hz), 5.26 (1H, d, J=5 Hz), 5.34 (1H, d, J=15 Hz), 5.85 (1H, d, J=5 Hz), 7.81 (1H, s), 9.54 (1H, s)

EXAMPLE 128

(6R,7R)-7-[(Z)-2-(5-Amino-1,2,4-thiadiazol-3-yl)-2-fluoromethoxyiminoacetamide]-3-(imidazo[5,1-b]thiazolium-6-yl)methyl- 3-cephem-4-carboxylate (internal salt)

92 mg (yield 34%) of the title compound was obtained from 407 mg of p-methoxybenzyl (6R,7R)-7-[(Z)-2-(5-tritylamino- 1,2,4-thiadiazol-3-yl)-2-fluoromethoxyiminoacetamide]-3-chloromethyl-3-cephem-4-carboxylic acid ester, 74 mg of imidazo[5,1-b]thiazole (Preparation 1) and 85 mg of sodium iodide in the same manner as in Example 44. NMR ($D_2O$) d (HDO=4.80): 3.24 (1H, d, J=18 Hz), 5.64 (1H, d, J=18 Hz), 5.15 (1H, d, J=14 Hz), 5.28 (1H, d, J=5 Hz), 5.30 (1H, d, J=14 Hz), 5.84 (2H, d, J=54 Hz), 5.90 (1H, d, J=5 Hz), 7.54 (1H, d, J=4 Hz), 7.77 (1H, s), 7.93 (1H, d, J=4 Hz), 9.37 (1H, s)

EXAMPLE 129

(6R,7R)-7-[(Z)-2-(5-Amino-1,2,4-thiadiazol-3-yl)-2-ethoxy- iminoacetamide]-3-{3-(carbamoylmethyl)imidazo[5,1-b]thiazolium- 6-yl}methyl-3-cephem-4-carboxylate (internal salt)

55 mg (yield 23%) of the title compound was obtained from 227 mg of p-methoxybenzyl (6R,7R)-7-[(Z)-2-(5-amino-1,2,4- thiadiazol-3-yl)-2-ethoxyiminoacetamide]-3-chloromethyl-3-cephem-4-carboxylic acid ester, 87 mg of 3-(carbamoylmethyl)-imidazo[5,1-b]thiazole (Preparation 51) and 68 mg of sodium iodide in the same manner as in Example 44. NMR ($D_2O$) d (HDO=4.80): 1.31 (3H, t, J=7 Hz), 3.22 (1H, d, J=18 Hz), 3.63 (1H, d, J=18 Hz), 4.05 (2H, s), 4.34 (2H, q, J=7 Hz), 5.16 (1H, d, J=14 Hz), 5.27 (1H, d, J=5 Hz), 5.31 (1H, d, J=14 Hz), 5.88 (1H, d, J=5 Hz), 7.42 (1H, s), 7.80 (1H, s), 9.41 (1H, s)

EXAMPLE 130

(6R,7R)-7-[(Z)-2-(5-Amino-1,2,4-thiadiazol-3-yl)-2-(2-fluoro- ethoxy)iminoacetamide]-3-{3-(carbamoylmethyl)

imidazo[5,1-b]- thiazolium-6-yl}methyl-3-cepham-4-carboxylate (internal salt)

97 mg (yield .40%) of the title compound was obtained from 331 mg of p-methoxybenzyl (6R,7R)-7-[(Z)-2-(5-tritylamino- 1,2,4-thiadiazol-3-yl)-2-(2-fluoroethoxy) iminoacetamide]-3-chloromethyl-3-cephem-4-carboxylic acid ester, 87 mg of 3-(carbamoylmethyl)imidazo[5,1-b]thiazole (Preparation 51) and 68 mg of sodium iodide in the same manner as in Example 44. NMR ($D_2O$) d ($\underline{H}DO$=4.80): 3.22 (1H, d, J=18 Hz), 3.62 (1H, d, J=18 Hz), 4.04 (2H, s), 4.57 (2H, dr, J=56 Hz, 4 Hz), 4.70 (2H, dr, J=72 Hz, 4 Hz), 5.14 (1H, d, J=14 Hz), 5.27 (1H, d, J=5 Hz), 5.85 (1H, d, J=14 Hz), 5.87 (1H, d, J=5 Hz), 7.41 (1H, s), 7.79 (1H, s), 9.40 (1H, s)

EXAMPLE 131

(6R,7R)-7-[(Z)-2-(5-Amino-1,2,4-thiadiazol-3-yl)-2-fluoromethoxyiminoacetamide]-3-{3-(carbamoylmethyl)imidazo[5,1-b]- thiazolium-6-yl}methyl-3-cephem-4-carboxylate (internal salt)

88 mg (yield 37%) of the title compound was obtained from 325 mg of p-methoxybenzyl (6R,7R)-7-[(Z)-2-(5-tritylamino- 1,2,4-thiadiazol-3-yl)-2-fluoromethoxyiminoacetamide]-3-chloromethyl-3-cephem-4-carboxylic acid ester, 87 mg of 3-(carbamoylmethyl)imidazo[5,1-b]thiazole (Preparation 51) and 68 mg of sodium iodide in the same manner as in Example 44. NMR ($D_2O$) d ($\underline{H}DO$=4.80): 3.41 (1H, d, J=18 Hz), 3.63 (1H, d, J=18 Hz), 4.04 (2H, s), 5.14 (1H, d, J=14 Hz), 5.28 (1H, d, J=5 Hz), 5.31 (1H, d, J=14 Hz), 5.82 (2H, d, J=54 Hz), 5.89 (1H, d, J=5 Hz), 7.41 (1H, s), 7.79 (1H, s), 9.40 (1H, s)

EXAMPLE 132

(6R,7R)-7-[(Z)-2-(5-Amino-1,2,4-thiadiazol-3-yl)-2-fluoromethoxyiminoacetamide]-3-{3-(2-hydroxyethyl)imidazo[5,1-b]- thiazolium-6-yl}methyl-3-cephem-4-carboxylate (internal salt)

40 mg (yield 17%) of the title compound was obtained from 325 mg of p-methoxybenzyl (6R,7R)-7-[(Z)-2-(5-tritylamino- 1,2,4-thiadiazol-3-yl)-2-fluoromethoxyiminoacetamide]-3-chloromethyl-3-cephem-4-carboxylic acid ester, 81 mg of 3-(2-hydroxyethyl) imidazo[5,1-b]thiazole (Preparation 52) and 68 mg of sodium iodide in the same manner as in Example 44. NMR ($D_2O$) d ($\underline{H}DO$=4.80): 3.12 (2H, t, J=6 Hz), 3.21 (1H, d, J=18 Hz), 3.63 (1H, d, J=18 Hz), 3.96 (2H, t, J=6 Hz), 5.14 (1H, d, J=14 Hz), 5.28 (1H, d, J=5 Hz), 5.30 (1H, d, J=14 Hz), 5.82 (2H, d, J=55 Hz), 5.88 (1H, d, J=5 Hz), 7.26 (1H, s), 7.76 (1H,. s), 9.42 (1H, s)

EXAMPLE 133

(6R,7R)-7-[(Z)-2-(5-Amino-1,2,4-thiadiazol-3-yl)-2-(2-fluoroethoxyimino) acetamide]3-cephem-4-carboxylate (internal salt)

0.064 g of the title compound was obtained from 0.248 g (0.30 mmol) of p-methoxybenzyl (6R,7R)-7-[(Z)-2-(5-tritylamino- 1,2,4-thiadiazol-3-yl)-2-(2-fluoroethoxyimino) acetamide]-3-chloromethyl-3-cephem-4-carboxylic acid ester, 0.045 g (0.36 mmol) of imidazo[5,1-b]thiazole (Preparation 1) and 0.090 g (0.60mmol) of sodium iodide in the same manner as in Example 31. NMR ($D_2O$) d ($\underline{H}DO$=4.80): 3.26 (1H, d, J=17.8 Hz), 3.66 (1H, d, J=17.8 Hz), 4.50–4.72 (3H, m), 4.84–4.88 (1H, m), 5.16 (1H, d, J=14.5 Hz), 5.29 (1H, d, J=4.9 Hz), 5.32 (1H, d, J=14.5 Hz), 5.89 (1H, d, J=4.9 Hz), 7.56 (1H, d, J=4.3 Hz), 7.79 (1H, s), 7.95 (1H, d, J=4.3 Hz), 9.38 (1H, s)

EXAMPLE 134

(6R,7R)-7-[(Z)-2-(5-Amino-1,2,4-thiadiazol-3-yl)-2-(2-fluoro- ethoxyimino)acetamide]-3-(5-hydroxymethylimidazo[5,1-b]- thiazolium-6-yl)methyl-3-cephem-4-carboxylate (internal salt)

0.0081 g of the title compound was obtained from 0.248 g (0.30 mmol) of p-methoxybenzyl (6R,7R)-7-[(Z)-2-(5-tritylamino- 1,2,4-thiadiazol-3-yl)-2-(2-fluoroethoxyimino) acetamide]-3-chloromethyl-3-cephem-4-carboxylic acid ester, 0.055 g (0.36 mmol) of 5-hydroxymethylimidazo[5,1-b]thiazole (Preparation 10) and 0.090 g (0.60 mmol) of sodium iodide in the same manner as in Example 31. NMR ($D_2O$) d ($\underline{H}DO$=4.80): 3.24 (1H, d, J=17.9 Hz), 3.57 (1H, d, J=17.9 Hz), 4.50–4.75 (3H, m), 4.85–4.90 (1H, m), 5.22 (2H, s), 5.28 (1H, d, J=15.9 Hz), 5.29 (1H, d, J=5.0 Hz), 5.30 (1H, d, J=15.9 Hz), 5.90 (1H, d, J=5.0 Hz), 7.70 (1H, d, J=4.4 Hz), 7.78 (1H, s), 8.08 (1H, d, J=4.4 Hz)

EXAMPLE 135

(6R,7R)-7-[(Z)-2-(5-Amino-1,2,4-thiadiazol-3-yl)-2-ethoxy- iminoacetamide]-3-(imidazo[5,1-b]thiazolium-6-yl)methyl-3- cephem-4-carboxylate (internal salt)

0.018 g of the title compound was obtained from 0.170 g (0.30 mmol) of p-methoxybenzyl (6R,7R)-7-[(Z)-2-(5-amino-1,2,4- thiadiazol-3-yl)-2-ethoxyiminoacetamide]-3-chloromethyl-3-cephem-4-carboxylic acid ester, 0.045 g (0.36 mmol) of imidazo-[5,1-b]thiazole (Preparation 1) and 0.090 g (0.60 mmol) of sodium iodide in the same manner as in Example 31. NMR ($D_2O$) d ($\underline{H}DO$=4.80): 1.33 (3H, t, J=7.1 Hz), 3.26 (1H, d, J=17.6 Hz), 3.66 (1H, d, J=17.6 Hz), 4.36 (2H, q, J=7.1 Hz), 5.17 (1H, d, J=14.3 Hz), 5.29 (1H, d, J=4.9 Hz), 5.32 (1H, d, J=14.3 Hz), 5.90 (1H, d, J=4.9 Hz), 7.56 (1H, d, J=4.3 Hz), 7.79 (1H, s), 7.95 (1H, d, J=4.3 Hz), 9.39 (1H, s)

EXAMPLE 136

(6R,7R)-7-[(Z)-2-(5-Amino-1,2,4-thiadiazol-3-yl)-2-ethoxy- iminoacetamide]-3-(5-hydroxymethylimidazo[5,1-b]thiazolium-6- yl)methyl-3-cephem-4-carboxylate (internal salt)

0.023 g of the title compound was obtained from 0.170 g (0.30 mmol) of p-methoxybenzyl (6R,7R)-7-[(Z)-2-(5-amino-1,2,4- thiadiazol-3-yl)-2-ethoxyiminoacetamide]-3-chloromethyl-3-cephem-4-carboxylic acid ester, 0.055 g (0.36 mmol) of 5-hydroxymethylimidazo[5,1-b]thiazole (Preparation 10) and 0.090 (0.60 mmol) of sodium iodide in the same manner as in Example 31. NMR ($D_2O$) d ($\underline{H}DO$=4.80): 1.34 (3H, t, J=7.1 Hz), 3.25 (1H, d, J=17.6 Hz), 3.57 (1H, d, J=17.6 Hz), 4.36 (2H, q, J=7.1 Hz), 5.22 (2H, s), 5.28 (1H, d, J=15.0 Hz), 5.28 (1H, d, J=4.9 Hz), 5.36 (1H, d, J=15.0 Hz), 5.89 (1H, d, J=4.9 Hz), 7.60 (1H, d, J=4.4 Hz), 7.78 (1H, s), 8.07 (1H, d, J=4.4 Hz)

EXAMPLE 137

(6R,7R)-7-[(Z)-2-(2-Aminothiazol-4-yl)-2-(2-hydroxyethoxy- imino)acetamide]-3-(imidazo[5,1-b]thiazolium-6-yl)methyl-3- cephem-4-carboxylate (internal salt)

0.0248 g of the title compound was obtained from 0.247 g (0.30 mmol) of p-methoxybenzyl (6R,7R)-7-[(Z)-2-(2-tritylamino- thiazol-4-yl)-2-(2-hydroxyethoxyimino) acetamide]-3-chloromethyl-3-cephem-4-carboxylic acid ester, 0.045 g (0.36 mmol) of imidazo[5,1-b]thiazole (Preparation 1) and 0.090 g (0.60 mmol) of sodium iodide in the same manner as in Example 1. NMR ($D_2O$) d (HDO=4.80): 3.26 (1H, d, J=17.6 Hz), 3.67 (1H, d, J=17.6 Hz), 3.88 (2H, m), 4.32 (2H, m), 5.14 (1H, d, J=14.4 Hz), 5.29 (1H, d, J=5.0 Hz), 5.33 (1H, d, J=14.4 Hz), 5.86 (1H, d, J=5.0 Hz), 6.96 (1H, s), 7.54 (1H, d, J=4.1 Hz), 7.79 (1H, s), 9.32 (1H, d, J=4.1 Hz), 9.38 (1H, s)

EXAMPLE 138

(6R,7R)-7-[(Z)-2-(5-Amino-1,2,4-thiadiazol-3-yl)-2-(2-fluoroethoxyimino) acetamide]-3-(5-formylaminomethylimidazo[5,1-b]- thiazolium-6-yl) methyl-3-cephem-4-carboxylate (internal salt)

0.0461 g of the title compound was obtained from 0.363 g (0.44 mmol) of p-methoxybenzyl (6R,7R)-7-[(Z)-2-(5-tritylamino- 1,2,4-thiadiazol-3-yl)-2-(2-fluoroethoxyimino) acetamide]-3-chloromethyl-3-cephem-4-carboxylic acid ester, 0.095 g (0.52 mmol) of 5-formylaminomethylimidazo [5,1-b]thiazole (Preparation 15) and 0.132 g (0.88 mmol) of sodium iodide in the same manner as in Example 59. NMR (D$_2$O) d (HDO=4.80): 3.17 (1H, d, J=17.9 Hz), 3.60 (1H, d, J=17.9 Hz), 4.50–4.75 (3H, m), 4.85–4.90 (1H, m), 5.04 (2H, s), 5.30 (1H, d, J=4.9 Hz), 5.30 (1H, d, J=15.3 Hz), 5.38 (1H, d, J=15.3 Hz), 5.89 (1H, d, J=4.9 Hz), 7.61 (1H, d, J=4.3 Hz), 7.75 (1H, s), 8.06 (1H, d, J=4.3 Hz), 8.22 (1H, s)

EXAMPLE 139

(6R,7R)-7-[(Z)-2-(2-Aminothiazol-4-yl)-2-ethoxyiminoacetamide]- 3-(imidazo[5,1-b]thiazolium-6-yl) methyl-3-cephem-4-carboxylate (internal salt)

0.033 g of the title compound was obtained from 0.242 g (0.30 mmol) of p-methoxybenzyl (6R,7R)-7-[(Z)-2-(2-tritylamino- thiazol-4-yl)-2-ethoxyiminoacetamide]-3-chloromethyl-3-cephem-4-carboxylic acid ester, 0.045 g (0.36 mmol) of imidazo[5,1-b]-thiazole (Preparation 1) and 0.090 g (0.60 mmol) of sodium iodide in the same manner as in Example 1. NMR (D$_2$O) d (HDO=4.80): 1.30 (3H, t, J=7.1 Hz), 3.26 (1H, d, J=17.9 Hz), 3.67 (1H, d, J=17.9 Hz), 4.26 (1H, q, J=7.1 Hz), 5.15 (1H, d, J=14.6 Hz), 5.29 (1H, d, J=4.8 Hz), 5.33 (1H, d, J=14.6 Hz), 5.86 (1H, d, J=4.8 Hz), 6.96 (1H, s), 7.55 (1H, d, J=4.3 Hz), 7.79 (1H, s), 7.94 (1H, d, J=4.2 Hz)

EXAMPLE 140

(6R,7R)-7-[(Z)-2-(2-Aminothiazol-4-yl)-2-ethoxyiminoacetamide]- 3-(5-formylaminomethylimidazo [5,1-b]thiazolium-6-yl)methyl-3- cephem-4-carboxylate (internal salt)

0.0171 g of the title compound was obtained from 0.242 g (0.30 mmol) of p-methoxybenzyl (6R,7R)-7-[(Z)-2-(2-tritylamino- thiazol-4-yl)-2-ethoxyiminoacetamide-]3-chloromethyl-3-cephem-4-carboxylic acid ester, 0.065 g (0.36 mmol) of 5-formylaminomethylimidazo[5,1-b] thiazole (Preparation 15) and 0.090 g (0.60 mmol) of sodium iodide in the same manner as in Example 1. NMR (D$_2$O) d (HDO=4.80): 1.30 (3H, t, J=7.0 Hz), 3.19 (1H, d, J=17.6 Hz), 3.61 (1H, d, J=17.6 Hz), 4.28 (2H, q, J=7.0 Hz), 5.05 (2H, s), 5.31 (1H, d, J=4.5 Hz), 5.31 (1H, d, J=15.6 Hz), 5.38 (1H, d, J=15.6 Hz), 5.87 (1H, d, J=4.5 Hz), 7.02 (1H, s), 7.62 (1H, d, J=4.3 Hz), 7.75 (1H, s), 8.07 (1H, d, J=4.3 Hz), 8.22 (1H, s)

EXAMPLE 141

(6R,7R)-7-[(Z)-2-(2-Aminothiazol-4-yl)-2-(2-fluoroethoxyimino)- acetamide]-3-(5-formylaminomethylimidazo[5, 1-b]thiazolium-6-yl)methyl-3-cephem-4-carboxylate (internal salt)

0.0261 g of the title compound was obtained from 0.248 g (0.30 mmol) of p-methoxybenzyl (6R,7R)-7-[(Z)-2-(2-tritylamino- thiazol-4-yl)-2-(2-fluoroethoxyimino) acetamide]-3-chloromethyl-3-cephem-4-carboxylic acid ester, 0.065 g (0.36 mmol) of 5-formylaminomethylimidazo [5,1-b]thiazole (Preparation 15) and 0.090 g (0.60 mmol) of sodium iodide in the same manner as in Example 1. NMR (D$_2$O) d (HDO=4.80): 3.18 (1H, d, J=17.6 Hz), 3.61 (1H, d, J=17.6 Hz), 4.4–4.7 (3H, m), 4.85 (1H, m), 5.05 (2H, s), 5.31 (1H, d, J=4.9 Hz), 5.31 (1H, d, J=15.9 Hz), 5.37 (1H, d, J=15.9 Hz), 5.87 (1H, d, J=4.9 Hz), 7.05 (1H, s), 7.61 (1H, d, J=4.4 Hz), 7.75 (1H, s), 8.07 (1H, d, J=4.4 Hz), 8.22 (1H, s)

EXAMPLE 142

(6R, 7R)-7-[(Z)-2-(2-Aminothiazol-4-yl)-2-(2-fluoroethoxyimino)- acetamide]-3-(imidazo[5,1-b] thiazolium-6-yl)methyl-3-cephem-4- carboxylate (internal salt)

0.0512 g of the title compound was obtained from 0.248 g (0.30 mmol) of p-methoxybenzyl (6R,7R)-7-[(Z)-2-(2-tritylamino- thiazol-4-yl)-2-(2-fluoroethoxyimino) acetamide]-3-chloromethyl-3-cepham-4-carboxylic acid ester, 0.045 g (0.36 mmol) of imidazo[5,1-b]thiazole (Preparation 1) and 0.090 g (0.60 mmol) of sodium iodide in the same manner as in Example 1. NMR (D$_2$O) d (HDO=4.80): 3.26 (1H, d, J=17.9 Hz), 3.67 (1H, d, J=17.9 Hz), 4.4–4.7 (3H, m), 4.85 (1H, m), 5.16 (1H, d, J=14.6 Hz), 5.29 (1H, d, J=4.8 Hz), 5.32 (1H, d, J=14.6 Hz), 5.87 (1H, d, J=4.8 Hz), 7.04 (1H, s), 7.56 (1H, d, J=4.3 Hz), 7.79 (1H, s), 7.95 (1H, d, J=4.3 Hz), 9.39 (1H, s)

EXAMPLE 143

(6R,7R)-7-[(Z)-2-(2-Aminothiazol-4-yl)-2-(2-fluoroethoxyimino)- acetamide]-3-(3-carbamoylimidazo[5, 1-b]thiazolium-6-yl)methyl- 3-cephem-4-carboxylate (internal salt)

0.0442 g of the title compound was obtained from 0.248 g (0.30 mmol) of p-methoxybenzyl (6R,7R)-7-[(Z)-2-(2-tritylamino- thiazol-4-yl)-2-(2-fluoroethoxyimino) acetamide]-3-chloromethyl-3-cephem-4-caboxylic acid ester, 0.060 g (0.36 mmol) of imidazo[5,1-b]thiazole-3-carboxyamide (Preparation 12) and 0.090 g (0.60 mmol) of sodium iodide in the same manner as in Example 25. NMR (D$_2$O) d (HDO=4.80): 3.26 (1H, d, J=18.1 Hz), 3.67 (1H, d, J=18.1 Hz), 4.4–4.7 (3H, m), 4.85 (1H, m), 5.19 (1H, d, J=15.0 Hz), 5.30 (1H, d, J=4.8 Hz), 5.36 (1H, d, J=15.0 Hz), 5.87 (1H, d, J=4.8 Hz), 7.00 (1H, s), 7.90 (1H, s), 8.39 (1H, s), 9.80 (1H, s)

EXAMPLE 144

(6R,7R)-7-[(Z)-2-(2-Aminothiazol-4-yl)-2-ethoxyiminoacetamide]- 3-(3-carbamoylimidazo[5,1-b] thiazolium-6-yl)methyl-3-cephem-4-carboxylate (internal salt)

0.0581 g of the title compound was obtained from 0.242 g (0.30 mmol) of p-methoxybenzyl (6R,7R)-7-[(Z)-2-(2-tritylamino- thiazol-4-yl)-2-ethoxyiminoacetamide]-3-chloromethyl-3-cephem-4-carboxylic acid ester, 0.060 g (0.36 mmol) of imidazo-[5,1-b]thiazole-3-carboxyamide (Preparation 12) and 0.090 g (0.60mmol) of sodium iodide in the same manner as in Example 25. NMR (D$_2$O) d (HDO=4.80): 1.30 (3H, t, J=7.2 Hz), 3.26 (1H, d, J=17..5 Hz), 3.67 (1H, d, J=17.5 Hz), 4.26 (2H, q, J=7.2 Hz), 5.19 (1H, d, J=14.7 Hz), 5.30 (1H, d, J=5.2 Hz), 5.35 (1H, d, J=14.7 Hz), 5.86 (1H, d, J=5.2 Hz), 6.97 (1H, s), 7.91 (1H, s), 8.39 (1H, s), 9.80 (1H, s)

EXAMPLE 145

(6R,7R)-7-[(Z)-2-(2-Aminothiazol-4-yl)-2-fluoromethoxyimino- acetamide]-3-(5-formylaminomethylimidazo[5,1-b]thiazolium-6- yl)methyl-3-cephem-4-carboxylate (internal salt)

0.0208 g of the title compound was obtained from 0.243 g (0.30. mmol) of p-methoxybenzyl (6R,7R)-7-[(Z)-2-(2-tritylamino-thiazol-4-yl)-2-fluoromethoxy-iminoacetamide]-3-chloromethyl-3-cephem-4-carboxylic acid ester, 0.065 g (0.36 mmol) of 5-formylaminomethylimidazo-[5,1-b]thiazole (Preparation 15) and 0.090 g (0.60 mmol) of sodium iodide in the same manner as in Example 1. NMR (D$_2$O) d (HDO=4.80): 3.19 (1H, d, J=17.7 Hz), 3.62 (1H, d, J=17.7 Hz), 5.05 (2H, s), 5.31 (1H, d, J=15.3 Hz), 5.32 (1H, d, J=4.7 Hz), 5.38 (1H, d, J=15.3 Hz), 5.80 (2H, d, J=55 Hz), 5.88 (1H, d, J=4.7 Hz), 7.19 (1H, s), 7.61 (1H, d, J=4.4 Hz), 7.75 (1H, s), 8.07 (1H, d, J=4.4 Hz), 8.22 (1H, s)

EXAMPLE 146

(6R,7R)-7-[(Z)-2-(2-Aminothiazol-4-yl)-2-carbamoylmethoxyimino- acetamide]-3-(imidazo[5,1-b]thiazolium-6-yl)methyl-3-cephem-4- carboxylate (internal salt)

0.0409g of the title compound was obtained from 0.251 g (0.30 mmol) of p-methoxybenzyl (6R,7R)-7-[(Z)-2-(2-tritylamino-             thiazol-4-yl)-2-carbamoylmethoxyiminoacetamide]-3-chloromethyl-3-cephem-4-carboxylic acid ester, 0.045 g (0.36 mmol) of imidazo[5,1-b]thiazole (Preparation 1) and 0.090 g (0.60 mmol) of sodium iodide in the same manner as in Example 1. NMR (D$_2$O) d (HDO=4.80): 3.26 (1H, d, J=18.1 Hz), 3.68 (1H, d, J=18.1 Hz), 4.73 (2H, s), 5.15 (1H, d, J=15.0 Hz), 5.30 (1H, d, J=4.4 Hz), 5.33 (1H, d, J=15.0 Hz), 5.89 (1H, d, J=4.4 Hz), 7.10 (1H, s), 7.56 (1H, d, J=4.0 Hz), 7.79 (1H, s), 7.95 (1H, d, J=4.0 Hz), 9.39 (1H, s)

EXAMPLE 147

(6R,7R)-7-[(Z)-2-(5-Amino-1,2,4-thiadiazol-3-yl)-2-carbamoyl- methoxyiminoacetamide]-3-(imidazo[5,1-b]thiazolium-6-yl)methyl- 3-cephem-4-carboxylate (internal salt)

0.0433 of the title compound was obtained from 0.251 g (0.30 mmol) of p-methoxybenzyl (6R,7R)-7-[(Z)-2-(5-tritylamino-    1,2,4-thiadiazol-3-yl)-2-carbamoylmethoxyiminoacetamide]-3-chloromethyl-3-cephem-4-carboxylic acid ester, 0.045 g (0.36 mmol) of imidazo[5,1-b]thiazole (Preparation 1) and 0.090 g (0.60mmol) of sodium iodide in the same manner as in Example 59. NMR (D$_2$O) d (HDO=4.80): 3.26 (1H, d, J=17.4 Hz), 3.67 (1H, d, J=17.4 Hz), 5.16 (1H, d, J=14.6 Hz), 5.30 (1H, d, J=4.7 Hz), 5.32 (1H, d, J=14.6 Hz), 5.93 (1H, d, J=4.7 Hz), 7.56 (1H, d, J=4.1 Hz), 7.79 (1H, s), 7.96 (1H, d, J=4.1 Hz), 9.39 (1H, s)

EXAMPLE 148

(6R,7R)-7-[(Z)-2-(2-Aminothiazol-4-yl)-2-cyclopentyloxyimino-    acetamide]-3-(5-formylaminomethylimidazo[5,1-b]thiazolium-6- yl)methyl-3-cephem-4-carboxylate (internal salt)

0.0208 of the title compound was obtained from 0.254 g (0.30 mmol) of p-methoxybenzyl (6R,7R)-7-[(Z)-2-(2-tritylamino-             thiazol-4-yl)-2-cyclopentyloxyiminoacetamide]-3-chloromethyl-3-cephem-4-carboxylic acid ester, 0.065 g (0.36 mmol) of 5-formylaminomethylimidazo[5,1-b]thiazole (Preparation 15) and 0.090 g (0.60 mmol) of sodium iodide in the same manner as in Example 1. NMR (D$_2$O) d (HDO=4.80): 1.5–2.0 (8H, m), 3.17 (1H, d, J=17.5 Hz), 3.62 (1H, d, J=17.5 Hz), 5.05 (2H, s), 5.30 (1H, d, J=15.0 Hz), 5.31 (1H, d, J=5.0 Hz), 5.37 (1H, d, J=15.0 Hz), 5.82 (1H, d, J=5.0.Hz), 6.99 (1H, s), 7.62 (1H, d, J=4.1 Hz), 7.76 (1H, s), 8.08 (1H, d, J=4.1 Hz), 8.22 (1H, s)

EXAMPLE 149

(6R,7R)-7-[(Z)-2-(5-Amino-1,2,4-thiadiazol-3-yl)-2-fluoro-methoxyiminoacetamide]-3-(3-methylimidazo[5,1-b] thiazolium-6- yl)methyl-3-cephem-4-carboxylate (internal salt)

0.0516 of the title compound was obtained from 0.244 g (0.30 mmol) of p-methoxybenzyl (6R,7R)-7-[(Z)-2-(5-tritylamino-    1,2,4-thiadiazol-3-yl)-2-fluoromethoxyiminoacetamide]-3-chloromethyl-3-cephem-4-carboxylic acid ester, 0.050 g (0.36 mmol) of 3-methylimidazo[5,1-b]thiazole (Preparation 2) and 0.090 g (0.60 mmol) of sodium iodide in the same manner as in Example 59. NMR (D$_2$O) d (HDO=4.80): 2.51 (3H, s), 3.25 (1H, d, J=18.2 Hz), 3.66 (1H, d, J=18.2 Hz), 5.17 (1H, d, J=14.7 Hz), 5.30 (1H, d, J=4.6 Hz), 5.32 (1H, d, J=14.7 Hz), 5.85 (2H, d, J=54 Hz), 5.90 (1H, d, J=4.6 Hz), 7.14 (1H, s), 7.77 (1H, s), 9.36 (1H, s)

EXAMPLE 150

(6R,7R)-7-[(Z)-2-(5-Amino-1,2,4-thiadiazol-3-yl)-2-cyclopentyl-     oxyiminoacetamide]-3-(5-formylaminomethylimidazo[5,1-b]- thiazolium-6-yl=)methyl-3-cephem-4-carboxylate (internal salt)

0.0229 of the title compound was obtained from 0.255 g (0.30 mmol) of p-methoxybenzyl (6R,7R)-7-[(Z)-2-(5-tritylamino-    1,2,4-thiadiazol-3-yl)-2-cyclopentyloxyiminoacetamide]-3-chloromethyl-3-cepham-4-carboxylic acid ester, 0.065 g (0.36 mmol) of 5-formylaminomethylimidazo[5,1-b]thiazole (Preparation 15) and 0.090 g (0.60 mmol) of sodium iodide in the same manner as in Example 59. NMR (D$_2$O) d (HDO=4.80): 1.514 2.0 (8H, m), 3.16 (1H, d, J=17.6 Hz), 3.61 (1H, d, J=17.6 Hz), 4.93 (1H, m), 5.05 (2H, s), 5.30 (1H, d, J=15.0 Hz), 5.31 (1H, d, J=4.9 Hz), 5.37 (1H, d, J=15.0 Hz), 5.84 (1H, d, J=4.9 Hz), 7.62 (1H, d, J=4.1 Hz), 7.76 (1H, s), 8.07 (1H, d, J=4.1 Hz), 8.22 (1H, s)

EXAMPLE 151

(6R,7R)-7-[(Z)-2-(5-Amino-1,2,4-thiadiazol-3-yl)-2-(2-fluoro- ethoxyimino)acetamide]-3-(3-methylimidazo[5,1-b] thiazolium-6- yl)methyl-3-cephem-4-carboxylate (internal salt)

0.0570 g of the title compound was obtained from 0.248 g (0.30 mmol) of p-methoxybenzyl (6R,7R)-7-[(Z)-2-(5-tritylamino-    1,2,4-thiadiazol-3-yl)-2-(2-fluoromethoxyimino)acetamide]-3-chloromethyl-3-cephem-4-carboxylic acid ester, 0.050 g (0.36 mmol) of 3-methylimidazo[5,1-b]thiazole (Preparation 2) and 0.090 g (0.60 mmol) of sodium iodide in the same manner as in Example 59. NMR (D$_2$O) d (HDO=4.80): 2.52 (3H, s), 3.25 (1H, d, J=17.8 Hz), 3.65 (1H, d, J=17.8 Hz), 4.50–4.75 (3H, m), 4.85 (1H, m), 5.18 (1H, d, J=15.0 Hz), 5.29 (1H, d, J=4.7 Hz), 5.33 (1H, d, J=15.0 Hz), 5.90 (1H, d, J=4.7 Hz), ?.15 (1H, s), 7.77 (1H, s), 9.37 (1H, s)

EXAMPLE 152

(6R,7R)-7-[(Z)-2-(2-Aminothiazol-4-yl)-2-((S)-1-carboxyethoxy- imino)acetamide]-3-(5-formylaminomethylimidazo[5,1-b]- thiazolium-6-yl)methyl-3-cephem-4-carboxylate (internal salt)

0.0216 g of a monosodium salt of the title compound was obtained from 0.305 g (0.30 mmol) of p-methoxybenzyl (6R, 7R)-7- [(Z)-2-(2-tritylaminothiazol-4-yl)-2-((S)-1-diphenylmethoxy- carbonylethoxyimino)acetamide]-3-chloromethyl-3-cephem-4-carboxylic acid ester, 0.065 g (0.36 mmol) of 5-formylamino-methylimidazo[5,1-b]thiazole (Preparation 15) and 0.090 g (0.60 mmol) of sodium iodide in the same manner as in Example 1. NMR ($D_2O$) d (HDO=4.80): 1.47 (3H, d, J=6.9 Hz), 3.17 (1H, d, J=18.0 Hz), 3.60 (1H, d, J=18.0 Hz), 4.68 (1H, q, J=6.9 Hz), 5.05 (2H, s), 5.30 (1H, d, J=15.0 Hz), 5.31 (1H, d, J=5.0 Hz), 5.38 (1H, d, J=15.0 Hz), 5.89 (1H, d, J=5.0 Hz), 7.05 (1H, s), 7.61 (1H, d, J=4.4 Hz), 7.76 (1H, s), 8.07 (1H, d, J=4.4 Hz), 8.22 (1H, s)

EXAMPLE 153

(6R,7R)-7-[(Z)-2-(5-Amino-1,2,4-thiadiazol-3-yl)-2-fluoromethoxyiminoacetamide]-3-(5-acetoxymethylimidazo[5,1-b]- thiazolium-6-yl)methyl-3-cephem-4-carboxylate (internal salt)

0.0122 g of the title compound was obtained from 0.266 g (0.33 mmol) of p-methoxybenzyl (6R,7R)-7-[(Z)-2-(5-tritylamino- 1,2,4-thiadiazol-3-yl)-2-fluoromethoxyiminoacetamide]-3-chloromethyl-3-cephem-4-carboxylic acid ester, 0.077 g (0.39 mmol) of 5-acetoxymethylimidazo[5,1-b]thiazole (Preparation 53) and 0.098 g (0.65 mmol) of sodium iodide in the same manner as in Example 59. NMR ($D_2O$) d (HDO=4.80): 2.15 (3H, s), 3.24 (1H, d, J=17.5 Hz), 3.59 (1H, d, J=17.5 Hz), 5.29 (1H, d, J=4.7 Hz), 5.35 (1H, d, J=15.5 Hz), 5.44 (1H, d, J=15.5 Hz), 5.73 (2H, s), 5.86 (2H, d, J=54 Hz), 5.91 (1H, d, J=4.7 Hz), 7.65 (1H, d, J=4.3 Hz), 7.85 (1H, s), 8.13 (1H, d, J=4.3 Hz)

EXAMPLE 154

(6R,7R)-7-[(Z)-2-(5-Amino-1,2,4-thiadiazol-3-yl)-2-ethoxy- iminoacetamide]-3-(5-acetoxymethylimidazo[5,1-b]thiazolium-6- yl)methyl-3-cephem-4-carboxylate (internal salt)

0.0338 g of the title compound was obtained from 0.193 g (0.34 mmol) of p-methoxybenzyl (6R,7R)-7-[(Z)-2-(5-amino-1,2,4- thiadiazol-3-yl)-2-ethoxyiminoacetamide]-3-chloromethyl-3-cephem-4-carboxylic acid ester, 0.080 g (0.41 mmol) of 5-acetoxymethylimidazo[5,1-b]thiazole (Preparation 53) and 0.100 g (0.67 mmol) of sodium iodide in the same manner as in Example 44. NMR ($D_2O$) d ( HDO=4.80): 1.34 (3H, t, J=7.1 Hz), 2.15 (3H, s), 3.24 (1H, d, J=17.7 Hz), 3.58 (1H, d, J=17.7 Hz), 4.36 (2H, q, J=7.1 Hz), 5.28 (1H, d, J=4.9 Hz), 5.34 (1H, d, J=15.9 Hz), 5.45 (1H, d, J=15.9 Hz), 5.72 (2H, s), 5.90 (1H, d, J=4.9 Hz), 7.66 (1H, d, J=4.3 Hz), 7.84 (1H, s), 8.13 (1H, d, J=4.3 Hz)

EXAMPLE 155

(6R,7R)-7-[(Z)-2-(5-Amino-1,2,4-thiadiazol-3-yl)-2-cyanomethoxyiminoacetamide]-3-(imidazo[5,1-b]thiazolium-6-yl)methyl- 3-cephem-4-carboxylate (internal salt)

0.0231 g of the title compound was obtained from 0.164 g (0.20 mmol) of p-methoxybenzyl (6R,7R)-7-[(Z)-2-(5-tritylamino- 1,2,4-thiadiazol-3-yl)-2-cyanomethoxyiminoacetamide]3-chloromethyl-3-cephem- 4-carboxylic acid ester, 0.030 g (0.24 mmol) of imidazo[5,1-b]thiazole (Preparation 1) and 0.060 g (0.40mmol) of sodium iodide in the same manner as in Example 59. NMR ($D_2O$) d (HDO=4.80): 3.25 (1H, d, J=17.9 Hz), 3.66 (1H, d, J=17.9 Hz), 5.11 (2H, s), 5.14 (1H, d, J=15.5 Hz), 5.28 (1H, d, J=4.5 Hz), 5.32 (1H, d, J=15.5 Hz), 5.87 (1H, d, J=4.5 Hz), 7.54 (1H, d, J=4.1 Hz), 7.78 (1H, s), 7.93 (1H, d, J=4.1 Hz), 9.37 (1H, s)

EXAMPLE 156

(6R, 7R)-7-[(Z)-2-(5-Amino-1,2,4-thiadiazol-3-yl)-2-cyano methoxyiminoacetamide]-3-(5-formylaminomethylimidazo [5,1-b]- thiazolium-6-yl)methyl-3-cephem-4-carboxylate (internal salt)

0.0281 g of the title compound was obtained from 0.246 g (0.30 mmol) of p-methoxybenzyl (6R,7R)-7-[(Z)-2-(5-tritylamino- 1,2,4-thiadiazol-3-yl)-2-cyanomethoxyiminoacetamide]-3-chloromethyl-3-cephem-4-carboxylic acid ester, 0. 065 g (0.36 mmol) of 5-formylaminomethylimidazo[5,1-b]thiazole (Preparation 15) and 0.090 g (0.60 mmol) of sodium iodide in the same manner as in Example 59. NMR ($D_2O$) d (HDO=4.80): 3.18 (1H, d, J=18.0 Hz), 3.61 (1H, d, J=18.0 Hz), 5.04 (2H, s), 5.13 (2H, s), 5.30 (1H, d, J=4.9 Hz), 5.30 (1H, d, J=14.9 Hz), 5.37 (1H, d, J=14.9 Hz), 5.89 (1H, d, J=4.9 Hz), 7.61 (1H, d, J=4.4 Hz), 7.75 (1H, s), 8.06 (1H, d, J=4.4 Hz), 8.22 (1H, s)

EXAMPLE 157

(6R,7R)-7-[(Z)-2-(5-Amino-1,2,4-thiadiazol-3-yl)-2-cyanomethoxyiminoacetamide]-3-(3-carbamoylimidazo[5,1-b] thiazolium- 6-yl)methyl-3-cephem-4-carboxylate (internal salt)

0.0444 g of the title compound was obtained from 0.164 g (0.20 mmol) of p-methoxybenzyl (6R,7R)-7-[(Z)-2-(5-tritylamino- 1,2,4-thiadiazol-3-yl)-2-cyanomethoxyiminoacetamide]-3-chloromethyl-3-cephem-4-carboxylic acid ester, 0.040 g (0.24 mmol) of imidazo[5,1-b]thiazole-3-carboxyamide (Preparation 12) and 0.060 g (0.40 mmol) of sodium iodide in the same manner as in Example 44. NMR ($D_2O$) d (HDO=4.80): 3.26 (1H, d, J=17.3 Hz), 3.66 (1H, d, J=17.3 Hz), 5.12 (2H, s), 5.18 (1H, d, J=14.8 Hz), 5.29 (1H, d, J=4.7 Hz), 5.35 (1H, d, J=14.8 Hz), 5.88 (1H, d, J=4.7 Hz), 7.89 (1H, s), 8.39 (1H, s)

EXAMPLE 158

(6R,7R)-7-[(Z)-2-(5-Amino-1,2,4-thiadiazol-3-yl)-2-methoxy- iminoacetamide]-3-[5-[(R)-1-(formylamino)ethyl]imidazo[5,1-b]- thiazolium-6-yl)methyl-3-cephem-4-carboxylate (internal salt)

0.118 g of the title compound was obtained from 0.277 g (0.50 mmol) of p-methoxybenzyl (6R,7R)-7-[(Z)-2-(5-tritylamino- 1,2,4-thiadiazol-3-yl)-2-methoxyiminoacetamide]-3-chloromethyl-3-cephem-4-carboxylic acid ester, 0.117 g (0.6 mmol) of 5-[(R)-1-(formylamino)ethyl]imidazo[5,1-b]thiazole (Preparation 18) and 0.090 g (0.6 mmol) of sodium iodide in the same manner as in Example 31. NMR ($D_2O$) d (HDO=4.80): 1.69 (3H, d, J=7.1 Hz), 3.24 (1H, d, J=17.7 Hz), 3.50 (1H, d, J=17.7 Hz), 4.06 (3H, s), 5.24 (1H, d, J=4.7 Hz), 5.33 (1H, d, J=15.1 Hz), 5.48 (1H, d, J=15.1 Hz), 5.60 (1H, q, J=7.1 Hz), 5.87 (1H, J=4.7 Hz), 7.60 (1H, d, J=4.4 Hz), 7.70 (1H, s), 7.98 (1H, J=4.4 Hz), 8.12 (1H, s)

EXAMPLE 159

(6R,7R)-7-[(Z)-2-(5-Amino-1,2,4-thiadiazol-3-yl)-2-(2-fluoro- ethoxyimino)acetamide]-3-(5-((R)-1-formylamino)

ethylimidazo-[5,1-b]thiazolium-6-yl)methyl-3-cephem-4-carboxylate (internal salt)

0.063 g of the title compound was obtained from 0.247 g of p-methoxybenzyl (6R,7R)-7-[(Z)-2-(5-tritylamino-1,2,4-thiadiazol-3-yl)-2-(2-fluoroethoxyimino)acetamide]-3-chloromethyl-3-cephem-4-carboxylic acid ester, 0.061 g of 5-((R)-1-formylamino)ethylimidazo[5,1-b]thiazole (Preparation 18) and 0.047 mg of sodium iodide in the same manner as in Example 99. NMR (D$_2$O) d (HDO=4.80): 1.69 (3H, d, J=7 Hz), 3.24 (1H, d, J=18 Hz), 3.50 (1H, d, J=18 Hz), 4.45–4.85 (4H, m), 5.25 (1H, d, J=5 Hz), 5.33 (1H, d, J=15 Hz), 5.49 (1H, d, J=15 Hz), 5.60 (1H, q, J=17 Hz), 5.87 (1H, d, J=5 Hz), 7.60 (1H, d, J=4 Hz), 7.70 (1H, s), 7.98 (1H, d, J=4 Hz), 8.12 (1H, s)

EXAMPLE 160

(6R,7R)-7-[(Z)-2-(5-Amino-1,2,4-thiadiazol-3-yl)-2-fluoromethoxyiminoacetamide]-3-(5-((S)-1-formylamino) ethylimidazo-[5,1-b]thiazolium-6-yl)methyl-3-cephem-4-carboxylate (internal salt)

0.063 g of the title compound was obtained from 0.255 g of p-methoxybenzyl (6R,7R)-7-[(Z)-2-(5-tritylamino-1,2,4-thiadiazol-3-yl)-2-fluoromethoxyiminoacetamide]-3-chloromethyl-3-cephem-4-carboxylic acid ester, 0.061 g of 5-((S)-1-formylamino)ethylimidazo[5,1-b]thiazole (Preparation 17) and 0.047 mg of sodium iodide in the same manner as in Example 99. NMR (D$_2$O) d (HDO=4.80): 1.68 (1H, d, J=7 Hz), 3.23 (1H, d, J=18 Hz), 3.59 (1H, d, J=18 Hz), 5.27 (1H, d, J=5 Hz), 5.34 (2H, br-s), 5.64 (1H, q, J=7 Hz), 5.30 (1H, d, J=15 Hz), 5.83 (2H, d, J=54 Hz), 5.87 (1H, d, J=5 Hz), 7.59 (1H, d, J=4 Hz), 7.72 (1H, s), 7.97 (1H, d, J=4 Hz), 8.14 (1H, s)

Preparation 57

7-(formylamino)methylimidazo[5,1-b]thiazole a) 7-(phthalimido)methylimidazo[5,1-b]thiazole To a solution of 0.344 g (2.23 mmole) of 7-hydroxymethylimidazole (Preparation 38), 0.660 g (4.46 mmole) of phthalimide and 0.900 g (4.46mmole) of triphenylphosphine in 20 ml of anhydrous tetrahydrofuran was added 0.700 ml (4.46 mmole) of diethyl azodicarboxylate under argon at room temperature. After stirring at room temperature for 30 minutes, the reaction mixture was concentrated under reduced pressure. The residue was purified by flash column chromatography on silica gel (eluted with chloroform: ethyl acetate=1:1—solely ethyl acetate) to give 0.379 g of 7-(phthalimido)methylimidazo[5,1-b]thiazole. Yield 60%. NMR (CDCl$_3$) δ: 4.98 (2H, s), 6.80 (1H, d, J=4.3 Hz), 7.34 (1H, d, J=4.3 Hz), 7.64–7.84 (4H, m), 7.91 (1H, s).

b) 7-aminomethylimidazo[5,1-b]thiazole

To a suspension of 0.379 g (1.34 mmole) of 7-(phthalimido)methylimidazo[5,1-b]thiazole in 15 ml of ehtanol was added 0.063 ml (2.0mmle) of anhydrous hydrazine, and the mixture was heated under reflux for 1 hour. The reaction mixture was ice-cooled, and the resulting crystalline products were removed by filtration. After the filtrate was concentrated under reduced pressure, a small amount of dichloromethane was added, and insolubles were removed by filtration. The filtrate was concentrated under reduced pressure to give crude 7-aminomethylimidazo[5,1-b]thiazole.

c) 7-(formylamino)methylimidazo[5,1-b]thiazole

To the ice-cooled solution of the whole amount of the crude 7-aminomethyl-imidazo[5,1-b]thiazole in 5 ml of dichloromethane was added a mixture of 0.5 ml of formic acid and 0.5 ml of acetic anhydride which had been preliminarily sitrred and reacted at 50° C. for 10 minutes. The resulting mixture was stirred under ice-cooling for 30 minutes. To the reaction mixture were added 10 ml of water, 20 ml of dichloromethane and 5 ml of a 50% aqueous potassium carbonate solution, and the organic layer was separated. The aqueous layer was further extracted thrice with 20 ml of dichloromethane. The combined organic layer was purified by flash column chromatography on silica gel (eluted with chloroform: methanol=15:1) to give the title compound in a yield of 0.088 g (36%). NMR (CDCl$_3$) δ: 4.53 (2H, d, J=5.8 Hz), 6.84 (1H, d, J=4.2 Hz), 6.86 (1H, br), 7.38 (1H, d, J=4.2 Hz), 7.93 (1H, s), 8.26 (1H, s).

Preparation 58

5-((R)-1-Formylamino-2-hydroxyethyl)imidazo[5,1-b]thiazole a) 2-[(N-tert-Butoxycarbonyl-D-seryl)amino] methylthiazole To 2.052 g of N-tert-butoxycarbonyl-D-serine and 2.27 g of 1-hydroxybenzotriazole was added 50 ml of methylene chloride. To this mixture was added 1.49 g of dicyclohexylcarbodiimide with stirring and ice-cooling, and the resulting mixture was stirred for one hour with ice-cooling. To this was added a solution of 1.142 g of 2-aminomethylthiazole in 3 ml of methylene chloride, and the mixture was stirred for an additional 14 hours. The crystals were removed by filtration. The filtrate was washed with a 5% aqueous solution of sodium hydrogencarbonate, dried over anhydrous magnesium sulfate, and then concentrated under reduced pressure. The residue was purified by flash column chromatography using silica gel, eluting with ethyl acetate to give 2.309 g (yield 77%) of 2-[N-tert-butoxycarbonyl-D-seryl)amino]methylthiazole. NMR (CDCl$_3$) d: 1.46 (9H, s), 3.61–3.67 (1H, m), 3.98–4.18 m), 4.18–4.30 (1H, br), 4.78 (1H, dd, J=16.8 Hz, 6.4 Hz), 4.83 (1H, dd, J=16.8 Hz, 6.4 Hz), 5.56–5.70 (1H, br), 7.29 (1H, d, J=3.3 Hz), 7.30–7.44 (1H, br), 7.68 (1H, d, J=3.3 Hz)

b) 2-[(N-Trifluoroacetyl-D-seryl)amino]methylthiazole

To 2.00 g of the above-obtained 2-[(N-tert-butoxycarbonyl-D-seryl)amino]methylthiazole was added 20 ml of trifluoro-acetic acid, and the mixture was stirred for 30 minutes. The reaction solution was concentrated to dryness under reduced pressure. To the trifluoroacetic acid salt of 2-(D-seryl)-aminomethylthiazole thus obtained was added 50 ml of methylene chloride. To this mixture were added 3.36 g of triethylamine and 4.72 g of ethyl trifluoroacetate with stirring. The mixture was stirred at room temperature for 3 hours, and then concentrated under reduced pressure. The residue was purified by flash column chromatography using silica gel, eluting with ethyl acetate to give 1.965 g (quant.) of 2-[(N-trifluoroacetyl-D-seryl) amino]methylthiazole. NMR (CDCl$_3$) δ: 1.5–1.7 (1H, br), 3.69 (1H, dd, J=11.5 Hz, 6.9 Hz), 4.17 (1H, dd, J=11.5 Hz, 3.4 Hz), 4.57 (1H, td, J=6.9 Hz, 3.4 Hz), 4.76 (1H, dd, J=16.8 Hz, 5.6 Hz), 4.96 (1H, dd, J=16.8 Hz, 6.9 Hz), 7.00–7.07 (1H, br), 7.31 (1H, d, J=3.3 Hz), 7.68 (1H, J=3.3 Hz), 7.60–7.68 (1H, br)

c) 2-[(O-Acetyl-N-trifluoroacetyl-D-seryl)amino] methylthiazole

To a solution of 1.965 g of the above-obtained 2-[(N-trifluoroacetyl-D-seryl)amino]methylthiazole in 20 ml of pyridine was added 2 ml of acetic anhydride. The mixture was stirred at room temperature for 14 hours, and then concentrated to dryness under reduced pressure. The residue was dissolved in 50 ml of methylene chloride, and the solution was washed with 30 ml of a saturated aqueous solution of sodium hydrogencarbonate. The aqueous layer was extracted with 30 ml of methylene chloride. The combined organic layers were dried over anhydrous magnesium sulfate, and concentrated to dryness under reduced pressure to give 2.07 g (yield 92%) of 2-[(O-acetyl-N-trifluoroacetyl-D-seryl)amino]methylthiazole. NMR (CDCl$_3$) d: 2.05 (3H, s), 4.36–4.41 (1H, m), 4.77–4.85 (2H, m), 7.33 (1H, d, J=3.3 Hz), 7.42–7.52 (1H, br), 7.6–7.7 (1H, br), 7.72 (1H, d, J=3.3 Hz) MS (EI, CHCl$_3$, 160° C.): 339 (M$^+$)

d) 2-[(R)-2-acetoxy-1-(trifluoroacetylamino)ethyl]imidazo-[5,1-b]thiazole

To 0.506 g of the above-obtained 2-[(O-acetyl-N-trifluoroacetyl-D-seryl)amino]methylthiazole was added 10 ml of phosphorus oxychloride. The mixture was refluxed for 5 hours, cooled to room temperature, and then concentrated to dryness under reduced pressure. To the residue was added 50 ml of methylene chloride, and the mixture was thoroughly stirred. To this was added 30 ml of a saturated aqueous solution of sodium hydrogencarbonate with ice-cooling, and the mixture was stirred for an additional 30 minutes. Insoluble matters were removed by filtration. The organic layer was separated, and the aqueous layer was extracted with 30 ml of methylene chloride. The combined organic layers were dried over anhydrous magnesium sulfate, and concentrated under reduced pressure. The residue was purified by flash column chromatography using silica gel, eluting with a 2:1 mixture of ethyl acetate and hexane to give 0.319 g (yield 67%) of 5-[(R)-2-acetoxy-1-(trifluoroacetyl-amino)ethyl]imidazo[5,1-b]thiazole. NMR (CDCl$_3$) d: 2.08 (3H, s), 4.53 (1H, dd, J=11.6 Hz, 5.3 Hz), 4.57 (1H, dd, J=11.6 Hz, 7.8 Hz), 5.67 (1H, td, J=7.8 Hz, 5.3 Hz), 6.92 (1H, d, J=4.3 Hz), 7.05 (1H, s), 7.56 (1H, d, J=4.3 Hz), 7.64–7.74 (1H, br)

e) 5-((R)-1=Formylamino-2-hydroxyethyl)imidazo[5,1-b]thiazole

To a solution of 0.310 g of the above-obtained 5-[(R)-2-acetoxy-1-(trifluoroacetylamino)ethyl]imidazo[5,1-b]thiazole in 10 ml of methanol was added a solution of 0.160 g of sodium hydroxide in 5 ml of water, and the mixture was stirred at room temperature for 14 hours. The reaction solution was concentrated to dryness under reduced pressure to give a solid containing 5-[(R)-1-amino-2-hydroxyethyl]imidazo[5,1-b]-thiazole. To this was added 50 ml of methylene chloride, and the mixture was thoroughly stirred. To this suspension was added with ice-cooling a mixture of 2.0 g of acetic anhydride and 0.5 g of formic acid, which had been heated to 50° C. for 10 minutes and then cooled to room temperature. The mixture was stirred at room temperature for 30 minutes, and then cooled with ice. To this were added 4 ml of water and 4 g of potassium carbonate, and the mixture was stirred at room temperature for 30 minutes. To this mixture was added 4 ml of methanol, and the resulting mixture was stirred for an additional one hour. The organic layer was separated by decantation. The aqueous layer containing the crystals was washed with methylene chloride (30 ml×3). The combined organic layers were dried over anhydrous magnesium sulfate, and then concentrated to dryness to give 0.200 g (quant.) of 5-((R)-1-formylamino-2-hydroxyethyl)imidazo[5,1-b]thiazole. NMR (DMSO-d$_6$) d: 3.88 (2H, t, J=5.8 Hz), 5.01 (1H, t, J=5.8 Hz), 5.27 (1H, dr, J=8.4 Hz, 5.8 Hz), 6.97 (1H, s), 7.22 (1H, d, J=4.2 Hz), 7.80 (1H, d, J=4.2 Hz), 8.08 (1H, s), 8.61 (1H, d, J=8.4 Hz) MS (EI, DMSO, 200° C.): 211 (M$^+$)

Preparation 59

5-((R)-1-ureidoethyl)imidazo[5,1-b]thiazole

To 0.234 g of 5-[(R)-1-(formylamino)ethyl]imidazo[5,1-b]thiazole (Preparation 18) was added 3 ml of an aqueous solution of 2N sodium hydroxide, and the mixture was stirred at room temperature for 16 hours. After the reaction mixture was adjusted to pH 5 with 5N hydrochloric acid and heated to a temperature of 70° C., 0.160 g of sodium cyanate was added and the resulting mixture was stirred at 70° C. for 1 hour and at room temperature for further 16 hours. The reaction mixture was concentrated to dryness under reduced pressure. The residue was mixed with 50 ml of methylene chloride and 50 ml of methanol to stir well the mixture before removal of insolubles by filtration. The filtrate was concentrated under reduced pressure, and the residue was purified on Sephadex LH20 (eluent: chloroform-methanol= 1:1) to give 0.221 g of the title compound (yield 87%). NMR (DMSOd-6) δ: 1.45 (3H, d, J=6.9 Hz), 5.13 (1H, dq, J8.7 Hz, 6.9 Hz), 5.52 (2H, br), 6.45 (1H, d, J=8.7 Hz), 6.92 (1H, s), 7.20 (1H, d, J=4.2 Hz), 7.80 (1H, d; J=4.2 Hz).

Preparation 60

5-((S)-1-formylamino-2-hydroxyethyl)imidazo[5,1-b]thiazole a) 2-[(N-tert-butoxycarbonyl-L-ceryl)amino]methylthiazole In the same manner as in Preparation 58 (a), 2-[(N-tert-butoxycarbonyl-L-seryl)amino]methylthiazole was obtained in an amount of 2.399 g from 2.052 g of N-tert-butoxycarbonyl-L-serine, 2.27 g of 1-hydroxybenzotriazole, 1.49 g of dicyclohexylcarbodiimide and 1.142 g of aminomethylthiazole. Yield 80%. NMR (CDCl$_3$) δ: 1.45 (9H, s), 3.61–3.67 (1H, m), 4.05–4.30 (3H, m), 4.78 (1H, dd, J=16.8 Hz, 6.4 Hz), 4.83 (1H, dd, J=16.8 Hz, 6.4 Hz), 5.54–5.69 (1H, br), 7.29 (1H, d, J=3.3 Hz), 7.29–7.42 (1H, br), 7.67 (1H, d, J=3.3 Hz).

b) 2-[(N-trifluoroacetyl-L-seryl)amino]methylthiazole

A 1.540 g portion of 2-[(N-tert-butoxycarbonyl-L-seryl)amino]methylthiazole and 15 ml of trifluoroacetic acid were added, and the mixture was stirred for 30 minutes. The reaction mixture was concentrated to dryness under reduced pressure. To the solution of (L-seryl)aminomethylthiazole trifluoroacetatate salt thus obtained in 50 ml of methylene chloride were added with stirring 2.73 g of triethylamine and 3.84 g of ethyl trifluoroacetate. The mixture was stirred at room temperature for 3 hours, concentrated under reduced pressure and subjected to flash column chromatography on silica gel (eluted with ethyl acetate) to give 1.519 g of 2-[(N-trifluoroacetyl-L-seryl)amino]methylthiazole. Quantitative yield. NMR (CDCl$_3$) δ: 1.5–1.75 (1H, br), 3.69 (1H, dd, J=11.5 Hz, 6.7 Hz), 4.18 (1H, dd, J=11.5 Hz, 3.5 Hz), 4.58 (1H, td, J=11.5 Hz, 3.5 Hz), 4.75 (1H, dd, J=16.7 Hz, 5.5 Hz), 4.96 (1H, dd, J=16.7 Hz, 6.9 Hz), 7.01–7.07 (1H, br), 7.31 (1H, d, J=3.3 Hz), 7.60–7.70 (1H, br), 7.68 (1H, d, J=3.3 Hz).

c) 2-[(O-acetyl-N-trifluoroacetyl-L-seryl)amino]methylthiazole

To the solution of 1.518 g of 2-[(N-trifluoroacetyl-L-seryl)amino]methylthiazole in 18 ml of pyridine was added 1.8 ml of acetic anhydride, and the mixture was stirred at room temperature for 14 hours. After the reaction mixture was concentrated to dryness under reduced pressure, it was dissolved in 40 ml of methylene chloride and washed with 25 ml of a saturated aqueous sodium hydrogen carbonate solution. The aqueous layer was re-extracted with 30 ml of methylene chloride. The combined organic layer was dried with anhydrous magnesium sulfate and concentrated to dryness under reduced pressure to give 1.733 g of 2-[(O-acetyl-N-trifluoroacetyl-L-seryl)amino]methylthiazole.

Quantitative yield. NMR (CDCl$_3$) δ: 2.06 (3H, s), 4.36–4.40 (2H, m), 4.75–4.85 (3H, m), 7.17–7.26 (1H, br), 7.34 (1H, d, J=3.3 Hz), 7.73 (1H, d, J=3.3 Hz).

d) 5-[(S)-2-acetoxy-1-(trifluoroacetylamino)ethyl] imidazo[5,1-b]thiazole

To 1.733 g of 2-[(O-acetyl-N-trifluoroacetyl-L-seryl) amino]methylthiazole was added 20 ml of phosphorus oxychloride, and the mixture was heated under reflux for 5 hours. After the reaction mixture was cooled to room temperature, it was concentrated to dryness under reduced pressure. To this dried reaction mixture was added 100 ml of methylene chloride, followed by 60 ml of a saturated aqueous sodium hydrogen carbonate solution. The resulting mixture was further stirred for 30 minutes. After insolubles were removed by filtration, the organic layer was separated, and the aqueous layer was re-extracted with 50 ml of methylene chloride. The combined organic layer was dried with anhydrous magnesium sulfate, concentrated under reduced pressure and subjected to flash column chromatography on silica gel (eluted with ethyl acetate-hexane=2:1) to give 1.064 g of 5-[(S)-2-acetoxy-1-(trifluoroacetylamino) ethyl]imidazo[5,1-b]thiazole. Yield 65%. NMR (CDCl$_3$) δ: 2.08 (3H, s), 4.53 (1H, dd, J=11.6 Hz, 5.3 Hz), 4.57 (1H, dd, J=11.6 Hz, 7.8 Hz), 5.67 (1H, td, J=7.8 Hz, 5.3 Hz), 6.92 (1H, d, J=4.3 Hz), 7.05 (1H, s), 7.57 (1H, d, J=4.3 Hz), 7.68–7.78 (1H, bs).

e) 5-((S)-1-formylamino-2-hydroxyethyl)imidazo[5,1-b]thiazole

To the solution of 0.747 g of 5-[(S)-2-acetoxy-1-(trifluoroacetylamino)-ethyl]imidazo[5,1-b]thiazole in 10 ml of methanol was added 5 ml of an aqueous solution of 0.233 g of sodium hydroxide, and the mixture was then stirred at room temperature for 14 hours. The reaction mixture was concentrated to dryness under reduced pressure to give solid product containing 5-[(R)-1-amino-2-hydroxyethyl]imidazo[5,1-b]thiazole. To this product was added 50 ml of methylene chloride, and the mixture was stirred well. The mixture of 1.2 g of acetic anhydride and 2.7 g of formic acid which had been preliminarily heated to 50° C. for 10 minutes and cooled to room temperature was added to the suspension. After mixing at room temperature for 30 minutes, the mixture was cooled to room temperature. Water (5 ml) and potassium carbonate (5 g) were added, and the resulting mixture was stirred at room temperature for 30 minutes. Methanol (20 ml) was added, and the mixture was further stirred for i hour. The organic layer was separated by decantation. The aqueous layer containing crystalline products was washed five times with 20 ml of methylene chloride, and the methylene chloride layers were combined with the organic layer separated previously. The combined organic layer was dried with anhydrous potassium carbonate and concentrated to dryness, and the residue was purified on Sephadex LH20 (eluent: chloroform-methanol=1:1) to give 0.440 g of 5-((S)-1-formylamino-2-hydroxyethyl)imidazo [5,1-b]thiazole. Quantitative yield. NMR (CDCl$_3$) δ: 3.90 (1H, dd, J=11.6 Hz, 3.6 Hz), 4.42 (1H, dd, J=11.6 Hz, 2.0 Hz), 5.45 (1H, ddd, J=9.0 Hz, 3.6 Hz, 2.0 Hz), 6.8–6.9 (1H, br), 6.83 (1H, d, J=4.3 Hz), 6.97 (1H, s), 7.76 (1H, d, J=4.3 Hz), 8.26 (1H, s). MS (EI, DMSO, 200° C.): 211 (M$^+$).

Preparation 61

5-((R)-2-oxo-4-oxazolydinyl)imidazo[5,1-b]thiazole

To the solution of 0.358 g of 5-[(R)-2-acetoxy-1-(trifluoroacetylamino)ethyl]imidazo[5,1-b]thiazole (Preparation 58e) in 10 ml of methanol was added 5 ml of an aqueous solution of 0.20 g of sodium hydroxide at room temperature. The mixture was stirred for 14 hours and concentrated to dryness under reduced pressure. Mehtylene chloride (30 ml) was added to the residue, and the mixture was stirred well to form a suspension, to which 0.280 g of trichloromethyl carbonate and 1 ml of triethylamine were added in this sequence. After stirring at room temperature for 1 hour, the reaction mixture was concentrated to dryness under reduced pressure and subjected to flash column chromatography on silica gel (eluent: ethyl acetate, ethyl acetate-methanol=20:1) to give 0.099 g of the title compound. NMR (CDCl$_3$) δ: 4.55 (1H, dd, J=9.1 Hz, 6.3 Hz), 4.80 (1H, t, J=9.1 Hz), 5.38 (1H, ddd, J=9.1 Hz, 6.3 Hz, 1.2 Hz), 5.82 (1H, br), 6.95 (1H, d, J=4.3 Hz), 7.04 (1H, s), 7.49 (1H, d, J=4.3 Hz). MS (EI, DMSO, 270° C.): 209 (M$^+$).

Preparation 62

5-[(1R,2S)-1-(formylamino)-2-hydroxypropyl] imidazo[5,1-b]thiazole a) 5-[(1R,2S)-2-acetoxy-1-(trifluoroacetylamino)propyl] imidazo[5,1-b]thiazole Crude 2-[N-(tert-butoxycarbonyl-D-threonyl)amino]-methylthiazole was obtained from 3.0 g of N-tert-butoxycarbonyl-D-threonine, 2.59 g of 1-hydroxybenzotriazole, 3.96 g of dicyclohexylcarbodiimide and 1.56 g of 2-aminomethylthiazole in the same manner as in Preparation 16 (a).

The crude 2-[N-(tert-butoxycarbonyl-D-threonyl)amino]-methylthiazole was treated in the same manner as in Preparation 16 (b) to give crude 2-[N-trifluoroacetyl-D-threonyl) amino]-methylthiazole.

Then, 2.77 g of triethylamine and 2.6 ml of acetic anhydride were added to the solution of the crude 2-[N-trifluoroacetyl-D-threonyl)amino]methylthiazole in 20 ml of methylene chloride at 0° C., and the mixture was stirred at room temperature for 20 hours. To the reaction mixture was added 100 ml of methylene chloride, and the resulting mixture was washed with a saturated aqueous sodium hydrogen carbonate solution and saturated saline and dried with anhydrous magnesium sulfate. The methylene chloride solution was concentrated under reduced pressure, subjected to column chromatography on Sephadex LH-20 (50% aqueous methanol solution) and concentrated under reduced pressure. After the residue was treated in the same manner as in Preparation 16 (c) and extracted with 250 ml of methylene chloride, the organic layer was dried with anhydrous potassium carbonate and concentrated under reduced pressure. The residue thus obtained was purified by column chromatography on Sephadex LH-20 (chloroform-methanol=1:1) and flash chromatography on silica gel (ethyl acetate-n-hexane=1:3) to give 1.0 g of the title compound as pale yellow crystals. Yield 21%. NMR (CDCl$_3$) δ: 1.26 (3H, d, J=6 Hz), 2.07 (3H, s), 5.41 (1H, t, J=8 Hz), 5.61 (1H, quint, J=7 Hz), 6.91 (1H, d, J=4 Hz), 7.06 (1H, s), 7.52 (1H, d, J=4 Hz), 7.60 (1H, brs).

b) 5-[(1R,2S)-1-(formylamino)-2-hydroxypropyl] imidazo[5,1-b]thiazole

To the solution of 0.475 g of 5-[(1R,2S)-1-trifluoroacetylamino)-2-acetoxypropyl]imidazo[5,1-b] thiazole in 12 ml of dioxane-water=1:1 was added 0.2 g of sodium hydroxide, and the mixture was stirred at room temperature for 1.5 hours. The reaction mixture was concentrated under reduced pressure. The the residue were added 7 ml of water and 7 ml of methylene chloride, followed by the mixture of 0.6 ml of acetic anhydride and 1.2 ml of formic acid. The solution was then maintained at an alkaline pH and stirred for 3 hours. The reaction mixture was extracted with 200 ml of methylene chloride and washed with a saturated aqueous solution of potassium carbonate. The organic layer was dried with anhydrous magnesium sulfate, concentrated under reduced pressure and purified by flash chromatography on silica gel (ethyl acetate-hexane=2:1) to give 0.16 g of the title compound. Yield 53%. NMR (CDCl$_3$) δ: 1.31 (3H, d, J=6 Hz), 4.63 (1H, q, J=6 Hz), 5.29 (1H, d, J=9 Hz), 6.59 (1H, brd, J=9 Hz), 6.82 (1H, d, J=4 Hz), 6.97 (1H, s), 7.73 (1H, d, J=4 Hz), 8.34 (1H, s).

EXAMPLE 161

(6R,7R)-7-[(Z)-2-(5-Amino-1,2,4-thiadiazol-3-yl)-2-fluoromethoxyiminoacetamide]-3-[5-((R)-1-formylamino-2-hydroxyethyl)- imidazo[5,1-b]thiazolium-6-yl]methyl-3-cephem-4-carboxylate (internal salt)

0.048 g of the title compound was obtained from 0.224 g (0.30 mmol) of p-methoxybenzyl (6R,7R)-7-[(Z)-2-(5-trimethyl- amino-1,2,4-thiadiazol-3-yl)-2-fluoromethoxyiminoacetamide]-3-chloromethyl-3-cephem-4-carboxylic acid ester, 0.069 g (0.33 mmol) of 5-((R)-1-formylamino-2-hydroxyethyl)imidazo[5,1-b]-thiazole (Preparation 58) and 0.075 g (0.5 mmol) of sodium iodide in the same manner as in Example 74. NMR (D$_2$O) d ( $\underline{H}$DO=4.80): 3.24 (1H, d, J=17.7 Hz), 3.49 (1H, d, J=17.7 Hz), 4.10 (1H, dd, J=12.1 Hz, 4.7 Hz), 4.14 (1H, dd, J=12.1 Hz, 5.1 Hz), 5.25 (1H, d, J=4.8 Hz), 5.69 (1H, dd, J=5.1 Hz, 4.7 Hz), 5.82 (2H, d, J=54.4 Hz), 5.88 (1H, d, J=4.8 Hz), 7.57 (1H, d, J=4.4 Hz), 7.75 (1H, s), 8.02 (1H, d, J=4.4 Hz), 8.19 (1H, s)

EXAMPLE 162

(6R,7R)-7-[(Z)-2-(5-amino-1,2,4-thiadiazol-3-yl)-2-fluoromethoxyiminoacetamido]-3-(7-(formylamino) methylimidazo[5,1- b]thiazolium-6-yl)methyl-3-cephem-4-carboxylate (inner salt)

The title compound was obtained in an amount of 0.0229 g in the same manner as in Example 44 from 0.102 g (0.126 mole) of p-methoxybenzyl (6R,7R)-7-[(Z)-2-(5-tritylamino-1,2,4-thiadiazol- 3-yl)-2-fluoromethoxyiminoacetamido]-3-chloromethyl-3-cephem-4-carboxylate, 0.0274 g (0.151 mmole) of 7-(formylamino)methylimidazo[5,1-b]thiazole (Preparation 57) and 0.038 g (0.25 mmole) of sodium iodide. NMR (D$_2$O) δ ($\underline{H}$DO—4.80): 3.22 (1H, d, J=18.1 Hz), 3.60 (1H, d, J=18.1 Hz), 4.69 (1H, d, J=17.2 Hz), 4.76 (1H, d, J=17.2 Hz), 5.26 (1H, d, J=15.3 Hz), 5.31 (1H, d, J=4.7 Hz), 5.32 (1H, d, J=15.3 Hz), 5.85 (1H, d, J=54 Hz), 5.90 (1H, d, J=4.7 Hz), 7.55 (1H, d, J=4.1 Hz), 7.91 (1H, d, J=4.1 Hz), 8.27 (1H, s), 9.34 (1H, s).

EXAMPLE 163

(6R,7R)-7-[(Z)-2-(5-amino-1,2,4-thiadiazol-3-yl)-2-(2-fluoroethoxyimino)acetamido]-3-(7-(formylamino) methylimidazo[5,1- b]thiazolium-6-yl)methyl-3-cephem-4-carboxylate (inner salt)

The title compound was obtained in an amount of 0.0171 g in the same manner as in Example 44 from 0.087 g (0.105 mmole) of p-methoxybenzyl (6R,7R)-7-[(Z)-2-(5-tritylamino-1,2,4-thiadiazol- 3-yl)-2-(2-fluoroethoxyimino) acetamido]-3-chloromethyl-3-cephem-4-carboxylate, 0.0233 g (0.129 mmole) of 7-(formylamino)methylimidazo [5,1-b]thiazole (Preparation 57) and 0.032 g (0.21 mole) of sodium iodide. NMR (D$_2$O) δ ($\underline{H}$DO—4.80): 3.22 (1H, d, J=17.1 Hz), 3.60 (1H, d, J=17.1 Hz), 4.5–4.8 (4H, m), 5.22–5.36 (3H, m), 5.89 (2H, d, J=4.6 Hz), 7.55 (1H, d, J=4.1 Hz), 7.91 (1H, d, J=4.1 Hz), 8.27 (1H, s), 9.33 (1H, s).

EXAMPLE 164

(6R,7R)-7-[(Z)-2-(5-amino-1,2,4-thiadiazol-3-yl)-2-fluoromethoxyiminoacetamido]-3-[5-((R)-1-formylamino-2- hydroxyethyl]imidazo[5,1-b]thiazolium-6-yl)methyl-3-cephem-4-carboxylate (inner salt)

The title compound was obtained in an amount of 0.048 g in the same manner as in Example 74 from 0.224 g (0.30 mmole) of p-methoxybenzyl (6R,7R)-7-[(Z)-2-(5-trimethylamino-,1,2,4- thiadiazol-3-yl)-2-fluoromethoxyiminoacetamido]-3-chloromethyl-3-cephem-4-carboxylate, 0.224 g (0.30 mmole) of 5-((R)-1-formylamino-2-hydroxyethyl)-imidazo[5,1-b]thiazole (Preparation 58) and 0.069 g (0.33 mole) of sodium iodide. NMR (D$_2$O) δ ($\underline{H}$DO—4.80): 3.24 (1H, d, J=17.7 Hz), 3.49 (1H, d, J=17.7 Hz), 4.10 (1H, dd, J=12.1 Hz, 4.7 Hz), 4.14 (1H, dd, J=12.1 Hz, 5.1 Hz), 5.25 (1H, d, J=4.8 Hz), 5.69 (1H, dd, J=5.1 Hz, 4.7 Hz), 5.82 (2H, d, J=54.4 Hz), 5.88 (2H, d, J=4.8 Hz), 7.57 (1H, d, J=4.4 Hz), 7.75 (1H, s), 8.02 (1H, d, J=4.4 Hz), 8.19 (1H, s).

EXAMPLE 165

(6R,7R)-7-[(Z)-2-(5-amino-1,2,4-thiadiazol-3-yl)-2-methoxyiminoacetamido]-3-[5-((R)-1-ureidoethyl)imidazo [5,1- b]thiazolium-6-yl)methyl-3-cephem-4-carboxylate (inner salt)

The title compound was obtained in an Mount of 0.068 g in the same manner as in Example 74 from 0.166 g (0.30 mmole) of p-methoxybenzyl (6R,7R)-7-[(Z)-2-(5-tritylamino-1,2,4-thiadiazol-3- yl)-2-methoxyiminoacetamido]-3-chloromethyl-3-cephem-4-carboxylate, 0.069 g (0.33 mmole) of 5-((R)-1-ureidoethyl)imidazo[5,1-b]thiazole (Preparation 59) and 0.068 g (0.5 mmole) of sodium iodide. NMR (D$_2$O) δ ($\underline{H}$DO—4.80): 1.63 (3H, d, J=7.1 Hz), 3.19 (1H, d, J=17.6 Hz), 3.46 (1H, d, J=17.6 Hz), 4.05 (3H, s), 5.23 (1H, d, J=4.7 Hz), 5.25 (1H, d, J=15.9 Hz), 5.35 (1H, q, J=7.1 Hz), 5.45 (1H, d, J=15.3 Hz), 5.86.(1H, d, J=4.7 Hz), 7.55 (1H, d, J=4.4 Hz), 7.67 (1H, s), 8.01 (1H, d, J=4.4 Hz)

EXAMPLE 166

(6R,7R)-7-[(Z)-2-(5-amino-1,2,4-thiadiazol-3-yl)-2-methoxyiminoacetamido]-3-[5-((R)-1-formylamino-2- hydroxyethyl)imidazo[5,1-b]thiazolium-6-yl)methyl-3-cephem-4-carboxylate (inner salt)

The title compound was obtained in an amount of 0.034 g in the same manner as in Example 74 from 0.166 g (0.30 mmole) of p-methoxybenzyl (6R,7R)-7-[(Z)-2-(5-tritylamino-1,2,4-thiadiazol-3- yl)-2-methoxyiminoacetamido]-3-chloromethyl-3-cephem-4-carboxylate, 0.069 g (0.33 mmole) of 5-((R)-1-formylamino-2-hydroxyethyl)-imidazo[5,1-b]thiazole (Preparation 58) and 0.075 g (0.5 mmole) of sodium iodide. NMR (D$_2$O) δ (HDO—4.80): 3.24 (1H, d, J=17.6 Hz), 3.50 (1H, d, J=17.6 Hz), 4.05 (3H, s), 4.09 (1H, dd, J=12.2 Hz, 4.6 Hz), 4.14 (1H, dd, J=12.2 Hz, 5.2 Hz), 5.23 (1H, d, J=4.8 Hz), 5.43 (2H, s), 5.69 (1H, dd, J=5.2 Hz, 4.6 Hz), 5.87 (1H, d, J=4.8 Hz), 7.58 (1H, d, J=4.3 Hz), 7.76 (1H, s), 8.02 (1H, d, J=4.3 Hz), 8.19 (1H, s).

EXAMPLE 167

(6R,7R)-7-[(Z)-2-(5-amino-1,2,4-thiadiazol-3-yl)-2-methoxyiminoacetamido]-3-[5-((R)-2-oxo-4- oxazolidinyl)

imidazo[5,1-b]thiazolium-6-yl)methyl-3-cephem-4-carboxylate (inner salt)

The title compound was obtained in an amount of 0.023 g in the same manner as in Example 74 from 0.166 g (0.30 mole) of p-methoxybenzyl (6R,7R)-7-[(Z)-2-(5-tritylamino-1,2,4-thiadiazol-3- yl)-2-methoxyiminoacetamido]-3-chloromethyl-3-cepham-4-carboxylate, 0.069 g (0.33 mmole) of 5-((R)-2-oxo-4-oxazolidinyl)imidazo[5,1-b]thiazole (Preparation 61) and 0.075 g (0.5 mmole) of sodium iodide. NMR ($D_2O$) δ (HDO—4.80): 3.17 (1H, d, J=17.7 Hz), 3.55 (1H, d, J=17.7 Hz), 4.65 (1H, dd, J=9.9 Hz, 6.7 Hz), 4.95 (1H, t, J=9.9.Hz), 5.26 (1H, d, J=5.0 Hz), 5.29 (1H, d, J=15 Hz), 5.31 (1H, d, J=15 Hz), 5.82 (2H, d, J=54.4 Hz), 5.86 (1H, d, J=5.0 Hz), 6.03 (1H, dd, J=9.9 Hz, 6.7 Hz), 7.66 (1H, d, J=4.4 Hz), 8.81 (1H, s), 7.94 (1H, d, J=4.4 Hz).

EXAMPLE 168

(6R,7R)-7-[(Z)-2-(5-amino-1,2,4-thiadiazol-3-yl)-2-fluoroethoxyiminoacetamido]-3-[5-[(R)-1-(formyl-amino)-2-hydroxyethyl]imidazo[5,1-b]thiazolium-6-yl)methyl-3-cephem-4-carboxylate (inner salt)

To the solution of 0.25 g (0.3 mole) of p-methoxybenzyl (6R,7R)-7-[(Z)-2-(5-tritylamino-1,2,4-thiadiazol-3-yl)-2-fluoroethoxyiminoacetamido]-3-chloromethyl-3-cephem-4-carboxylate in 5 ml of acetone was added 0.17 g (1.4m mole) of sodium iodide, and the mixture was stirred in darkness at room temperature for 1 hour. After the acetone was removed under reduced pressure, the residue was dissolved in ethyl acetate and washed with a small amount of a saturated aqueous solution of sodium thiosulfate, and then saturated saline. The organic layer was dried over anhydrous magnesium sulfate and concentrated under reduced pressure. The residue thus obtained was dissolved in 3 ml of DMF. A solution of 0.07 g of 5-[(R)-1-(formylamino)-2-hydroxyethyl]imidazo[5,1-b]thiazole (Preparation 58) in 1 ml of DMF was added to the above solution, and the mixture was stirred in darkness at room temperature overnight. To the reaction mixture was added 20 ml of a 10% aqueous sodium trifluoroacetate solution, and the resulting sediments were collected by centrifugation, washed twice with a 10% aqueous sodium trifluoroacetate solution and dried in vacuum for 1 hour. To the residue thus obtained were added under ice-cooling 1 ml of anisole and 3 ml of trifluoroacetic acid, and the mixture was stirred for 1 hour. Twenty milliliter of isopropyl ether was added to the reaction mixture, and the resulting solids were sedimented by centrifugation. The precipitate were washed with isopropyl ether and then dried in vacuum. A 5% aqueous sodium hydrogen carbonate solution was added to the product to neutralize and dissolve it. The resulting solution was purified by column chromatography on Diaion HP-20 resin (eluent: 200 ml of water, 50 ml of 5% methanol-water, 50 ml of 10% methanol-water, 100 ml of 15% methanol-water, 100 ml of 20% methanol-water, 100 ml of 25% methanol-water, 100 ml of 30% methanol-water, 100 ml of 40% methanol-water). The fraction containing the aimed product was concentrated and lyophilized to give 0.016 g of the title compound. Yield 8%. NMR ($D_2O$) δ: 3.15 (1H, d, J=17 Hz), 3.41 (1H, d, J=17 Hz), 3.97–4.06 (2H, m), 4.40–4.51 (1H, m), 4.58–4.68 (1H, m), 5.15 (1H, d, J=5 Hz), 5.34 (2H, brs), 5.59–5.61 (1H, m), 5.78 (1H, d, J=4 Hz), 7.48 (1H, d, J=4 Hz), 7.66 (1H, s), 7.91–7.94 (1H, m), 8.05 (1H, s).

EXAMPLE 169

(6R,7R)-7-[(Z)-2-(5-amino-1,2,4-thiadiazol-3-yl)-2-fluoromethoxyiminoacetamido]-3-[5-(S)-1-(formylamino)-2- hydroxyethyl]imidazo[5,1-b]thiazolium-6-yl)methyl-3-cephem-4-carboxylate (inner salt)

The title compound was obtained in an amount of 0.038 g (20%) in the same manner as in Example 74 from 0.175 g (0.3 mmole) of p-methoxybenzyl; (6R,7R)-7-[(Z)-2-(5-amino-1,2,4-thiadiazol-3-yl)-2-fluoromethoxyiminoacetamido]-3-chloromethyl-3-cephem-4-carboxylate, 0.065 g (0.3 mmole) of 5-(S)-1-(formylamino)-2-hydroxyethyl]imidazo[5,1-b]thiazole (Preparation 60 ) and 0.17 g (1.14 mole) of sodium iodide. NMR ($D_2O$) δ: 3.13 (1H, d, J=18 Hz), 3.48 (1H, d, J=18 Hz), 3.98–4.00 (2H, m), 5.17 (1H, d, J=5 Hz), 5.24 (1H, d, J=15 Hz), 5.30 (1H, d, J=15 Hz), 5.59 (1H, t, J=5 Hz), 5.63 (1H, s), 5.77 (1H, d, J=5 Hz), 5.81 (1H, s), 7.47 (1H, d, J=4 Hz), 7.71 (1H, s), 7.90 (1H, d, J=4 Hz), 8.11 (1H, s).

EXAMPLE 170

(6R,7R)-7-[(Z)-2-(5-amino-1,2,4-thiadiazol-3-yl)-2-ethoxyiminoacetamido]-3-[5-(S)-1-(formylamino)-2-hydroxyethyl]imidazo[5,1-b]thiazolium-6-yl)methyl-3-cephem-4-carboxylate (inner salt)

The title compound was obtained in an amount of 0.032 g (17%) in the same manner as in Example 1 from 0.17 g (0.3 mole) of p-methoxybenzyl (6R,7R)-7-[(Z)-2-(5-amino-1,2,4-thiadiazol-3-yl)-2- ethoxyiminoacetamido]-3-chloromethyl-3-cephem-4-carboxylate, 0.07 g (0.3 mmole) of 5-(S)-1-(formylamino)-2-hydroxyethyl]imidazo[5,1-b]thiazole (Preparation 60) and 0.18 g (1.2 mole) of sodium iodide. NMR ($D_2O$) δ: 1.19 (3H, t, J=7 Hz), 3.13 (1H, d, J=18 Hz), 3.47 (1H, d, J=18 Hz), 3.99 (2H, dd, J=4 Hz, 1 Hz), 4.22 (1H, q, J=7 Hz), 5.16 (1H, d, J=5 Hz), 5.24 (1H, d, J=15 Hz), 5.31 (1H, d, J=15 Hz), 5.58 (1H, t, J=4 Hz), 5.75 (1H, d, J=5 Hz), 7.47 (1H, d, J=4 Hz), 7.71 (1H, s), 7.90 (1H, d, J=4 Hz), 8.11 (1H, s).

EXAMPLE 171

(6R,7R)-7-[(Z)-2-(5-amino-1,2,4-thiadiazol-3-yl)-2-fluoromethoxyiminoacetamido]-3-[5-[(1R,2S)-1-(formylamino)-2- hydroxypropyl]imidazo[5,1-b]thiazolium-6-yl)methyl-3-cephem-4-carboxylate (inner salt)

The title compound was obtained in an amount of 0.049 g (25%) in the same manner as in Example 1 from 0.175 g (0.31 mmole) of p-methoxybenzyl (6R,7R)-7-[(Z)-2-(5-amino-1,2,4-thiadiazol-3-yl)-2-fluoromethoxyiminoacetamido]-3-chloromethyl-3-cephem-4-carboxylate, 0.07 g (0.31 mmole) of 5-[(1R,2S)-1-(formylamino)-2-hydroxypropyl]imidazo[5,1-b]thiazole (Preparation 62) and 0.186 g (1.2 mole) of sodium iodide. NMR ($D_2O$) δ: 1.25 (3H, d, J=6 Hz), 3.14 (1H, d, J=18 Hz), 3.39 (1H, d, J=18 Hz), 4.24–4.28 (1H, m), 5.15 (1H, d, J=5 Hz), 5.37 (2H, brs), 5.47 (1H, d, J=3 Hz), 5.64 (1H, brs), 5.78–5.82 (2H, m), 7.46 (1H, d, J=4 Hz), 7.64 (1H, s), 7.92 (1H, d, J=4 Hz), 8.13 (1H, s).

EXAMPLE 172

(6R,7R)-7-[(Z)-2-(5-amino-1,2,4-thiadiazol-3-yl)-2-ethoxyiminoacetamido]-3-[5-[(1R,2S)-1-(formylamino)-2-hydroxypropyl]imidazo[5,1-b]thiazolium-6-yl)methyl-3-cephem-4-carboxylate (inner salt)

The title compound was obtained in an amount of 0.046 g (31%) in the same manner as in Example 1 from 0.176 g (0.31 mole) of p-methoxybenzyl (6R,7R)-7-[(Z)-2-(5-amino-1,2,4-thiadiazol-3-yl)- -ethoxyiminoacetamido]-3-chloromethyl-3-cephem-4-carboxylate, 0.070 g (0.31 mmole) of 5-[(1R,2S)-1-(formylamino)-2-hydroxypropyl]

imidazo[5,1-b]thiazole (Preparation 62) and 0.186 g (1.2 mmole) of sodium iodide. NMR (D$_2$O) δ: 1.19–1.27 (6H, m), 3.15 (1H, d, J=18 Hz), 3.39 (1H, d, J=18 Hz), 4.20–4.31 (3H, m), 5.30 (1H, d, J=5 Hz), 5.37 (2H, brs), 5.47 (1H, d, J=4 Hz), 5.78 (1H, d, J=5 Hz), 7.47 (1H, d, J=4 Hz), 7.65 (1H, s), 7.93 (1H, d, J=4 Hz), 8.14 (1H, s).

EXAMPLE 173

(6R,7R)-7-[(Z)-2-(5-amino-1,2,4-thiadiazol-3-yl)-2-ethoxyiminoacetamido]-3-[5-((R)-1-(formylamino)-2-hydroxy) ethylimidazo[5,1-b]thiazolium-6-yl ]methyl-3-cephem-4-carboxylate (inner salt)

The title compound was obtained in an amount of 0.046 g in the same manner as in Example 25 from 0.161 g of p-methoxybenzyl (6R,7R)-7-[(Z)-2-(5-amino-1,2,4-thiadiazol-3-yl)-2- ethoxyiminoacetamido]-3-chloromethyl-3-cephem-4-carboxylate, 0.061 g of 5-((R)-1-formylamino-2-hydroxy)ethylimidazo[5,1-b]thiazole (Preparation 60) and 0.047 g of sodium iodide. NMR (D$_2$O) δ (HDO—4.80): 1.26 (1H, t, J=7 Hz), 3.20 (1H, d, J=18 Hz), 3.46 (1H, d, J=18 Hz), 4.0–4.2 (1H, m), 4.29 (2H, q, J=7 Hz), 5.20 (1H, d, J=5 Hz), 5.39 (2H, brs), 5.64 (1H, brs), 5.30 (1H, d, J=15 Hz), 5.83 (2H, d, J=5 Hz), 7.55 (1H, d, J=4 Hz), 7.71 (1H, s), 7.97 (1H, d, J=4 Hz), 8.14 (1H, s).

Preparation 63

5-[1-(formylamino)-1-methylethyl]imidazo[5,1-b] thiazole a) 2-[[[(1-methyl-1-[(trifluoroacetyl)amino]propanoyl] amino]-methyl]thiazole To 2.5 g (0.024m mole) of 2-amino-2-methylpropanoic acid was added under ice-cooling 17 ml (0.122 mole) of triethylamine, followed by 15 ml (0.14 mole) of ethyl trifluoroacetate, and the mixture was stirred for 1 hour. Six milliliter (0.05 mole) of ethyl trifluoroacetate was added, and the mixture was further stirred for 20 hours. The reaction mixture was concentrated to dryness under reduced pressure. To the solution of the residue thus obtained in methylene chloride (20 ml) was added 5 g (0.036 mole) of 1-hydroxybenzotriazole at a temperature of 3° C., followed by 38 ml (0.036 mole) of 1.0M dicyclohexylcarbodiimide and 2.85 g (0.025 mole) of 2-aminomethylthiazole. The mixture was treated in the same manner as in Preparation 16 (a) to give 4.9 g of the title compound. Yield 66%. NMR (CDCl$_3$) δ: 1.71 (6H, s), 4.80 (2H, d, J=5.6 Hz), 7.03 (1H, brs), 7.33 (1H, d, J=3.3 Hz), 7.72 (1H, d, J=3.3 Hz), 7.81 (1H, brs).

b) 5-[1-methyl-1-[(trifluoroacetyl)amino]ethyl]imidazo [5,1-b]thiazole

To 1.8 g (0.6 mmole) of 2-[[[(1-methyl-1-[ (trifluoroacetyl)amino]propanoyl]-amino]methyl]thiazole was added under ice-cooling 20 ml of phosphorus oxychloride, and the mixture was stirred at 110° C. for 19 hours. The reaction mixture was concentrated under reduced pressure, and the residue was dissolved in the mixture of 100 ml of water and 100 ml of methylene chloride. Furthermore, 60 g of sodium hydrogen carbonate was added, and insolubles were removed by filtration. The methylene, chloride layer was separated, and the aqueous layer was washed with 50 ml of methylene chloride. The combined methylene chloride layer was dried with anhydrous magnesium sulfate and concentrated to dryness under reduced pressure. The residue was purified by flash chromatography on silica gel (ethyl acetate-chloroform=1:2) to give 1.14 g of the title compound. Yield 67%. NMR (CDCl$_3$) δ: 1.90 (6H, s), 6.91 (1H, d, J=4.3 Hz), 7.01 (1H, s), 7.45 (1H, d, J=4.3 Hz), 8.38 (1H, brs).

c) 5-[1-(formylamino)-1-methylethyl]imidazo[5,1-b] thiazole

To the solution of 1 g (3.6 mole) of 5-[1-methyl-1-[ (trifluoroacetyl)amino]-ethyl]imidazo[5,1-b]thiazole in 3 ml of methanol was added 0.72 g (0.018 mole) of sodium hydroxide, and the mixture was stirred at 50° C. for 10 hours. The reaction mixture was concentrated, and the residue thus obtained was dissolved in 100 ml of ethyl acetate and washed twice with 100 ml of a saturated aqueous potassium hydrogen carbonate solution. The organic layer was dried over anhydrous magnesium sulfate and concentrated to dryness to give 0.74 g of crude 5-(1-amino-1-methylethyl)imidazo[5,1-b]thiazole. The mixture of 0.74 g of the crude product, 3 ml of formic acid and 1.5 ml of acetic anhydride was stirred in the absence of solvents for 3 hours and treated in the same manner as in Preparation 15 (c) to give 0.63 g of the title compound. Yield 83%. NMR (CDCl$_3$) δ: 1.74 (6H, s), 6.95 (1H, s), 7.11 (1H, d, J=4.8 Hz), 7.71 (1H, d, J=4.8 Hz), 8.01 (1H, s).

Preparation 64

5-[(1R)-1-(formylamino)-2-methylpropyl]imidazo[5, 1-b]thiazole a) 2-[(N-tert-butoxycarbonyl-D-valyl)amino] methylthiazole The title compound was obtained in an amount of 1.603 g (quantitatively) in the same manner as in Preparation 16 (a) from 1.086 g of N-tert-butoxycarbonyl-D-valine, 0.743 g of 1-hydroxybenzotriazole, 1.135 g of dicyclohexylcarbodiimide and 0.571 g of 2-aminomethylthiazole. NMR (CDCl$_3$) δ: 0.92 (3H, d, J=6.8 Hz), 0.97 (3H, d, J=6.9 Hz), 1.43 (9H, s), 2.1–2.3 (1H, m), 3.98 (1H, dd, J=8.5 Hz, 6.0 Hz), 4.78 (2H, d, J=5.8 Hz), 5.0–5.1 (1H, br), 6.85–6.95 (1H, br), 7.29 (1H, d, J=3.3 Hz), 7.71 (1H, d, J=3.3 Hz).

b) 2-[(N-trifluoroacetyl-D-valyl)amino]methylthiazole

The title compound was obtained in an amount of 1.423 g (92%) by treating 1.599 g of 2-[(N-tert-butoxycarbonyl-D-valyl)amino]methylthiazole in the same manner as in Preparation 16 (b). NMR (CDCl$_3$) δ: 0.98 (3H, d, J=6.8 Hz), 0.99 (3H, d, J=6.8 Hz), 2.1–2.25 (1H, m), 4.45 (1H, dd, J=8.7 Hz, 6.1 Hz), 4.76 (1H, dd, J=16.2 Hz, 5.5 Hz), 4.84 (1H, dd, J=16.2 Hz, 5.6 Hz),), 6.65–6.8 (1H, br), 7.1–7.2 (1H, br), 7.33 (1H, d, J=3.3 Hz), 7.73 (1H, d, J=3.3 Hz).

c) 5-[(1R)-2-methyl-1-(trifluoroacetylamino)propyl] imidazo[5,1-b]thiazole

The title compound was obtained in an amount of 1.037 g (77%) by treating 1.420 g of 2-[(N-trifluoroacetyl-D-valyl)amino]methylthiazole in the same manner as in Preparation 16 (c). NMR (CDCl$_3$) δ: 0.93 (3H,d, J=6.7 Hz), 1.05 (3H, d, J=6.8 Hz), 2.35–2.55 (1H, m), 5.08 (1H, t, J=8.6 Hz), 6.87 (1H, d, J=4.3 Hz), 7.04 (1H, s), 7.49 (1H, d, J=4.3 Hz), 7.6–7.75 (1H, br).

d) 5-[(1R)-1-(formylamino)-2-methylpropyl]imidazo[5, 1-b]thiazole

The title compound was obtained in an amount of 0.649 g (82%) by treating 1.028 g of 5-[(1R)-2-methyl-1-(trifluoroacetylamino)propyl]imidazo [5, 1-b]thiazole in the same manner as in Preparation 16 (d). NMR (CDCl$_3$) δ: 0.96 (3H,d, J=6.7 Hz), 1.06 (3H, d, J=6.8 Hz), 2.3–2.5 (1H, m), 5.22 (1H, t, J=8.8 Hz), 6.55–5.65(1H, br), 6.82 (1H, d, J=4.3 Hz), 7.01 (1H, s), 7.51 (1H, d, J=4.3 Hz), 8.24 (1H, s).

EXAMPLE 174

(6R,7R)-7-[(Z)-2-(5-amino-1,2,4-thiadiazol-3-yl)-2-fluoromethoxyiminoacetamido]-3-[5-[(1-formylamino)-1- methylethyl]imidazo[5,1-b]thiazolium-6-yl)methyl-3-cephem-4-carboxylate (inner salt)

The title compound was obtained in an amount of 17 g (7%) in the same manner as in Example 74 from 0.325 g (0.4 mmole) of p-methoxybenzyl (6R,7R)-7-[(Z)-2-(5-amino-1,2,4-thiadiazol-3-yl)-2- fluoromethoxyiminoacetamido]-3-chloromethyl-3-cephem-4-carboxylate, 0.092 g (0.4 mmole) of 5-[1-(formylamino)-1-methylethyl]imidazo-[5,1-b]-thiazole (Preparation 63) and 0.180 g (1.2 mmole) of sodium iodide. NMR ($D_2O$) δ: 1.97 (6H, s), 3.15 (1H, d, J=18 Hz), 3.57 (1H, d, J=18 Hz), 5.28 (1H, d, J=4.4 Hz), 5.38 (1H, brs), 5.74 (1H, brs), 5.89 (2H, d, J=4.4 Hz), 5.92 (1H, s), 7.57 (1H, d, J=4.7 Hz), 7.67 (1H, s), 8.09 (1H, s), 8.11 (1H, d, J=4.7 Hz).

EXAMPLE 175

(6R,7R)-7-[(Z)-2-(5-amino-1,2,4-thiadiazol-3-yl)-2-fluoromethoxyiminoacetamido]-3-[5-[(1R)-1-(formylamino)-2- methylpropyl]imidazo[5,1-b]thiazolium-6-yl)methyl-3-cephem-4-carboxylate (inner salt)

The title compound was obtained in an amount of 0.104 g in the same manner as in Example 74 from 0.407 g (0.50 mmole) of p-methoxybenzyl (6R,7R)-7-[(Z)-2-(5-tritylamino-1,2,4-thiadiazol-3-yl)-2-fluoromethoxyiminoacetamido]-3-chloromethyl-3-cephem-4-carboxylate, 0.0134 g (0.60m mole) of 5-[(1R)-1-(formylamino)-2-methylpropyl]-imidazo-[5,1-b]-thiazole (Preparation 64) and 0.120 g (0.8 mmole) of sodium iodide. NMR ($D_2O$) δ (HDO=4.80): 0.81 (3H, d, J=6.6 Hz), 1.17 (3H, d, J=6.5 Hz), 2.4–2.6 (1H, m), 3.27 (1H, d, J=17.6 Hz), 3.45 (1H, d, J=17.6 Hz), 5.17(1H, d, J=10.2 Hz), 5.23 (1H, d, J=4.8 Hz), 5.33 (1H, d, J=15.1 Hz), 5.59 (1H, d, J=15.1 Hz), 5.82 (2H, d, J=54.3 Hz), 7.87 (1H, d, J=4.8 Hz), 7.61 (1H, d, J=4.4 Hz), 7.71(1H, s), 7.97 (1H, d, J=4.4 Hz), 8.14 (1H, s).

The structures of the compounds obtained in the above Examples are shown in the following Tables.

TABLE 1

| | X | $R^1$ | $R^2$ | $R^3$ | $R^4$ | $R^5$ | n |
|---|---|---|---|---|---|---|---|
| 1 | CH | $CH_3$ | H | H | H | H | 0 |
| 2 | CH | —CHCOOH (S)\| $CH_3$ | H | H | H | H | 0 |
| 3 | CH | $CH_3$ \| —CHCOOH \| $CH_3$ | H | H | H | H | 0 |
| 4 | CH | $CH_3$ | H | $CH_3$ | H | H | 0 |
| 5 | CH | —CHCOOH (S)\| $CH_3$ | H | $CH_3$ | H | H | 0 |
| 6 | CH | $CH_3$ | H | H | $CH_3$ | H | 0 |
| 7 | CH | —CHCOOH (S)\| $CH_3$ | H | H | $CH_3$ | H | 0 |
| 8 | CH | $CH_3$ | H | $C_2H_5$ | H | H | 0 |
| 9 | CH | —CHCOOH (S)\| $CH_3$ | H | $C_2H_5$ | H | H | 0 |
| 10 | CH | $CH_3$ | $CH_3$ | $CH_3$ | H | H | 0 |
| 11 | CH | —CHCOOH (S)\| $CH_3$ | $CH_3$ | $CH_3$ | H | H | 0 |
| 12 | CH | $CH_3$ | —$CH_2$—$CH_2$—$CH_2$— | | H | H | 0 |
| 13 | CH | —CHCOOH (S)\| $CH_3$ | —$CH_2$—$CH_2$—$CH_2$— | | H | H | 0 |
| 14 | CH | —CHCOOH (S)\| $CH_3$ | H | H | $COOC_2H_5$ | H | 0 |
| 15 | CH | —CHCOOH (S)\| $CH_3$ | H | H | $CH_2OH$ | H | 0 |
| 16 | CH | $CH_3$ | $CH_3$ | H | H | H | 0 |

TABLE 1-continued

| | X | $R^1$ | $R^2$ | $R^3$ | $R^4$ | $R^5$ | n |
|---|---|---|---|---|---|---|---|
| 17 | CH | —CHCOOH (S)\|CH$_3$ | CH$_3$ | H | H | H | O |
| 18 | CH | —CHCOOH (S)\|CH$_3$ | H | COOC$_2$H$_5$ | H | H | O |
| 19 | CH | —CHCOOH (S)\|CH$_3$ | H | CH$_2$OH | H | H | O |
| 20 | CH | —CHCOOH (S)\|CH$_3$ | H | CH$_2$F | H | H | O |
| 21 | CH | —CHCOOH (S)\|CH$_3$ | H | CONHCH$_3$ | H | H | O |
| 22 | CH | —CHCOOH (S)\|CH$_3$ | H | CN | H | H | O |
| 23 | CH | CH$_3$ | H | H | H | CH$_3$ | O |
| 24 | CH | —CHCOOH (S)\|CH$_3$ | H | H | H | CH$_3$ | O |
| 25 | CH | —CHCOOH (S)\|CH$_3$ | H | CONH$_2$ | H | H | O |
| 26 | CH | —CHCOOH (S)\|CH$_3$ | H | CONH$_2$ | CH$_3$ | H | O |
| 27 | CH | CH$_3$ | H | CONH$_2$ | H | H | O |
| 28 | N | —CHCOOH (S)\|CH$_3$ | H | CONH$_2$ | H | H | O |
| 29 | CH | —CHCOOH (S)\|CH$_3$ | H | CONH$_2$ | CH$_2$OH | H | O |
| 30 | N | CH$_3$ | H | H | H | H | O |
| 31 | N | CH$_3$ | H | H | CH$_2$OH | H | O |
| 32 | N | CH$_3$ | H | CH$_3$ | H | H | O |
| 33 | N | CH$_3$ | H | H | CH$_3$ | H | O |
| 34 | N | CH$_3$ | H | H | CH$_2$NHCHO | H | O |
| 35 | N | CH$_3$ | H | H | H | CH$_3$ | O |
| 36 | N | CH$_3$ | H | CH$_2$OH | H | H | O |
| 37 | N | CH$_3$ | H | CH$_2$F | H | H | O |
| 38 | N | CH$_3$ | H | CONHCH$_3$ | H | H | O |
| 39 | N | CH$_3$ | H | CN | H | H | O |
| 40 | N | CH$_3$ | H | H | CH$_2$COOCH$_3$ | H | O |
| 41 | N | CH$_3$ | H | H | CH$_2$CONH$_2$ | H | O |
| 42 | N | CH$_3$ | CH$_3$ | CH$_3$ | H | H | O |
| 43 | N | CH$_3$ | CH$_3$ | H | H | H | O |
| 44 | N | CH$_3$ | H | CONH$_2$ | H | H | O |
| 45 | N | CH$_3$ | H | CONH$_2$ | CH$_3$ | H | O |
| 46 | N | CH$_3$ | H | CONH$_2$ | CH$_2$OH | H | O |
| 47 | N | C$_2$H$_5$ | H | CONH$_2$ | H | H | O |
| 48 | N | CH$_2$CH$_2$F | H | CONH$_2$ | H | H | O |
| 49 | N | C$_2$H$_5$ | H | H | CH$_2$NHCHO | H | O |
| 50 | CH | CH$_3$ | H | H | CH$_2$NHCHO | H | O |
| 51 | CH | H | H | H | CH$_3$ | H | O |
| 52 | N | CH$_3$ | H | H | CH$_2$NH$_2$ | H | O |
| 53 | N | CH$_3$ | H | CH$_3$ | CH$_2$OH | H | O |
| 54 | N | CH$_3$ | H | CH$_3$ | CH$_2$NHCHO | H | O |
| 55 | N | C$_2$H$_5$ | H | CH$_3$ | CH$_2$NHCHO | H | O |
| 56 | N | C$_2$H$_5$ | H | (5-)—CH$_2$—NH—CO—(3-) | | H | O |

TABLE 1-continued

| | X | R¹ | R² | R³ | R⁴ | R⁵ | n |
|---|---|---|---|---|---|---|---|
| 57 | N | C₂H₅ | H | H | —CHNHCHO (S)\|CH₃ | H | O |
| 58 | N | C₂H₅ | H | H | —CHNHCHO (R)\|CH₃ | H | O |
| 59 | N | CH₂CH₂OH | H | H | H | H | O |
| 60 | N | C₂H₅ | H | H | CH₂NHCOCF₃ | H | O |
| 61 | N | C₂H₅ | H | CONH₂ | CH₂NHCHO | H | O |
| 62 | N | C₂H₅ | H | H | CONH₂ | H | O |
| 63 | N | CH₂CH₂OH | H | H | CH₂NHCHO | H | O |
| 64 | N | C₂H₅ | H | H | CH=CHCONH₂ | H | O |
| 65 | N | CH₂CH₂OH | H | CONH₂ | H | H | O |
| 66 | N | CH₂F | H | H | —CHNHCHO (R)\|CH₃ | H | O |
| 67 | N | CH₃ | H | H | CH₂CH₂OH | H | O |
| 68 | N | CH₃ | H | H | CH₂CH₂NHCHO | H | O |
| 69 | N | CH₃ | H | H | COOH | H | O |
| 70 | N | C₂H₅ | H | H | CH₂CH₂OH | H | O |
| 71 | N | C₂H₅ | H | H | CH₂CH₂NHCHO | H | O |
| 72 | N | C₂H₅ | H | H | CN | H | O |
| 73 | N | C₂H₅ | H | H | NHCOCH₃ | H | O |
| 74 | N | C₂H₅ | H | H | CH₂NHCONH₂ | H | O |
| 75 | N | C₂H₅ | H | H | CH₂OCH₃ | H | O |
| 76 | N | CH₂F | H | H | CH₂CH₂OH | H | O |
| 77 | N | CH₂F | H | H | CH₂NHCONH₂ | H | O |
| 78 | N | C₂H₅ | H | H | CH(OCH₃)₂ | H | O |
| 79 | N | C₂H₅ | H | H | CHO | H | O |
| 80 | N | C₂H₅ | H | H | CH₃\|CH₂N—CHO | H | O |
| 81 | N | C₂H₅ | H | H | CH₃\|CH₂NCONH₂ | H | 0 |
| 82 | N | CH₂F | H | H | CHO | H | O |
| 83 | N | C₂H₅ | H | H | H | CH₂OH | O |
| 84 | N | CH₂CH₂F | H | H | CHO | H | O |
| 85 | N | CH(CH₃)₂ | H | H | H | H | O |
| 86 | N | CH(CH₃)₂ | H | CONH₂ | H | H | O |
| 87 | N | CH(CH₃)₂ | H | H | CH₂NHCHO | H | O |
| 88 | N | CH₂CH₂CH₃ | H | H | H | H | O |
| 89 | N | CH₂CH₂CH₃ | H | H | CH₂NHCHO | H | O |
| 90 | N | CH₂CH₂CH₃ | H | CONH₂ | H | H | O |
| 91 | N | CH₂CH₂CH₃ | H | H | CH₂CH₂OH | H | O |
| 92 | N | CH₂CH₃ | H | CH₃ | H | H | O |
| 93 | N | CH₂CH₃ | H | CH₂OCONH₂ | H | H | O |
| 94 | N | CH₂CH₂F | H | CH₂OCONH₂ | H | H | O |
| 95 | N | CH₂F | H | CH₂OCONH₂ | H | H | O |
| 96 | N | CH₂CH₃ | H | H | SCH₃ | H | O |
| 97 | N | CH₂F | H | H | SCH₃ | H | O |
| 98 | N | H | H | CONH₂ | H | H | O |
| 99 | N | CH₃ | H | CH₂NHCHO | H | H | O |
| 100 | N | CH₃ | H | CH₂NH₂ | H | H | O |
| 101 | N | CH₂CHF₂ | H | CONH₂ | H | H | O |
| 102 | N | C₂H₅ | H | CH₂F | H | H | O |
| 103 | N | CH₂CH₂F | H | CH₂F | H | H | O |
| 104 | N | CH₂F | H | CONH₂ | H | H | O |
| 105 | N | CH₂F | H | H | CH₂NHCHO | H | O |
| 106 | CH | CH₂F | H | H | H | H | O |
| 107 | CH | CH₂F | H | CONH₂ | H | H | O |
| 108 | CH |  | H | H | H | H | O |

TABLE 1-continued

| | X | R¹ | R² | R³ | R⁴ | R⁵ | n |
|---|---|---|---|---|---|---|---|
| 109 | CH |  | H | CONH₂ | H | H | O |
| 110 | N | CH₂CH₂CH₂F | H | H | H | H | O |
| 111 | N | CH₂CH₂CH₂F | H | CONH₂ | H | H | O |
| 112 | N |  | H | H | H | H | O |
| 113 | N |  | H | CONH₂ | H | H | O |
| 114 | N | C₂H₅ | H | CH₂OH | H | H | O |
| 115 | N | CH₂F | H | CH₂OH | H | H | O |
| 116 | N | CH₂CH₂F | H | CH₂OH | H | H | O |
| 117 | N |  | H | CH₂OH | H | H | O |
| 118 | N | CH₂F | H | CHO | H | H | O |
| 119 | N | CH₂F | H | CHF₂ | H | H | O |
| 120 | N | CH₂F | H | CH=N—OH | H | H | O |
| 121 | N | CH₂F | H | C₂H₅ | H | H | O |
| 122 | N | CH₂F | H | CH₂OCOCH₃ | H | H | O |
| 123 | N | CH₂F | H | CH₂OCH₃ | H | H | O |
| 124 | N | CH₂F | H | CN | H | H | O |
| 125 | N | CH₂F | CONH₂ | CH₃ | H | H | O |
| 126 | N | C₂H₅ | CONH₂ | CH₃ | H | H | O |
| 127 | N | CH₂CH₂F | CONH₂ | CH₃ | H | H | O |
| 128 | N | CH₂F | H | H | H | H | O |
| 129 | N | C₂H₅ | H | CH₂CONH₂ | H | H | O |
| 130 | N | CH₂CH₂F | H | CH₂CONH₂ | H | H | O |
| 131 | N | CH₂F | H | CH₂CONH₂ | H | H | O |
| 132 | N | CH₂F | H | CH₂CH₂OH | H | H | O |
| 133 | N | CH₂CH₂F | H | H | H | H | O |
| 134 | N | CH₂CH₂F | H | H | CH₂OH | H | O |
| 135 | N | C₂H₅ | H | H | H | H | O |
| 136 | N | C₂H₅ | H | H | CH₂OH | H | O |
| 137 | CH | CH₂CH₂OH | H | H | H | H | O |
| 138 | N | CH₂CH₂F | H | H | CH₂NHCHO | H | O |
| 139 | CH | C₂H₅ | H | H | H | H | O |
| 140 | CH | C₂H₅ | H | H | CH₂NHCHO | H | O |
| 141 | CH | CH₂CH₂F | H | H | CH₂NHCHO | H | O |
| 142 | CH | CH₂CH₂F | H | H | H | H | O |
| 143 | CH | CH₂CH₂F | H | CONH₂ | H | H | O |
| 144 | CH | C₂H₅ | H | CONH₂ | H | H | O |
| 145 | CH | CH₂F | H | H | CH₂NHCHO | H | O |
| 146 | CH | CH₂CONH₂ | H | H | H | H | O |
| 147 | N | CH₂CONH₂ | H | H | H | H | O |
| 148 | CH |  | H | H | CH₂NHCHO | H | O |
| 149 | N | CH₂F | H | CH₃ | H | H | O |
| 150 | N |  | H | H | CH₂NHCHO | H | O |
| 151 | N | CH₂CH₂F | H | CH₃ | H | H | O |
| 152 | CH | —CHCOOH (S)\|CH₃ | H | H | CH₂NHCHO | H | O |

TABLE 1-continued

| | X | R¹ | R² | R³ | R⁴ | R⁵ | n |
|---|---|---|---|---|---|---|---|
| 153 | N | CH₂F | H | H | CH₂OCOCH₃ | H | 0 |
| 154 | N | C₂H₅ | H | H | CH₂OCOCH₃ | H | 0 |
| 155 | N | CH₂CN | H | H | H | H | 0 |
| 156 | N | CH₂CN | H | H | CH₂NHCHO | H | 0 |
| 157 | N | CH₂CN | H | CONH₂ | H | H | 0 |
| 158 | N | CH₃ | H | H | —CHNHCHO(R)\|CH₃ | H | 0 |
| 159 | N | CH₂CH₂F | H | H | —CHNHCHO(R)\|CH₃ | H | 0 |
| 160 | N | CH₂F | H | H | —CHNHCHO(S)\|CH₃ | H | 0 |
| 161 | N | CH₂CH₃ | H | H | H | CH₂NHCHO | 0 |
| 162 | N | CH₂F | H | H | H | CH₂NHCHO | 0 |
| 163 | N | CH₂CH₂F | H | H | H | CH₂NHCHO | 0 |
| 164 | N | CH₂F | H | H | —CHNHCHO(R)\|CH₂OH | H | 0 |
| 165 | N | CH₃ | H | H | —CHNHCONH₂(R)\|CH₃ | H | 0 |
| 166 | N | CH₃ | H | H | —CHNHCHO\|CH₂OH | | 0 |
| 167 | N | CH₃ | H | H | 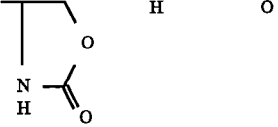 | H | 0 |
| 168 | N | CH₂CH₂F | H | H | —CHNHCHO(R)\|CH₂OH | H | 0 |
| 169 | N | CH₂F | H | H | —CHNHCHO(S)\|CH₂OH | H | 0 |
| 170 | N | CH₂CH₃ | H | H | —CHNHCHO(S)\|CH₂OH | H | 0 |
| 171 | N | CH₂F | H | H | —CHNHCHO(R)\|(S)CHOH\|CH₃ | H | 0 |
| 172 | N | CH₂CH₃ | H | H | —CHNHCHO(R)\|(S)CHOH\|CH₃ | H | 0 |
| 173 | N | CH₂CH₃ | H | H | —CHNHCHO(R)\|CH₂OH | H | 0 |
| 174 | N | CH₂F | H | H | 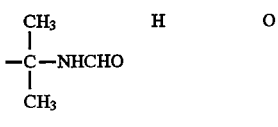 | H | 0 |
| 175 | N | CH₂F | H | H | —CHNHCHO\|CH(CH₃)₂ | H | 0 |

PREPARATION EXAMPLES

Preparation for Injection

A pharmaceutical composition containing a compound according to the present invention is aseptically charged into vials so that each vial may contain 1000 mg (potency) of the compound of the invention.

|  | Minimum Inhibition Concentration (μg/ml) | | | | | | | | | | |
|---|---|---|---|---|---|---|---|---|---|---|---|
|  | Example | | | | | | | | | | |
| Strain | 2 | 30 | 31 | 44 | 48 | 49 | 112 | 133 | 164 | CAZ | CPR |
| S. Aureus 209P JC-1 | 6.25 | 0.39 | 0.78 | 0.78 | 0.39 | 0.78 | 0.39 | 0.39 | 0.78 | 6.25 | 0.20 |
| S. Aureus 133* | 100 | 12.5 | 6.25 | 12.5 | 6.25 | 6.25 | 3.13 | 6.25 | 6.25 | 100 | 6.25 |
| S. Aureus 126* | >100 | 25 | 12.5 | 25 | 12.5 | 6.25 | 3.13 | 12.5 | 6.25 | >100 | 50 |
| S. epidermidis ATCC14990 | 6.25 | 0.39 | 0.78 | 0.78 | 0.39 | 0.78 | 0.20 | 0.39 | 0.78 | 6.25 | 0.39 |
| E. coli NIHJ JC-2 | 0.05 | 0.05 | ≦0.025 | ≦0.025 | ≦0.025 | 0.05 | 0.78 | ≦0.025 | ≦0.025 | 0.39 | 0.05 |
| K. pneumoniae PC1602 | ≦0.025 | 0.05 | 0.05 | ≦0.025 | ≦0.025 | 0.05 | 0.78 | ≦0.025 | ≦0.025 | 0.10 | 0.05 |
| P. vulgaris GN76 | ≦0.025 | 0.39 | 0.39 | 0.20 | 0.20 | 0.39 | 3.13 | 0.20 | 0.20 | 0.05 | 0.20 |
| M. morganii 1510/S-1 | ≦0.025 | 0.10 | 0.05 | 0.05 | ≦0.025 | ≦0.025 | 0.39 | ≦0.025 | ≦0.025 | 0.20 | ≦0.025 |
| C. freundii GN346/16 | 0.39 | 0.10 | 0.10 | 0.10 | 0.10 | 0.05 | 0.78 | 0.10 | ≦0.025 | 0.39 | 0.05 |
| E. cloacae G-0008 | 0.05 | 0.05 | 0.05 | 0.05 | ≦0.025 | 0.05 | 0.78 | ≦0.025 | 0.05 | 0.20 | 0.05 |
| S. marcescens No. 1 | ≦0.025 | 0.05 | 0.05 | 0.05 | ≦0.025 | 0.10 | 1.56 | ≦0.025 | ≦0.025 | 0.05 | ≦0.025 |
| P. aeruginosa GN10362 | 0.78 | 1.56 | 3.13 | 1.56 | 0.78 | 1.56 | 3.13 | 0.78 | 0.78 | 1.56 | 3.13 |
| P. aeruginosa E-2 | 0.78 | 3.13 | 3.13 | 1.56 | 0.78 | 1.56 | 3.13 | 0.78 | 0.78 | 1.56 | 3.13 |

*Methicillin-resistant Staphylococcus (MRSA)
CAZ: Ceftazidime
CPR: Cefpirome

Capsulated Preparation

| Compound of the Invention | 250 parts (potency) |
|---|---|
| Milk sugar | 60 parts (potency) |
| Magnesium stearate | 5 parts (potency) |

The above ingredients are homogeneously mixed, and the mixture is charged into capsules so that each capsule way contain 250 mg (potency) of the compound of the invention.

Soft Capsulated Preparation for Rectal Administration

| Olive oil | 160 parts |
|---|---|
| Polyoxyethylene lauryl ether | 10 parts |
| Sodium hexamethaphosphate | 5 parts |

To a base which is a homogeneous mixture of the above-ingredients is added 25 parts (potency) of a compound according to the present invention, and the mixture was homogeneously mixed. The resulting mixture is charged into soft capsules for rectal administration so that each capsule may contain 250 mg (potency) of the compound of the invention.

Antibacterial Activity Test

The antibacterial activity of the compounds according to the present invention was demonstrated by the minimum inhibitory concentrations of the compounds against various bacteria, measured by a conventional two-fold dilution method. The measurement was carried out in the following manner: $10^6$ CFU/ml of a bacterium to be tested was inoculated on a Medium N for disc susceptibility test (manufactured by Nissui Pharmaceutical Co., Ltd.), and cultivated at 35° C. for 18 to 20 hours. The results are as shown in Table 11.

Acute Toxicity Test 0.5 ml of a pharmaceutical solution prepared by dissolving a compound of the present invention in a physiological saline solution for injection (80 mg/ml) was injected to the caudal veins of ICR mice (4 weeks old, male, body weight: approx. 20 g). Two weeks after the administration, the mice were observed whether they were dead or not. The mice to which the compound of Example 49 had been administered were all (3 cases) alive. Therefore, the $LD_{50}$ of this compound is >2 g/kg (>40 mg/mouse).

What is claimed is:

1. A cephem derivative represented by the formula (I):

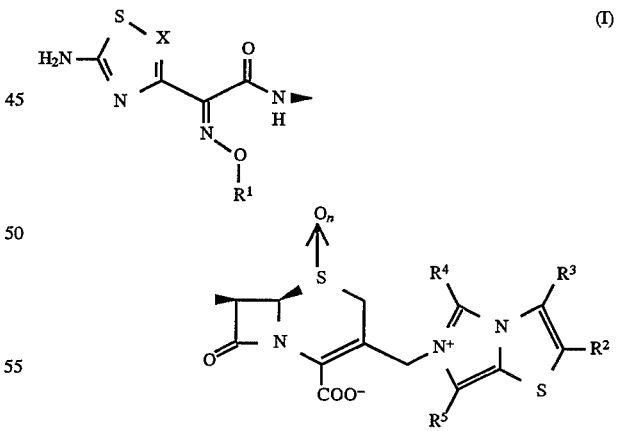

wherein X represents CH or N, $R^1$ represents a hydrogen atom; $C_{1-4}$ alkyl in which one or more hydrogen atoms may be substituted by a group selected form a group consisting of halogen, hydroxyl, carboxyl, $C_{1-4}$ alkoxycarbonyl, carbamoyl, N-$C_{1-4}$ alkylcarbamoyl, cyano, amino and $C_{1-4}$ alkylamino group; $C_{2-4}$ alkenyl; $C_{2-4}$ alkynyl; or $C_{3-6}$ cycloalkyl, $R^2$, $R^3$, $R^4$ and $R^5$, which may be the same or different, each independently represent hydrogen; $C_{1-4}$ alkoxy;

$C_{1-4}$ alkylthio; cyano; carboxyl; $C_{1-4}$ alkoxycarbonyl; carbamoyl; N-$C_{1-4}$ alkylcarbamoyl; formyl; amino in which one or more hydrogen atoms may be substituted by a group selected from a group consisting of formyl, $C_{1-4}$ alkylcarbonyl and $C_{1-4}$ alkylsulfonyl; halogen; $C_{1-4}$ alkyl in which one or more hydrogen atoms may be substituted by a group selected from a group consisting of hydroxyl, $C_{1-4}$ alkoxy, mercapto, $C_{1-4}$ alkylthio, cyano, halogen, carboxyl, $C_{1-4}$ alkoxycarbonyl, carbamoyl, N-$C_{1-4}$ alkylcarbamoyl, formyl, alkylcarbonyl, hydroxyimino, $C_{1-4}$ alkoxyimino, amino, formylamino, $C_{1-4}$ alkylcarbonylamino, $C_{1-4}$ alkylcarbonylamino (which may be substituted by a halogen atom), carbamoyloxy, N-$C_{1-4}$ alkylcarbamoyloxy, $C_{1-4}$ alkylsulfonylamino, ureido, N-$C_{1-4}$ alkylureido, $C_{1-4}$ alkoxycarbonylamino and imino $C_{1-4}$ alkylamino; $C_{3-6}$ cycloalkyl; $C_{2-4}$ alkenyl; or $C_{2-4}$ alkynyl; or a saturated five-membered heterocyclic ring which contains one oxygen atom and one nitrogen atom and may be substituted by oxo (=O), or any two of $R^2$, $R^3$, $R^4$ and $R^5$ may form $C_{3-6}$ alkylene, where one or more methylene groups in this alkylene group may be substituted by —NH—, —O—, —S— or —CO—, and n is 0 or 1; and a pharmaceutically acceptable salt thereof.

2. The compound according to claim 1, wherein $R^2$, $R^4$ and $R^5$ represent a hydrogen atom, and $R^3$ represents a hydrogen atom or a methyl group.

3. The compound according to claim 1, wherein $R^3$ represents a group selected from the group consisting of carbamoyl, hydroxymethyl, fluoromethyl, (carbamoyloxy) methyl, (N-methylcarbamoyloxy)methyl, 2-(carbamoyloxy) ethyl, cyano, difluoromethyl, formyl, (hydroxyimino) methyl and methoxymethyl.

4. The compound according to claim 3, wherein $R^2$, $R^4$ and $R^5$ represent a hydrogen atom.

5. The compound according to claim 1, wherein $R^4$ represents a group selected from the group consisting of hydroxymethyl, (formylamino)methyl, (R)-1-(formylamino)ethyl, (S)-1-(formylamino)ethyl, (N-formyl-N-methylamino)methyl, ureidomethyl, aminomethyl, 2-hydroxyethyl, formyl, dimethoxymethyl, 2-(formylamino)ethyl, carbamoylmethyl, 2-(carbamoyloxy) ethyl, methylthio, carbamoyl, methoxymethyl, acetoxymethyl, (N-methylureido)methyl, (acetylamino) methyl, (trifluoroacetylamino)methyl, cyano, carboxyl, ethoxycarbonyl and 2-oxo-4-oxazolidinyl.

6. The compound according to claim 5, wherein $R^2$, $R^3$ and $R^5$ represent a hydrogen atom.

7. The compound according to claim 1, wherein $R^2$ represents a hydrogen atom, $R^3$ represents a methyl group, $R^4$ represents a (formylamino)methyl group, and $R^5$ represents a hydrogen atom.

8. The compound according to claim 1, wherein $R^3$ represents a carbamoyl group, and $R^4$ represents a (formylamino)methyl group.

9. The compound according to claim 8, wherein $R^2$ and $R^5$ represent a hydrogen atom.

10. The compound according to claim 1, wherein $R^3$ and $R^4$ are combined to represent 1-oxo-2-azapropanone.

11. The compound according to claim 10, wherein $R^2$ and $R^5$ represent a hydrogen atom.

12. The compound according to claim 1, wherein $R^5$ represents a hydroxymethyl group.

13. The compound according to claim 12, wherein $R^2$, $R^3$ and $R^4$ represent a hydrogen atom.

14. The compound according to claim 1, wherein $R^2$ represents a carbamoyl group.

15. The compound according to claim 14, wherein $R^3$ represents a methyl group, and $R^4$ and $R^5$ represent a hydrogen atom.

16. A pharmaceutical composition comprising the compound according to claim 1 together with a pharmaceutically acceptable carrier.

17. A method for treating infectious diseases caused by Gram positive or Gram negative bacteria, comprising administering the compound of any one of claims 1 to 15.

18. A method for preparing an antibacterial agent which comprises admixing the compound of any one of claims 1 to 15 together with a pharmaceutically acceptable carrier.

19. The compound according to claim 1, selected from the group consisting of:

(6R,7R)-7-[(Z)-2-(5-amino-1,2,4-thiadiazol-3-yl)-2-methoxyimino acetamide]-3-(5-(formylamino) methylimidazo[5,1-b]thiazolium-6- yl)methyl-3-cephem-4-carboxylate (internal salt), (6R,7R)-7-[(Z)-2-(5-amino-1,2,4-thiadiazol-3-yl)- 2-(2-fluoroethoxyimino)-acetamide]-3-(imidazo[5,1-b] thiazolium -6-yl)methyl-3-cephem-4-carboxylate (internal salt), (6R,7R)-7-[(Z)-2-(5-amino-1,2,4-thiadiazol-3-yl)-2-fluoro- methoxyiminoacetamide]-3-(5-((S)-1-formylamino)ethylimidazo- [5,1-b]thiazolium-6-yl) methyl-3-cephem-4-carboxylate (internal salt), (6R,7R)-7-[(Z)-2-(5-amino-1,2,4-thiadiazol-3-yl)-2-fluoro- methoxyiminoacetamide]-3-(5-((R)-1-formylamino-2-hydroxyethyl)- imidazo[5,1-b] thiazolium-6-yl]methyl-3-cephem-4-carboxylate (internal salt), (6R,7R)-7-[(Z)-2-(5-Amino-1,2,4-thiadiazol-3-yl)-2-ethoxyimino -acetamide]-3-[5-(formylamino) methylimidazo[5,1-b]thiazolium-6-yl]methyl-3-cephem-4-carboxylate (internal salt), (6R,7R)-7-[(Z)-2-(5-Amino-1,2,4-thiadiazol-3-yl)-2-(fluoro- methoxyimino)acetamide]-3-[5-[(R)-1-(formylamino)ethyl]imidazo -[5,1-b]thiazolium-6-yl] methyl-3-cephem-4-carboxylate (internal salt), and (6R,7R)-7-[(Z)-2-(5-amino-1,2,4-thiadiazol-3-yl)-2-fluoromethoxyiminoacetamido]-3-[5-(S)-1-(formylamino)-2- hydroxyethyl]imidazo[5,1-b] thiazolium-6-yl)methyl-3-cephem-4-carboxylate (inner salt).

20. A method for treating infectious diseases caused by *Pseudomonas aeruginosa* comprising administering the compound according to any one of claims 1–15 and 19.

21. A method for treating infectious diseases caused by methicillin-resistant *Staphylococcus aureus* (MRSA) comprising administering the compound according to any one of claims 1–15 and 19.

* * * * *